US012802779B2

(12) United States Patent
Biggins et al.

(10) Patent No.: US 12,802,779 B2
(45) **Date of Patent: *Nov. 17, 2026**

(54) HUMAN THERAPEUTIC TARGETS AND MODULATORS THEREOF

(71) Applicant: LifeMine Therapeutics, Inc., Watertown, MA (US)

(72) Inventors: John Baxter Biggins, Long Beach, NY (US); Brian Roger Bowman, New Rochelle, NY (US); Gregory L. Verdine, Newton, MA (US)

(73) Assignee: LifeMine Therapeutics, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/040,032

(22) Filed: Jan. 29, 2025

(65) Prior Publication Data

US 2026/0011401 A1 Jan. 8, 2026

Related U.S. Application Data

(63) Continuation of application No. 18/221,761, filed on Jul. 13, 2023, now Pat. No. 12,243,623, which is a continuation of application No. 16/646,978, filed as (Continued)

(51) Int. Cl.
*G16B 20/00* (2019.01)
*G16B 35/10* (2019.01)

(52) U.S. Cl.
CPC ............ *G16B 20/00* (2019.02); *G16B 35/10* (2019.02)

(58) Field of Classification Search
None
See application file for complete search history.

(56) References Cited

U.S. PATENT DOCUMENTS 6,432,648 B1 * 8/2002 Blumenfeld ........... G16B 20/20 536/23.5
8,065,089 B1 11/2011 Najarian
(Continued)

FOREIGN PATENT DOCUMENTS

WO 02077179 A2 10/2002
WO 2007139871 A2 12/2007
(Continued)

OTHER PUBLICATIONS

International Search Report for PCT/U52018/051134 (Human Therapeutic Targets and Modulators Thereof, filed Sep. 14, 2018), issued by ISA/US, 6 pages (Feb. 21, 2019).
(Continued)

*Primary Examiner* — Eliyah S. Harper
(74) *Attorney, Agent, or Firm* — Elmore Patent Law Group, P.C.; Carolyn S. Elmore; Jia Kang

(57) ABSTRACT

Among other things, the present disclosure provides technologies for efficient and effective identification of ETaGs, for example, from fungi genomes. In some embodiments, provided technologies are particularly useful for identifying mammalian targets of biosynthetic products of fungi. In some embodiments, provided technologies are particularly useful for identifying and/or prioritizing human targets for drug development. In some embodiments, provided technologies are particularly useful for developing modulators for human targets based on biosynthetic products of fungi.

19 Claims, 40 Drawing Sheets

Specification includes a Sequence Listing.

*Thermomyces lanuginosus*: 4 genomic Ras isoforms

Related U.S. Application Data application No. PCT/US2018/051134 on Sep. 14, 2018, now Pat. No. 11,749,375.

(60) Provisional application No. 62/558,744, filed on Sep. 14, 2017.

(56) References Cited

U.S. PATENT DOCUMENTS

| | | | | |
|---|---|---|---|---|
| 12,243,623 | B2 * | 3/2025 | Biggins | G16B 30/10 |
| 2001/0039014 | A1 * | 11/2001 | Bass | C12N 15/1031 702/20 |
| 2002/0164588 | A1 * | 11/2002 | Eisenberg | G16B 20/30 435/6.16 |
| 2004/0058872 | A1 | 3/2004 | Keller et al. | |
| 2004/0076981 | A1 * | 4/2004 | Yoder | C12Q 1/6895 435/254.2 |
| 2004/0265865 | A1 | 12/2004 | Mattick et al. | |
| 2006/0205017 | A1 | 9/2006 | Handelsman et al. | |
| 2007/0003999 | A1 | 1/2007 | Keller et al. | |
| 2007/0117749 | A1 * | 5/2007 | Dawson | C07K 14/32 435/69.3 |
| 2009/0011476 | A1 | 1/2009 | Hoffmeister et al. | |
| 2009/0191602 | A1 | 7/2009 | Tang et al. | |
| 2009/0191636 | A1 * | 7/2009 | Ramage | C12N 15/8277 435/469 |
| 2011/0076682 | A1 | 3/2011 | Keller et al. | |
| 2011/0091454 | A1 | 4/2011 | Diber et al. | |
| 2012/0028816 | A1 | 2/2012 | Warren et al. | |
| 2012/0190038 | A1 | 7/2012 | Tang et al. | |
| 2012/0315680 | A1 | 12/2012 | Tang et al. | |
| 2014/0273144 | A1 | 9/2014 | Hawkins et al. | |
| 2015/0037862 | A1 | 2/2015 | Keller et al. | |
| 2015/0203884 | A1 | 7/2015 | Tang et al. | |
| 2015/0218531 | A1 | 8/2015 | Tang et al. | |
| 2015/0310168 | A1 * | 10/2015 | Machida | G16B 40/00 702/19 |
| 2016/0224748 | A1 | 8/2016 | Apte et al. | |
| 2016/0237443 | A1 | 8/2016 | Keller et al. | |
| 2017/0029790 | A1 | 2/2017 | Tang et al. | |
| 2017/0121719 | A1 | 5/2017 | Oakley et al. | |
| 2018/0068062 | A1 | 3/2018 | Zhang et al. | |
| 2019/0130999 | A1 | 5/2019 | Oppenheim et al. | |
| 2019/0194098 | A1 | 6/2019 | Cheung et al. | |
| 2020/0143907 | A1 | 5/2020 | Engreitz et al. | |
| 2020/0194098 | A1 | 6/2020 | Hannigan et al. | |
| 2020/0206283 | A1 | 7/2020 | Segal et al. | |
| 2020/0211673 | A1 | 7/2020 | Biggins et al. | |
| 2021/0230611 | A1 | 7/2021 | Naughton et al. | |
| 2021/0257056 | A1 | 8/2021 | Liu et al. | |

FOREIGN PATENT DOCUMENTS

| | | | |
|---|---|---|---|
| WO | 2011044496 | A2 | 4/2011 |
| WO | 2014071182 | A1 | 5/2014 |
| WO | 2017100917 | A1 | 6/2017 |
| WO | 2017205387 | A1 | 11/2017 |
| WO | 2018094110 | A2 | 5/2018 |
| WO | 2018175635 | A1 | 9/2018 |
| WO | 2019055816 | A1 | 3/2019 |
| WO | 2023081396 | A1 | 5/2023 |
| WO | 2023081413 | A2 | 5/2023 |
| WO | 2023091950 | A1 | 5/2023 |

OTHER PUBLICATIONS

Written Opinion for PCT/U52018/051134 (Human Therapeutic Targets and Modulators Thereof, filed Sep. 14, 2018), issued by ISA/US, 11 pages (Feb. 21, 2019).

"BUSCO Software", https://busco.ezlab.org/.

Abe, Y., "Effect of Increased Dosage of the ML-236B (Compactin) Biosynthetic Gene Cluster on ML-236B Production in *Penicillium citrinum*", Mol. Genet. Genomics, 268(1), 2002, 130-137.

Alanjary, M., "The Antibiotic Resistant Target Seeker (ARTS), an Exploration Engine for Antibody Cluster Prioritization and Novel Drug Target Discovery", Nucleic Acids Research, 45(W1), https://doi.org/10.1093/nar/gkx360, Jul. 3, 2017, W42-W48.

Almeida, H., "TOUCAN: A Framework for Fungal Biosynthetic Gene Cluster Discovery", NAR Genomics and Bioinformatics, 2(4), https://doi.org/10.1093/nargab/lqaa098, Nov. 27, 2020, 1-11.

Bailey, T., "The MEME Suite", Nucleic Acids Res., 43(W1), May 7, 2015, W39-W49.

Baran, R., "Detecting Horizontally Transferred and Essential Genes Based on Dinucleotide Relative Abundance", DNA Res., 15, DOI: 10.1093/dnares/dsn021, Sep. 16, 2008, 267-276.

Basson, M., "Structural and Functional Conservation Between Yeast and Human 3-Hydroxy-3-Methylglutaryl Coenzyme A Reductases, The Rate-Limiting Enzyme of Sterol Biosynthesis", Mol. Cell. Biol., 8(9), Sep. 1, 1988, 3797-3808.

Bat-Erdene, U., "Iterative Catalysis in the Biosynthesis of Mitochondrial Complex II Inhibitors Harzianopyridone and Atpenin B", J. Am. Chem. Soc., 142(19), DOI: 10.1021/jacs.0c03438, May 13, 2020, 8550-8554.

Berge, S. M, "Pharmaceutical Salts", J. Pharm. Sci., 66(1), Jan. 1977, 1-19.

Blin, K., "AntiSMASH 4.0—Improvements in Chemistry Prediction and Gene Cluster Boundary Identification", Nucleic Acids Res, 45(W1), doi: 10.1093/nar/gkx319, Jul. 3, 2017, W36-W41.

Blin, K., "antiSMASH 6.0: Improving Cluster Detection and Comparison Capabilities", Nucleic Acids Res., 49(W1), DOI: 10.1093/nar/gkab335, Jul. 2, 2021, W29-W35.

Chiang, Y., "A Gene Cluster Containing Two Fungal Polyketide Synthases Encodes the Biosynthetic Pathway for a Polyketide, Asperfuranone, in *Aspergillus nidulans*", J. ACS, 13(18), 2009, 2965-2970.

Choffnes, E., "The Science and Applications of Synthetic and Systems Biology: Workshop Summary", Institute of Medicine (US) Forum on Microbial Threats. Washington (DC): National Academies Press (US); 2011. https://www.ncbi.nlm.nih.gov/books/NBK84445/, doi: 10.17226/13239, 1-570.

Chung, K., "Determination of a Transcriptional Regulator-Like Gene Involved in Biosynthesis of Elsinochrome Phytotoxin by the Citrus Scab Fungus, *Elsinoe fawcettii.*", Microbiology, 154(11), 2008, 3556-3566.

Cimermancic, P., "Insights into Secondary Metabolism from a Global Analysis of Prokaryotic Biosynthetic Gene Clusters", Cell, 158(2), 2014, 412-421.

Clevenger, K., "A Scalable Platform to Identify Fungal Secondary Metabolites and their Gene Clusters", Nat. Chem. Bio., 13(8), 2017, 895-901.

Costanzo, M., "A Global Genetic Interaction Network Maps a Wiring Diagram of Cellular Function", Sci., 353(6306), doi: 10.1126/science.aaf1420, Sep. 23, 2016, 1-34.

Dixon, S., "Identifying Druggable Disease-Modifying Gene Products", Curr. Opin. Chem. Biol., 13(5-6), 2009, 549-555.

Ehrlich, K., "Aflatoxin Biosynthesis Gene clusters and Flanking Regions", J.Applied Microbiol., 99(3), 2005, 518-527.

Emms, D., "OrthoFinder: Solving Fundamental Biases in Whole Genome Comparisons Dramatically Improves Orthogroup Inference Accuracy", Genome Biology 16(157), Aug. 6, 2015, 1-14.

Fischbach, M., "Prokaryotic Gene Clusters: A Rich Toolbox For Synthetic Biology", Biotechnol. J., 5(12), https://doi.org/10.1002/biot.201000181, Dec. 10, 2010, 1277-1296.

Gilchrist, C., "Clinker & Clustermap.js: Automatic Generation of Gene Cluster Comparison Figures", Bioinformatics, 37(16), DOI: 10.1093/bioinformatics/btab007, Aug. 25, 2021, 2473-2475.

Gonzalez-Valbuena, E., "Metrics to Estimate Differential Co-Expression Networks", BioData Mining, 10(32), doi: 10.1186/s13040-017-0152-6, Nov. 10, 2017, 1-15.

Hannigan, G., "A Deep Learning Genome-Mining Strategy for Biosynthetic Gene Cluster Prediction", Nucleic Acids Res., 47(18), Aug. 10, 2019, e110.

Harvey, C., "Precursor-Directed Biosynthesis of Macrolide Antibiotics", Dissertation as submitted to the Department of Chemistry and the Committee on Graduate Studies of Stanford University in

(56) References Cited

OTHER PUBLICATIONS

Partial Fulfillment of the Requirements for the Degree of Doctor of Philosophy, 176 pages (Apr. 2012).
Heinz, S., "Simple Combinations of Lineage-Determining Transcription Factors Prime cis-Regulatory Elements Required for Macrophage and B Cell Identities", Mol. Cell, 38(4), doi: 10.1016/j.molcel.2010.05.004, May 28, 2010, 576-589.
Huang, L., "KinOrtho: A Method For Mapping Human Kinase Orthologs Across The Tree of Life and Illuminating Understudied Kinases", BMC Bioinformatics, 22(446), Sep. 8, 2021, 1-31.
Kapasa, M., "Phylogenetic And Regulatory Region Analysis of Wnts Genes Reveals Conservation of a Regulatory Module With Put.Alive Implication in Pancreas Development", Biol. Direct, 5(49), https://doi.org/10.1186/1745-6150-5-49, Aug. 4, 2010, 1-13.
Katz, L., "Natural Product Discovery: Past, Present, and Future", J. Ind. Microbiol. Biotechnol., 43(2-3), DOI: 10.1007/s10295-015-1723-5, Jan. 6, 2016, 155-176.
Kautsar, S., "Big-Slice: A Highly Scalable Tool Maps The Diversity of 1.2 Million Biosynthetic Gene Clusters", GigaScience, 10(1), DOI: 10.1093/gigascience/giaa154, Jan. 13, 2021, 1-31.
Kautsar, S., "MIBiG 2.0: A Repository for Biosynthetic Gene Clusters of Known Function", Nucleic Acids Research, 48(D1), https://doi.org/10.1093/nar/gkz882, Oct. 15, 2019, D454-D458.
Keller, N., "Fungal Secondary metabolism: Regulation, Function and Drug Discovery", Nat. Chem. Biol., 17(3), Mar. 2019, 167-180.
Keller, N. P, "Translating Biosynthetic Gene Clusters Into Fungal Armor and Weaponry", Nat. Chem. Biol., 11(9), doi: 10.1038/nchembio.1897, Sep. 2015, 671-677.
Kennedy, J., "Modulation of Polyketide Synthase Activity by Accessory Proteins During Lovastatin Biosynthesis", Science, 284(5418), May 21, 1999, 1368-1372.
Khaldi, N., "SMURF: Genomic Mapping of Fungal Secondary Metabolite Clusters", Fungal Genet. Biol., 47(9), doi: 10.1016/j.fgb.2010.06.003, Jun. 8, 2010, 736-741.
Naerbolling, I. , "Resistance Gene-Directed Genome Mining of 50 *Aspergillus* Species", mSystems, 4(4):e00085-19, doi: 10.1128/mSystems.00085-19, 2019.
Kloosterman, A., "Expansion of RiPP Biosynthetic Space Through Integration of Pan-Genomics and Machine Learning Uncovers a Novel Class of Lanthipeptides", PLoS Biol., 18(12):e3001026, doi: 10.1371/journal.pbio.3001026, Dec. 22, 2020.
Li, L., "OrthoMCL: Identification of Ortholog Groups for Eukaryotic Genomes", Genome Res., 13(9), doi: 10.1101/gr.1224503, Sep. 2003, 2178-2189.
Libis, V., "Multiplexed mobilization and expression of biosynthetic gene clusters", Nature Comm., 13(1), DOI: 10.1038/s41467-022-32858-0, Sep. 6, 2022.
Lim, F., "Fungal Isocyanide Synthases and Xanthocillin Biosynthesis in *Aspergillus fumigatus*" mBio, 9(3):e00785-18, doi: 10.1128/mBio.00785-18, May 29, 2018, 1-17.
Liu, J., "Transcriptomic Analysis on the Formation of the Viable Putative Non-Culturable State of Beer-Spoilage *Lactobacillus acetotolerans*", Sci. Rep., 6(36753), https://doi.org/10.1038/srep36753, Nov. 7, 2016, 1-11.
Lowther, W., "The Anti-Angiogenic Agent Fumagillin Covalently Modifies a Conserved Active-Site Histidine in the *Escherichia coli* Methionine Aminopeptidase", PNAS, 95(21), Oct. 13, 1998, 12153-12157.
Manni, M., "BIJSCO Update: Novel and Streamlined WorkflowsAlong With Broader and Deeper Phylogenetic Coverage for Scoring of Eukaryotic, Prokaryotic, and Viral Genomes", Mol. Biol. Evol., 38(10), doi: 10.1093/molbev/msab199, Sep. 27, 2021, 4647-4654.
Medema, M., "anti SMASH: Rapid Identification, Annotation and Analysis of Secondary Metabolite Biosynthesis Gene Clusters in Bacterial and Fungal Genome Sequences", Nucleic Acids Res., 39, doi: 10.1093/nar/gkr466, Jun. 14, 2011, W339-W346.
Montiel, D., "Yeast Homologous Recombination-Based Promoter Engineering for the Activation of Silent Natural Product Biosynthetic Gene Clusters", PNAS, 112(29), Jul. 6, 2015, 8953-8958.
Moreno-Hagelsieb, G., "Choosing BLAST Options for Better Detection of Orthologs as Reciprocal Best Hits", Bioinformatics, 24(3), https://doi.org/10.1093/bioinformatics/btm585, Nov. 26, 2007, 319-324.
Naughton, L., "Identification of Secondary Metabolite Gene Clusters in the *Pseudovibrio* Genus Reveals Encouraging Biosynthetic Potential towards the Production of Novel Bioactive Compounds", Front. Microbiol., 8, https://doi.org/10.3389/fmich.2017.01494, Aug. 18, 2017, 1-15.
Newman, D., "Natural Products as Sources of New Drugs from 1981 to 2014", J. Nat. Prod., 79(3), doi: 10.1021/acs.jnatprod.5b01055, Mar. 25, 2016, 629-661.
Orvis, J., "Ergatis: A Web Interlace and Scalable Software System for Bloinformatics Workflow", Bioinformatics, 26(12), DOI: 10.1093/bioinformatics/btq167, Jun. 15, 2010, 1488-1492.
Palazzotto, E., "Omics and Multi-Omics Approaches to Study The Biosynthesis of Secondary Metabolites in Microorganisms", Curr. Opin. Microbiol., 45, doi: 10.1016/j.mib.2018.03.004, Apr. 12, 2018, 109-116.
Piel, J., "Metabolites From Symbiotic Bacteria", Nat. Prod. Rep., 26(3), doi: 10.1039/b703499g, Dec. 5, 2008, 338-362.
Powers, S., "Genes In *S. cerevisiae* Encoding Proteins With Domains Homologous to The Mammalian Ras Proteins", Cell, 36(3), DOI: 10.1016/0092-8674(84)90340-4, Mar. 1984, 607-612.
Regueira, T., "Molecular Basis for Mycophenolic Acid Biosynthesis in *Penicillium brevicompactum*", Appl. Environ. Microbiol., 77(9), Mar. 11, 2011, 3035-3043.
Scherlach, K., "Mining and Unearthing Hidden Biosynthetic Potential", Nat. Commun., 12(1):3864, https://doi.org/10.1038/s41467-021-24133-5, Jun. 23, 2021, 1-12.
Sharp, P., "The Codon Adaptation Index—A Measure of Directional Synonymous Codon Usage Bias, and Its Potential Applications", Nucleic Acids Res., 15(3), doi: 10.1093/nar/15.3.1281, Feb. 11, 1987, 1281-1295.
Steenwyk, J., "An Orthologous Gene Coevolution Network Provides Insight Into Eukaryotic Cellular and Genomic Structure and Function", Sci. Adv., 8(18), DOI: 10.1126/sciadv.abn0105, May 4, 2022, 1-13.
Stockwell, B., "Outsmarting Cancer. A Biologist talks About What Makes Disease-Causing Proteins so Difficult to Target with Drugs", Sci. Am., 305(20), Oct. 1, 2011.
Subazini, T., "Characterization of Lovastatin Biosynthetic Cluster Proteins In *Aspergillus terreus* Strain ATCC 20542", Bioinformation, 6(7), doi: 10.6026/97320630006250, Jun. 23, 2011, 250-254.
Suresh, A., "Evolutionary Dynamics Based on Comparative Genomics of Pathogenic *Escherichia coli* Lineages Harboring Polyketide Synthase (pks) Island", mBio., 12(1): e03634-20, doi: 10.1128/mBio.03634-20, Mar. 2, 2021, 1-21.
Tang, X., "Identification ofThiotetronic Acid Antibiotic Biosynthetic Pathways by Target-Directed Genome Mining", ACS Chem. Biol., 10(12), Oct. 21, 2015, 2841-2849.
Tatusov, R., "A Genomic Perspective on Protein Families", Science, 278, doi: 10.1126/science.278.5338.631, Oct. 24, 1997, 631-637.
Thaker, M., "Antibiotic Resistance-Mediated Isolation of Scaffold-Specific Natural Product Producers", Nature Protocols, 9(6), May 29, 2014, 1459-1479.
Tommasi, S., "RASSF3 and NORE1: Identification and Cloning of Two Human Homologues of he Putative Tumor Suppressor Gene RASSF1", Oncogene, 21, https://doi.org/10.1038/sj.onc.1205365, Apr. 24, 2002, 2713-2720.
Tran, P. N, "Detecting and prioritizing biosynthetic gene clusters for bioactive compounds in bacteria and fungi", Appl Microbiol Biotechnol, 103(8), doi: 10.1007/s00253-019-09708-z, 2019, 3277-3287.
Trivedi, R., "Substitution Scoring Matrices for Proteins—An Overview", Protein Sci., 29(11), doi: 10.1002/pro.3954, Oct. 12, 2020, 2150-2163.
Vandova, G., "Identification Of Polyketide Biosynthetic Gene Clusters That Harbor Self-Resistance Target Genes", Retrieved from https://web.archive.org/web/20200711060946ld/https://www.biorxiv.org/ontentlbiorxiv/early/2020/06/02/2020.06.01.128595.full.pdf, https://doi.org/10.1101/2020.06.01.128595doi, Jun. 2, 2020, 1-37.

(56) References Cited

OTHER PUBLICATIONS

Vesth, T. C, "FunGeneClusterS: Predicting Fungal Gene Clusters from Genome and Transcriptome Data", Synth. Syst. Biotechnol., 1(2), http://dx.doi.org/10.1016/j.synbio.2016.01.002, Feb. 23, 2016, 122-129.
Vignolle, G. A, "FunOrder: A robust and semi-automated method for the identification of essential biosynthetic genes through computational molecular co-evolution", PLOS Computational Biol., 17(9), OI: 10.1371/journal.pcbi.1009372, Sep. 27, 2021.
Wall, D., "Ortholog Detection Using The Reciprocal Smallest DistanceAlgorithm", Methods Mol. Biol., 396, doi: 10.1007/978-1-59745-515-2_7, 2007, 95-110.
Wasil, Z., "OryzinesA & B, Maleidride Congeners from *Aspergillus oryzae* and Their Putative Biosynthesis", J. Fungi, 4(3):96, doi: 10.3390/jof4030096, Aug. 13, 2018, 1-12.
Weber, T., "An Introduction to Genome Mining Using antiSMASH", antiSMASH5, antiSMASH Database Manual,, 2019, 1-26.
Yan, Y., "Recent Developments in Self-Resistance Gene Directed Natural Product Discovery", Nat. Prod. Rep., 37(7), doi: 10.1039/c9np00050j, Jul. 1, 2021, 879-892.
Yan, Y., "Resistance-Gene-Directed Discovery of a Natural-Product Herbicide with a New Mode of Action", Nature, 559, Jul. 11, 2018, 415-418.
Yeh, H., "Resistance Gene-Guided Genome Mining: Serial Promoter Exchanges in *Aspergillus nidulans* Reveal the Biosynthetic Pathway for Fellutamide B, a Proteasome Inhibitor", ACS Chem. Biol., 11(8), Aug. 19, 2016, 2275-2284.
Zhu, S., "Computational advances in biosynthetic gene cluster discovery and prediction", Biotechnol Adv, 79:108532, doi: 10.1016/j.biotechadv.2025.108532, 2025, Feb. 7, 2025.
Navarro-Munoz, J., "A computational framework to explore large-scale biosynthetic diversity", Nat Chem Biol., 16(1), DOI: 10.1038/S41589-019-0400-9, Nov. 25, 2019, 60-68.

* cited by examiner

```
                                                        10                  20          30          40
KRAS             M---------------------------TEYKLVVVGAGG------VGKSALTIQLIQNHFVDEYDPTIEDSYRKQVVIDG
HRAS             M---------------------------TEYKLVVVGAGG------VGKSALTIQLIQNHFVDEYDPTIEDSYRKQVVIDG
NRAS             M---------------------------TEYKLVVVGAGG------VGKSALTIQLIQNHFVDEYDPTIEDSYRKQVVIDG
ANHP_459_5       MQP-------------------------RREYHIVVLGA--------------AQFVQNVWIESYDPTIEDSYRKQIEVDG
KB73344_288_17   MSQ-------------------------REYHIVVLGSGG------VGKSCLTAQFVQNVWIESYDPTIEDSYRKVLEVDG
CM004463         MAS-----------------------KFLREYKLVVVGGGG------VGKSCLTIQLIQSHFVDEYDPTIEDSYRKQCVIDE
KV42800_485_5    MSRS-----AAQA-------------SFLREYKLVVVGGGGMSLVSPVGKSALTIQFIQSHFVDEYDPTIEDSYRKQCVIDD
AACS_391_8       MPEVMNAMYATKGGIFDVSENDKAQFLREYKLVVVGGGG------VGKSALTIQFIQSHFVDEYDPTIEDSYRKQCIIDD
JH97138_360_5    MANN----------AASRAA---QAQFLREYKLVVVGGGG------VGKSALTIQFIQSHFVDEYDPTIEDSYRKQCVIDE
KI911109_c052    M---------------------------TLYKLVVLGDGG------VGKTALTIQLCLNHFVETYDPTIEDSYRKQVVIDQ
KE54696_c00122   MDAP-----------PYLL--------KFLREYKLVVVGGGG------VGKSCLTIQLIQSHFVDEYDPTIEDSYRKQCVIDE

KRAS             ETCLLDILDTAGQEEYSAMRDQYMRTGEGFLCVFAINNTKSFEDIHHYREQIKRVKDSE---------------------
HRAS             ETCLLDILDTAGQEEYSAMRDQYMRTGEGFLCVFAINNTKSFEDIHQYREQIKRVKDSD---------------------
                   50     60        70       80       90       100
NRAS             ETCLLDILDTAGQEEYSAMRDQYMRTGEGFLCVFAINNSKSFADINLYREQIKRVKDSD---------------------
ANHP_459_5       RQCILEILDTAGTEQF-----------------IPSITSMSSLNELSEIREQILPIKDDD--------------------
KB73344_288_17   RHVILEILDTAGTEQFK-----LYMKTGQGFLLVFSITSESSFWELAELREQIRRIKEDS---------------------
CM004463         EVALLDVLDTAGQEEYSAMREQYMRTGEGFLLVYSITSRQSFEEITTFQQQILRVKDKD---------------------
KV42800_485_5    EVALLDVLDTAGQEEYGAMREQYMRTGEGFLLVYSITSRNSFEEISTFHQQILRVKDKD---------------------
AACS_391_8       EVALLDVLDTAGQEEYGAMREQYMRTGEGFLLVYSITSRNSFEEISIFHQQILRVKDQD---------------------
JH97138_360_5    EVALLDVLDTAGQEEYGAMREQYMRTGEGFLLVYSITARSSFEEINQFYQQILRVKDQD---------------------
KI911109_c052    Q-SMLEVLDTAGQEEYTALRDQWIRDGEGFVLVYSITSPASFARIPKFYNQIKMVKESASSGSPAGASYLTSPINSPSGP
KE54696_c00122   EVALLDVLDTAGQEEYSAMREQYMRTGEGFLLVYSITSPQSFEEMLTFQQQILRVKDRD---------------------
```

Boldface: Nucleotide binding residues of KRAS

FIG. 13

```
                                                       10             20        30        40
KRAS                M--------------------------TEYKLVVVGAGG------VGKSALTIQLIQNHFVDEYDPTIEDSYRKQVVIDG
HRAS                M--------------------------TEYKLVVVGAGG------VGKSALTIQLIQNHFVDEYDPTIEDSYRKQVVIDG
NRAS                M--------------------------TEYKLVVVGAGG------VGKSALTIQLIQNHFVDEYDPTIEDSYRKQVVIDG
ANHP_459_5          MQP-----------------------RREYHIVVLGA---------------AQFVQNVWIESYDPTIEDSYRKQIEVDG
KB73344_288_17      MSQ------------------------REYHIVVLGSGG------VGKSCLPAQFVQNVWIESYDPTIEDSYRKVLEVDG
CM004463            MAS---------------------KFLREYKLVVVGGGG------VGKSCLTIQLIQSHFVDEYDPTIEDSYRKQCVIDE
KV42800_485_5       MSRS----AAQA------------SFLPEYKLVVVGGGGMSLVSPVGKSALTIQFIQSHFVDEYDPTIEDSYRKQCVIDD
AACS_391_8          MPEVMNAMYATKGGIFDVSENDKAQFLPEYKLVVVGGGG------VGKSALTIQFIQSHFVDEYDPTIEDSYRKQCIIDD
JN97138_360_5       MANN--------AASRAA----QAQFLREYKLVVVGGGG------VGKSALTIQFIQSHFVDEYDPTIEDSYRKQCVIDE
KI911109_c052       M--------------------------TLYKLVVLGDGG------VGKTALTIQLCLNHFVETYDPTIEDSYRKQVVIDQ
KE54696_c00122      MDAD----------PYLL------KFLREYKLVVVGGGG------VGKSCLTIQLIQSHFVDEYDPTIEDSYRKQCVIDE

KRAS                EPCLLDILDTAGQEEYSAMRDQYMRTGEGFLCVFAINNTKSFEDIHHYREQIKRVKDSE---------------------
HRAS                ETCLLDILDTAGQEEYSAMRDQYMRTGEGFLCVFAINNTKSFEDIHQYREQIKRVKDSD---------------------
                      50        60        70        80        90       100
NRAS                ETCLLDILDTAGQEEYSAMRDQYMRTGEGFLCVFAINNSKSFADINLYREQIKRVKDSD---------------------
ANHP_459_5          RQCILEILDTAGTEQF----------------IFSITSMSSLNELSEIREQILRIKDDD---------------------
KB73344_288_17      RHVILEILDTAGTEQFK----LYMKTGQGFLLVFSITSESSFWELAELREQIRRIKEDS---------------------
CM004463            EVALLDVLDTAGQEEYSAMREQYMRTGEGFLLVYSITSRQSFEEITTFQQQILRVKDKD---------------------
KV42800_485_5       EVALLDVLDTAGQEEYGAMREQYMRTGEGFLLVYSITSPNSFEEISTFHQQILRVKDKD---------------------
AACS_391_8          EVALLDVLDTAGQEEYGAMREQYMRTGEGFLLVYSITSPNSFEEISIFHQQILRVKDQD---------------------
JN97138_360_5       EVALLDVLDTAGQEEYGAMREQYMRTGEGFLLVYSITARSSFEEINQFYQQILRVKDQD---------------------
KI911109_c052       Q-SMLEVLDTAGQEEYTALRDQWIRDGEGFVLVYSITSRASFARIPKFYNQIKMVKESASSGSPAGASYLTSPINSPSGP
KE54696_c00122      EVALLDVLDTAGQEEYSAMREQYMRTGEGFLLVYSITSRQSFEEMLTFQQQILRVKDRD---------------------
```

Boldface: KRAS residues w/ 4 Å of BRAF, PDB: 4G0N

FIG. 14

```
                                                              10         20        30        40
KRAS             M-------------------------TEYKLVVVGAGG------VGKSALTIQLIQNHFVDEYDPTIEDSYRKQVVIDG
HRAS             M-------------------------TEYKLVVVGAGG------VGKSALTIQLIQNHFVDEYDPTIEDSYRKQVVIDG
NRAS             M-------------------------TEYKLVVVGAGG------VGKSALTIQLIQNHFVDEYDPTIEDSYRKQVVIDG
ANHP_459_5       MQP-----------------------REYHIVVLGA--------------AQFVQNVWIESYDPTIEDSYRKQIEVDG
KB73344_288_17   MSQ-----------------------REYHIVVLGSGG------VGKSCLTAQFVQNVWIESYDPTIEDSYRKVLEVDG
CM004463         MAS---------------------KFLREYKLVVVGGGG------VGKSCLTIQLIQSHFVDEYDPTIEDSYRKQCVIDE
KV42800_485_5    MSRS-----AAQA-----------SFLREYKLVVVGGGGMSLVSRVGKSALTIQFIQSHFVDEYDPTIEDSYRKQCVIDD
AACS_391_8       MPEVMNAMYATKGGIFDVSENDKAQFLREYKLVVVGGGG------VGKSALTIQFIQSHFVDEYDPTIEDSYRKQCIIDD
JH97138_360_5    MANN--------AASRAA---QAQFLREYKLVVVGGGG------VGKSALTIQFIQSHFVDEYDPTIEDSYRKQCVIDE
KI911109_c052    M-------------------------TLYKLVVLGDGG------VGKTALTIQLCLNHFVETYDPTIEDSYRKQVVIDQ
KE54696_c00122   MDAD--------PYLL-------KFLREYKLVVVGGGG------VGKSCLTIQLIQSHFVDEYDPTIEDSYRKQCVIDE

KRAS             ETCLLDILDTAGQEEYSAMRDQYMRTGEGFLCVFAINNTKSFEDIHHYREQIKRVKDSE--------------------
HRAS             ETCLLDILDTAGQEEYSAMRDQYMRTGEGFLCVFAINNTKSFEDIHQYREQIKRVKDSD--------------------
                   50        60        70        80        90        100
NRAS             ETCLLDILDTAGQEEYSAMRDQYMRTGEGFLCVFAINNSKSFADINLYREQIKRVKDSD--------------------
ANHP_459_5       RQCILEILDTAGTEQF-----------------IFSITSMSSLNELSEIREQILRIKDDD-------------------
KB73344_288_17   RHVILEILDTAGTEQFK----LYMKTGQGFLLVFSITSESSFWELAELREQIRRIKEDS--------------------
CM004463         EVALLDVLDTAGQEEYSAMREQYMRTGEGFLLVYSITSPQSFEEITTFQQQILRVKDKD--------------------
KV42800_485_5    EVALLDVLDTAGQEEYGAMREQYMRTGEGFLLVYSITSRNSFEEISTFRQQILRVKDKD--------------------
AACS_391_8       EVALLDVLDTAGQEEYGAMREQYMRTGEGFLLVYSITSRNSFEEISIFHQQILRVKDQD--------------------
JH97138_360_5    EVALLDVLDTAGQEEYGAMREQYMRTGEGFLLVYSITARSSFEEIKQFYQQILRVKDQD--------------------
KI911109_c052    Q--SMLEVLDTAGQEEYTALRDQWIRDGEGFVLVYSITSPASFARIPKFYNQIKMVKESASSGSPAGASYLTSPINSPSGP
KE54696_c00122   EVALLDVLDTAGQEEYSAMREQYMRTGEGFLLVYSITSPQSFEEMLTFQQQILRVKDRD--------------------
```

Boldface: KRAS residues w/ 4 Å of rasGAP, PDB: 1WQ1

FIG. 15

```
                                                                  10             20        30        40
KRAS             M---------------------------TEYKLVVVGAGG------VGKSALTIQLIQNHFVDEYDPTIEDSYRKQVVIDG
HRAS             M---------------------------TEYKLVVVGAGG------VGKSALTIQLIQNHFVDEYDPTIEDSYRKQVVIDG
NRAS             M---------------------------TEYKLVVVGAGG------VGKSALTIQLIQNHFVDEYDPTIEDSYRKQVVIDG
ANHP_459_5       MQP------------------------RREYHIVVLGA---------------AQFVQNVWIESYDPTIEDSYRKQIEVDG
KB73344_288_17   MSQ-------------------------REYHIVVLGSGG------VGKSCLTAQFVQNVWIESYDPTIEDSYRKVLEVDG
CM004463         MAS---------------------KFLREYKLVVVGGGG------VGKSCLTIQLIQSHFVDEYDPTIEDSYRKQCVIDE
KV42800_485_5    MSRS-----AAQA-----------SFLREYKLVVVGGGGMSIVSRVGKSALTIQFIQSHFVDEYDPTIEDSYRKQCVIDD
AACS_391_8       MPEVMNAMYATKGGIFDVSENDKAQFLREYKLVVVGGGG------VGKSALTIQFIQSHFVDEYDPTIEDSYRKQCIIDD
JH97138_360_5    MANN----------AASRAA---QAQFLREYKLVVVGGGG------VGKSALTIQFIQSHFVDEYDPTIEDSYRKQCVIDE
KI911109_c052    M----------------------------       VVLGDGG----
KE54696_c00122   MDAD----------PYLL------KFLREYKLVVVGGGG------VGKSCLTIQLIQSHFVDEYDPTIEDSYRKQCVIDE

                  50        60        70        80        90        100
KRAS             ETCLLDILDTAGQEEYSAMRDQYMRTGEGFLCVFAINNTKSFEDIHHYREQIKRVKDSE---------------------
HRAS             ETCLLDILDTAGQEEYSAMRDQYMRTGEGFLCVFAINNTKSFEDIHQYREQIKRVKDSD---------------------
NRAS             ETCLLDILDTAGQEEYSAMRDQYMRTGEGFLCVFAINNSKSFADINLYREQIKRVKDSD---------------------
ANHP_459_5       RQCILEILDTAGTEQF------------------IFSITSMSSLNELSEIREQILRIKDDD---------------------
KB73344_288_17   RHVILEILDTAGTEQFX----LYMKTGQGFLLVFSITSESSFWELAELREQIRRIKEDS---------------------
CM004463         EVALLDVLDTAGQEEYSAMREQYMRTGEGFLLVYSITSRQSFEEITTFQQQILRVKDKD--       ------------
KV42800_485_5    EVALLDVLDTAGQEEYGAMREQYMRTGEGFLLVYSITSRNSFEEISTFHQQILRVKDKD---------------------
AACS_391_8       EVALLDVLDTAGQEEYGAMREQYMRTGEGFLLVYSITSRNSFEEISIFHQQILRVKDQD---------------------
JH97138_360_5    EVALLDVLDTAGQEEYGAMREQYMRTGEGFLLVYSITARSSFEEINQFYQQILRVKDQD---------------------
KI911109_c052    Q-SMLEVLDTAGQEEYTALRDQWIRDGEGFVLVYSITSRASFARIPKFYNQIKMVKESASSGSPAGASYLTSPINSPSGP
KE54696_c00122   EVALLDVLDTAGQEEYSAMREQYMRTGEGFLLVYSITSRQSFEEMLTFQQQILRVKDRD---------------------
```

Boldface: KRAS residues w/ 4 Å of SOS, PDB:1BKD

FIG. 16

```
Human_ARNOSec7_Ter  LEANEGSK-------TLQRNRKMA----------MGPKKFNMDPKKGIQFLVENELLQNTP--EE---IARFLYKGEGLNKT
Human_GBF1Sec7      ------------------DPRELIEIKNKKKLLITGTEQFNQKPKKGIQFLQEKGLL-TIP--MDNTEVAQWLRENPRLDKK
ETaGSec7_NCBI       --------DPNALRQQRSRKSMIM----------KGASKFNEKPKAGIAFLVAQGVIQEPENPKN---IAEFIKGTTRIDKK

Human_ARNOSec7_Ter  AIGDYLGEREELNLAVLHAFVDLHEFTDLNLVQALRQFLWSFRLPGEAQKIDRMMEAFAQRYCLCNPGVFQS---TDTC--
Human_GBF1Sec7      MIGEFVSDR--KNIDLLESFVSTFSFQGLRLDEALRLYLEAFRLPGEAPVIQRLLEAFTERWMNCNGSPFAN--SDAC--
ETaGSec7_NCBI       ILGEFISKK--TNENILNEFMKLFNFAGKRIDEALRELLGAFRLPGESALIERIVEVFAAQYM----DDAKPAGIADSTAA

Human_ARNOSec7_Ter  YVLSYSVIMLNTDLHNPNVR--DK---MGLERFVAMNRGINEGG-DLPEELLRNLYDSIRNEPFKIPEDDGND
Human_GBF1Sec7      FSLAYAVIMLNTDQHNHNVR--KQNAPMTLEEFRKNLKGVNGGK-DFEQDILEDMYHAIKNEEIVMPEEQT--
ETaGSec7_NCBI       FVLVYATILLNTDQHNPNFRGQKR---MTIENFAQNLRGV-NDQGDFDSNFLQEIFDSIRTHEIILPEEHD--
```

Boldface: ARNOSec7 residues w/4 Å of Brefeldin A, PDB: 1R8Q

PANEL A

FIG. 19

```
                        50
Human_ARNOSec7_Ter   LEANEGSK-------FLQRNRKMA------------MGRKKFNMDPKKGIQFLVENELLQNTP--EE---IARFLYKGEGLNKT
Human_GBF1Sec7       ----------------------DPRELIEIKNKKKLLITGTEQFNQKPKKGIQFLQEKGLL-TIP---MDNTEVAQWLRENPPLDKK
ETaGSec7_NCBI        --------DPNALRQQRSRKSMIM-----------KGASKFNENPKAGIAFLVAQGVIQEPENPKN---IAEFIKGTTRIDKK

Human_ARNOSec7_Ter   AIGDYLGEREELNLAVLHAFVDLHEFTDLNLVQALRQFLWSFRLPGEAQKIDRMMEAFAQRYCLCNPGVFQS--TDTC--
Human_GBF1Sec7       MIGEFVSDR--KNIDLLESFVSTFSFQGLRLDEALRLYLEAFRLPGEAPVIQRLLEAFTERWMKCNGSPFAK--SDAC--
ETaGSec7_NCBI        ILGEFISKK--TNENILNEFMKLFNFAGKRIDEAIRELLGAFRLPGESALIERIVEVFAAQYM---DDAKPAGIADSTAA

Human_ARNOSec7_Ter   YVLSYSVIMLNTDLHNPNVR--DK---MGLERFVAMNRGINEGG-DLPEELLRNLYDSIRNEPFKIPEDDGND
Human_GBF1Sec7       FSLAYAVIMLNTDQHNHNVR--KQNAPMTLEEFRKNLKGVNGGK-DFEQDILEDMYHAIKNEEIVMPEEQT--
ETaGSec7_NCBI        FVLVYATILLNTDQHNPNFRGQKR---MTIENFAQNLRGV-NDQGDFDSNFLQEIFDSIRTHEIILPEEHD--
```

Boldface: Matched and conserved residues

PANEL B

FIG. 19 (CONTINUED)

ETaG RasGAP Cluster (Terpene)

*Acremonium furcatum*

SEQUENCE LISTING

```
Sequence total quantity: 55
SEQ ID NO: 1            moltype = DNA  length = 1044
FEATURE                 Location/Qualifiers
source                  1..1044
                        mol_type = other DNA
                        organism = Thermomyces lanuginosus
SEQUENCE: 1
atgcagccgc ggtgagtgtt ggtcgcgctc cttggcaaag gtcaatacta attggacaca  60
ggcgggaata tcatattgtc gtcctgggag ctggtatgtc gagaagagat tcgccacagc  120
ctatcagtcg atatgtgtcc ctaacaatgt tatacaggag gcgtcgggaa gagctgcttg  180
acaggtatgg acgcgatgga ctgcggcgac aacatgcgac cgatggctca ctaacttatc  240
tcatagctca atttgtacaa aatgtttgga ttgagagtta cgacccgaca attgaagatt  300
cctatcgaaa gcagattgaa gtcgatgtga gttcccgtgg cattgatgcg attataccac  360
ctgcttacga tattctattc gcagggtcga caatgcattc tcgagatgta cgtctctctt  420
cagagctgtc gcggagctat ttcatcttac tgatcaccgt gcagtctgga cacagccgga  480
acagagcaat tcagtacgtc ttaacctccc aactccgatg aaaaggacca tccactaacg  540
atgacgacag ctgcgatgag gtattacacg tcaatgcggc gcacatggcc aatgaagttg  600
acatgactgt ccagggaaat ttacatgaaa caagggcagg gattcctgct agtcttctcg  660
atcaccagca tgtcatcgct gaacgagtta tcggaaatcc gggagcagat cctccgcatc  720
aaggacgatg acaaggtccc tatggtgatc gtcggcaaca agtccgatct cgaggaaaac  780
cgagctgtgc ctcgtagcaa agcgtttgcg ctctcgcaga gctggggcaa cgctccttac  840
tacgaaacat ccgctcgacg gcgagcaaac gtcaacgagg tcttcattga cctgtgccga  900
cagatcatcc gcaaggatct gcaagctaca caggcaaagc aagcggaagc cagacaagtt  960
aagcgagagg cgactcctcg caatgacagg agcaagaagg atagaaaatc cacaaggcgt  1020
cggcatcaat gcgcgattat gtga                                        1044

SEQ ID NO: 2            moltype = DNA  length = 2143
FEATURE                 Location/Qualifiers
source                  1..2143
                        mol_type = other DNA
                        organism = Talaromyces leycettanus
SEQUENCE: 2
atgctggaag tgctagacac agcgggccag gaagagtaca ccgcactgag agaccagtgg  60
atccgcgatg gtgaagggtt cgttctcgtc tatagcatca catcgcgagc gtcgttcgcc  120
cgcataccca agttctacaa tcagatcaag atggttaaag aatcggcaag ctccgggtca  180
cccgctggag ccagctactt gacgtcgccg atcaattctc cctcgggacc cccgcttcct  240
gtgccggtaa tgttggttgg caacaagagc gacaaggcga tggaccgcgc cgtctctgcg  300
```

-continued

```
caggaaggcc aagctcttgc caaggagctg gggtgcgaat tcgtcgaggc ttccgccaag  360
aactgtatca atgtcgaaaa ggctttctac gacgtcgtga ggatgcttcg gcagcagcga  420
caacagcaac agggaggacg ggcgcaggag cggcgacccg ccgctttcgg atcagggcca  480
atgcgcgatc gggacgccgg tcccgagtac ccaaagtcgt ttcgtccgga tcgatcaagg  540
catcgcaatg gcctcaaatg cgttatccta tgagctcccc ccgatgagtg ttccgatcgg  600
cggatctttc cagcttctga cctccgctta ttcatgaccg ttgctctcta gaatggatgg  660
tgtctagctc cgtgtttctc tttctcggag cgtgtgagcg agcttgagga cagtcgttcc  720
acttgtgccc cctcctatcc gccgcaggcc cttgtcgctg ccgctttgcg gaccgctcgt  780
tttgtctacg ttgtactcga aagcacggcc tctgctttcg tggaagtctc cctttatgcc  840
agctttgggt gcggtggtcg atatgcagat actgtgttct atgctcgctg catgcgattc  900
agaggcgtct tgattccccg tgtcagtatg gggtgttctc gctattcagg gaatcatctg  960
aaaccaattt ttctcatccg ttctgttttt gggaatcgga acacgggggg gatgtctgga  1020
aatctggacc tataactata gaaatgtttc tcaccacctt tctcactcaa ccctcttgat  1080
gaatatccgc ccggcgtctt ctactacttc ctaccgtcta ctaccaccaa tctctattct  1140
tcttaccacc caccttctga gccacttctt acacatcatt ctcgtttggt ttgacagcaa  1200
agcggggaga gttcgaagga cagatcccat gcaggattgg aggacgagag gggaagagtc  1260
gaagggagaa aaataattaa aaaaaagaaa ggtgcggggg cagaaggagg caggtttggt  1320
tgagagttgc gaatcggtcc tgtcgcagtc aagtcccaaa aaagaaaaga tcgcagtcgg  1380
cgcattagca ggcattttga tacgatgata ccctacagcc gagcttcgag tttttgtgtt  1440
ccttttcctt ttttgcaaat gctgatttaa aaaaataaca atagagctac atactgaatg  1500
tggatttttt tgacctctca tctttttgtt gcagggatga ccgccaattg gtaaattcat  1560
ccccagtcat aatccgagcg caggatgcat gaactccagt acctcatcat atcgcctgca  1620
cgttcaagtt ccatcaatca ttcggcggcg cctactctgt acgactaagt ctacggagtt  1680
tgttcttgtt gcggggaagg aagcgaaagc cacgactcca acaaacaaac tcagggtgaa  1740
ttgaatcctc agtttctact ctgtagccga agagccatca ttaccattca ggggaagagc  1800
ctaaagagct tgcgaggttg ggctgagctg ctgtgcagtg agcaatatat ttggtcgatg  1860
ttttggatac gttatctgga atgcgcagat gcagtggtta tgcatatcct cacgtactcg  1920
attctgatga ttcacgggac catacggagt cgataccgag actctcgcta caaacctgtc  1980
aattgatatc gtgtacagag taccggagcc gagactggga aatagcacag tctcagtctc  2040
aggtagctat cgatcaattt gacaaggtta gaagtatctc gctagtaatt gccagatgat  2100
tcattcccgg ttgaaaactt ttccattggc cttcttcgct tag                    2143

SEQ ID NO: 3           moltype = DNA  length = 989
FEATURE                Location/Qualifiers
source                 1..989
                       mol_type = other DNA
                       organism = Sistotremastrum niveocremeum
SEQUENCE: 3
atgtcgagag tgagtatttc tgtttattgc ggctctatct tgatctcact cgtcgctagt  60
ctgctgctca ggcttcgttc cttcgcgaat acaagctcgt cgtcgtcggt ggtggtggta  120
tgagccttgt ctctcgttct ctgcaatcaa aatctcactc gcttttctct tgtgctgcct  180
aggtgttggc aaatccgctc tgaccattca attcatccaa agtcatttcg ttgacgagta  240
tgaccctact atcgaaggtc agccgaccgc taggcaacca ttatctgatc aaacagctca  300
tctcgcactc gacagattct tacagaaagc aatgtgtcat cgatgatgaa gttgcccttt  360
tggatgtgtt agataccgct gggcaggaag aatatgggtg agctcgtctc gcagcccgat  420
tcccacgctt attgctaaca cgacatcggc agcgcaatgc gagaacagta tatgcgaacg  480
ggagaaggat tcttgcttgt ctactcgata acgtcgcgga actctttcga agaaatcagc  540
actttccatc agcaaattct tcgagtaaaa gacaaggatg cgttcccggt tatcgtggta  600
gccaacaagt gtgaccttga atatgagcga caagtcggca tgaacggtgc gtttttagtg  660
ttgtttcaat caacattgtg actcatcctt cgtcagaggg ccgtgacctg gccaagcact  720
tcaactgcaa atttatcgag acctcggcga agcagcgaat caacgttgat gaggcctttt  780
cgaaccttgt tcgagagatt cgcaaattca acaaggtatg taagcccaaa cccgacggaa  840
ctcccggcct gatctcttta caggaacaac agaccggacg tcctgcgacc atggctccga  900
gcggccctgt gggtgcattc ggtggtcccc ccggcatgga agatggacct catgacgctg  960
gttgctgctc tggatgtgtc gttgtataa                                   989

SEQ ID NO: 4           moltype = DNA  length = 989
FEATURE                Location/Qualifiers
source                 1..989
                       mol_type = other DNA
                       organism = Sistotremastrum suecicum
SEQUENCE: 4
atgtcgagag tgagtatttc tgtttattgc ggctctatct tgatctcact cgtcgctagt  60
ctgctgctca ggcttcgttc cttcgcgaat acaagctcgt cgtcgtcggt ggtggtggta  120
tgagccttgt ctctcgttct ctgcaatcaa aatctcattc gcttttctct tgtgctgcat  180
aggtgttggc aaatccgctc tgaccattca attcatccaa agtcatttcg ttgacgagta  240
tgaccctact atcgaaggtc agccgaccgc taggcaacca ttatctgatc taacagctca  300
tctcgcactc gacagattct tacagaaagc aatgtgtcat cgatgatgaa gttgcccttt  360
tggatgtgtt agataccgct gggcaggaag aatatgggtg agctcgtctc gcagcccgat  420
tcccacgctt attgctaaca cgacatcggc agcgcaatgc gagaacagta tatgcgaacg  480
ggagaaggat tcttgcttgt ctactcgata acgtcgcgga actctttcga agaaatcagc  540
actttccatc agcaaattct tcgagtaaaa gacaaggatg cattccctgt tatcgtggta  600
gccaacaagt gtgaccttga atatgagcga caagttggca tgaacggtgc gattctagtg  660
ttgtttctgt cgatattggg acttatcccc cttcagaggg ccgtgatttg gccaagcact  720
tcaactgcaa atttatcgag acatcggcga agcagcgaat caacgttgat gaggcctttt  780
ccaaccttgt tcgagagatt cgcaaattca acaaggtatg taagcccaaa cccgacggaa  840
ctcccggcct gatctcttta caggaacaac agaccggacg tcctgcgacc atggctccga  900
gcggccctgt gggtgcattc ggtggtcccc ccggcatgga agatggacct catgacgctg  960
gttgctgctc tggatgtgtc gttgtataa                                   989
```

```
SEQ ID NO: 5           moltype = DNA  length = 1127
FEATURE                Location/Qualifiers
source                 1..1127
                       mol_type = other DNA
                       organism = Agaricus bisporus
SEQUENCE: 5
atggcaaaca acgctgcgtc cagagtatgt cctccccaca aaccaccctc agttgcctgg  60
cttatgctct atttcaggct gctcaggccc agttcctgag agaatacaag ctcgtagtgg  120
tcggaggagg aggcaagtgc tacccgccct tacaagctag caagtcctaa agtcgtgtac  180
aggtgttgga aaatctgcat tgactatcca attcattcaa agccatttcg tggacgagta  240
cgacccaact atcgagggtg agcttctttc tcaccaatca atccccttcc aggttatgac  300
atttcggaac atttgtgcta acattctcgt cttaaaacag actcgtacag gaaacaatgc  360
gtcattgatg aagaggtcgc ccttctcgat gtcctggata ccgctggtca agaagaatat  420
gggtcagtgt gctctcctga ataaattccg aagcagtccc cgattttttt tcctttcgtc  480
tcgtgattcg actatgaaaa tggtcttcca cgaggcgaag ctttcatttc ccggcataat  540
tcagttatac gaccctggat ctaaccctat atgtacttat tttccagtgc catgcgggag  600
caatacatgc gtactgggga gggatttctt ctcgtctaca gcatcaccgc gcgtagctcc  660
tttgaagaaa tcaaccagtt ttaccagcaa attttgaggg tcaaagatca agattctttc  720
cctgttattg tcgttgcaaa caagtgcgat ttggaatatg aacgccaagt tggtatgaac  780
ggtatgttat caaaccttgg agtatatcag ggccccagta gtgacgcaac ctacagaggg  840
ccgagatctc gcgagacatt ttggctgcaa attcatcgag acgtctgcca aacaacgaat  900
aaacgtggat gaagctttca gcaatcttgt tcgtgaaatc cgaaaatata acaaggtcgg  960
ttttccgcat cacacgcaga gattttacaa actcattggt gcttttatag gaccaacaaa  1020
caggccgccc tctccacggc agcggtggtg gagccggcgg ttatggtggc aaggaccaca  1080
atgacgatgg aggtgctggc tgctgcggcg gttgcgttat tctttaa                1127

SEQ ID NO: 6           moltype = DNA  length = 1681
FEATURE                Location/Qualifiers
source                 1..1681
                       mol_type = other DNA
                       organism = Coprinopsis cinerea
SEQUENCE: 6
atgcctgagg tgatgaatgc tatgtacgcc acgaaaggcg gtatcttcga cgtcagcgag  60
aatgataagg tttggcgttt gcagtgtttc aaagctggcc tctgttgtgt tggagaatac  120
tcggatgctg atatacatat ggtttatcga atacaagtac gcgtataagg aaagctgggg  180
tagacaaggg actatagctg gatcttaact cccaggaggg gacgagatga gagaatgcgg  240
tctacagcaa ttctgatgct cgaaaatcca tcagcagagg tcaaccttgg gtttctagcg  300
aaaagaaggg agataggaag cccggaatat caaaacacgc gtcggattgt ggtccaaatt  360
gaaaaatgac cgagagcctc gagctcgtgt cgcgagatgt ttgcacttga gatttaaact  420
ccgctgatga tggcctttga agtgagtttg gttacgatgt ttagaggaac ccagtcgccc  480
cctgctcccg ctcaactccc taaataccct tcctgaccat cttctttctt tcccaaatct  540
ttttcttctc tttcaacaga tttcatttct gaagcatggc tgccagggtc cgtcaaatcc  600
cacagtctgc accgtggaac ctcagcaaac tcacacagcg tccaacaggc tcagttcttg  660
agggagtaca agctcgtcgt cgtaggtggt ggtggtatgt tgcacagctc ttagaacgga  720
atgtagtctc acctgtggtg ccccaggtgt tggaaagtcg gccctgacta ttcagttcat  780
ccaatcccac ttcgtggatg aatatgaccc gactatcgaa ggtccgtata acaaggcctt  840
ctctcgcaag gatgcaatag cttatgctta ttcgacacag actcgtacag aaaacagtgc  900
atcatcgacg acgaggtcgc actcctcgac gttctcgata ccgccggaca ggaagagtat  960
gggtgagtac ccgcgctgca cccctctatt ttccaccgaa tgcttcgtgg acagcccaac  1020
ttttgatcct cgtatcccat accaccgctt tccttgttcc cggaatcttt gcatcaccac  1080
ctctccacct tgccctcttc ttcgggacgt tccgtgatta acacacacct acagagccat  1140
gcgggagcaa tacatgcgca cgggcgaagg cttccttctc gtctactcta tcacctccag  1200
aaactcgttt gaggaaatca gcattttcca ccaacaaatt ttgcgagtca aggaccagga  1260
ttccttcccc gtcattgttg tggctaacaa gtgcgatctc gaatatgaac gtcaagttgg  1320
catgaacggt gtgtagtcca tctttatgtc ccttgccgac atgacatgaa caacgtattg  1380
cagaggggcg tgatctcgcc aaacactttg gttgcaaatt catcgaaacc tcggccaagc  1440
aacgaatcaa cgtcgacgag gcattcagca acctcgttcg ggagattcgc aagtcaacag  1500
ggtgagcaat cctctcttcc aaggtattct gactagcatt caaactgtct catgcccccca  1560
ggaacaacaa accggtcgtc ctgccatcgc agcaggtgga ggtggtccag ccggctccta  1620
cacccaggac aggcaccacg atgaggcacc tggatgctgt gccggatgtg ttattgccta  1680
a                                                                  1681

SEQ ID NO: 7           moltype = DNA  length = 961
FEATURE                Location/Qualifiers
source                 1..961
                       mol_type = other DNA
                       organism = Colletotrichum higginsianum
SEQUENCE: 7
atggcgtcca aggttcgtcg tcgccacctc ccgtttccct tcatttcttt tgccgcctcg  60
tcgctccatc gctccatcgc cccatcgatc cgttgctaac cagttgccat ctcgcagttt  120
ctgagggagt acaagttggt cgtcgtcggc ggcggtggtg tcggtaaatc ctgcttgacc  180
atccaattga ttcagagcca ctttgtcgac gaatatgacc cgacgatcga aggtgcgtcg  240
tcccgaactt cttgctccac cgttcgatgc gacggcttcg aatcaatcgc atgctaatgt  300
ggatctcacc catttcagat tcctaccgca agcagtgcgt catcgacgag gaggtcgctc  360
tactcgatgt cctcgacacg gccggtcagg aggagtactc cgccatgagg gagcagtaca  420
tgaggacggg agagggtttc cttctggttt actccatcac ttcgcgacag agcttcgagg  480
agatcaccac attccagcag cagattctga gagtaaagga caaggactac ttccccatgg  540
tcgtcgtcgg caacaagtgc gatctggaga gcgagagaga agtcacacga caaggtatga  600
```

```
ttctgattcc tgctgtgccg cgacaccgca tgaggcggct cctttcgagg cccaggcccg  660
gtgtggattc attgatggaa tgaaaagtag ctgacatcat tcactcgtgc gcgctacaga  720
gggagaggcc cttgccaagt cattcggctg caagttcatc gagacgtcgg ccaagtctcg  780
catcaacgtc gacaaggctt tctatgatat tgtccgagaa atccgtcggt acaaccgcga  840
gatgcagggc tactctaccg gcagtggcgg cgcctcgggc atcaacggcc ccccgaagcc  900
catggacgtc gagaacggcg agcaagaggc aggctgctgc tccaagtgcg tactaatgtg  960
a                                                                  961

SEQ ID NO: 8           moltype = DNA  length = 326
FEATURE                Location/Qualifiers
source                 1..326
                       mol_type = other DNA
                       organism = Gyalolechia flavorubescens
SEQUENCE: 8
atggcttcaa aggtaagtcc atctgtctct ttagagtatt ctcattgctc tttgctaccg  60
agcttctcca tggacgctga cccttacctg ctcaagttcc tacgggaata caagctcgtc  120
gtcgttggcg gaggaggtgt gggcaagtcc tgcttgacca tccagctcat ccagagtcac  180
ttcgtcgacg aatacgatcc caccattgaa ggtaaataga ttcgtcctat ccacccattg  240
cgcttttact gatcgaagcg atttgcaaga ctcctaccgg aagcaatgcg tcatcgacga  300
agaagtcgcc ttactcgatg tactag                                       326

SEQ ID NO: 9           moltype = DNA  length = 809
FEATURE                Location/Qualifiers
source                 1..809
                       mol_type = other DNA
                       organism = Bipolaris maydis
SEQUENCE: 9
atgttcttgc ctcaactcta ctccctcaac cctgccttgg ctgccaaaca tgctgatcct  60
cttgctccta cagcccagtt tgtgcaaaac gtgtggatag agagctatga tcccaccatc  120
gaggactcgt accgaaaggt cctcgaagta gacgtgcgta cacgacactc ttactagccg  180
cgttttttc actgacccac tctccctccc agggccgtca tgtcattctc gagatcttgg  240
atactgccgg cacagagcag tttagtaagt gattacatac atagccccac cccacgtgga  300
cccaagacta acacgacaat agctgccatg aggtagagtt tcctactacc cccttactcg  360
gtaaacatca aaacttacac ggatgcagag aactgtacat gaaaacgggc caaggattcc  420
ttttggtctt cagcatcaca tcagaatctt ccttttggga gcttgccgag ctgcgtgagc  480
agatacgacg catcaaggaa gacagcaacg tacccatggt tctcattggc aacaagtcgg  540
acctagaaga cgaccgtgcc gtgccgcgcc cacgagcatt tgccatttcg cgtgaatgga  600
acgttcctta tttcgaaacc agtgctcgaa ggagagccaa tgtcgacgaa gcctttgtcg  660
acctctgcag gcaaatcatc cgcaaggatc agaacgaacg aaaccgcatg gccccaccgg  720
attccccgag gcctggcggt cccaggagca gaactcacac gggacggcca aagcgcaagg  780
ctcaccggcc ccattgtacc attctttaa                                    809

SEQ ID NO: 10          moltype = DNA  length = 2244
FEATURE                Location/Qualifiers
source                 1..2244
                       mol_type = other DNA
                       organism = Penicillium vulpinum
SEQUENCE: 10
atggaagttg aaaggccgga tggttggcat catcactgct gaccacgaac agacatcacg  60
aaatatgaca cacctgctct actacacccc ttcctccaag taatacgatc atcctcaacc  120
tctgctgcga tcacctccct cgctctcatc gccatcacga aattcctctc ctacaaaata  180
atctccggtg actccgctcg gctggctgaa gccatgcagc tcctctcatc agctctcacg  240
cactgccggt tcgaggcaag cgattcagca acggacgaaa ttgtactcct gcaggtactg  300
aatctcatgg aaagcattat cttgagtcca ggaggtgaat ctctctgcaa tgagagcgtt  360
tctgagatga tgcaaactgg actgagcatg tgctgccaac ccaggctttc ggaactccta  420
cgacagtctg ctgagattgc catggtctct atttgccaat tggtcttcga gcgatggaag  480
cacctagaag aagaggtggg cgaagagcta ggggccttgg atcaggatgt cagggccgat  540
atgggcacga tgaagctcct tgattcaaaa atgcagacct ccttgaccgg tccaaactcc  600
aagaatctta aatctgagga gaagacacgg tcttttgcga gcgtggagaa gctgatcaat  660
gagtccacag ggatgacact gcaaaagggc gacgccacaa ttgatctacc gtcaatgcac  720
gatgaacagg atgaaggcga ggcgctccca atcaagccat actccctgac gttgatacga  780
gagcttcttg tgatcctcat caatatacta gatcctgagg acaagaaaca aacagacaca  840
atgcgtatca cggcactgcg cattctgcat gttgtgttgg aagtagcggg cccatcaata  900
tggaagttga aaggccggat ggttggcatc atcactgctg accacgaaca gacatcacga  960
aatatgacac acctgctcta ctacacccct tcctccaagt aatacgatca tcctcaacct  1020
ctgctgcgat cacctccctc gctctcatcg ccatcacgaa attcctctcc tacaaaataa  1080
tctccggtga ctccgctcgg ctggctgaag ccatgcagct cctctcatca gctctcacgc  1140
actgccggtt cgaggcaagc gattcagcaa cggacgaaat tgtactcctg caggtactga  1200
atctcatgga aagcattatc ttgagtccag gaggtgaatc tctctgcaat gagagcgttt  1260
ctgagatgat gcaaactgga ctgagcatgt gctgccaacc caggctttcg gaactcctac  1320
gacagtctgc tgagattgcc atggtctcta tttgccaatt ggtcttcgag cgatggaagc  1380
acctagaaga agaggtgggc gaagagctag gggccttgga tcaggatgtc agggccgata  1440
tgggcacgat gaagctcctt gattcaaaaa tgcagacctc cttgaccggt ccaaactcca  1500
agaatcttaa atctgaggag aagacacggt cttttgcgag cgtggagaag ctgatcaatg  1560
agtccacagg gatgacactg caaaagggcg acgccacaat tgatctaccg tcaatgcacg  1620
atgaacagga tgaaggcgag gcgctcccaa tcaagccata ctccctgacg ttgatacgag  1680
agcttcttgt gatcctcatc aatatactag atcctgagga caagaaacaa acagacacaa  1740
tgcgtatcac ggcactgcgc attctgcatg ttgtgttgga agtagcgggc ccatcaatag  1800
ctcacagctg tagattctgc gaatattgct gaatcttttt ataaattctt tgataccctc  1860
```

```
ctcgttctcc tcagctcgca aatcgcttga acttccatct atcccgctac aaagccccac  1920
tcagatcatc aacaaagatg atagagcagc ggacaccagc ctgttttatg cctttgcttc  1980
ttatgtttcg agtttcgcga acggtgagcc accggaacct tcagacgaag agattgagaa  2040
caccttgtgt acaatcgata ctatcagcgc ttgttcgttg gacgaaatca catccaacat  2100
cttgtaagtc ataaaccgcg tggctaatca ggacatgaat taacaagacc tctagcgaca  2160
tgtccacaga ggctttgaga cctctgttca tggcgctttt gtcacgacta cccgaagata  2220
catcgctcca cggtattgca gtaa                                        2244

SEQ ID NO: 11          moltype = DNA  length = 1044
FEATURE                Location/Qualifiers
source                 1..1044
                       mol_type = other DNA
                       organism = Thermomyces lanuginosus
SEQUENCE: 11
atgcagccgc ggtgagtgtt ggtcgcgctc cttggcaaag gtcaatacta attggacaca  60
ggcgggaata tcatattgtc gtcctgggag ctggtatgtc gagaagagat tcgccacagc  120
ctatcagtcg atatgtgtcc ctaacaatgt tatacaggag gcgtcgggaa gagctgcttg  180
acaggtatgg acgcgatgga ctgcggcgac aacatgcgac cgatggctca ctaacttatc  240
tcatagctca atttgtacaa aatgtttgga ttgagagtta cgacccgaca attgaagatt  300
cctatcgaaa gcagattgaa gtcgatgtga gttcccgtgg cattgatgcg attataccac  360
ctgcttacga tattctattc gcagggtcga caatgcattc tcgagatgta cgtctctctt  420
cagagctgtc gcggagctat ttcatcttac tgatcaccgt gcagtctgga cacagccgga  480
acagagcaat tcagtacgtc ttaacctccc aactccgatg aaaaggacca tccactaacg  540
atgacgacag ctgcgatgag gtattacacg tcaatgcggc gcacatggcc aatgaagttg  600
acatgactgt ccagggaaat ttacatgaaa caagggcagg gattcctgct agtcttctcg  660
atcaccagca tgtcatcgct gaacgagtta tcggaaatcc gggagcagat cctccgcatc  720
aaggacgatg acaaggtccc tatggtgatc gtcggcaaca agtccgatct cgaggaaaac  780
cgagctgtgc ctcgtagcaa agcgtttgcg ctctcgcaga gctggggcaa cgctccttac  840
tacgaaacat ccgctcgacg gcgagcaaac gtcaacgagg tcttcattga cctgtgccga  900
cagatcatcc gcaaggatct gcaagctaca caggcaaagc aagcggaagc cagacaagtt  960
aagcgagagg cgactcctcg caatgacagg agcaagaagg atagaaaatc cacaaggcgt  1020
cggcatcaat gcgcgattat gtga                                        1044

SEQ ID NO: 12          moltype = DNA  length = 1054
FEATURE                Location/Qualifiers
source                 1..1054
                       mol_type = other DNA
                       organism = Aspergillus rambelli
SEQUENCE: 12
atgctgggaa tagcggtcac taataatgcc tccttcggtg tgaccggtag acgggaatat  60
cacattgtcg tgttgggtgc tggaggagtg ggaaaaagtt gtcttactgg tatgattctc  120
ggtcgcgtcg gcttcgtgct tgcctcggaa ggccgtctct gctctctaga ccaatcagtc  180
gcttacttgt ggcagcgcaa tttgtgcaaa acgtttggat tgaaagctat gatccgacga  240
ttgaagactc ttatcgcaag catatcgagg tagatgtatg tttatcctgc tctcaacttc  300
attctcgggt tcattctcaa gtcgctgaca ttttctaggg ccgacaatgt attctggaaa  360
tgtatgtcac aaggaacacg gatggtggtt cggaattgcg ctttacgtgt aaacaaacac  420
ggctggctga cccttgacct gtcaacagac ttgatacagc ggggacagaa caatttagtg  480
agttatcttg ctcttgatgc tgggttttct ctccactaac gttttcccag cggccatgag  540
gtaatgaatg ctatatccat ggggtcatcg ggactcacat ctctcagttg ccagatctcg  600
atcgctaaca tgtgaatcct gcagagaact atatatgaag caaggccagg gctttttgct  660
tgtattctct atcactagca tgtcgtctct gaacgagctg tccgaattac gagaacaaat  720
tattcgcatt aaagacgacg agaaagttcc catcgtcatt gtgggcaata aatcggattt  780
ggaggaagac cgcgcagtcc cacgtgctcg tgcatttgct ctttctcaga gctggggcaa  840
cgctccctac tatgaaacat cggcgcgtcg acgagccaat gttaatgagg tcttcattga  900
cctgtgtcga cagattatac ggaaggacct ccagggaagt tcgaccagcg attatgatgc  960
tgccgcacgt aaacgcgagg gtcaaacccg acaagaccga aagcgagaga gaaaacgaca  1020
agtgcggcga aagggtcctt gtgtcattct ctaa                             1054

SEQ ID NO: 13          moltype = DNA  length = 1054
FEATURE                Location/Qualifiers
source                 1..1054
                       mol_type = other DNA
                       organism = Aspergillus ochraceoroseus
SEQUENCE: 13
atgctgggaa tagcggtcac taataatgcc tccttcggtg tgaccggtag acgggaatat  60
cacattgtcg tgttgggtgc tggaggagtg ggaaaaagtt gtcttactgg tatgattctc  120
ggtcgcgtcg gcttcgtgct tgcctcggaa ggccgtctct gctctctaga ccaatcagtc  180
gcttacttgt ggcagcgcaa tttgtgcaaa acgtttggat tgaaagctat gatccgacga  240
ttgaagactc ttatcgcaag catatcgagg tagatgtatg tttatcctgc tctcaacttc  300
attctcgggt tcattctcaa gtcgctgaca ttttctaggg ccgacaatgt attctggaaa  360
tgtatgtcac aaggaacacg gatggtggtt cggaattgcg ctttacgtgt aaacaaacac  420
ggctggctga cccttgacct gtcaacagac ttgatacagc ggggacagaa caatttagtg  480
agttatcttg ctcttgatgc tgggttttct ctccactaac gttttcccag cggccatgag  540
gtaatgaatg ctatatccat ggggtcatcg ggactcacat ctctcagttg ccagatctcg  600
atcgctaaca tgtgaatcct gcagagaact atatatgaag caaggccagg gctttttgct  660
tgtattctct atcactagca tgtcgtctct gaacgagctg tccgaattac gagaacaaat  720
tattcgcatt aaagacgacg agaaagttcc catcgtcatt gtgggcaata aatcggattt  780
ggaggaagac cgcgcagtcc cacgtgctcg tgcatttgct ctttctcaga gctggggcaa  840
cgctccctac tatgaaacat cggcgcgtcg acgagccaat gttaatgagg tcttcattga  900
```

```
cctgtgtcga cagattatac ggaaggacct ccagggaagt tcgaccagcg attatgatgc  960
tgccgcacgt aaacgcgagg gtcaaacccg acaagaccga aagcgagaga gaaaacgaca  1020
agtgcggcga aagggtcctt gtgtcattct ctaa                              1054

SEQ ID NO: 14          moltype = DNA  length = 1127
FEATURE                Location/Qualifiers
source                 1..1127
                       mol_type = other DNA
                       organism = Agaricus bisporus
SEQUENCE: 14
atggcaaaca acgctgcgtc cagagtatgt cctccccaca aaccaccctc agttgcctgg  60
cttatgctct atttcaggct gctcaggccc agttcctgag agaatacaag ctcgtagtgg  120
tcggaggagg aggcaagtgc tacccgccct tacaagctag caagtcctaa agtcgtgtac  180
aggtgttgga aaatctgcat tgactatcca attcattcaa agccatttcg tggacgagta  240
cgacccaact atcgagggtg agcttctttc tcaccaatca atccccttcc aggttatgac  300
atttcggaac atttgtgcta acattctcgt cttaaaacag actcgtacag gaaacaatgc  360
gtcattgatg aagaggtcgc ccttctcgat gtcctggata ccgctggtca agaagaatat  420
gggtcagtgt gctctcctga ataaattccg aagcagtccc cgattttttt tcctttcgtc  480
tcgtgattcg actatgaaaa tggtcttcca cgaggcgaag ctttcatttc ccggcataat  540
tcagttatac gaccctggat ctaaccctat atgtacttat tttccagtgc catgcgggag  600
caatacatgc gtactgggga gggatttctt ctcgtctaca gcatcaccgc gcgtagctcc  660
tttgaagaaa tcaaccagtt ttaccagcaa attttgaggg tcaaagatca agattctttc  720
cctgttattg tcgttgcaaa caagtgcgat ttggaatatg aacgccaagt tggtatgaac  780
ggtatgttat caaaccttgg agtatatcag ggccccagta gtgacgcaac ctacagaggg  840
ccgagatctc gcgagacatt ttggctgcaa attcatcgag acgtctgcca aacaacgaat  900
aaacgtggat gaagctttca gcaatcttgt tcgtgaaatc cgaaaatata acaaggtcgg  960
ttttccgcat cacacgcaga gattttacaa actcattggt gcttttatag gaccaacaaa  1020
caggccgccc tctccacggc agcggtggtg gagccggcgg ttatggtggc aaggaccaca  1080
atgacgatgg aggtgctggc tgctgcggcg gttgcgttat tctttaa                1127

SEQ ID NO: 15          moltype = DNA  length = 1124
FEATURE                Location/Qualifiers
source                 1..1124
                       mol_type = other DNA
                       organism = Agaricus bisporus
SEQUENCE: 15
atggcaaaca acgctgcgtc cagagtatgt cctccccaca aaccgccctc agtttcttgg  60
cttatgctct atttcaggct gctcaggccc agttcctgag agaatacaag ctcgtagtgg  120
tcggaggagg aggcaagtgc tacccgccct tacaagctag caagtcctaa agtcgtgtac  180
aggtgttgga aagtctgcat tgactatcca attcattaaa agccatttcg tggacgagta  240
cgacccaact attgagggtg agcttctttc tcaccaatca atccccctcc aggttatgac  300
atttcggaac atttgtgcta acattctcgt cttaaaacag actcgtacag gaaacaatgc  360
gtcattgatg aagaggtcgc ccttctcgat gtcctggata ctgctggtca agaagaatat  420
gggtcagtgt gctctcctga ataaattccg aagcagtccc cgattttttt tcctttcgtc  480
tcgtgattcg actatgaaaa tggtcttcca cgaggcgaag ctttcatttc ccggcataat  540
tcagttatac gaccctggat ctaaccctat atgtacttat tttccagtgc catgcgggag  600
caatacatgc gtactgggga gggatttctt ctcgtctaca gcatcaccgc gcgtagctcc  660
tttgaagaaa tcaaccagtt ttaccagcaa attttgaggg tcaaagatca agattctttc  720
cctgttattg tcgttgcaaa caagtgcgat ttggaatatg aacgccaagt tggtatgaac  780
ggtatgttgt taaaccttgg agtatatcag ggcccagtag tgacgcaacc tacagagggc  840
cgagatctcg cgagacactt tggctgcaaa ttcatcgaga cgtctgccaa acaacgaata  900
aacgtggatg aagctttcag caatcttgtt cgtgaaatcc gaaaatataa caaggtcggt  960
tttccacatc acacgcagat tttacaaact cattggtact tttataggac caacaaacag  1020
gccgccctct ccacggcagc ggtggtggag ccggcggtta tggtggcaag gaccacaatg  1080
acgatggagg tgctggctgc tgcggcggtt gcgttattct ttaa                   1124

SEQ ID NO: 16          moltype = DNA  length = 1681
FEATURE                Location/Qualifiers
source                 1..1681
                       mol_type = other DNA
                       organism = Coprinopsis cinerea
SEQUENCE: 16
atgcctgagg tgatgaatgc tatgtacgcc acgaaaggcg gtatcttcga cgtcagcgag  60
aatgataagg tttggcgttt gcagtgtttc aaagctggcc tctgttgtgt tggagaatac  120
tcggatgctg atatacatat ggtttatcga atacaagtac gcgtataagg aaagctgggg  180
tagacaaggg actatagctg gatcttaact cccaggaggg gacgacatga gagaatgcgg  240
tctacagcaa ttctgatgct cgaaaatcca tcagcagagg tcaaccttgg gtttctagcg  300
aaaagaaggg agataggaag cccggaatat caaaacacgc gtcggattgt ggtccaaatt  360
gaaaaatgac cgagagcctc gagctcgtgt cgcgagatgt ttgcacttga gatttaaact  420
ccgctgatga tggcctttga agtgagtttg gttacgatgt ttagaggaac ccagtcgccc  480
cctgctcccg ctcaactccc taaataccct tcctgaccat cttctttctt tcccaaatct  540
ttttcttctc tttcaacaga tttcatttct gaagcatggc tgccagggtc cgtcaaatcc  600
cacagtctgc accgtggaac ctcagcaaac tcacacagcg tccaacaggc tcagttcttg  660
agggagtaca agctcgtcgt cgtaggtggt ggtggtatgt tgcacagctc ttagaacgga  720
atgtagtctc acctgtggtg ccccaggtgt tggaaagtcg gccctgacta ttcagttcat  780
ccaatcccac ttcgtggatg aaatatgacc gactatcgaa ggtccgtata acaaggcctt  840
ctctcgcaag gatgcaatag cttatgctta ttcgacacag actcgtacag aaaacagtgc  900
atcatcgacg acgaggtcgc actcctcgac gttctcgata ccgccggaca ggaagagtat  960
gggtgagtac ccgcgctgca cccctctatt ttccaccgaa tgcttcgtgg acagcccaac  1020
```

```
ttttgatcct cgtatcccat accaccgctt tccttgttcc cggaatcttt gcatcaccac  1080
ctctccacct tgccctcttc ttcgggacgt tccgtgatta acacacacct acagagccat  1140
gcgggagcaa tacatgcgca cgggcgaagg cttccttctc gtctactcta tcacctccag  1200
aaactcgttt gaggaaatca gcattttcca ccaacaaatt ttgcgagtca aggaccagga  1260
ttccttcccc gtcattgttg tggctaacaa gtgcgatctc gaatatgaac gtcaagttgg  1320
catgaacggt gtgtagtcca tctttatgtc ccttgccgac atgacatgaa caacgtattg  1380
cagaggggcg tgatctcgcc aaacactttg gttgcaaatt catcgaaacc tcggccaagc  1440
aacgaatcaa cgtcgacgag gcattcagca acctcgttcg ggagattcgc aagtcaacag  1500
ggtgagcaat cctctcttcc aaggtattct gactagcatt caaactgtct catgcccca  1560
ggaacaacaa accggtcgtc ctgccatcgc agcaggtgga ggtggtccag ccggctccta  1620
cacccaggac aggcaccacg atgaggcacc tggatgctgt gccggatgtg ttattgccta  1680
a                                                                  1681

SEQ ID NO: 17          moltype = DNA  length = 1031
FEATURE                Location/Qualifiers
source                 1..1031
                       mol_type = other DNA
                       organism = Hypholoma sublateritum
SEQUENCE: 17
atggctgcta gggtacgtcc cttcacataa ctagccaacg tcgcgtagct catgccctct  60
caggctcagt tcttgcgaga atacaagttg gtggtggtgg gcggaggagg tcagcaaatc  120
ctggcgccat ttcccggtct ttctcctgct cacagtttcc ttcaggtgtc ggaaagtctg  180
ctttgactat tcagttcatt caaagccatt tcgttgacga gtacgatccc accatcgagg  240
gtgagagttt cgtgcttcca gtgccgccgc gacgctgacc gaagtcaaga ttcgtaccgt  300
aagcaatgcg taatcgacga ggaggttgct ctcctcgacg ttctggacac tgctggtcag  360
gaggagtacg ggtacgtgtc tgtctttacc attaacattg tcctcccccct gttcttttt  420
ggctcgcgcc tcgaggcgcg ttcttgctct ggtgctattc ttatcatggc tgttctctga  480
cggaaatacg tatagtgcta tgcgcgaaca atacatgcgt accggcgagg gtttcttgct  540
cgtctactcc attacatccc gcgactcctt cgaggaaata agcacattcc accaacagat  600
tctgcgggtc aaggaccagg actcgttccc cgttatcgtt gttgcgaaca agtgcgattt  660
ggagtacgag cgccaggttg gcatgaatgg tacggcagta gaccaccagg ctggaagatg  720
ctaatcaact atctctctca gagggccgtg accttgccaa gcacttcggt tgcaagttca  780
tcgaaacgtc agccaagcag cggatcaacg tcgatgaggc tttcagcaac cttgttcgcg  840
agattcggaa gtataataag gttagtacgt tatgttattc tacctctccc tatctgacag  900
atattgtcca ccaggaacaa caaactggtc gcccggccct tgccggcaat ggaggaagca  960
ctggcgcata cgatgggaaa gaccagcacg atgatactcc tgggtgttgt tccggctgtg  1020
ttgtcctcta a                                                       1031

SEQ ID NO: 18          moltype = DNA  length = 989
FEATURE                Location/Qualifiers
source                 1..989
                       mol_type = other DNA
                       organism = Sisotremastrum niveocremeum
SEQUENCE: 18
atgtcgagag tgagtatttc tgtttattgc ggctctatct tgatctcact cgtcgctagt  60
ctgctgctca ggcttcgttc cttcgcgaat acaagctcgt cgtcgtcggt ggtggtggta  120
tgagccttgt ctctcgttct ctgcaatcaa aatctcactc gcttttctct tgtgctgcct  180
aggtgttggc aaatccgctc tgaccattca attcatccaa agtcatttcg ttgacgagta  240
tgaccctact atcgaaggtc agccgaccgc taggcaacca ttatctgatc aaacagctca  300
tctcgcactc gacagattct tacagaaagc aatgtgtcat cgatgatgaa gttgcccttt  360
tggatgtgtt agataccgct gggcaggaag aatatgggtg agctcgtctc gcagcccgat  420
tcccacgctt attgctaaca cgacatcggc agcgcaatgc gagaacagta tatgcgaacg  480
ggagaaggat tcttgcttgt ctactcgata acgtcgcgga actctttcga agaaatcagc  540
actttccatc agcaaattct tcgagtaaaa gacaaggatg cgttcccggt tatcgtggta  600
gccaacaagt gtgaccttga atatgagcga caagtcggca tgaacggtgc gtttttagtg  660
ttgtttcaat caacattgtg actcatcctt cgtcagaggg ccgtgacctg gccaagcact  720
tcaactgcaa atttatcgag acctcggcga agcagcgaat caacgttgat gaggcctttt  780
cgaaccttgt tcgagagatt cgcaaattca acaaggtatg taagcccaaa cccgacggaa  840
ctcccggcct gatctcttta caggaacaac agaccggacg tcctgcgacc atggctccga  900
gcggccctgt gggtgcattc ggtggtcccc ccggcatgga agatggacct catgacgctg  960
gttgctgctc tggatgtgtc gttgtataa                                    989

SEQ ID NO: 19          moltype = DNA  length = 989
FEATURE                Location/Qualifiers
source                 1..989
                       mol_type = other DNA
                       organism = Sisotremastrum suecicum
SEQUENCE: 19
atgtcgagag tgagtatttc tgtttattgc ggctctatct tgatctcact cgtcgctagt  60
ctgctgctca ggcttcgttc cttcgcgaat acaagctcgt cgtcgtcggt ggtggtggta  120
tgagccttgt ctctcgttct ctgcaatcaa aatctcattc gcttttctct tgtgctgcat  180
aggtgttggc aaatccgctc tgaccattca attcatccaa agtcatttcg ttgacgagta  240
tgaccctact atcgaaggtc agccgaccgc taggcaacca ttatctgatc taacagctca  300
tctcgcactc gacagattct tacagaaagc aatgtgtcat cgatgatgaa gttgcccttt  360
tggatgtgtt agataccgct gggcaggaag aatatgggtg agctcgtctc gcagcccgat  420
tcccacgctt attgctaaca cgacatcggc agcgcaatgc gagaacagta tatgcgaacg  480
ggagaaggat tcttgcttgt ctactcgata acgtcgcgga actctttcga agaaatcagc  540
actttccatc agcaaattct tcgagtaaaa gacaaggatg cattccctgt tatcgtggta  600
gccaacaagt gtgaccttga atatgagcga caagttggca tgaacggtgc gattctagtg  660
```

```
ttgtttctgt cgatattggg acttatcccc cttcagaggg ccgtgatttg gccaagcact  720
tcaactgcaa atttatcgag acatcggcga agcagcgaat caacgttgat gaggcctttt  780
ccaaccttgt tcgagagatt cgcaaattca acaaggtatg taagcccaaa cccgacggaa  840
ctcccggcct gatctcttta caggaacaac agaccggacg tcctgcgacc atggctccga  900
gcggccctgt gggtgcattc ggtggtcccc ccggcatgga agatggacct catgacgctg  960
gttgctgctc tggatgtgtc gttgtataa                                   989

SEQ ID NO: 20          moltype = DNA  length = 2143
FEATURE                Location/Qualifiers
source                 1..2143
                       mol_type = other DNA
                       organism = Talaromyces leycettanus
SEQUENCE: 20
atgctggaag tgctagacac agcgggccag gaagagtaca ccgcactgag agaccagtgg  60
atccgcgatg gtgaagggtt cgttctcgtc tatagcatca catcgcgagc gtcgttcgcc  120
cgcataccca agttctacaa tcagatcaag atggttaaag aatcggcaag ctccgggtca  180
cccgctggag ccagctactt gacgtcgccg atcaattctc cctcgggacc cccgcttcct  240
gtgccggtaa tgttggttgg caacaagagc gacaaggcga tggaccgcgc cgtctctgcg  300
caggaaggcc aagctcttgc caaggagctg gggtgcgaat tcgtcgaggc ttccgccaag  360
aactgtatca atgtcgaaaa ggctttctac gacgtcgtga ggatgcttcg gcagcagcga  420
caacagcaac agggaggacg ggcgcaggag cggcgacccg ccgctttcgg atcagggcca  480
atgcgcgatc gggacgccgg tcccgagtac ccaaagtcgt ttcgtccgga tcgatcaagg  540
catcgcaatg gcctcaaatg cgttatccta tgagctcccc ccgatgagtg ttccgatcgg  600
cggatctttc cagcttctga cctccgctta ttcatgaccg ttgctctcta gaatggatgg  660
tgtctagctc cgtgtttctc tttctcggag cgtgtgagcg agcttgagga cagtcgttcc  720
acttgtgccc cctcctatcc gccgcaggcc cttgtcgctg ccgctttgcg gaccgctcgt  780
tttgtctacg ttgtactcga aagcacggcc tctgctttcg tggaagtctc cctttatgcc  840
agctttgggt gcggtggtcg atatgcagat actgtgttct atgctcgctg catgcgattc  900
agaggcgtct tgattccccg tgtcagtatg gggtgttctc gctattcagg gaatcatctg  960
aaaccaattt ttctcatccg ttctgttttt gggaatcgga acacgggggg gatgtctgga  1020
aatctggacc tataactata gaaatgtttc tcaccacctt tctcactcaa ccctcttgat  1080
gaatatccgc ccggcgtctt ctactacttc ctaccgtcta ctaccaccaa tctctattct  1140
tcttaccacc caccttctga gccacttctt acacatcatt ctcgtttggt ttgacagcaa  1200
agcggggaga gttcgaagga cagatcccat gcaggattgg aggacgagag gggaagagtc  1260
gaagggagaa aaataattaa aaaaaagaaa ggtgcggggg cagaaggagg caggtttggt  1320
tgagagttgc gaatcggtcc tgtcgcagtc aagtcccaaa aaagaaaaga tcgcagtcgg  1380
cgcattagca ggcattttga tacgatgata ccctacagcc gagcttcgag tttttgtgtt  1440
ccttttcctt ttttgcaaat gctgatttaa aaaaataaca atagagctac atactgaatg  1500
tggatttttt tgacctctca tctttttgtt gcagggatga ccgccaattg gtaaattcat  1560
ccccagtcat aatccgagcg caggatgcat gaactccagt acctcatcat atcgcctgca  1620
cgttcaagtt ccatcaatca ttcggcggcg cctactctgt acgactaagt ctacggagtt  1680
tgttcttgtt gcggggaagg aagcgaaagc cacgactcca acaaacaaac tcagggtgaa  1740
ttgaatcctc agtttctact ctgtagccga agagccatca ttaccattca ggggaagagc  1800
ctaaagagct tgcgaggttg ggctgagctg ctgtgcagtg agcaatatat ttggtcgatg  1860
ttttggatac gttatctgga atgcgcagat gcagtggtta tgcatatcct cacgtactcg  1920
attctgatga ttcacgggac catacggagt cgataccgag actctcgcta caaacctgtc  1980
aattgatatc gtgtacagag taccggagcc gagactggga aatagcacag tctcagtctc  2040
aggtagctat cgatcaattt gacaaggtta gaagtatctc gctagtaatt gccagatgat  2100
tcattcccgg ttgaaaactt ttccattggc cttcttcgct tag                    2143

SEQ ID NO: 21          moltype = DNA  length = 677
FEATURE                Location/Qualifiers
source                 1..677
                       mol_type = other DNA
                       organism = Thermoascus crustaceus
SEQUENCE: 21
atgacccaac aatcgaaggt tggtcaccgt taagcaaacc acgatgggag cgtcccgacc  60
atgatggctc attagatctc ttcttctcca gactcgtacc gcaagcagtg tgttattgac  120
gatgaggtcg ccctgttgga cgtcctggat accgccggcc aggaggaata ctcagccatg  180
cgagaacagt acatgagaac gggagagggg ttccttctgg tgtactctat aacttcgcgt  240
cagtcgttcg aggaaatcat gaccttccaa caacagatct tgcgagtcaa ggacaaggat  300
tatttcccca tcattgtcgt cggcaacaag tgtgatctgg agaaggagag agtggtcacg  360
caagaaggta tgtctttaag ctctccgtcg gcttttgaaa cttggctgga gtgccttgct  420
aatcacatta ccgcttctca acagagggtg aggctctcgc gaagcaattc ggctgcaaat  480
tcctggaaac ctcggcgaag tcgcgtatta atgttgaaaa cgcgttctac gaacttgtgc  540
gtgagatccg ccgctacaac aaagagatgt catcctcgtc cggtggcggt gcgggcgcgc  600
gcgcccctga gggcaagatg gatgttaatg acccaggcga gagcgctggc tgctgtggaa  660
agtgcattgt tatgtaa                                                 677

SEQ ID NO: 22          moltype = DNA  length = 809
FEATURE                Location/Qualifiers
source                 1..809
                       mol_type = other DNA
                       organism = Bipolaris maydis
SEQUENCE: 22
atgttcttgc ctcaactcta ctccctcaac cctgccttgg ctgccaaaca tgctgatcct  60
cttgctccta cagcccagtt tgtgcaaaac gtgtggatag agagctatga tcccaccatc  120
gaggactcgt accgaaaggt cctcgaagta gacgtgcgta cacgacactc ttactagccg  180
cgtttttttc actgacccac tctccctccc agggccgtca tgtcattctc gagatcttgg  240
```

```
atactgccgg cacagagcag tttagtaagt gattacatac atagccccac cccacgtgga  300
cccaagacta acacgacaat agctgccatg aggtagagtt tcctactacc cccttactcg  360
gtaaacatca aaacttacac ggatgcagag aactgtacat gaaaacgggc caaggattcc  420
ttttggtctt cagcatcaca tcagaatctt ccttttggga gcttgccgag ctgcgtgagc  480
agatacgacg catcaaggaa gacagcaacg tacccatggt tctcattggc aacaagtcgg  540
acctagaaga cgaccgtgcc gtgccgcgcc cacgagcatt tgccatttcg cgtgaatgga  600
acgttcctta tttcgaaacc agtgctcgaa ggagagccaa tgtcgacgaa gcctttgtcg  660
acctctgcag gcaaatcatc cgcaaggatc agaacgaacg aaaccgcatg gccccaccgg  720
attccccgag gcctggcggt cccaggagca gaactcacac gggacggcca aagcgcaagg  780
ctcaccggcc ccattgtacc attctttaa                                    809

SEQ ID NO: 23          moltype = DNA  length = 961
FEATURE                Location/Qualifiers
source                 1..961
                       mol_type = other DNA
                       organism = Colletotrichum higginsianum
SEQUENCE: 23
atggcgtcca aggttcgtcg tcgccacctc ccgtttccct tcatttcttt tgccgcctcg  60
tcgctccatc gctccatcgc cccatcgatc cgttgctaac cagttgccat ctcgcagttt  120
ctgagggagt acaagttggt cgtcgtcggc ggcggtggtg tcggtaaatc ctgcttgacc  180
atccaattga ttcagagcca ctttgtcgac gaatatgacc cgacgatcga aggtgcgtcg  240
tcccgaactt cttgctccac cgttcgatgc gacggcttcg aatcaatcgc atgctaatgt  300
ggatctcacc catttcagat tcctaccgca agcagtgcgt catcgacgag gaggtcgctc  360
tactcgatgt cctcgacacg gccggtcagg aggagtactc cgccatgagg gagcagtaca  420
tgaggacggg agagggtttc cttctggttt actccatcac ttcgcgacag agcttcgagg  480
agatcaccac attccagcag cagattctga gagtaaagga caaggactac ttccccatgg  540
tcgtcgtcgg caacaagtgc gatctggaga gcgagagaga agtcacacga caaggtatga  600
ttctgattcc tgctgtgccg cgacaccgca tgaggcggct cctttcgagg cccaggcccg  660
gtgtggattc attgatggaa tgaaaagtag ctgacatcat tcactcgtgc gcgctacaga  720
gggagaggcc cttgccaagt cattcggctg caagttcatc gagacgtcgg ccaagtctcg  780
catcaacgtc gacaaggctt tctatgatat tgtccgagaa atccgtcggt acaaccgcga  840
gatgcagggc tactctaccg gcagtggcgg cgcctcgggc atcaacggcc ccccgaagcc  900
catggacgtc gagaacggcg agcaagaggc aggctgctgc tccaagtgcg tactaatgtg  960
a                                                                  961

SEQ ID NO: 24          moltype = DNA  length = 326
FEATURE                Location/Qualifiers
source                 1..326
                       mol_type = other DNA
                       organism = Gyalolechia flavorubescens
SEQUENCE: 24
atggcttcaa aggtaagtcc atctgtctct ttagagtatt ctcattgctc tttgctaccg  60
agcttctcca tggacgctga cccttacctg ctcaagttcc tacgggaata caagctcgtc  120
gtcgttggcg gaggaggtgt gggcaagtcc tgcttgacca tccagctcat ccagagtcac  180
ttcgtcgacg aatacgatcc caccattgaa ggtaaataga ttcgtcctat ccacccattg  240
cgcttttact gatcgaagcg atttgcaaga ctcctaccgg aagcaatgcg tcatcgacga  300
agaagtcgcc ttactcgatg tactag                                       326

SEQ ID NO: 25          moltype = DNA  length = 3190
FEATURE                Location/Qualifiers
source                 1..3190
                       mol_type = other DNA
                       organism = Lecanosticta acicola
SEQUENCE: 25
atggagctcc ctttcgagaa cccgaccgca acaactgaac caggcccgcg agatcgaaat  60
aatttctttg tccccgacca gacacggcca cctccagagc tgatggcgcg tggctttgag  120
cgggatgagg acgagtacga tggatctgca tcggaggcag aaggagagtc actgatgtta  180
ggctcgcatg actcgatttc tcgccgacgc cagtccgtga tggatggagt atcccctgcc  240
acgtccatgg attccttgta cgccgcagga tctaaagatt tcaaaacgcc gcagccgccg  300
agcaagagcc cgcaaaagtc acacagcctc ggcggaaaca gtaccagcac atctgtgacc  360
gaaagctttt ccagaccttc tatttcctcc aacccccctc aacactttgt cgacgatggc  420
ttcgcaccgc caatcacctg gcctttgctt gtcgataata tgcggtacgc cgtggaagcc  480
tatcgccagg tgcttttcaa cggtgagcgt gcagagtacg taagaaaggc cgaggacata  540
tctgaccatc ttcgcatgct gctggctgct ggatctgaca cgacggataa ccactctggt  600
aacccatcta tcatttccac aaacaaggcg ctatatcctt acttccggga catgatgtct  660
aagttctcga agctggttct ttcatcacat attgccgccg ctgattggcc tggtgccgac  720
tcggccaata aatgtttgca ggaggccgat ggagttatgc aaggcgtgta tggctatgtg  780
caagtggctc aacatcagcg cggcgatgcc atccatcgca tcgtgcctgg cttcgtcagc  840
ggcagctctt cgggtggtag ctggcagaac aacggtgttt ccttgaatac ttcaggcccg  900
acatcattcc tcgttccgga tggaggggac tcgcgagtag agccatcggt ctctcttgac  960
accgcctttt tggattcaat cgacatcctc agaagatctt ttgttggtag tattcggcga  1020
ctagaagaac ggctggttat aaaccggaat atcgttacag tggaggaaca tggagacatt  1080
gccgatgcga tctcagctgc tgcaatcaag gtgattgaac agttccgccc atggatctcc  1140
tcggtggagt cgatgaattt agctccgttg ggaaccagct tccagaaccc ccagctagta  1200
gacttcagct tgcaaaagca gagagtctac gatgctattg gagattttgt cctgagctgt  1260
caagcagtct ctgcccctct ggctgatgag tgggcagagc tccgtggtaa ttctctcgac  1320
gatcgtgtga atgccgtgcg aggcatcgtt agacagttgg agaactatgt ctcccagatt  1380
ggcttctcat tgtcgctgct cctcgagcaa atccccaccg aaccagcatc atctctaaga  1440
cgggatagcc gccaagaagc ggaagatgag tcgtacaaga taatgcatag ccgaggcgag  1500
```

```
tccaaggcca agattgccac agagtcaatc gggattccgt cctcctacgc tcctgaaaag  1560
gaaagtggca cagataaagt acgaagaaat atggacaagg cacaacgttt ctttggccag  1620
gcaccccaa cggctatcac ccgagagcca atccgtgagc cagtccgtga gcccgaagaa  1680
actccctggt tcttgaaaat ggcccatgaa ggcgaagtgt tctacgataa caagggagac  1740
ttgcccatcc tcaaatgtgg aacactcgcc ggattggttg aacacctcac ccgccacgat  1800
aagcttgatg catccttcaa caacacattc ctcctcacct atcgctcttt cactactgcc  1860
accgaactat ttgaattgct tgtccagcgg tttaacattc agcctccatt tggcctgaat  1920
caagatgaca tgcaaatgtg gattgaccgg aaacagaagc cgattagatt ccgtgtcgtc  1980
aacattctta agagctggtt cgatcacttc tggatggagc ccaatgatga actgcacatg  2040
gatctcctgc gacgtgtcca taccttacc agcgactcca tcgctaccac gaagacccca  2100
ggaaccccta cattattggc cgtgatcgaa caacgacttc gaggacaaga taccactgtt  2160
aagcgccttg ttccgactca gagcaccgcc gcaccaacac caatcatccc taagaatatg  2220
aagaaactga agttcctcga cattgatcca acggagtttg ctcggcagtt gaccatcatt  2280
gagtcgcgcc tctactccaa aatccggccc actgagtgtt tgaacaagac atggcagaag  2340
aaggtcggcc ctgatgagcc ggaaccatct cccaatgtca aggccttgat tcttcactcg  2400
aaccagctta ccaactgggt cgcggaaatg attctcgccc aaggcgatgt taagaagcgg  2460
gttgtagtca tcaaacactt tgtgaacgtg gctgatgtat gtgtttactc tgcttgcttg  2520
acaaatcccg gcctcactaa ctcaatcata cagaaatgtc gccatctgaa caattattct  2580
accctgactt ccatcatctc ggctcttgga actgcaccca ttcatcgtct aggtagaacg  2640
tggggccagg ttagcggacg cacgtccgca attctggaac agatgcgccg gcttatggct  2700
agtacgaaga actttggcga ataccgagaa accctgcatc tcgctaaccc gccctgtatt  2760
ccatttttcg gtatgcgtca cggtcatttc aagcagattc aagttgtctt ggagtatctc  2820
accccttga ctctgtagct aacacatctt aggtgtctat ctcacggatt tgaccttcat  2880
tgaagacggt atcccgtctc taacaccatc agaattgatc aacttcaata agcgggccaa  2940
gaccgcagaa gtcatccggg atatccaaca ataccagaac gtgccttacc ttttgcaacc  3000
cgtcggcgaa cttcaagatt acatcctcag taacctccaa ggtgctggcg atgtacatga  3060
catgtacgac cggagtctgg agatcgagcc tagggagcgc gaggacgaaa agattgcaag  3120
gtatgctgaa gccacaagca gagacaaggg ctccttgtta tttgcatcca ccgtcgctat  3180
cttgcgataa                                                         3190
```

```
SEQ ID NO: 26          moltype = DNA  length = 3190
FEATURE                Location/Qualifiers
source                 1..3190
                       mol_type = other DNA
                       organism = Penicillium chrysogenum
SEQUENCE: 26
atggagctcc ctttcgagaa cccgaccgca acaactgaac caggcccgcg agatcgaaat  60
aatttctttg tccccgacca gacacggcca cctccagagc tgatggcgcg tggctttgag  120
cgggatgagg acgagtacga tggatctgca tcggaggcag aaggagagtc actgatgtta  180
ggctcgcatg actcgatttc tcgccgacgc cagtccgtga tggatggagt atcccctgcc  240
acgtccatgg attccttgta cgccgcagga tctaaagatt tcaaaacgcc gcagccgccg  300
agcaagagcc cgcaaaagtc acacagcctc ggcggaaaca gtaccagcac atctgtgacc  360
gaaagctttt ccagaccttc tatttcctcc aaccccctc aacactttgt cgacgatggc  420
ttcgcaccgc caatcacctg gcctttgctt gtcgataata tgcggtacgc cgtggaagcc  480
tatcgccagg tgcttttcaa cggtgagcgt gcagagtacg taagaaaggc cgaggacata  540
tctgaccatc ttcgcatgct gctggctgct ggatctgaca cgacggataa ccactctggt  600
aacccatcta tcatttccac aaacaaggcg ctatatcctt acttccggga catgatgtct  660
aagttctcga agctggttct ttcatcacat attgccgccg ctgattggcc tggtgccgac  720
tcggccaata aatgtttgca ggaggccgat ggagttatgc aaggcgtgta tggctatgtg  780
caagtggctc aacatcagcg cggcgatgcc atccatcgca tcgtgcctgg cttcgtcagc  840
ggcagctctt cgggtggtag ctggcagaac aacggtgttt ccttgaatac ttcaggcccg  900
acatcattcc tcgttccgga tggaggggac tcgcgagtag agccatcggt ctctcttgac  960
accgcctttt tggattcaat cgacatcctc agaagatctt ttgttggtag tattcggcga  1020
ctagaagaac ggctggttat aaaccggaat atcgttacag tggaggaaca tggagacatt  1080
gccgatgcga tctcagctgc tgcaatcaag gtgattgaac agttccgccc atggatctcc  1140
tcggtggagt cgatgaattt agctccgttg ggaaccagct tccagaaccc ccagctagta  1200
gacttcagct tgcaaaagca gagagtctac gatgctattg gagattttgt cctgagctgt  1260
caagcagtct ctgcccctct ggctgatgag tgggcagagc tccgtggtaa ttctctcgac  1320
gatcgtgtga atgccgtgcg aggcatcgtt agacagttgg agaactatgt ctcccagatt  1380
ggcttctcat tgtcgctgct cctcgagcaa atccccaccg aaccagcatc atctctaaga  1440
cgggatagcc gccaagaagc ggaagatgag tcgtacaaga taatgcatag ccgaggcgag  1500
tccaaggcca agattgccac agagtcaatc gggattccgt cctcctacgc tcctgaaaag  1560
gaaagtggca cagataaagt acgaagaaat atggacaagg cacaacgttt ctttggccag  1620
gcaccccaa cggctatcac ccgagagcca atccgtgagc cagtccgtga gcccgaagaa  1680
actccctggt tcttgaaaat ggcccatgaa ggcgaagtgt tctacgataa caagggagac  1740
ttgcccatcc tcaaatgtgg aacactcgcc ggattggttg aacacctcac ccgccacgat  1800
aagcttgatg catccttcaa caacacattc ctcctcacct atcgctcttt cactactgcc  1860
accgaactat ttgaattgct tgtccagcgg tttaacattc agcctccatt tggcctgaat  1920
caagatgaca tgcaaatgtg gattgaccgg aaacagaagc cgattagatt ccgtgtcgtc  1980
aacattctta agagctggtt cgatcacttc tggatggagc ccaatgatga actgcacatg  2040
gatctcctgc gacgtgtcca taccttacc agcgactcca tcgctaccac gaagacccca  2100
ggaaccccta cattattggc cgtgatcgaa caacgacttc gaggacaaga taccactgtt  2160
aagcgccttg ttccgactca gagcaccgcc gcaccaacac caatcatccc taagaatatg  2220
aagaaactga agttcctcga cattgatcca acggagtttg ctcggcagtt gaccatcatt  2280
gagtcgcgcc tctactccaa aatccggccc actgagtgtt tgaacaagac atggcagaag  2340
aaggtcggcc ctgatgagcc ggaaccatct cccaatgtca aggccttgat tcttcactcg  2400
aaccagctta ccaactgggt cgcggaaatg attctcgccc aaggcgatgt taagaagcgg  2460
gttgtagtca tcaaacactt tgtgaacgtg gctgatgtat gtgtttactc tgcttgcttg  2520
acaaatcccg gcctcactaa ctcaatcata cagaaatgtc gccatctgaa caattattct  2580
```

```
accctgactt ccatcatctc ggctcttgga actgcaccca ttcatcgtct aggtagaacg  2640
tggggccagg ttagcggacg cacgtccgca attctggaac agatgcgccg gcttatggct  2700
agtacgaaga actttggcga ataccgagaa accctgcatc tcgctaaccc gccctgtatt  2760
ccatttttcg gtatgcgtca cggtcatttc aagcagattc aagttgtctt ggagtatctc  2820
accccccttga ctctgtagct aacacatctt aggtgtctat ctcacggatt tgaccttcat  2880
tgaagacggt atcccgtctc taacaccatc agaattgatc aacttcaata agcgggccaa  2940
gaccgcagaa gtcatccggg atatccaaca ataccagaac gtgccttacc ttttgcaacc  3000
cgtcggcgaa cttcaagatt acatcctcag taacctccaa ggtgctggcg atgtacatga  3060
catgtacgac cggagtctgg agatcgagcc tagggagcgc gaggacgaaa agattgcaag  3120
gtatgctgaa gccacaagca gagacaaggg ctccttgtta tttgcatcca ccgtcgctat  3180
cttgcgataa                                                          3190

SEQ ID NO: 27          moltype = DNA  length = 4030
FEATURE                Location/Qualifiers
source                 1..4030
                       mol_type = other DNA
                       organism = Magnaporthe oryzae
SEQUENCE: 27
atggtaatgc ccggcgacca ttccatgcag cgggcgagcc ttcaagtggc acccctcgcc  60
atccgtaaca agggctcccg tctcggccac ggctctgaca ccgagaacga tgcttctttc  120
acgtcagtct cgagcaacaa cagtgacgcc accatcacgg actcgaggtc cgacgcaaca  180
aacctcaaca agacaacagc aaccaccacc accaccacaa caacaacgac caccacgagc  240
acaaccaaga aaccaaacgc cgcgatcgat tcgtccaacg gctcccacat gaagtcgtcg  300
tcgcgcaatg gctcgcgaga ggaaccgctg gaggcggatc cggacatggc tccgcccgtc  360
ttccacaact tcttgcgggc cttcttccac ttcaagccga gcttcctcat gacggactcg  420
actgttacac tgccgctggc cgagggcgac gtaatcctgg tgcactcgat acacaccaat  480
ggctgggcag acggcaccct gctggcaacc ggcgccagag gctggctgcc gaccaactac  540
tgcgaaccat acggacccga cgaactcacg aacctttttga acgccttgct taacttttgg  600
gatcttttgc gtagcacgtc ggtcaacgac cacgagatat tcagcaacca ggagttcatg  660
aagggcataa tagccggcgt ccgataccta ctggtaggtt tttgctcttt gtttttcttt  720
tgtcttttta tgactttgct tagccccgag ccttgcgcct ggcgtgggat gaaaaaaaag  780
accaaaaagc cctccgaggc ctgtgcgact gacgctgatt aattgggtgg cacaggaacg  840
cacaaactct cttactagag aggcccctct cattcagcgc cacgagggcc tcagacgcag  900
caggaaatcg ctattgtccg agcttagctc gctggtcaag acggccaaac gcctccagga  960
gcaccagcgt atgattcagc ccattgagga cactaacgat atcattgacg agatgatcct  1020
caaggcattc aagattgtga ccaagggtac tcgctttcta gacattctgg atgaggacag  1080
gaaatctcga gcaccatcag tcacggtcat ggcaaccgtc atggaggagg tgacgccgcc  1140
cgtcgacgga aagcctgcaa atagcgaaca ggcaaaggca ctgcgggcgt tgacggcagg  1200
tgcaggcgaa gactcgtctg ccgtggacga caccacggag cagacggtcg ttgtacgtcc  1260
tactaacagg cgcatgtcga ccatcacatc gccaatttcg gcaaccaaca cgaggagaat  1320
gtcgctgggt agcaaccccc accgggtgtc gacggcaatc tcgcaccgag tctcgcttgt  1380
cccatcacca tccaccaagg cccagaacct catctcacag caattgagcg acagccacga  1440
taccttcctg tcatacctgg gttcgttcat cggccgcctg cacctgcagt cccagtctag  1500
gccgcatttg gcgcttgccg tcaagcagtc ggcaacgtcg ggtggcgagc tgctggtggt  1560
tgtcgatgtg gtgtgcgccc acaaccgcat gagccaggat ttccttgatg cttaccgcga  1620
tgccatgttt gcacgtctcc gagaccttgt cttggcggca caggatgtcc tgaccagccg  1680
cggtcgcgag atggaggacg tcatctttcc ccaggacaac agcagactgc ttcaggcggc  1740
cacgggttgc gtgcgggcca cgggcgagtg tgttgccaag accaaatggt tcctcgaaaa  1800
gattggcgac tttgagtttg agctggaacg gggagcttcg gctctgaaca tggatcttgg  1860
gtttttggag attaaagttg ccgaggagag ggataaggag caggggatgg aggggaccag  1920
catcgccgag tccaacaaat caggctctac cgaaacctcg acggtaacgg caactacgac  1980
acagtccgcc gcgtcgacaa ccgccacggt gcggccgacg gccctggcca ccaacaagcc  2040
gcttcctgag gtgccccaat ccacaacccc cgacgaggag gccccgcggc ctcaacgatc  2100
ccccgcttcc tcacgaccga cctcgcttgt ggaggagggc cctgccagca tggcttcctc  2160
tgtggcgtcg ctgcgtccta tgctgccgcc tctgcccagg ctttccacct cgcttatgac  2220
gcaggatgag tacagcccgt cggagcactc ggctggccac gacagcgaca actaccatgg  2280
ctcgttccgc tctgagagca tgacagcctc cagctccgga accggcagca catatatcag  2340
ccgcgactcg gagtcaagcc tggtctcaca gtcgtcaacg cgtgcgacaa cgccagacat  2400
tcccttggcg aaccaaaagt cgctctcgga tattagcaac tctggcagcg gagcttgtgt  2460
ggttgaggag gatgacgtcg agtcgaggct gctcgagagg agatatgcgc acgagctcat  2520
gttcaacaag gaggggcaag ttaccggcgg ctcactcccc gctctggtcg agaggctgac  2580
cactcacgag tccacccccg acgccatgtt cgtgtcgacc ttttacttga ctttcaggct  2640
cttctgcaca cccgtaaaat tggccgagag cttgatcgac cgattcgact acgttgccga  2700
gtctgctcac atggcaggtc ccgttcgtct gcgtgtctac aacgtcttca agggctggct  2760
cgagtcccac tggagggacg agacggaccg cgaagccctg agtctcatcg agccgtttgc  2820
tactttcaaa cttggcgagg tgcttccctc ggccggcaag cgtatcctcg agcttgtcga  2880
tcgcgtctct gcgtgcggcg gtggtgcatt ggtcccacgc ctggtgtctt cgatgggcaa  2940
gaccaacaca tccatctctc aatacgttcc cgccgacact cccctgccaa acccggtatt  3000
caccaagagc cacgcgcacc tgctggccaa ctggaggaac ggcggcagct gccctagcat  3060
cctcgacctt gatgctctcg agattgcccg gcagcttacc atcaagcaga tgaacatctt  3120
ttgctcgata atgcccgagg agctcctagg ctctcagtgg atgaagaatg gaggtgccga  3180
gtcgcccaac gtcaaggcca tgtcgacctt ttccaacgac ttgtcctcgc tggtgtcgga  3240
cacaatcctg cactacaacg aggtcaagaa gcgtgcagcc gtgctcaagc agtggatcaa  3300
gattgcccac cagtgcctgg acttgaacaa ctatgacgcc ctcatggcga tcatctgcag  3360
tctcaacagc tccaccatca cgcgcctccg gcgcacatgg gaggccgtct cgcctcgtcg  3420
ccgtgagctc ctcaagcagc tccaagccat tgtcgagccg tctcagaaca acaaggtcct  3480
gcgcggtcgc ttggccggcc acgtcccgcc ctgcctgcca ttcctcggca tgttcctcac  3540
cgacctgacc tttgtcgaca ttggcaaccc ggccatcaag cagctccctg gtaacgaggg  3600
cgacggcaag gctccggcca tcaccgtcat caactttgac aagcacgccc gcacggccaa  3660
```

```
gatcatcggc gagctgcagc gcttccagat tccttaccgg ctgcaggagc ttaccgaggt  3720
gcaggagtgg atccaggccc agattgcacg actccgcgag ctcgagacgc ccaacgataa  3780
cgtccaggtc gcctactacc gcaagagtct gctgctcgag ccccgcgagg tcacggccac  3840
gccccagacg ctacggaact cgtccgagac gttttcctcg tcgtcggcca cgctcgcacc  3900
tccaagcgcc agagactcga ccgctgccaa cggcagagca gcagagagaa ctgctcagtc  3960
gcagaggacg gattattttg gctggatgcg aggatctggg ggcagccaca gagatcatcc  4020
tgctgcttga                                                         4030

SEQ ID NO: 28          moltype = DNA  length = 3669
FEATURE                Location/Qualifiers
source                 1..3669
                       mol_type = other DNA
                       organism = Arthroderma gypseum
SEQUENCE: 28
atggctgctc gcgatggcta ctccagccag ggcgctgctg gtgcggcgaa tgacgatggt  60
ctgtaccaaa atttacttcc tcttcttccg gttctaccca cgtcgtatta accgcatttc  120
acaggctacg tatcaccaac agaggcgcct ccggctctct atgttagagc tctgtacaag  180
tacacctcag acgaccacac cagccttagc ttcgagcaag gcgacattat tcaggtgctg  240
aatcagctcg agaccggctg gtgggacggt gtgattggtg atgtccgtgg ctggttccca  300
agtaactact gcgctgtcgt tcctgggccc gaggctctca acgagcacgc cggtgatgcc  360
agtgccgaat ctggcgcaga cgatgactac gaggacgacg ttgacggcct tgacactacc  420
ctgagagacg acgacctgcc tattgaaagc aatggagcag acggcggcga gcccgaagag  480
gccgccttct ggatccccca ggccaccgca gacgggcgcc tgttctacta caacacattg  540
accggctaca gcacaatgga acttcccctg gagacgccga cttccgtcaa cgagtctggc  600
cctcgggacc gtacaaacgt ctacgtgccc gaacacacca ggctgccacc tgagatgatg  660
gccccgtggca tcgatcgcta cgaagatgac tatgatggct ctgcctcaga ggctgaaggt  720
gactccctct taatggcatc gcagcgccga cattcgttca tttctgatgg cgtctctcct  780
gctacatcct taggttccgt caatccttca ccaatcacca aacactatga tctcaaatca  840
gcttatcctc cccatttcgt tgcaaacggt ggaaacgctg gcatggactc tatccctatc  900
atgggcactc ccatgtccac ccactcgaac gcgactgatc gatctctgcc ctttggcatc  960
tcaacctcta tccctcgcta tttcctggat gactccaccg ctcctcatcc tacctggaac  1020
tcgctcgtca gcaacatgcg agatgcaatt gaggcgtatc gacaggccat catcgaaggt  1080
cggcggtcag agtacgttcg cagggccgag gatgtgtccg atcacctgcg gatgcttctc  1140
gcggcaggct ccgatactac agataaccac tcgggcaacc cgtcaatcat ctctacaaac  1200
aaggcgctat acccgcattt ccgcgatatg atgtccaaat tctccaagct cgtcctatcc  1260
tcacatattg ccgcggctga ctggccggga ccagactctg cgaccaaatg tctccatgaa  1320
gccgagggcg ttctacaggg cgtttacggc tacgtcgaag tggccaagca gcagcgagga  1380
gacgatatcc gccgtctgac acctggcttt gtcgccggca gcacttctgg cggtcactgg  1440
cagaacaaca acctcgctcg aagggatcca acgtctttcc tcgagcatga ctctgagtct  1500
caccgcactc cgtcggtctc gcttgactca aagcttctag agcgaatcga agagcttcgc  1560
aagatgctag ctgtcagctc ccgcaggcta gaagagcagc tctcatcctt caagggtaaa  1620
attgttacgc caaaaagcca tgccgagatt ggcgacgctg tatgtgaagc tggcgtgccg  1680
atagtcgaaa actttcgccc gtgggtggcg ctcatcgagt ctatcgactt gtcacacttt  1740
ggctctgatc tccagaaccc gcaattagcg gacttcagcg ttcagaagca gcgcgtgtac  1800
gacagcatct cggacctcgt tatgagctgc cagcacatct ctgctccgct aggcgacgag  1860
tgggccgaga tcaggggcga ttcgcttgag actcgtctaa ataatacccg catgatgtca  1920
aggcagctca ctaattgcgt tcaacagatt ggattctcgt tgaccttact attggaacaa  1980
gctccacaac aacaaataca aaatggagat ggatataaca aatctgctcc caaggtacgc  2040
aagagtccgc catcatctat tggcatacct tccagctatg gcgtgggcga tgaccatgat  2100
aagccaccac ggtctctgga taaggcgcag cggttctttg gccaacccgt gccgagggag  2160
ccgacttctg ccagagaacc cgaggaaaca ccgtggttcc tgaaactcga ccatgaggcc  2220
gaggtgtttt acgacgtcaa gggtgacgtg cagcagctca agtgcggtac gctggcagga  2280
ctagttgaac agcttacccg ccatgacaag cttgatccct ccttcaagga taccttcctt  2340
ctcacatacc ggtccttcac cacggcttcg gagcttttg agatggtggt acatcgcttc  2400
acactccagc ctccctacgg cctgaccaaa gcagagctac aaatctggac cgaacaaaag  2460
caaataccca tccggatccg tgtcgtcaac atcctcaaga gttggttcga gaacttctgg  2520
atggaaccaa atgatgaggc aaacacacat ttacttggcc gtatacactc cttcgttacc  2580
gaggcagttg catcgactaa gacgcctggc gcgcaacaac tagtcagttt gatagagcaa  2640
cgcctacgtg gagaagaaac taccgccaaa cgcctggtac ccaccattag ctccaatgca  2700
cccactccca tcacacccaa gaacatgagg aggatcaagt tcttggatat cgacccaacg  2760
gagtttgcgc gccagttgac tatcatcgag tcgcggctgt atgctaagat taagcctacg  2820
gagtgtttga ataagacctg gcagaaaaag gctggaccag gcgaggccga gccggcgccg  2880
aacgtcaagg ctcttattct acattctaac cagcttacca actgggtggc tgagatgatt  2940
ttgacccagt cggacgtcag gagacgagtc gtcgttatca aacactttgt ctccgttgct  3000
gatgtaagtt gatttatctt cttacccccct taacacataa aaattatgct aacaaatttg  3060
atagaaatgc cgacaactta acaattattc tactttgaca tctattatct ctgcgcttgg  3120
caccgcgcca atccatcgac tggctcgtac atgggcgcaa gtcagccaga gaaccgctgg  3180
aaccctcgag atgatccgca aactcatggc tagcacaaag aactttggcg aataccgtga  3240
aacccttcac ctagccaatc ccccttgcat tcctttcttc ggtaacgaca atttcctatt  3300
ttttttatc ggcgcagagc cactaacaca cgcacaggtg tctacctaac ggatcttacc  3360
ttcatcgaag acggcattcc ctcactcact caatccgatc taatcaactt caacaaacgc  3420
accaagaccg cggaggtgat ccgcgatatc cagcagtacc agaatgcgcc ttaccagctc  3480
attcccgtgc cggagctgca ggagtacgtg ctgaataata tgcaggctgc aggcgatgtg  3540
cacgacatgt acgaccgcag tcttgaaatc gaaccccgag aaagggaaga cgagaaaatc  3600
gcaaggtatg gtaaacacta ctacgaccca tcggtcgttg cactctccct gacggttggc  3660
atacattga                                                          3669

SEQ ID NO: 29          moltype = DNA  length = 1571
FEATURE                Location/Qualifiers
```

```
source                  1..1571
                        mol_type = other DNA
                        organism = Endocarpon pusillum
SEQUENCE: 29
atggaggaga atgacggaga gagcaggaag cttctcgaca ggatctactc atttgctaaa  60
gactcaattg ccacgaccaa gacaccaggc tcaggacctt tgatggcggt ggttgagcag  120
aggctgaagg gtcaggacac ttctgctaaa agacttgtgc taacattgac gaattctgct  180
cccgccccga tcttgccaaa aaatatgaag aagctcaagt tcctcgacat agacgcaaca  240
gaattcgcac gacagcttac cattatcgag tctaagctct atggaaagat caaaccaact  300
gaatgtttgg gcaagacgtg gcagaaaaag gttggtcctg aggagcccga cccagcaccc  360
aatgtgaagt ccttgatcct ccattccaac cagctcacga actgggttgc ggagatgata  420
ctatcacagt ccgaggttaa gaagcgagta ctcgtcatca agcactttgt ttcgattgca  480
gatgtgagtc cagccgtaaa cgccaattcg caaagactga cccatacaga aatgccgcaa  540
catgaataat ttctcaaccc ttacctctat tgtttctgct ctgggaactg ctccaataca  600
ccggcttaat cgaacatgga cccaagtcag cccaaagacc atgacttctc tgagtgtgat  660
gcgacagctt atggccagca ccaagaactt tggtgaatat cgggagaggc tacgccgggc  720
aaacccgcca tgcataccct tcctaggtgt ttatcttacg gatctgacat tcattgaaga  780
tggaatcgcg tcgatcgtca agaactccaa cctcattaat tttgccaagc ggaccaagac  840
ggccgaggtc attcgtgaca tccagcagta ccagaacgta ccgtactcgc tcaaccctgt  900
tcctgatctt caggagtata tactcagcaa catgagagaa gctggcgatg tacatgagat  960
gtatgataag agcttgcaaa tcgaaccaag ggagcgagag gatgagaaga tcgcaaggtg  1020
agtgtgtaca aggaaatctt cacaccccca acgatgcaga tgggtctgac tcacgtctct  1080
cctcgattat agattgctgt ctgagtctgg tttcctttga tccgtgagca ggactcgcga  1140
ttcgctggtt tctcaacata ccttttgagt tgaatagccg cggggtttgc aggtgccgaa  1200
tctcccttgt ccctaactat gatgtcaatt ctacataagt actggggatg ctacacaagg  1260
ccggtcctac gtaacaagcc attgcatgga tacttggatg gttgggggtt tttctggtag  1320
atatctgatt caggcttggt ggcatggtat tggacgtctg acatgaaatt gcacgagcaa  1380
acgagtcgat gagacactta tctggacatg gtcaaacatc aacgaagctc atggatagga  1440
gcgatactaa ttcaggctga tctcggagct tgtgatgggg aatctgcgat atctagtgct  1500
tttgaatata catttttgtt gctaatgcag aatgagtagc tgcatttttg cgcagtcgat  1560
cggttttcta g                                                       1571

SEQ ID NO: 30           moltype = DNA  length = 3012
FEATURE                 Location/Qualifiers
source                  1..3012
                        mol_type = other DNA
                        organism = Fistulina hepatica
SEQUENCE: 30
atgtacgatc tcgtacacga aattgttgcc attgtgtgca agctacttac catcgcggac  60
gctgtaatgc tgcacccaga catcccgcca aacaaagtca agaacctcag ccactcaaag  120
aatgcgctgt acgattcgac gacggcattg atggaatgtg tccagacgtt gacgcaacca  180
ctcgcgccga cggtgacgga agaggatgag aagagcgcgt tactggtcac cgccacatcc  240
gcagtaaagg ttggtgcaga ctgcgtggcc gcgatcaaga tgtgcctgtc gcgttcggtg  300
ggcgaacggc cattcgtact gcagctgccc gacaagaatc accctcctgt ggcagtgcct  360
ttacaacgac caaagctcgg caaggcaaca agccttggct cgttgaatac gtccactaac  420
gtgcctgaag accacgatga caccatccgg ccgcccgtac caccacttcc acaacagtgt  480
tcgcgtgatc tttcttctgg atcggaaaag agcgacgcgt cggcacagag ttcgacgagc  540
tcacgagaca caggctttac gtcgttggac gccttgaagc tggtttcacc gaaagagaag  600
cctctgcccg ctctccttaa gcttacaaaa gccgccgtcg aaaaagatct cccctcgccc  660
acatctcttg ctcccactga agctgcaagt acatgggaag gtgctccatc acattacttg  720
cactcgctcg gtaaatcatc aaccacttca tcaaatgcgg cgctcagctt gcaatctatc  780
ccacaatcct tgccatcact gccggcgctt gtcaatgcac atgactattc cgacgacgag  840
gtggcatgca atagcgaggg acacatcgtc ggtgcaacga tgagcgtgtt agtggcacgg  900
atgacgccac atgacaatct cgtcgatgcc gccttcgccg cagtcttctt catgacgttc  960
cgcttgtttt cgtcgcccga agagctcgtt gacactctga tagctcggta caacatccag  1020
ccgcctgaat tcctgagtca ggcggacaag gagttgtgga tgcatcaaaa gggcatgccc  1080
attcgacttc gtgcggcgaa ccttgtaaag agctgggttg aaagttattg gcgccctggt  1140
gttgacgatg cagtgtcgca gaccatctac gaatttgcag agacttgtgt gcataagacc  1200
tttgcgtcgg tcgccaaccg tattgtggaa ctgctggagg tgcggcaaac gacaagtaac  1260
gcggtaatca cgccgaaagg cgatcgcaca cgcgaccccg gcatgtcaat taaccctccg  1320
attgtgaatt cgccgtccga aattccgcga ccgatcgtgt ccaaaccatt gtttgcggcg  1380
ttgaggaatc ggaatttctc gtcgatcagt gtgcttgact tcgatgcatt ggaattggcc  1440
cgccaactca cgcttatgga atgcacgctc tattgtgcaa tacggccgga ggaagtgctc  1500
gaacctggcc agccgggaaa gccgaacatg aatgtcaagg cgatgagcac gctgagcact  1560
gttatcacag gttgggtaac tgagtctata ctcagtgaac aagatgcgaa gaaacggact  1620
acgctggtta agttcttcgt caaggtcgca gatgtacgtg ttcgttctat gtcaaccgtc  1680
tgtaaagatt ttgaactcct tgtcagagat gtgtctcact gaacaatttc agtacctcgt  1740
ggtcccttct agcggctctc gattcttcta ccatttcacg gcttcatcag acctggaccg  1800
taagtaccaa atttgtctct tgttctctcg ttaaaatatg attcttgctt ccagggcctg  1860
cctcagaaga atcggcaaca gcttgatgca cttcgcaagt tatcggaccg tgctcggaat  1920
taccgcgagt acagaaataa attgcggaac accgcgccgc cagctgttcc gttcttgggt  1980
ttgtgcactg tttctgctcc ttttcgcgat gagacggatt aacaatggtt ttcaggcctc  2040
tacctgacgg atgtgacatt ttgtcgtgag ggcaatccct ccactaaacc gtcgcctcta  2100
gatcccaata agcagctcat caacttcaat aaatatcata agttggcgcg aatcgtgcaa  2160
ggtattttca catgcgcgtg ccgcactatg tcataatgct tgaacttcgg tttgcagata  2220
tgcagcgttt ccaagtgcct tacaatttca aggctatacc tgttatccag gaatatttga  2280
acgtcgcgtt cgagacttcg aagaagaaca gcgatcttca agacttgtac cgtcgtaggc  2340
aagtacacag tatgaattct tctgtggcca taatcgctga tgatgtgctc agtcttatga  2400
tcgagccaaa gcggccggtc gacacgccac ccgcgagcgc gagcgatacg cgattgttcc  2460
```

```
attgggcttc gaagtcccaa acaccatctc agactgtagc tgctccattc tagatgtccc  2520
tgcttatttg tactattttc actatgttta tacatgggtt ccgtgcacac ggttgctcat  2580
atttgtgtct ctttcttttt tttggcggac ccgttcgcgt gttttcgatg actttctctc  2640
tccgtcctcg gtgttcacat attaactcga ctctctgtct ctctgtctct ttcgctcttg  2700
ttattcattt cgctttgttg ttaggttata tatacattat attgtcaagc catctgtacg  2760
ttcacccatc cactgcattg gtttagcctc actacttttg tctgcttgaa tacactggtt  2820
cgtccatcac ccgtgtcgtc tctggccagt agggaaggga gcacgcatcg tttcactata  2880
cataggtcag tcaggtcgag tctttcttct tctgggttca tccctcaggt catgaggtgc  2940
gtcatgcagc gacttgttat tctcaatctg attatggtca gttatatcag cggtgaaact  3000
cttcacgaat ag                                                      3012

SEQ ID NO: 31          moltype = DNA  length = 1658
FEATURE                Location/Qualifiers
source                 1..1658
                       mol_type = other DNA
                       organism = Aureobasidium pullulans
SEQUENCE: 31
atggtgacaa ccccttcagc ctccacaaat ccgcccctcg acattgacac gaatttggac  60
gaatcacgcg acgacattac agactcatct cgttctgagc acgcctcctc atctgaggat  120
ggcggtcttg atgtcgatag tcaatcagag gccccatccg atgagcgggg atactccttt  180
gacaacctcg tcgaccgtct cctggggcta ccgcgatcaa aagccgacac acgattcggc  240
tctgtctttc ttgccctcta tcggaaattc gctgcacccg gacagttgct ggaagctata  300
gttcatcgct tcgaagcctt ggaaaaagaa aactgtcctt tcatgacaaa gactgtctca  360
caattacgct acttatctgt cattgagcaa tggattggaa cataccctgg agactttgca  420
cacacaaaaa cccgccgtcg catgcgcatc ttcgtcgcca agctgtccaa cacacgcatc  480
ttctctgctg ccgctcgtga gatgagctgt gacttggacg ttgtgacaga agacgatgat  540
acaaattggg cttgttgtga catggatcgt gaaaaacgcg gtctcctgag ccccgatctc  600
ggctggtcat cccgtgtgag cacactcctg gacgatcccg aatttgactt tagcgacaac  660
ctgggaagcc tgtctctcga tggcggccag ggtagaaatg cagcccattc cttacatacc  720
gactttggca tgctgcagac cgtggacgca gcacgtagac aaggcccatc tctggttccc  780
gtccccaaga ttccaatcag caagatgcat tggcacatgc ttatggaaac accaacggat  840
cacatcgctt gcgaactgac acgcattgac tggatcatgt tcagtgcagt acgtccgcgt  900
gatttggtgc ggcacgtttc cttatcgcaa actcagaagg cacagtgcaa atccatagta  960
catgtcagcc gcatgatcga ccatttcaat cacattcgag actgggtggc caacttcatc  1020
ttgcttagag agaaggcgaa acaccgtgta ctgatgttgg aaaagctcat gcatgtcgcc  1080
cgtaagctgc gagagatgaa caactacaac tcgctggggg cgttccttgc cggtatcagc  1140
agtgcagccg tacaccgact tgccgctact cgagaactgg tttcacccga gaccggcaag  1200
gattggatga agctggagat attgatgtct cccactcgct cttattctgc ttatcgcctg  1260
gcttgggaga actcaagcgg agagagaatc cctttcctcc ctctacccat ccgagatctt  1320
gtggccgccg aggaaggcaa caagaccttt gtcggcgacg aagtgaatgg cagaatcaac  1380
tggcgcaagt tcgaagtcat gggagaaacg gtcgtcggga ttcaaaaggc gcaaggtctg  1440
ccttatagga actccatgct cggccctagg aatgatgagt tgagagcatt gatcctgaac  1500
agtaacatga tcagagatga cgaggtaagt tcttcagaga tcaaggtatt tgcagacaca  1560
cgactaactg aatcttccag gctctttatg accgtagctg ttctctcgaa tctaccaacg  1620
acagaagggg gctgcgagat atcttcagac gcgcatag                          1658

SEQ ID NO: 32          moltype = DNA  length = 2510
FEATURE                Location/Qualifiers
source                 1..2510
                       mol_type = other DNA
                       organism = Acremonium furcatum
SEQUENCE: 32
atgtctgtga tgctgcaagc tccttcccga gcctccactg catcctcctc ctccatccag  60
cccctctccc gacagaacac catgtcttcc tacgatggct cgcggtccgc ccgccagtcg  120
aagcggtact ccatgtccgc gctgtacatg tccatgtcag ccaacgacgg agagctcgag  180
atcgaagacg atctggccaa aggtaggcta catgcattcc cagttgcact acgactggat  240
tctctcgcta acacgctcaa aacacagccc agaaaatcct gcgagaactc aagtccaaga  300
tctcctccca gtccaagaag aacttcgtcc tcgagaagga tgttcgatat ctcgactctc  360
gaatcgccct tctcatccag aaccgcatgg ctctggagga acagaacgaa gtcgccagcc  420
atcttgaaga cgccacagac atgcaagagg gagccttccc gaacgacgac aagacccaga  480
aatatggcaa cctcatgttt ttgctgcagt ccgagccgag gcacatcgcc catctgtgcc  540
gtcttgtgtc catggctgag atcgactcgc tgctccagac cgtcatgttc acgatctatg  600
gaaatcagta cgagagccgc gaagagcacc tgcttcttac catgttccag gtccgcctgc  660
ctacctgcac tatatcagat cattgctaac aaggacttcc agtctgttct gacctatcag  720
ttcgacaaca cccctgagta ctcctcgctc ctgcgcgcaa atacccccgt ctctcgcatg  780
atgacgacat acacgaggag aggccctgga cagagtttcc tcaagtctgt tctggccgat  840
aggatcaaca gcctgatcga actgaaggac ctcgaccttg aaatcaaccc cttgaaggtg  900
tatgagcgca tgatcgagca gatcgaagag gacacaggaa gcctacccgc atccctgcca  960
aagggaatca ctgctgagca ggcggcggaa aaccctcaag tccaggccat catcgaaccc  1020
cgtctgacga tgctgacgga tctcgccaat ggcttcttgt cgaccatcat cgaggggctc  1080
gatgaagctc cttatgggat ccgttggatt tgcaagcaga tccgcagctt gaccaagcgc  1140
aagtatcctg atgctaatga tcaggttgtt tgcaccctca tcggcggttt cttcttcctg  1200
cgcttcatca accctgccat tgtcacgccc aagtcctaca tgctcatcga aggccagcct  1260
gccgagcgac ccaggcgcac cttgacctac attgccaaga tgctccagaa cctggccaac  1320
aagccctcgt atgccaagga gccgtacatg gcgaagcttc agcccttcat tcagcacaac  1380
aaggaccggg tcaacaagtt catgctcgac ctctgcgagg tgcaagattt ctacgaaagc  1440
ctcgagatgg acaactacgt ggccctgtcc aagaaggacc tggagctgtc catcacactg  1500
aacgaaatct acgccatgca ctcactgatc gagaagcatc atgatgagct ctgcaaggac  1560
gccaattctc acctggcaat catcatgtct gaactgtctt cggccccggc ccaagtccca  1620
```

```
cgcaaggaga acagggtcgt caacttgccc ctattcagtc gctgggagac agccatggat  1680
gacctcactg ccgcacttga cattacgcaa gaggaggtgt tctttatgga agccaagtcc  1740
atcttcgtac agatcatgcg gtccatcccg tccaacagca gcgtttctcg acgccccctg  1800
cgcctcgaga ggatcgctga cgcagcagcc accagccgaa acgatgcggt tatggtccgc  1860
aagggcattc gagccatgga gctgctttca cagcttcagg agctgagggt cattgataag  1920
agcgaccatt tcagtctgct ccgcgatgag gtggagcaag agctgcagca cctggggtcg  1980
ctcaaggaag ccgtcatccg tgagacatcg aagctcgagg aggttttcaa gaccattcgc  2040
gaccataaca cgtacctggt cggccagctc gagacgtaca aaagctatct tcacaacgtc  2100
cgctcgcaga gcgaaggaac gaagaggaag cagcagaagc agcaggtcct tggtccttac  2160
aagttcaccc atcagcagct tgaaaaggag ggcgtcatcc agaagagcaa tgtccccgac  2220
aaccgacggg cgaacattta cttcaacttc acgagccctt tgccgggcac tttcgtcatt  2280
tcccttcact acaagggtga gtattcctca ttgccgcgcc ctcattgatt catgcttaca  2340
actgcgtagg acgcaaccga ggattgctgg agcttgatct caagctggac gaccttctgg  2400
agatgcagaa ggacgggcaa gacgacctcg accttgagta cgtgcagttc aatgtgccca  2460
aggtcctggc gctcttgaac aagcgcttcg cgaggaagaa ggggtggtaa              2510

SEQ ID NO: 33           moltype = DNA  length = 5325
FEATURE                 Location/Qualifiers
source                  1..5325
                        mol_type = other DNA
                        organism = Purpureocillium lilacinum
SEQUENCE: 33
atggtcaggg actcagggtc acgtccagga cgggaagacg tctggctgtt ggctgtcttt  60
ctcgtcgccc caagaaaggg tagggagtct tggctgctcc gcagagactt gtatttgcat  120
ggccgccatc ccatcggcgc cgtgtgtggc atggcacggg tgctgctgcg tgcttcgttc  180
gaatggggtc gatgatgccc aattcctcgg ggatcctcgt cgtggtatat taccttacct  240
ttgcatctac ctaatcgacg gcggcggcgc caggcaaatg gaagctggcc gccggcaagg  300
tcaccgccca cggcacccct aatcgtcaat tacgacagac gcccgaccaa cgacacccac  360
ctctgtggcc ggggctgcac acccgagtgt aggttcaagg ttgatcttgc gtacctcacg  420
gagtacaggc gaggtactgc agcgcgtgcc ttccttgccc gtggccggac cgcgccaaca  480
ccgacgagta cctgccccgt actccgtgga gtgctccgcg ccgtgccttg cttgcctcga  540
gtacaaagcc agggtacttc cgtacattgc ccctcgacca ggccaccacc cagacccgca  600
aaaaagacaa cgacaagaca acagcgtcac ccttcccctt gtccgtgctc cagcaagccc  660
gcttgtcctc gaccggtgct gtctcgccgg cgcgcgcgcc tcgataccat accctctctt  720
ttctacaatt gcactcactt tccccatccg tcggggcttt gcgtttttcg gcccagaata  780
gccgtcgacg gtactgtgcg ccattgccag agagcttgat ctgttgttgc ggcgccaaac  840
accgaacgct ctttatactt tcctgtgccc cttgacctga acgcagtcgc agcgttctcg  900
cccttcgacc ccggcatcga gcttggaaac cgacaagcag ctccccccaca atcctggcct  960
gccgctttct ccgcatcgcc tcgtccgcct ttcgtaacga ctgcttcgtc gcccgcgttc  1020
gactccgcct ggcctcgaac ctcgaggcgc ctgcgtgtaa gtcagtcacc ttgcgtgctt  1080
tgatcctgcg gctcagctgc agccccccca ccagcagttt gcccttgctt caggtcctgc  1140
tgtcatgtcg tccacgctct cagcagttct cttgtacttc ttagttcacc ctgcattcct  1200
cgccacgccc gccccgtccc cctctggcct gcattccaga cacgggtcat tggctcttgc  1260
cacaacatcc aggtcgcgct ccggccttgc taacatccaa tctcgcctcc agacaaacga  1320
gcgtcgcgta catctcacaa ctgctggttg cgcccacctg cgttgacctg cgcctcggtg  1380
gtcgcggccg tcgttgtcac atccctgggt cctcgccagc accagcatac cccccctcaa  1440
aaagaacgaa ctgtcacgga accccccccct ggggctcctc cactgcgctc tttggataac  1500
caaagcactt actttggaac cagggcgcgg ctggccgtcg ctctgggacg ggccgtcgac  1560
gctagaccgc gaggcctcga ccagatgatc ttgacactcg tctctacctt ctcacaggcg  1620
caatgctgag cgaccaaccg tcgcgaactg ctttacacgt ggccccgctg gagataccccg  1680
cgtcgcagcc acaggacggt gccaatggct tgtgccatca agaacatcag acgaatctct  1740
actcacagac ccctatgact ccgccggaaa cacctaacgg ctcccaggag gacctgacgc  1800
cggagcctct cgccccgccc gtctttcaca atttccttag ggccttctac ccgtttcacc  1860
ccggctacgc cttgtccgac tcgagcgtca cgctgccact ggacgaaggc gatgtcgtac  1920
ttatacactc tgtacacacc aatggttggg cggacggtac tcttttggca accggcgcca  1980
ggggctggct gccaactaac tactgcgatg cctacgagcc cgaggatatg cggagccttc  2040
tgaaggcgct tctcaacttt tgggacctcc tacgtagcgc atcagtaaac aatgagatct  2100
tcaggaacca agaatttatg aagggcgtca tagctggagt tcggtttctc ttggtaggct  2160
tgcgctatct tctcccccac aagggctcat tgtctttgct aatgacaatg tgctcaggaa  2220
cgcacaaact gcttaaaccg agaatcgacc atcattcagc gcagtgacag tttaaggaga  2280
tgtcgcaaat cattgctctc agaactctca tcattggtca agacagcgaa gaaaacacag  2340
gagtgccaaa aggggacact ccacccaccg caggatgtca acgacatcat tgacgagatg  2400
atactcaagg cattcaagat tgtcaccaaa ggcgtccggt ttctcgatgt tctcgaggac  2460
gaacggaggg ctcgcgcacc agcagctgtc actgtcatgg ccactgtcgc cgaggaatca  2520
tacattccac ctacaccccc tgcggagcgc ttggctttcg acgatcaaag tttgaacaat  2580
ggcagcgaga cggcttcccg cggaacggcc gacagtgtgg ttggcagcag cgccacttcg  2640
gaacccagcg ttgcatcact caatccatgg aacaggcgca tgtcgtctct gggtggatct  2700
caaggcacgg cggcccagaa tcgatggtct caaggaagtc tccaacaagt caaccgtttg  2760
tccacaagta tggcgcacag agtctcgctg gccggcccat ccccgctgtc gaggcctcaa  2820
catttggtat cggagcgcct caaccgcagc catgacaaat tcctctcgca cctcggatct  2880
ttcattgggc gactgcactt gcagtcacac tcgcaaccgg aactggcact cgcgatcaag  2940
caatctgcca catcgggcgg tgaattactg gcagtcatcg acggtgtctg cgagtacaac  3000
agctctagtg ccgcggcgct cgctattgtc cgagatgcca tgtttgagcg cattcagatc  3060
ttggtccact ctgccagaga tattttggcc aatgccgcta ctgaagggggc cgacataatc  3120
ctgccacaag acaatggggt tttgctcatg gcagccactg gttgcgtgaa agccgcagga  3180
gaatgcgtcg ccaaggccaa ggccgccatt gagagggcgg gggacttcga gttcgagctg  3240
gaagagaaca cgctcgggat agacctgagc atcttggaca ttgtcgtgga cgagcgggcg  3300
agaacgccct cggtaacgga tcgatcggac cctatgagca gcgttgcaga atcgttccag  3360
acccccgaat cgactgttca gcctcaaaag cggccgatcg cacccgccgt cgacaagccg  3420
```

```
cttccccaag tacccagaat caccatcccc gcagactcgc acagtcgtca aagcaactcc  3480
ccagtgtcct ctcgaccccc gtccctcaac gaggacaatg cttctagcgt cgcgtcgtct  3540
gtttcgtcta ttcgccctgt tctcccgccc ctccctgagg tttccacaac accgcagcct  3600
ctggatcgcg atggttccga cacgacaaca atcgagtcgg acgcccatac ctcgaggttc  3660
gacgccttgg cggcgtccag cgcgggcagc agtaccactt acctcagccg ggactctgaa  3720
acgagcatga tgtcgcagac gtcgacgcga gcgacgacgc cggatcacac cttggtgcct  3780
cgcagccagc cctcgatgtc ggagctgagt acggccggca gcttctccca ggccgaagag  3840
gcggatgacg tcgaaacaag acttatggag aggacgtacg ctcacgagct catgttcaat  3900
aaggaaggtc aagtcactgg cggatcgctc caggctctgg tcgaacgtct caccacgcac  3960
gagtcgactc cggacgcggc ttttgtctcg actttctacc tcacattccg actgttttgc  4020
tcaccggtca ggttgacgga agcgctcatc gaacgtttcg attacgttgg agaatcgcct  4080
cacatgtcgg gccccgtgcg tttgagggta tacaatgctt tcaaaggctg gctggaatcc  4140
cactggaagg agcagactga tcgagacgca ctacagctca tgattccctt tgcggaagga  4200
aagctggctt cggttctgcc atcagcggga cgccgcctgt ccgagctggc caagcgtgtc  4260
tccggagaag ggtctctggt gccgcggctt gtctcgtcaa tgggaaagac gagcacgtcc  4320
attgctcaat ttgtcccggc tgatagcccc gtgccgcagc ctatcatttc aaaaagccag  4380
cagaatttgc ttacgtcctt caaaattggc agtgggatgc caaccatcct cgactttgac  4440
cctctcgagc tggcacgaca gatcactctg aggcagatgg gcattttctg ctccatccaa  4500
ccggaagagc tgcttgcatc gcagtggatg aagaacggtg gtgtagatgc accacacgtc  4560
aaggctatgt cagcgctgtc gacggacttg tcgaatctgg tggcagagac catccttcag  4620
tacaccgaga tcaagaagcg agccgctgcc atcaagcagt ggattaagat cgcccataaa  4680
tgccacgaac tgcacaacta cgacgggctc atggccataa tttgcagcct gaacagcagc  4740
acgatcagcc gccttcgcaa aacctgggac gcgatttctg caaagcgaaa ggaggtgtta  4800
cgcgcactgc aggagatcgt ggaaccatct cagaacaaca aagttctgcg gacgcgacta  4860
cacgatcacg tacctccttg cctgcccttc ctcggcatgt acctcacgga tctcaccttt  4920
gtggacattg gcaaccccgc gacgaagcag atgtccctgg gcacccagtc ggaagaggac  4980
agcacgggcg gcttgactgt tgtcaacttt gacaagcaca gtcgcactgc caaaatcatt  5040
ggcgagcttc aacgtttcca aatcccgtat cggctggtgg aagtgtctga catgcaggac  5100
tggctggccg ctcaggtgcg gcgtgtgcgc gaaggtgacc aaggcaacgt ccaggtcact  5160
tactatcgca agagcctgct cctggaaccc cgcgagagcg cttcgcgacg cgaagccgag  5220
ccgcctacac ctggttcaac tggtgttggc agctctcgca ccgacttgtt tggctggatg  5280
tcccgcgacc gaagcggaca aaccgctaca ccagcacccg tatag                    5325
```

```
SEQ ID NO: 34           moltype = DNA  length = 1585
FEATURE                 Location/Qualifiers
source                  1..1585
                        mol_type = other DNA
                        organism = Fusarium sp.
SEQUENCE: 34
atgcacaagg gcaccggtgc tgtgcaaaat tgcctgattg cagctgaaag gcagtctaca  60
aagcgtttga cgaccatcga tgaaactagt gacgcccgtc gtccaagctt gagggacgat  120
tcactatccc atccccgact tcatctgaac gagaacgctg aggtgactgg aggcaccctt  180
ccgggccttg tgggccatct cacctctcga caatccgcat ccgacatcat gttcccgtac  240
gctttctttc ttacattccg acaattctgc aagccacgag agctcgcaga acagcttgtc  300
gagagattcg atagtgccaa cgactcttcc tttgccgaag atacgcagtt gagggtctgc  360
gacggtttca agctttggct cgaaatgtac tggcgagtgg agactgacca agaggctcta  420
ccggttatca agcccttat cacatcgagc ttgtcttcta tcatcccagc cgcgagtagg  480
aagctagctc ggttgatcga gcaccttcca gctcgagagc cttgtttgtt gcctctagca  540
gatcatgata aactcataac aactgttttt gactcaccta gagtcaggag acatcgagct  600
cagcctaatg attcagcgac gcatcaatgg ggctttttga ggacgctgag gaacagtaaa  660
agctcgtcga ctttcctcag ctttggctgt atagagtttg cccgacagtt gagcattgag  720
cagacgactc tattctgccg cattcctccc caagagttcc tgggttgtgc gtgggtatgc  780
aaaactggca acatggcgcc taatatcaga gcaatggtgt ctttcactag tcagctttca  840
aaccttgtgg tggaaaccat tctcgaccat caaacggctc gcaagcgggc tgctgccatt  900
aaccactggg tcaacatcgc acaggagtgc tcaaactttc gcaactacga tggccttgtg  960
gccctcctct caggcttggg ccacagtgcc attctccggc tacgtcagac atggaatctg  1020
gtatcaccca agtacataaa caccttacaa ttccttaaga cgcgtatgga ccgctccgat  1080
aatcacaaat cacttcgcgc attattggaa acccatgaca acccatgtct gccctttctt  1140
ggcatgtatc taacagagct ggcttttgtg gagatgggtc agtcttggat cgatccgcaa  1200
aatcctcacg acgaaacaac atctgagcag ccctttattg actttgctaa atatgctcgg  1260
acggctaaga ttgtaaggca gcttcagcgt ttccagacgc catccaagtt aacagctcac  1320
cctcgtctac aaaattggtt gtcttttaaa atctcagaac ttgattgcaa taatgaccct  1380
aaactggatg ttagcttttt tgatagaagt gtgtcattgg agccgtacag gataaaaaag  1440
tagttgtggc ccgctctctc taaataaaat aatcgtaatg tctaaagcag tgtttgttta  1500
atccgtgcca gtatatgacc cttatttgcg gattccttgc gctcaaatag ccgtaaacat  1560
gcgttctagt cccccaagct aggcg                                        1585
```

```
SEQ ID NO: 35           moltype = DNA  length = 4366
FEATURE                 Location/Qualifiers
source                  1..4366
                        mol_type = other DNA
                        organism = Corynespora cassiicola
SEQUENCE: 35
atggaccaaa caaggcagag tcggcgcaac aggagggaga ttggcgctcc ggaagcaact  60
cagcctctgc cacgcgacca acggcgagac gatcgcggct cgtacaattc ggcgacgatc  120
cgtaccgtca cccccgattc catcccagag gacagcgttg ccagccagac gtacactacc  180
tccccgccca tctcgccgcg ctccaacagt acctcccagt ccgcccgcaa cagcaacccg  240
cgcacctttg ttgcccgcgc aaactcgaac gacgcagaat actcgctcag ggctgcccgt  300
gagactcaga ctcgtccgcg gaccaggacc ctggaggagc gctcaacgcg cgatcgctct  360
```

```
ccgccgaatc tattcgtaac cagccgccac cgcatcggct cggtgcacag cgctgcgccc  420
tccaatttcc agagcctcga ggagtcggtc gtcacctcca tcggccatcc ctctaccata  480
tccgccggcc ctaccgcccc tccgcctcga acctcgagca gcaaccgaag ccgcatcata  540
aaacagcagg cccagccgca accgccccag cgtgccacct cgcccacctc ctcgaccgcc  600
gtctctccca atgcccagca gccagactcg tgggtgtcgc ctgtgccggc ttcagacgcc  660
cgcaaggtcc tgaagctcat gcgcgccaca tgcggcaaga tgcagggcat gctggccttc  720
cgcagaggag agtcgaatcc gtggtcgctc tcctactgct acatcaatga ggaggccggg  780
agcttggtgt acgagccaaa gagtgacaca tcgtaccaca ggacgctggt gccggacctg  840
cgcggctgtc gtgtcaagac tgcctacgat gccgagtcgt acaccgccta cattcacgtt  900
ctgggccaca actccaagct cgaggtgttt ttgcgcccgc ccacccaaga agaatttgac  960
tcttggtttg ccgcacttct ctgctggggc cccatccgcc ccaagggcat ccacaacaag  1020
atggcgaagc cccagacgcc aatggtgacg gaacggcgac tcgccgatag caggagacac  1080
tccgaggtgt ctctgctcaa agaggcgccc atcatcaaag tcggaaagat gatctactgg  1140
gataccagcg tgacatatag caacacagga accccaagg ccactggagt cgccaggccc  1200
caagcctacc ggatacaaag ccatggctcc cgcaggtgga gaagagtatc gtgcaccttg  1260
cgagagaacg gagagctcaa gctatactcc gacactgatg tcactctagt ctcggtcgtt  1320
cagctttccc agctgtcgcg gtgcgccgtc cagcgcctgg acccatctgt tctggataac  1380
gaattctgca tcgctatcta cccgcaatac acctcgacgt cgacgtcatt atcactacta  1440
cgccccattt tcctatcgct ggaatcacga gttctttacg aagtgtggat tgttctgtta  1500
cgagcattta ccattccgca actctacggc ccgaaacagc cgaccctaaa cgacgaaggc  1560
gccctctcgc cttcgttcgg tacacaagac atgttccgca tggagcgttc gctactggtc  1620
agagtcatcg aggcaaggtt gataccaccg ataagcccca aggtctcaga aaacagcggg  1680
cggccgacgt cctcggcgaa tatgaacgcc ggaggttact acgtcgaagt cttgttggat  1740
ggagaagcgc gagcccggac catggccaag aatgagggca acaatccatt ttggcgggag  1800
gaatttgagt ttcttgacct acctgcagtc ctctcaacag cttctttgct gttgaagaag  1860
cgacctccga gccaagcccg caacgacaag aacttttacg agacacagct caactccgaa  1920
tccttcaact cggacggtgc aggtggctat gccggcatct ctttcgatca gacatgcggc  1980
aagacagaca tctatcttga cgacctgggt ccgaatcagg aagttgagaa gtggtggccg  2040
cttgtcaaca tgtacggcaa cagtgtcggc gaagtcctcg tcaaggttag cgctgaagag  2100
tgtgtcattc tcatggctcg agattaccag cccatgtcgg agcttctgca tcgcttctcc  2160
aatggtctga cattgcagat tgcgcagatg atcccgaatg agctcaagaa gctgtcagaa  2220
tacctcctca atatatttca agtttcgggc caggccggcg agtggatcat ggctcttgtt  2280
gaggaagaga ttgatggcac cctcaaggaa agcccggcga gtcgtctgcg tttcagcaag  2340
agactgggat ctagcgagtc tagcgagtcc ttcggctcgt cgagtgaccg cgaactcttt  2400
ttgagagaca tgggcaacaa tgctaagctg gaggcgaact tgttgttccg cggcaacacc  2460
ctcttgacta agtccctgga cttccacatg aaacggctcg gaaaggagta cctggaagag  2520
actcttagcg aaagactgcg agagatcaac gaaaaggacc ccgagtgcga ggtggatcca  2580
aacaagatca catcccaaaa tgagcttgac cgcaactgga ggagactcat caacatcacc  2640
gaggatctct ggcgtgccat ttacaattcc gtctcgcgtt gcccccagga actgaggctg  2700
atctttcgac acattcaagc ttgtgccgag gatcgttatg gcgatttcct caggacggtc  2760
aagtacagca gcgtttcggg ctttcttttc ctccgcttct tcgtcccagc cgtgcttaat  2820
ccgaagctgt tcggcttact gaaaggtatg tggtgacttc ttgccaacag gttgggcgat  2880
actaaataat gcagaccacc cgaaacccag agcacgcaga acatttacac tggtagccaa  2940
gtccctacag ggccttgcca acatgtcatc ttttggtaca aaagaggcat ggatggagcc  3000
gatgaactcc ttcctctcat cgcaccgtca agagttcaag acttacctag acaacatctg  3060
ctccatctcc tcgacaacct cgcctgcccc tcctatacct ccttcgtaca gcacccctct  3120
tgcgattctg cagcgcctac cacccacttc tcgagaaggt tttccttctc ttccgtatct  3180
catcgaccat gcacgcaact ttgctgctct ggtagaccta tggctccaga atacgagaag  3240
cagcgcgccg aatatccagt caacagatgg cgatcttctc cgctttcaca acatctgcgt  3300
ggctctacat gaacgcacag atgattgcct gaacagggca gaacgtgccg aacgtcctag  3360
ctcgtcgttg agtgtcaaat gggaagagtt ggtcgagcaa ctgcagggtt ctgcaagctt  3420
tgacagctca aggggcgctg ccacaaggaa tcgaggagca acaatcaaag aagaggagag  3480
ggagtatctg ccaatatccc cgggaacgtg cgacgaaatg actagttcct cgtccacgag  3540
cacccctgtg accatgaagc ctgttcgaca acccaagggg cggcatcagc agaacagttc  3600
catatctgcg tctactaatt cagtcgccag caataactca ggcaccatga cctttccaaa  3660
cccctttgca ccaaagactg cccgcagtgc aggttatccg ccctcagtaa acgattcggt  3720
atccgcttcc cagtctgcat cggcctccgc cagcgcatct gcatccgcaa atgaggaaac  3780
gccacctggg agctccgatg gcttgcacat ggcacctgcc cctgcttatc cacagactca  3840
tacccaccca tccgcctcta cgaattcttt cacgtatgcg aaccccaatg cacacattaa  3900
cacggggacg atggcatcag gagcccttac acgccctcct cgtagtgcag gcggccacag  3960
tctggaaaac tccgatgcag gaagcacgca cgaggaagag tacactacgg cactccctgc  4020
cttctccaag gactcgcaga aggagaagaa ggagcgtggc ttccgcggtg ttttgccatt  4080
ccaacgcaag cgtaaagaca aggataagga taaggacaag gataaggaca aggacaggga  4140
aaaggataaa gacaaagata aagacaggga gaaggacaaa gacaaggaca aagacaagga  4200
gaggggcaaa gaaaaagaca gggacaaaga gaaagaaaaa gacaagggca agctccgaga  4260
aagggaacga agcgtggaac ggaatgaccg tggtggacac tctgccatgg gcgaatacca  4320
cagccacagt agccttcggg gtcgagcgca gaacgaagag ttctga                4366
```

```
SEQ ID NO: 36          moltype = DNA  length = 4768
FEATURE                Location/Qualifiers
source                 1..4768
                       mol_type = other DNA
                       organism = Magnaporthe oryzae
SEQUENCE: 36
atgtctaaga agcatgagcg cggacagagt ctggacatga gcaaactcgc catcttcgaa  60
caagagaaga cggtcacacc cgcaccagcg ccgccgccca ggatggggag cttgcggcca  120
acgtcgatgc tcctcactcg atctgacacg atcaaccgag ggggaagtgc cgctgtcgcc  180
catgcccatg gccccgcctc gcctccgccc ttgcaccatc cacaggcagt ccaactgccc  240
ggatccgatc ttgagatcct tggccgctca tccacaaacc aacttcgtac cctctcgaaa  300
```

```
cttgcacagt ctggagaggc tgatgagttt gccatcacgt caccggcgca agaggttgtc  360
ggactaaaag gccgccgcag gcttcagaga gccgacaggt caaatgctgg ccgcctcggt  420
cagaagtcta gcggatatgg gtgggaaggg agaaattgga tggacaaaca acgacaattc  480
cttcaggcat acgaatatct ttgtcacatc ggtgaggcaa aagagtggat cgaagatgtt  540
atgaacaaat ctattggtga gattgtgaag ctggaagagg agcttaggaa cggcgagact  600
ctggcggagg tggttcaagc gctgaacccg gaccgaagat atcgtatttt ccggcaccct  660
cgtctacagt accgccattc ggacaacatt gcaatcttct tccggtacct cgacgaggtt  720
gaactacccg acctcttccg atttgaactg atcgatcttt acgaaaagaa aaacatccca  780
aaggtcatct actgcataca tgctctcagc tggctcttat accgcaaagg aattgtcgat  840
ttccgaatcg gaaacctggt tggtcaactt gagtttgagc accacgatct tgaagctatg  900
cagaagggcc tggataagct aggggccagt atgccgacct ttggtgacat gggcgctgac  960
tttggggttg agccggaacc ggaacccgaa gaaacggaag aggagcggat agaaagggaa  1020
cttggagaaa atgaggagtc catcgtcgag ctgcaagctc aagtacgcgg tgcattattg  1080
cgaatgcggc ttggggagac aatgcaggaa ctctgggact cggagaactg gcttgtcgac  1140
cttcaggccc ggattcgtgg tgattttgcg cgccagatca tcgactaccg actaaacatg  1200
aggcgcttcg cagtgaatct acagagtgcc gcacgcgggt tcctcgttcg gtcgcggcaa  1260
gcagagagag agtacatgtg gaagcgctca gagcccgccg ttctgaagct acagagtctc  1320
ttccgggctg caaaggtccg cgatgaggta cgagacgtgc gatctcaatt gtcagaggct  1380
acaggtcctg tacgcgagat ccaagcggtt atgcgaggct ttctcgcccg caagggtgtg  1440
cgcacccagg tgcaagagac gagtcgaacg tcgggagccg caccgggtct ccaggcggcc  1500
attcgtggta tgctgctgag gaacaggctt gatcatgaca gggctattct tgccgaggaa  1560
gctgtttcga tctgcagctt tcaggccgcc tcccgtgcct tgctcacaag aaaacaggtc  1620
gcccttcaac gggagtcact agcaagcttc acggcgcagt gggagggtct tcaatccgcc  1680
tccaggggga tgttcgccag gaacagcatc catgtcacca aggcggagct ccggggacac  1740
tctcctgcca ttggcctcct gcaggctttt tcaagggccg gtgctgtacg acgtgaaacg  1800
acccgggtgt tggacgccat cgctgtacac gagccgcagg tggttgagct tcagggcttg  1860
atccgcggcg ccattcaacg ccaacgtatt gccgccgact accaggacct tgaggaacaa  1920
gtccctcaga ttaccgacct gcagtctcag atccgtggta tgctctgccg caaagagcaa  1980
ggtgagcttc ttgatcagct ccagagcaac gaagagcaaa tcatcacttt gcaggcccag  2040
atcagggcta tgatcctgcg aaacaacttg gatgtagtgc tggccgagct cgaagagcaa  2100
gaagggacga ttgtgcagct gcaggctgcg gccaggggtg tgattgtacg caagaggttc  2160
gaggagaaga agcgtcactt caaggagaac atgtccaagg tcatcaagat ccaaagtttt  2220
gttcgtggaa agctccaagg tgaagcctac aagagcctca caacaggcaa gagcccgccc  2280
gtcagtgccg tcaagaactt tgtccatctg ctgaacgaca gcgattttga cttcaacgag  2340
gaggttgagt ttgagcggat gcgcaagact gtggtacaac aggtgcggca aaacgagatg  2400
ttggagcagt acatcgacca gctggacatc aagatcgctc tgctcgtcaa gaacaagatc  2460
actctggacg aggtagttag gcaccagagc aactttggtg gccacaccag caatctgata  2520
gcgaacagct ccatcgcttc agtgaaccag tatgatctca aggccctgaa caagacgtcg  2580
aggaagaagc tcgagtcata ccagcatctc ttctacaacc tacaaacgca accgcaatat  2640
ctggcacgcc tgttccgcag gatacgtgag caaggcacgg ccgagaagga gtgcaagcgc  2700
atcgagcatc tcatcatggg tctctttggg tatgcacaaa agaggagaga agagtactac  2760
ctcctcaagc taatttctcg ctctatctgg gaggaggttg aagctagcca catggtacaa  2820
gactcactac gtggtaacct cttctggtct aagctcctag gcaactattc gaggtcacct  2880
cgcgacagga agtacctgcg agacctgctc ggccctctga ttcgtgacaa cattatcgag  2940
gaccctgctc tcgaccttga aagcgatcct ctccagatct atcgatccgc catcaacaac  3000
gaggagctgc ggacgggcat gccaagccaa aggccactcg acgtccccag ggaagtagcc  3060
atcaaggatc ccgagacgag ggagctgttc attgatcatc ttcgggatct ccgtgagatt  3120
tgcgaccagt tcttgcttgc cctcgaagac ctgcttcctc gactgccata tggcctcaga  3180
tacatatgcc gccagatgtt tgatgccttg tgccaacatt tcaagcgtga gccgcagcac  3240
atattgctac agatggtggg caactggttc tggcgctttt acctgcagcc tgccctgacg  3300
gctcctgaga acgtcggcgt gatggagaag gggttgagcc cgctgcagaa gcgcaacctg  3360
ggtgaggttg ccaaggttct cggccaggta gcctctggcc gtccgtttgg cggtgataat  3420
atctacctgc agccattaaa cgcctttgtc gctgagtcca tggagcgttt aggccatatc  3480
ctgggcgagc tgatctcagt cgccgatgcc gaaagtacat ttgacattga tgagttcaac  3540
gacctttacg ccaaaaaccg gcccacgctt tatatcaagc ttgcagatat cttcgccata  3600
cacaacctga tctcgtcaga ccttcccact atttgtccca accgcgacga catgctccgg  3660
gagatcatgc aggagctcgg tagtgccaag aacaacgaga gtgagatgag ggctaccggc  3720
tcgtccgaca tccagatgtt cctcactccc aagctgcacg atgtcgaaga tcccgaggca  3780
gagatcaagg ctctcttcat ggagacgaag cgctgcatcc tgtacattat tcgtgtccag  3840
tcaggctcaa ccctcctcga gatcctggtc aagcccgtca cgcaagagga cgagcgcaag  3900
tggatggcgg tgctgcacga cgactttagt gacggcgggt ccacaaaggg agcttattcc  3960
gacgttaata tggtcgacgt tacccgtatg tcgtacctcg acctcaagcg cacggcactc  4020
gagaacgtca tgaggctgga gcacgccggc aggatctcca agcacaacca ctaccaagat  4080
atattgaacg ccattgcact cgatatccgg accaaaagca ggaggagagt tcagaggcag  4140
cgcgagctcg acggggtccg catgacgctt tctaatctcc acgagaaggc aaagtaccta  4200
gagcaacagc gcaagagcta cgatgactac attgagcagg ccatggcgac tctgcagaat  4260
aggaaagggt aagtcgacct acgataccaa catgcttctc gtctgaacaa gtaaaggcta  4320
acctcgttgg tttgttaact ttgaacagca agaaacggtt cctgcttcca ttcacaaagc  4380
agtacaacca ccaacgcgag ctcgagcgta gcggccgggt gcccaagttc ggatcgtaca  4440
agtacagcgc acgccagctc gccgacaagg gcgtacttgt cagctgggcg ggagtgtcgg  4500
agcgcgacct gagccagatc aacctcacta tctcttgcga cgaggtgggc gtatttgtca  4560
tcgagggctc gcgtggccac atccagatcc ccggcgcgag tgccctagtc cctatcgagg  4620
acctgctgca agcccagttt gagtcgcatc agttcatgaa cctcttcgag ggcaacctga  4680
ggctcaatgt caatatcttg ctgcatctgc tttataagaa attttatagg acacaataaa  4740
tggtcggggc gaattgggga gggtctaa                                   4768
```

```
SEQ ID NO: 37          moltype = DNA  length = 1361
FEATURE                Location/Qualifiers
source                 1..1361
```

```
                        mol_type = other DNA
                        organism = Colletotrichum acutatum
SEQUENCE: 37
atgtccgtca tgctccaaac accatctcga gcttctaccg cctcctcctc ctccttccaa  60
ccccttttccc gccaaaacac catgtcttct tacgatggat cgcggtccgc ccgccaatcg  120
aagcgttact ccatgtccgc gctgtacatg tccatgtcag cgaacgagac tgatctggag  180
attgaggatg acttggccaa aggtaggctc tgtaacctcc gcagtttcct tgcccttttg  240
ccctactgac gatggatttt acagcccaga agattctcag agagctcaag tccaagatct  300
cttcgcagtc caaaaagaac ttcgtactgg aaaaggatgt acgatatctt gattcacgaa  360
tcgccctcct catccagaac cgaatggctc tcgaggaaca gaacgaagtc gcgagccact  420
tggaagacgc gacggatatg caagaaggcg cctttcctaa cgacgacaag acgcaaaagt  480
atggcaactt gatgttcttg ttgcaatccg agccgaggca tattgcacac ctctgccgtc  540
tggtgtcaat gtcggaaatc gactctctgc tgcagactgt catgttcacc atctacggaa  600
accaatacga gagtcgcgaa gaacatctgc tcttgactat gttccaggtt tgtgacccgt  660
gactatacta cgcgatctgg caagctgact cttgacccat tagtctgttc tgacctacca  720
attcgacaac acccccgaat attcttcgct tctgcgtgcg aacacccccg tctcgagaat  780
gatgaccacg tatacgcgga gaggaccagg acagagcttt ctcaagtcag ttctcgctga  840
tagaatcaac agtctgatcg agttgaagga tctcgacctg gagatcaacc ccctcaaggt  900
ctacgagcgc atgattgagc aaattgagga ggacactggc agtctgcctg catcgcttcc  960
caagggcgtt actgctgagc aggctgcgga gaacccccaa gttcaagcca tcatcgagcc  1020
gcgtctgaca atgctcaccg agattgctaa tggcttcttg acaaccatca ttgacggact  1080
cgacgaagcg ccgtacggta ttcggtggat ttgcaaacag attcgcagct tgacgaagcg  1140
caagtaccct gatgccaatg atcaggtcat ttgcactctt atcggcggat tcttcttctt  1200
gcggttcatc aacccggcaa tcgtgacacc aaagtcatac atgctcattg acggtcagcc  1260
ggctgatcgc ccgagaagaa cgctgacttt gattgcaaag atgctgcaaa accttgctaa  1320
caagccctcc tacgccaagg agccatacat ggccaagctg c                      1361

SEQ ID NO: 38           moltype = DNA  length = 1727
FEATURE                 Location/Qualifiers
source                  1..1727
                        mol_type = other DNA
                        organism = Hypoxylon sp.
SEQUENCE: 38
atgactacct acactaggcg tggaccagga cagagcttct tgcgaacggt actggcgcaa  60
agaatcaaca gcctaattga gttgacagat ctagaccttg agatcaaccc cttgaaagtc  120
tatgaacgca tgtgtcaaca aattgaagaa gacaccggta gtcttccccc ctctctacct  180
agaggaatca caggcgaaca agctgccgag aatccccaag tgcaagccat catagagcct  240
cgtttaacga tgctaacgga gattgccaat ggcttcctga ccacaattat cgagggcctc  300
gaagaggctc cctatggcat tagatggata tgcaagcaga ttcggagttt gaccaaacga  360
aaatatcctg atgcgaatga ccaggtcatt tgcacactga tcggcggctt tttcttcctg  420
cgctttatca atcctgctat cgttacaccc aagtcctaca tgctcatcga tggagtgcct  480
tctgaacgac cacgccgaac gttaaccctg gttgccaaga tgcttcagaa cttggccaat  540
aaaccatcgt atgctaaaga accgtacatg gcgaagttgc aaccatttat ccagcagaac  600
aaggatcgtg tcaacaagtt tatgcttgat ctctgcgagg tccaggactt ctacgagagt  660
ctcgagatgg acaactatgt tgcactttca aagaaagacc tagagctctc cattacgctg  720
aatgagatat acgccatgca cgccttgatc gaaaagcaca gtggagaact ctgtagggac  780
gagaactccc acttgtcaca aatcatccag gagctcggca aagcacccgc gcaggtacct  840
cggaaggaga atagggcgat taatcttccc ctgtttagcc gatgggagac agctatagat  900
gatttgactg ccgccctaga tatcacgcag gaggaagtgt atttcatgga agcaaagtca  960
atctttgtac aagttatgcg gtccattcct gctaacagct cggttgctcg gcgacctcta  1020
cgcctagaga gaattgctga tgcggctgcc acatcaagga acgacgcagt gatggtccgg  1080
aaaggtatcc gggccatgga gctgcttagt caactacagg agatgaaggt tattgataag  1140
tcagaccagt tcagcctcct gagggatgag gtcgaacaag agttacaaca tctaggttcc  1200
ctgaaggatg gtgtcattgc cgaaaccgcg aagctcgaag aggtttacaa gacgattagg  1260
gatcataact cgtacctcgt cggccagcta gagacttaca agagctatct ccacaacgtg  1320
cgaagtcagt ccgaaggcac gagacggaaa cagcaaaagc agcaagttct cgggccttac  1380
aagtttactc accagcaact agagaaggaa ggcgtcatcc agaagagtaa tgttccggac  1440
aatagaaggg ctaacatcta cttcaatttc acaagtcctt tacctggaac ttttgtgatt  1500
tcattacact acaaaggtca gtcagaaggg acattccact tcagtcacgg gctaacaaat  1560
gaataggacg caatcgtggt cttctagaac tcgaccttaa gttggacgat ctgttagaaa  1620
tgcagaagga caatcaagat gacttggacc tcgaatacgt gcagttcaac gtcacgaagg  1680
tattggcctt gttaaacaag cgctttgcca ggaagaaggg ctggtaa                1727

SEQ ID NO: 39           moltype = DNA  length = 2880
FEATURE                 Location/Qualifiers
source                  1..2880
                        mol_type = other DNA
                        organism = Diaporthe ampelina
SEQUENCE: 39
atgtctgtga tgctgcaaac tccttcccgg gcctcaaccg catcctcctc ctcctaccag  60
gccctctccc gccagaacac catgtcttcc tacgatggct cgcggtcagc ccgccaatcg  120
aaacggtact ccatgtcggc attgtacatg tccatgtcgg cacaggaaac cgacttggaa  180
atagaagacg atcttgctaa aggtttgttc ccaacccctc tcatccaggc cgaaatcttg  240
accgaagtcc cattacttac tgtccccagc ccaaaagata ctacgggact tgaagtccaa  300
gatttcctcc caatccaaga agaacttcgt gcttgaaaag gacgtgcggt acctcgactc  360
acgtattgca ttgctgattc agaatcgcat ggctttggag gagcagaacg aagtcgccag  420
ccacttagaa gacgcgacag atattcagga aggggtcttt ccaaacgacg acaagacgca  480
gagatatggc aacctcatgt ttctcttgca atcagagccc aggcacattg cgcatctctg  540
ccggcttgtg tccatgtccg agatcgactc cctgctgcag acagtcatgt tcaccatcta  600
```

```
tggaaaccag tacgagagcc gagaagagca tctgctgcta actatgtttc aggtttgcct  660
accttctatt tcaacgtgag tgctcatgct aactcttgcc accagtccgt tttgacgtat  720
cagttcgata acacgcctga atattcgtcg ctgcttcgcg ccaacacacc agtctcccgg  780
atgatgacaa catacacgag gagaggcccg ggtcagagtt ttttgagatc ggtgcttgcg  840
cacaggatta atggccttat cgagctgcac gatctggatc tcgagatcaa ccccctcaaa  900
gtttacgagc gcatgtgcga acaaatcgag caggacacgg gcagccttcc gccgtctctg  960
ccaaagggca tcactgctga acaggccgcg gagaatgctc aggtccaagc tatcatcgag  1020
ccgagactca ccatgcttac cgagatcgcg aatggctttt tgtcgaccat catcgacggc  1080
ctggacgaag cgccgtacgg aattcgatgg atctgcaaac aaattcgcag cttgacgaag  1140
cggaagtacc ccgatgccaa cgaccaggtc atttgtacac tgatcggagg atttttcttc  1200
ctgcgcttca taaaccctgc catcgttacg ccgaagtcgt acatgctgat agatggaaca  1260
ccggcggatc ggccgaggag gaccttgacg ctgatcgcaa aaatgctgca aaaccttgcg  1320
aacaagccat cctacgcgaa ggagccctac atggccaagc tgcagccgtt tatccaatcg  1380
aacaaagaac ggatcaacaa gttcatgctt gatctttgcg atgtgcaaga cttctacgaa  1440
agtctggaga tggacaacta cgtggcgctt tcaaagaagg atctggagct gtccataaca  1500
ctgaacgaga tctatgccat gcacggcctc attgacaagc accggaatga aatttgcaag  1560
gacgagaact cgcacctaca catcatcatg tccgagcttg gcccttctcc tccgcaggtg  1620
cccaggaagg agaaccgggt gatcaactta ccactgttca gcagatggga gtcggccatg  1680
gatgacttga ccgccgcgct cgatatcacc caggaggaga tttatttcat ggaggccaaa  1740
aacgtatttg tacagatcat gcgttccatt ccatcgaata actcggttca gcgaaggcct  1800
cttcgcctcg agcgtatcgc cgatgcagca gcgacatctc ggaacgacgc ggttatggtc  1860
cgcaaaggta tccgtgctat ggaactgctg agtcaactcc aggagctgcg agtcatagac  1920
aaatccgacc agttcagcct gctacgagat gaggtcgagc aagagctaca gcatctgggc  1980
tctcttaagg atgcggtcct tgtggagact tccaagcttg acgaggtcta caagacaatc  2040
cgcgaccaca acacgtatct ggtcggccag ctggaaacgt acaagagcta tctgcacaat  2100
gtccgcagcc agagtgaggg tacacggcgg aaacagcaga agcagcaggt tctcggtccc  2160
tacaagttca cacaccaaca attggagaag gaaggggtta tccagaagag caatgtgccg  2220
gacaacaggc gggccaacat atatttcaac ttcacaagcc cccttccggg aacattcgtg  2280
atttctctgc actacaaggg caagtatagc agctcgaggg ctgaggacca tccggcatca  2340
ttcgtgaatt tattactgac atccatccca gggcgtaacc gcgggctctt ggagcttgat  2400
ctcaagctcg acgatctcct ggagatgcag aaagacggac aggacgagct ggacctcgag  2460
tatgtccaat tcaatgtgcc gaaagtgctc gcccttctga acaagcggtt cgctcggaag  2520
aagggttggt aaataacgga ttgccacacg ttattctgcc ttgtgtgcat cctagaagat  2580
gaggcaagcg gtggtccatc cacagtggcc tacttcttca caacacatat ctcacgatcg  2640
atcattctgc catctccaac atacaacatc atgtatcgct aagggactgt cggcgttttg  2700
gggccggcgt gcacttttat aatccttgat accatcgtct atacgcaaca tcgtctttca  2760
ggtcgcccgc ctacaccttc acctttcccc actatatatc ccgaccgaga gagccctctc  2820
tcgtactgca cgcccccgc cccctggggc agcacatcaa cagcctctat caatatctaa  2880

SEQ ID NO: 40           moltype = DNA  length = 2789
FEATURE                 Location/Qualifiers
source                  1..2789
                        mol_type = other DNA
                        organism = Talaromyces piceae
SEQUENCE: 40
ttcgacaaca cgcccgagta ctcgtcgctt ctccgtcaaa acacccccgt ttcccgcatg  60
atgaccacct acacccgccg cggtcccggt caaagctacc tgaaacatgt cttggctgaa  120
cagatcaata cgctcattga cttgcacgat gtcgatctcg agatcaaccc cttgaaggtg  180
tacgaaagta tggtgcagca gcttcaggaa gacacgggca gtttgcccga ctacctgccc  240
cgagcagtca ccgccgaagt cgctgccgag aacgagcagg tccaggcgat tattgctccg  300
cgcctgaaga tgttgacgga ccttgccaac aattttctca acaccatcat cgagggggctc  360
gaagatgctc cgtacgggat ccgctggatc tgcaaacaaa tccgaagtct ctcccgacgc  420
aagtacccgg acgctcagga ccagaccatc tgcacgctta tcggcggctt ctttttcctt  480
cgcttcatca acccggccat tgtgacgcct cggtcgtaca tgctcattga ggcgaccccg  540
accgacaagc cccgccggac cttgaccctg atcgccaaga tgctgcagaa cttggccaat  600
aagccgtcgt acgccaaaga accgtacatg gccaaattga gcccctttat cgacgagaac  660
aaagaccgcg tgaacaaatt cttgctcgat ctgtgtgaag tccaggactt ttacgagagc  720
ctggagatgg acaactatgt cgccctgacg aagcgggacc tggagctgca gatcacgttg  780
aacgaggtgt atgccacaca cgcgctgctg gagaaacaca gcgccagcct ggcggcttca  840
gaccaacact ctcacttgca agctcttctc caggaactag ggccggcacc gagccaggtt  900
ccccggaaag acaatcgcgc gatcaacctg ccgctgttta gcaagtggga gacctcggtc  960
gacgatctca cggcggccct ggatatcacc caggaagaga ttttctttat ggaagccaag  1020
tcgacctttg tccagatcct gcgttcgcta ccctccaact cggctgtcat gcggcgtcct  1080
ttgcggctgg atcgcatcgc cgaggccgcg gcaactctga agaacgatgc cgtcatggtt  1140
cgaaagggga ttcgtacgat ggagctcctg agccagctcc aggagctggg cgtgattgat  1200
cgatccgatg agtttgggct gttgcgcgac gaagtcgaac aggaactcgt ccatctgggt  1260
tcgctcaagg agaaagtggt gcaagagact cggcagttgg aggaagtgta caagaccatt  1320
cgcgatcaca acgcctactt ggtcggccag ctcgaaacct acaagtcgta tctgcacaac  1380
gtgcgcagcc agtccgaagg caaatcccgg aacaaaaagg agaagaacca ggagctcggt  1440
ccgtacaagt ttacccacca gcaacttgaa aaggagggag tcatccgcaa aagcaacgtg  1500
cccgagaatc ggcgtgccaa catctatttt atgttcaaga gtccgctgcc gggcacattt  1560
gtcatcagtc tacactacaa aggtgagctt tcgtcctttt gttttcctgg tttgctgaag  1620
ccccgcccca aactaactat caccaggacg agcccgcggt cttctcgagc tcgacttgaa  1680
actggacgac cttttggaga tgcaaaaaga caaccaagag gaccttgatc ttgaatacgt  1740
tcaattcaac gtcaccaaag tactgaccct gctgaacaag cgctttgcgc gtaaaaaggg  1800
gtggtaatgg ccccttgacg actttccatg accctggcac cccgttgtgc tttacctaac  1860
ccgtatcctt ttgttttcga aacacagtgc ttgcgttgtc cgtgtgagtt caacagcttg  1920
ccatgatacc ccgctccggc tcgaatttag tctacatctt gattatgcta ttgatcgttt  1980
gcgcataccc ctgttggttt tttggttcac ctgaattgtt ggtttgattt ttggaaaatg  2040
```

```
gattaaaaaa agcacaaaaa aaaagaagaa gaagaagaaa aagaggaaaa aaaaaaaaaa  2100
aagaggaagt caaagtctcc atggggatat cctgttatgg atgtcgggaa atgtggtgaa  2160
ttgcttacat gacttgcgtc caccgttcgc tggctcgaaa ggtgtattgt ttgtgtttgg  2220
tgattgtttg cgtgtcgtgc gctttggtgt ttgagtctct ggaccgtata cagagcggct  2280
tgaagcattt tttgtttgcg tgcgtttcga tggttgggat tgttatgctg atccgaccac  2340
gtgtaataat atatatatat atatatatat atcaatcata ggctttcatg acaatcactt  2400
cttgtctctc ctccccttgg tccatatcgc catatctggt cagaccaggg tggcgagcga  2460
atcagcacag acaaccaaac taggcaaagc tagtcgcaac tttgccgcca actgcaacac  2520
cagccacaac tgccgcccgc cgctgctccc ccagcccact tggcccgatc agcgcacgcc  2580
agacctttgt tttctagttt ctcctcagct gcaatcacac tttacccttc agaccgcaac  2640
ttcagacttg tgtgttctgc aattccttcc cttttcctct tttcctcgct gtgtcctcta  2700
tccgcacctg ccgggcacaa atcgaattga ccgcagtcat catcgactca ccaccagtca  2760
atctcgccgg accccgctat cccgcttga                                   2789

SEQ ID NO: 41          moltype = DNA  length = 2633
FEATURE                Location/Qualifiers
source                 1..2633
                       mol_type = other DNA
                       organism = Sporothrix insectorum
SEQUENCE: 41
atgtctgtca tgctgcagac gccttctcga gcctccactg cctcttcttc gtcctttcaa  60
cccatctcca gacagaacac catgtcgtcc tacgatggca cgcggtccgc ccgccaatcc  120
aagcggattt ccatgtccgc cctctacatg tccatgtcgg ccaacgaaac cgacttggag  180
attgaggacg agctggccaa aggttggtcc aaagcccctg cctgctgctg ccttctgtgg  240
acgtttttgt ctggtttgca aactgcccat gatgtactaa tgccgtgttc tcttctccct  300
gccacagcac aaaagaagct tcgcgatctc aaagccaaaa tctcgatgca atcgaaacag  360
aactttgtcc tcgagaagga cgtgcggtat ctcgattcga gaattgcctt gctgattcaa  420
aatcgcatgg ccttggaaga ggtatgcatt gaagcggctg cggattacag aaacaacaaa  480
tgacccatac tccgttgttg ttgatgtcgt tcttgttctc ttgttccctt tcctaacgcc  540
aattgtgctt tagcaaaacg aagtggcgag ccgtctcgaa gacgcactcg aattgcaagt  600
cggcgccttt ccgaacgaca tgcaaaccca aaaatacggc aacctgatgt tcctgctaca  660
gtccgagcct cggcacattg cgcatctctg ccgcctggtg tccatgtccg aaatcgactc  720
actgctgcag acggtcatgt tcaccatcta cggcaaccag tacgagagcc gcgaagagca  780
cctgctcctg accatgtttc agtctgtgct cacctaccaa ttcgacaaca cccccgaata  840
ctcctcgctg ctgcgggcca acaccccgt ctcgcgcatg atgacgacgt acacgcgacg  900
cggacccggc cagagctttc tcaagaccat cctcgccgac cggatcaaca gcctcatcga  960
gctccaagac ctcgacctgg aaatcaaccc gctcaaggtc tacgagcgca tggtcgccca  1020
gatcgaagaa gacacgggca gcctccccgc gtccctcccc aagggcatca cggccgaaca  1080
ggccgccgaa aacccacagg tccaggccat catcgagccg cgcctgacca tgctcaacga  1140
gatcgccaac gggttcctcg ccaccatcat tgacggcctg gaggaggcgc cgtacggcat  1200
ccgctggatc tgcaagcaga tccgcagcct cacgaagcgc aagtaccccg acgccaacga  1260
ccaggccatc tgcaccctga tcggcggctt cttcttcctg cgcttcatca acccggccat  1320
tgtcaccccc aagtcgtaca tgctgatcga cggcacgccc gccgaccggc cgcgccggac  1380
cttgacgctg atcgccaaga tgctgcagaa cctggccaac aagccctcgt acgccaagga  1440
gccgtacatg tccaagctgc agcccttcat ccaccacaac aaagaccgtg tcaacaagtt  1500
catgctggac ctgtgcgagg tgcaggattt ctacgagagc ctggagatgg acaactacgt  1560
ggcgctgtcc aagaaggacc tcgagctgtc catcaccctc aacgagatct acgccatgca  1620
cggcctgatc gaaaagcaca gcggcgagct ctgcagcgac gcgaactcgc atctggccgt  1680
catgatggcc gacctcggtg ccgcgcccgc gcagctcccc cgcaaggaaa atcgcgtgat  1740
caacctgccc ctgttcagcc gctgggaagc cgcgctcgac gacctgacgg cggcgctcga  1800
catcacccag gaggaggtgt acttcatgga ggccaagtcc atctttgtgc aaatcatgcg  1860
gtccatcccg cagaactcgt ccgtggcgcg ccggcccctg cgcctcgaac gcatcgccga  1920
cgccgcggcc acgttcaaaa acgacgccgt catggtgcgc aagggcatcc gcgccatgga  1980
gctactgagc cagttgcagg agatgaaggt caccgataag tccgatggct tctctctgtt  2040
gcgcgacgag gtggagcagg agctgcagca cctcggctcg ctgaaggagg gcgtcctcac  2100
cgaaacgaag aagctgtccg aggtgtttgc gaccatcacc gaccacaaca cgtacctgaa  2160
cggccagctc gagacgtaca agagctacct gcacaacgtg cgcagccaga gcgaaggcac  2220
gcgccggaaa ccccagaaac agcaggtact cggcccgtac aagttcacac accagcagct  2280
agagaaggag ggcgtcatcc agaagagcaa tgtccccgac aaccgccgag ccaacatcta  2340
cttcaacttt accagtcctc tgccgggcac ctttgtcatc tccctgcatt ataaaggtaa  2400
ggcgctcctc tgccgcattt gcgttgtccc attatgcatt tgtacggttt cggtactcac  2460
taacgcatgc agggcgcacc cggggcctgt tggagctgga tctcaaactc gacgatctcc  2520
tggagatgca gaaaaacaac ttggacgagc tcgatttgga atacgttcgg ttcaacgtcc  2580
ccaaggtgct ggccctgttg aacaagcgct ttgcaaggaa gaagggctgg tag         2633

SEQ ID NO: 42          moltype = AA  length = 107
FEATURE                Location/Qualifiers
source                 1..107
                       mol_type = protein
                       organism = Homo sapiens
SEQUENCE: 42
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSE                107

SEQ ID NO: 43          moltype = AA  length = 107
FEATURE                Location/Qualifiers
source                 1..107
                       mol_type = protein
                       organism = Homo sapiens
```

```
SEQUENCE: 43
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHQYREQI KRVKDSD                107

SEQ ID NO: 44          moltype = AA  length = 101
FEATURE                Location/Qualifiers
source                 1..101
                       mol_type = protein
                       organism = Homo sapiens
SEQUENCE: 44
MQPRREYHIV VLGAAQFVQN VWIESYDPTI EDSYRKQIEV DGETCLLDIL DTAGQEEYSA  60
MRDQYMRTGE GFLCVFAINN SKSFADINLY REQIKRVKDS D                      101

SEQ ID NO: 45          moltype = AA  length = 85
FEATURE                Location/Qualifiers
source                 1..85
                       mol_type = protein
                       note = Ras ETaG sequence
                       organism = unidentified
SEQUENCE: 45
MQPRREYHIV VLGAAQFVQN VWIESYDPTI EDSYRKQIEV DGRQCILEIL DTAGTEQFIF  60
SITSMSSLNE LSEIREQILR IKDDD                                        85

SEQ ID NO: 46          moltype = AA  length = 105
FEATURE                Location/Qualifiers
source                 1..105
                       mol_type = protein
                       note = Ras ETaG sequence
                       organism = unidentified
SEQUENCE: 46
MSQREYHIVV LGSGGVGKSC LTAQFVQNVW IESYDPTIED SYRKVLEVDG RHVILEILDT  60
AGTEQFKLYM KTGQGFLLVF SITSESSFWE LAELREQIRR IKEDS                  105

SEQ ID NO: 47          moltype = AA  length = 112
FEATURE                Location/Qualifiers
source                 1..112
                       mol_type = protein
                       note = Ras ETaG sequence
                       organism = unidentified
SEQUENCE: 47
MASKFLREYK LVVVGGGGVG KSCLTIQLIQ SHFVDEYDPT IEDSYRKQCV IDEEVALLDV  60
LDTAGQEEYS AMREQYMRTG EGFLLVYSIT SRQSFEEITT FQQQILRVKD KD          112

SEQ ID NO: 48          moltype = AA  length = 123
FEATURE                Location/Qualifiers
source                 1..123
                       mol_type = protein
                       note = Ras ETaG sequence
                       organism = unidentified
SEQUENCE: 48
MSRSAAQASF LREYKLVVVG GGGMSLVSRV GKSALTIQFI QSHFVDEYDP TIEDSYRKQC  60
VIDDEVALLD VLDTAGQEEY GAMREQYMRT GEGFLLVYSI TSRNSFEEIS TFHQQILRVK  120
DKD                                                                123

SEQ ID NO: 49          moltype = AA  length = 133
FEATURE                Location/Qualifiers
source                 1..133
                       mol_type = protein
                       note = Ras ETaG sequence
                       organism = unidentified
SEQUENCE: 49
MPEVMNAMYA TKGGIFDVSE NDKAQFLREY KLVVVGGGGV GKSALTIQFI QSHFVDEYDP  60
TIEDSYRKQC IIDDEVALLD VLDTAGQEEY GAMREQYMRT GEGFLLVYSI TSRNSFEEIS  120
IFHQQILRVK DQD                                                     133

SEQ ID NO: 50          moltype = AA  length = 121
FEATURE                Location/Qualifiers
source                 1..121
                       mol_type = protein
                       note = Ras ETaG sequence
                       organism = unidentified
SEQUENCE: 50
MANNAASRAA QAQFLREYKL VVVGGGGVGK SALTIQFIQS HFVDEYDPTI EDSYRKQCVI  60
DEEVALLDVL DTAGQEEYGA MREQYMRTGE GFLLVYSITA RSSFEEINQF YQQILRVKDQ  120
D                                                                  121

SEQ ID NO: 51          moltype = AA  length = 127
FEATURE                Location/Qualifiers
source                 1..127
```

-continued

```
                        mol_type = protein
                        note = Ras ETaG sequence
                        organism = unidentified
SEQUENCE: 51
MTLYKLVVLG DGGVGKTALT IQLCLNHFVE TYDPTIEDSY RKQVVIDQQS MLEVLDTAGQ  60
EEYTALRDQW IRDGEGFVLV YSITSRASFA RIPKFYNQIK MVKESASSGS PAGASYLTSP  120
INSPSGP                                                           127

SEQ ID NO: 52           moltype = AA  length = 117
FEATURE                 Location/Qualifiers
source                  1..117
                        mol_type = protein
                        note = Ras ETaG sequence
                        organism = unidentified
SEQUENCE: 52
MDADPYLLKF LREYKLVVVG GGGVGKSCLT IQLIQSHFVD EYDPTIEDSY RKQCVIDEEV  60
ALLDVLDTAG QEEYSAMREQ YMRTGEGFLL VYSITSRQSF EEMLTFQQQI LRVKDRD     117

SEQ ID NO: 53           moltype = AA  length = 203
FEATURE                 Location/Qualifiers
source                  1..203
                        mol_type = protein
                        organism = Homo sapiens
SEQUENCE: 53
LEANEGSKTL QRNRKMAMGR KKFNMDPKKG IQFLVENELL QNTPEEIARF LYKGEGLNKT  60
AIGDYLGERE ELNLAVLHAF VDLHEFTDLN LVQALRQFLW SFRLPGEAQK IDRMMEAFAQ  120
RYCLCNPGVF QSTDTCYVLS YSVIMLNTDL HNPNVRDKMG LERFVAMNRG INEGGDLPEE  180
LLRNLYDSIR NEPFKIPEDD GND                                         203

SEQ ID NO: 54           moltype = AA  length = 203
FEATURE                 Location/Qualifiers
source                  1..203
                        mol_type = protein
                        organism = Homo sapiens
SEQUENCE: 54
DPRELIEIKN KKKLLITGTE QFNQKPKKGI QFLQEKGLLT IPMDNTEVAQ WLRENPRLDK  60
KMIGEFVSDR KNIDLLESFV STFSFQGLRL DEALRLYLEA FRLPGEAPVI QRLLEAFTER  120
WMNCNGSPFA NSDACFSLAY AVIMLNTDQH NHNVRKQNAP MTLEEFRKNL KGVNGGKDFE  180
QDILEDMYHA IKNEEIVMPE EQT                                         203

SEQ ID NO: 55           moltype = AA  length = 203
FEATURE                 Location/Qualifiers
source                  1..203
                        mol_type = protein
                        organism = Homo sapiens
SEQUENCE: 55
DPNALRQQRS RKSMIMKGAS KFNENPKAGI AFLVAQGVIQ EPENPKNIAE FIKGTTRIDK  60
KILGEFISKK TNENILNEFM KLFNFAGKRI DEAIRELLGA FRLPGESALI ERIVEVFAAQ  120
YMDDAKPAGI ADSTAAFVLV YATILLNTDQ HNPNFRGQKR MTIENFAQNL RGVNDQGDFD  180
SNFLQEIFDS IRTHEIILPE EHD                                         203
```

HUMAN THERAPEUTIC TARGETS AND MODULATORS THEREOF

CROSS-REFERENCE TO RELATED APPLICATIONS

This application is a continuation of U.S. application Ser. No. 18/221,761, filed Jul. 13, 2023, which is a continuation of U.S. application Ser. No. 16/646,978, filed Mar. 12, 2020, now U.S. Pat. No. 11,749,375, issued Sep. 5, 2023, which is a national stage application under 35 U.S.C. § 371 of International Application No. PCT/US2018/051134, filed internationally on Sep. 14, 2018, which claims priority to U.S. Provisional Application No. 62/558,744, filed Sep. 14, 2017, the disclosures of which are herein incorporated by reference in their entirety.

REFERENCE TO AN ELECTRONIC SEQUENCE LISTING

The contents of the electronic sequence listing (232992000601SEQLIST.xml; Size: 131,098 bytes; and Date of Creation: Aug. 23, 2023) is herein incorporated by reference in its entirety.

BACKGROUND

Identification of so-called "druggable" targets within the human proteome has been described as "a significant challenge". See, for example, Dixon et al *Curr. Opin. Chem. Biol.* 13:549, 2009. As of 2011, reports estimated that only about 2% of human proteins had been successfully targeted by approved drugs, and furthermore that only 10-15% of human proteins are even susceptible to targeting (i.e., are "druggable"). See, for example, Stockwell *Sci. Am* 305:20, 2011.

SUMMARY

Evidence is emerging that some microbial biosynthetic gene clusters sometimes contain genes (referred to herein as "passenger" genes) that appear not to be involved in synthesis of the relevant biosynthetic products produced by the enzymes encoded by the clusters. In some cases, such passenger genes have been described as "self-protective" because they encode proteins that apparently can render the host organism resistant to the relevant biosynthetic product. For example, in some cases, genes encoding transporters of the biosynthetic products, detoxification enzymes that act on the biosynthetic products, or resistant variants of proteins whose activities are targeted by the biosynthetic products, have been reported. See, for example, Cimermancic et al *Cell* 158:412, 2014; Keller *Nat. Chem. Biol.* 11:671, 2015. Researchers have proposed that identification of such genes, and their functions, could be useful in determining the role of the biosynthetic products synthesized by the enzymes of the clusters. See, for example, Yeh et al. *ACS Chem. Biol.* 11:2275, 2016; Tang et al. *ACS Chem. Biol.* 10:2841, 2015; Regueira et al. *Appl, Environ. Microbiol.* 77:3035, 2011; Kennedy et al., *Science* 284:1368, 1999; Lowther et al., *Proc. Natl. Acad. Sci. USA* 95:12153, 1998; Abe et al, *Mol. Genet. Genomics* 268:130, 2002.

Among other things, the present disclosure offers a different perspective on non-biosynthetic genes present in biosynthetic gene clusters, or in proximity zones relative to biosynthetic genes of the clusters as described herein, and provides new insights regarding potential usefulness of certain such genes in human therapeutics. In some embodiments, the present disclosure provides technologies that utilize such insights to develop and/or improve human therapeutics.

Among other things, the present disclosure provides an insight that certain non-biosynthetic genes present in biosynthetic gene clusters, or in proximity zones relative to biosynthetic genes of the clusters, and particularly in eukaryotic (e.g., fungal, as contrasted with bacterial) biosynthetic gene clusters, may represent homologs of human genes that represent targets of therapeutic interest. The present disclosure defines parameters that characterize such non-biosynthetic genes of interest, herein referred to as "embedded target genes" or "ETaGs". The present disclosure provides technologies for identifying and/or characterizing ETaGs, databases including biosynthetic gene cluster and/or ETaG gene sequences (and optionally relevant annotations), systems for identifying and/or characterizing human target genes corresponding to ETaGs, as well as methods of making and/or using such human target genes and/or systems that contain and/or express them, etc.

The present disclosure contributes a further insight that relationship between ETaGs and their related biosynthetic gene clusters (biosynthetic gene clusters that contain biosynthetic genes in proximity zones relative to which the ETaGs are within) informs the identification, design, and/or characterization of effective modulators of the corresponding human target genes. The present disclosure provides technologies for such identification, design, and/or characterization, and also provides agents that achieve modulation of relevant human target genes, as well as methods of providing and/or using such agents.

As noted above, the present disclosure encompasses the insight that an ETaG can serve as a functional homolog (e.g., an ortholog) of a human target of medical (e.g., therapeutic) relevance. According to the present disclosure, sequences of passenger (i.e., non-biosynthetic) genes within eukaryotic (e.g., fungal) biosynthetic gene clusters, or in proximity zones relative to biosynthetic genes of the clusters, can be compared with those of human genes. Nucleic acid sequence similarity, peptide sequence similarity and/or phylogenetic relationships can be determined (e.g., quantitatively assessed and/or through evolutionary tree visualization) for the compared sequences. Alternatively or additionally, conservation of known structural and/or protein effector elements can be assessed. In some embodiments, those passenger genes with relatively high homology to human sequences and/or conserved structural and/or protein effector elements may be prioritized as ETaGs of interest as human drug targets.

In some embodiments, the present disclosure provides methods comprising steps of:

- querying a set of nucleic acid sequences, each of which is found in a fungal strain and comprises a biosynthetic gene cluster; and
- identifying within at least one of the fungal nucleic acid sequences an embedded target gene (ETaG) sequence characterized in that it:
  - is within a proximity zone relative to at least one gene in the cluster; and
  - is optionally co-regulated with at least one biosynthetic gene in the cluster.

Typically, a biosynthetic gene cluster comprises one or more biosynthetic genes. In some embodiments, a biosynthetic gene cluster comprises one or more biosynthetic genes and one or more non-biosynthetic genes. In some embodiments, a non-biosynthetic gene is regulatory, e.g., transcription factors. In some embodiments, in a biosynthetic gene cluster identified by bioinformatics, a non-biosynthetic gene may be a hypothetical gene. In some embodiments, borders of biosynthetic gene clusters are defined by bioinformatics methods, for example, antiSMASH. In some embodiments, biosynthetic genes and non-biosynthetic genes are designated based on bioinformatics. In some embodiments, non-biosynthetic gene might have biosynthetic functions even though they are identified as non-biosynthetic gene by bioinformatics methods (and/or indicated as non-biosynthetic gene in the present disclosure).

In some embodiments, the present disclosure provides methods comprising steps of:

- querying a set of nucleic acid sequences, each of which is found in a fungal strain and comprises a biosynthetic gene cluster; and
- identifying within at least one of the fungal nucleic acid sequences an embedded target gene (ETaG) sequence characterized in that it:
  - is within a proximity zone relative to at least one biosynthetic gene in the cluster; and
  - is optionally co-regulated with at least one biosynthetic gene in the cluster.

In some embodiments, the present disclosure encompasses the recognition that ETaGs from eukaryotic fungi can bear more similarities to mammalian genes than, for example, their counterparts, if any, in prokaryotes such as certain bacteria. In some embodiments, fungi contain ETaGs that are more therapeutically relevant, and/or contain more therapeutically relevant ETaGs, than organisms that are evolutionarily more distant from human.

In some embodiments, the present disclosure provides methods comprising steps of:

- querying a set of nucleic acid sequences, each of which is found in a fungal strain and comprises a biosynthetic gene cluster; and
- identifying within at least one of the fungal nucleic acid sequences an embedded target gene (ETaG) sequence characterized in that it:
  - is within a proximity zone relative to at least one gene in the cluster;
  - is homologous to an expressed mammalian nucleic acid sequence; and
  - is optionally co-regulated with at least one biosynthetic gene in the cluster.

In some embodiments, the present disclosure provides methods comprising steps of:

- querying a set of nucleic acid sequences, each of which is found in a fungal strain and comprises a biosynthetic gene cluster; and
- identifying within at least one of the fungal nucleic acid sequences an embedded target gene (ETaG) sequence characterized in that it:
  - is within a proximity zone relative to at least one biosynthetic gene in the cluster;
  - is homologous to an expressed mammalian nucleic acid sequence; and
  - is optionally co-regulated with at least one biosynthetic gene in the cluster.

In some embodiments, a proximity zone is no more than 1-100, for example, no more than 1, 2, 3, 4, 5, 6, 7, 8, 9, 10, 15, 20, 30, 40, 50, 60, 70, 80, 90, or 100 kb upstream or downstream of a biosynthetic gene in a cluster. In some embodiments, a proximity zone is no more than 1-100, for example, no more than 1, 2, 3, 4, 5, 6, 7, 8, 9, or 10 kb upstream or downstream of a biosynthetic gene in a cluster. In some embodiments, an ETaG is within a biosynthetic gene cluster. In some embodiments, a proximity zone is between two biosynthetic genes of a biosynthetic gene cluster.

In some embodiments, an ETaG sequence is homologous to a mammalian nucleic acid sequence. In some embodiments, a mammalian sequence is a human nucleic acid sequence. In some embodiments, an ETaG sequence is homologous to a human nucleic acid sequence. In some embodiments, an ETaG sequence is homologous to an expressed mammalian nucleic acid sequence. In some embodiments, an ETaG sequence is homologous to an expressed human nucleic acid sequence. In some embodiments, a mammalian nucleic acid, e.g., a human nucleic acid sequence, is related to a human disease, disorder, or condition. In some embodiments, such a human nucleic acid sequence is an existing target of therapeutic interest. In some embodiments, such a human nucleic acid sequence is a novel target of therapeutic interest. In some embodiments, such a human nucleic acid sequence is a target previously considered not susceptible to targeting by, e.g., small molecules. In some embodiments, a biosynthetic product produced by enzymes encoded by the related biosynthetic gene cluster, or an analog thereof, is a modulator (e.g., an activator, an inhibitor, etc.) of a human target.

In some embodiments, an ETaG sequence is homologous to an expressed mammalian nucleic acid sequence in that its sequence, or a portion thereof, is at least 50%, 60%, 70%, 80%, or 90% identical to that of an expressed mammalian nucleic acid sequence. In some embodiments, an ETaG sequence is homologous to a mammalian nucleic acid sequence in that mRNA produced from an ETaG, or a portion thereof, is homologous to that of a mammalian nucleic acid sequence. In some embodiments, a homologous portion is at least 50, 100, 150, or 200 base pairs in length. In some embodiments, a homologous portion encodes a conserved protein, or a conserved portion of protein, such as a protein domain, a set of residues that relates to a function (e.g., interaction to another molecule (e.g., a protein, a small molecule, etc.), enzymatic activity, etc.), etc., from fungi to a mammal.

In some embodiments, an ETaG sequence is homologous to a mammalian nucleic acid sequence in that a product encoded by an ETaG, or a portion thereof, is homologous to that encoded by a mammalian nucleic acid sequence. In some embodiments, an ETaG sequence is homologous to a mammalian nucleic acid sequence in that a protein encoded by an ETaG, or a portion thereof, is homologous to that encoded by a mammalian nucleic acid sequence. In some embodiments, an ETaG sequence is homologous to a mammalian nucleic acid sequence in that a portion of a protein encoded by an ETaG is homologous to that encoded by a mammalian nucleic acid sequence.

In some embodiments, a portion of a protein is a protein domain. In some embodiments, a protein domain is an enzymatic domain. In some embodiments, a protein domain interacts with one or more agents, e.g., small molecules, lipids, carbohydrates, nucleic acids, proteins, etc.

In some embodiments, a portion of a protein is a functional and/or structural domain that defines a protein family that the protein belongs to. Amino acid resides that within specific catalytic or structural domain defining patent families can be selected based on predictive subfamily domain architecture, and optionally verified by various assays, for use in alignment analysis of homology.

In some embodiments, a portion of a protein is a set of key residues, either consecutive or not consecutive, that are important for a function of a protein. In some embodiments, a function is an enzymatic activity, and a portion of a protein is a set of residues that are required for the activity. In some embodiments, a function is an enzymatic activity, and a portion of a protein is a set of residues that interact with a substrate, an intermediate, or a product. In some embodiments, a set of residues interact with a substrate. In some embodiments, a set of residues interact with an intermediate. In some embodiments, a set of residues interact with a product.

In some embodiments, a function is an interaction with one or more agents, e.g., small molecules, lipids, carbohydrates, nucleic acids, proteins, etc., and a portion of a protein is a set of residues that are required for the interaction. In some embodiments, a set of residues each independently contact an interacting agent. For example, in some embodiments, each of the residues of a set independently contacts an interacting small molecule. In some embodiments, a protein is a kinase and an interacting small molecule is or comprises a nucleobase, and a set of residues each independently contact the nucleobase via, e.g., hydrogen bonding, electrostatic forces, van der Waals forces, aromatic stacking, etc. In some embodiments, an interacting agent is another macromolecule. In some embodiments, an interaction agent is a nucleic acid. In some embodiments, a set of residues are those that contact an interacting nucleic acid, for example, those in transcription factors. In some embodiments, a set of residues are those that contact an interacting protein.

In some embodiments, a portion of a protein is or comprises an essential structural element of protein effector recruitment and/or binding, for example, based on tertiary protein structures of human targets.

Portions of proteins, such as protein domains, sets of residues responsible for biological functions, etc., can be conserved from species to species, for example, in some embodiments from fungi to human as illustrated in the present disclosure.

In some embodiments, protein homology is measured based on exact identity, e.g., the same amino acid residues at given positions. In some embodiments, homology is measured based on one or more properties, e.g., amino acid residues bearing one or more identical or similar properties (e.g., polar, non-polar, hydrophobic, hydrophilic, size, acidic, basic, aromatic, etc.). Exemplary methods for assessing homology are widely known in the art and can be utilized in accordance with the present disclosure, for example, MUSCLE, TCoffee, ClustalW, etc.

In some embodiments, a protein encoded by an ETaG, or a portion thereof (e.g., those described in the present disclosure), is at least 50%, 60%, 70%, 80%, 85%, 90%, 91%, 92%, 93%, 94%, 95%, 96%, 97%, 98%, or 99%, or 100% (when 100% it is identical) homologous to that encoded by a mammalian nucleic acid sequence. In some embodiments, a protein encoded by an ETaG, or a portion thereof, is at least 50%, 60%, 70%, 80%, 85%, 90%, 91%, 92%, 93%, 94%, 95%, 96%, 97%, 98%, or 99%, or 100% homologous to that encoded by an expressed mammalian nucleic acid sequence.

In some embodiments, an ETaG is co-regulated with at least one biosynthetic gene in the biosynthetic gene cluster. In some embodiments, an ETaG is co-regulated with two or more genes in the biosynthetic gene cluster. In some embodiments, an ETaG is co-regulated with the biosynthetic gene cluster in that expression of the ETaG is increased, or turned on, when a biosynthetic product produced by the enzymes encoded by the biosynthetic gene cluster (a biosynthetic product of the biosynthetic gene cluster) is produced. In some embodiments, an ETaG is co-regulated with the biosynthetic gene cluster in that expression of the ETaG is increased, or turned on, when level of a biosynthetic product of the biosynthetic gene cluster is increased.

In some embodiments, an ETaG gene sequence is optionally more than about 10%, 20%, 30%, 40%, 50%, 60%, 70%, 80%, 85%, 90%, 95%, or 99% homologous to one or more gene sequences in the same genome. In some embodiments, an ETaG gene sequence is optionally more than about 10%, 20%, 30%, 40%, 50%, 60%, 70%, 80%, 85%, 90%, 95%, or 99% homologous to 2, 3, 4, 5, 6, 7, 8, 9 or more gene sequences in the same genome. In some embodiments, the homology is more than 10%. In some embodiments, the homology is more than 20%. In some embodiments, the homology is more than 30%. In some embodiments, the homology is more than 40%. In some embodiments, the homology is more than 50%. In some embodiments, the homology is more than 60%. In some embodiments, the homology is more than 70%. In some embodiments, the homology is more than 80%. In some embodiments, the homology is more than 90%. Certain examples are presented in the Figures.

In some embodiments, an ETaG gene sequence is optionally no more than about 10%, 20%, 30%, 40%, 50%, 60%, 70%, 80%, 85%, 90%, 95%, or 99% identical to any expressed gene sequence in at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% fungal nucleic acid sequence in the set that is from a different fungal strain and comprises a homologous biosynthetic gene cluster. In some embodiments, an ETaG gene sequence is optionally no more than about 10%, 20%, 30%, 40%, 50%, 60%, 70%, 80%, 85%, 90%, 95%, or 99% identical to at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% fungal gene sequence that is within a proximity zone relative to a biosynthetic gene of a homologous biosynthetic gene cluster from a different fungal strain. In some embodiments, an ETaG gene sequence is optionally no more than about 10%, 20%, 30%, 40%, 50%, 60%, 70%, 80%, 85%, 90%, 95%, or 99% identical to at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% fungal gene sequence that is within a proximity zone relative to a biosynthetic gene of a homologous biosynthetic gene cluster from a different fungal strain. In some embodiments, an ETaG gene sequence is optionally no more than about 10%, 20%, 30%, 40%, 50%, 60%, 70%, 80%, 85%, 90%, 95%, or 99% identical to any expressed gene sequence in any fungal nucleic acid sequence in the set that is from a different fungal strain and comprises a homologous biosynthetic gene cluster. In some embodiments, an ETaG gene sequence is optionally no more than about 10%, 20%, 30%, 40%, 50%, 60%, 70%, 80%, 85%, 90%, 95%, or 99% identical to any expressed gene sequence that is within a proximity zone relative to a biosynthetic gene of a homologous biosynthetic gene cluster from a different fungal strain. In some embodiments, it is no more than about 10% identical. In some embodiments, it is no more than about 20% identical. In some embodiments, it is no more than about 30% identical. In some embodiments, it is no more than about 40% identical. In some embodiments, it is no more than about 50% identical. In some embodiments, it is no more than about 60% identical. In some embodiments, it is no more than about 70% identical. In some embodiments, it is no more than about 80% identical. In some embodiments, it is no more than about 90% identical.

In some embodiments, a human target gene and/or a product thereof is susceptible to modulation by a biosynthetic product, or an analog thereof, of a biosynthetic gene cluster, wherein the human target gene has its homologous ETaGs within the biosynthetic gene cluster or in a proximity zone relative to a biosynthetic gene of the cluster. In some embodiments, a protein encoded by a human target gene is susceptible to modulation by a biosynthetic product, or an analog thereof, of a biosynthetic gene cluster, wherein the human target gene has its homologous ETaGs within the biosynthetic gene cluster or in a proximity zone relative to a biosynthetic gene of the cluster. Thus, in some embodiments, the present disclosure not only provides novel human target, but also provides methods and agents for modulating such human targets.

In some embodiments, the present disclosure provides technologies, e.g., methods, databases, systems, etc., for identifying ETaGs and/or their medical relevance, e.g., their therapeutic relevance. In some embodiments, the present disclosures provide databases, optionally with various annotations, that are structured for efficient identification, search, use, etc. of ETaGs, related biosynthetic gene clusters, related biosynthetic products and/or analogs thereof of the biosynthetic gene clusters, the related homologous mammalian nucleic acid sequences (e.g., human genes), etc. Among other things, the present disclosure provides databases and/or sequences structured to improve computing efficiency and/or accuracy for, e.g., ETaG identification.

For example, in some embodiments, a provided database was constructed so that all the biosynthetic gene clusters were identified and annotated. Nucleic acid sequences for these clusters were then computationally excised from the rest of the nucleic acid sequences in the fungal genomes and databased. The resulting database of biosynthetic gene cluster was then used for ETaG searches. Among other things, when a hit in an ETaG search was identified using such a database, the hit was an ETaG because only sequences that were in biosynthetic clusters (or proximity zones thereof) were searched. Separating biosynthetic gene cluster sequences from the whole genome sequences improves the signal to noise ratio and vastly speeds up ETaG search processes. Among other things, compared to using provided databases, searches for ETaGs in whole fungal genome sequences frequently led to false positives where identified hits were "house-keeping" gene located in the genomes but not in biosynthetic gene cluster or proximity zones thereof. In some embodiments, an identified hit, e.g., ETaG, from provided technologies (e.g., methods, databases, etc.) is not a house-keeping gene. In some embodiments, an identified hit, e.g., ETaG, from provided technologies is or comprises a sequence that shares homology with a second nucleic acid sequence (e.g., a gene) or a portion thereof in the same genome. Sequence homology for sequences in the present disclosure can be at least 20%, 30%, 40%, 50%, 60%, 70%, 75%, 80%, 85%, 90%, 91%, 92%, 93%, 94%, 95%, 96%, 97%, 98%, 99% or 99.5%. In some embodiments, the homology is at least 50%; in some embodiments, at least 60%; in some embodiments, at least 70%; in some embodiments, at least 75%; in some embodiments, at least 80%; in some embodiments, at least 85%; in some embodiments, at least 90%; and in some embodiments, at least 95%. A portion of a sequence of the present disclosure can comprise at least 5, 6, 7, 8, 9, 10, 15, 20, 25, 30, 35, 40, 45, 50, 60, 70, 80, 90, 100, 150, 200, 250, 300, 350, 400, 450, 500, 600, 700, 800, 900 or 1000 amino acid residues for a protein sequence or nucleobases for a nucleic acid sequence. In some embodiments, a portion of a nucleic acid sequence is at least 10, 15, 20, 25, 30, 35, 40, 45, 50, 60, 70, 80, 90, 100, 150, 200, 250, 300, 350, 400, 450, 500, 600, 700, 800, 900 or 1000 nucleobases in length. In some embodiments, the length is at least 20 nucleobases. In some embodiments, the length is at least 30 nucleobases. In some embodiments, the length is at least 40 nucleobases. In some embodiments, the length is at least 50 nucleobases. In some embodiments, the length is at least 100 nucleobases. In some embodiments, the length is at least 150 nucleobases. In some embodiments, the length is at least 200 nucleobases. In some embodiments, the length is at least 300 nucleobases. In some embodiments, the length is at least 400 nucleobases. In some embodiments, the length is at least 500 nucleobases. In some embodiments, an identified hit, e.g., ETaG, from provided technologies is or comprises a sequence that encodes a product, e.g., a protein, that shares homology (e.g., at least 50%, 60%, 70%, 75%, 80%, 85%, 90%, 91%, 92%, 93%, 94%, 95%, 96%, 97%, 98%, 99% or 99.5%) with a product, or a portion thereof (e.g., a set of key residues of a protein, a protein domain, etc., as described in the present disclosure), encoded by a second nucleic acid sequence (e.g., gene) in the same genome. As described herein, homology/similarities can be assessed using a variety of technologies as appreciated by those skilled in the art. In some embodiments, a second nucleic acid sequence is or comprises a house-keeping gene. In some embodiments, a second nucleic acid sequence is shared among two or more species. In some embodiments, an ETaG while homologous to a second nucleic acid sequence differs from the second nucleic acid sequence in that the ETaG encodes a product (e.g., a protein) that provides resistance to a product of its corresponding biosynthetic cluster (e.g., a small molecule) while the second nucleic acid sequence does not.

In some embodiments, the present disclosure provides a system comprising:

- one or more non-transitory machine-readable storage media storing data representing a set of nucleic acid sequences, each of which is found in a fungal strain and comprises a biosynthetic gene cluster.

In some embodiments, the present disclosure provides a system comprising:

- one or more non-transitory machine-readable storage media storing data representing a set of nucleic acid sequences, each of which is or comprises a ETaG sequence.

In some embodiments, at least 10, 20, 50, 100, 200, or 500, or at least 5%, 10%, 20%, 30%, 40%, 50%, 60%, 70%, 80%, 90%, or 95%, or all, of the nucleic acid sequences of a set comprise ETaGs, which are indexed and/or annotated. In some embodiments, provided systems can greatly improve computing efficiency, as it is structured to greatly reduce the amount of data to be processed. For example, instead of processing all genomic or biosynthetic gene cluster sequence data of one or more (in some cases, hundreds or thousands or even more) fungi genomes to search for an ETaG, provided systems can search only genes indexed/marked as ETaGs, thereby saving time and cost used for processing sequences not indexed as ETaGs. Additionally and alternatively, an ETaG can be independently annotated with information such as its related biosynthetic gene cluster (which contains a biosynthetic gene the proximity zone relative to which the ETaG is within), structures of the biosynthetic products of the related biosynthetic gene cluster, and/or human homologs of the ETaG, etc. In some embodiments, at least 10, 20, 50, 100, 200, or 500, or at least 5%, 10%, 20%, 30%, 40%, 50%, 60%, 70%, 80%, 90%, or 95%, or all, of ETaGs of a set are independently annotated, with at least one of the following: a related biosynthetic gene cluster, and a human homolog of the ETaG. In some embodiments, at least 10, 20, 50, 100, 200, or 500, or at least 5%, 10%, 20%, 30%, 40%, 50%, 60%, 70%, 80%, 90%, or 95%, or all, of ETaGs of a set are independently annotated, with at least one of the following: a related biosynthetic gene cluster, a biosynthetic product of the related biosynthetic gene cluster, and a human homolog of the ETaG. In some embodiments, by structuring sequence data with ETaG index and annotation, provided systems can provide a number of advantages. For example, in some embodiments, provided systems provide fast access to ETaGs with useful related information, for example, their related biosynthetic gene clusters and human homologs, and vice versa, while maintaining data size and cost low.

In some embodiments, provided methods and systems are useful for human target identification and/or characterization, as, among other things, provided methods and systems provide connections between biosynthetic gene clusters, ETaGs, and human target genes. In some embodiments, the present disclosure provides insights particularly into targets that were considered undruggable prior to the present disclosure, by providing their homologous ETaGs in fungi and the related biosynthetic gene clusters. In some embodiments, the present disclosure greatly improves drugability of targets that were considered undruggable prior to the present disclosure, in some cases, essentially converting them into druggable targets, by, for example, their homologous ETaGs in fungi, the related biosynthetic gene clusters, the biosynthetic products of the related biosynthetic gene clusters (which can be directly used as modulators, and/or whose analogs can be used as modulators, of the human targets).

In some embodiments, the present disclosure provides methods for identifying and/or characterizing a human target of a biosynthetic product of a biosynthetic gene cluster, or an analog of the product.

In some embodiments, the present disclosure provides methods comprising:

- identifying a human homolog of an ETaG that is within a proximity zone relative to at least one gene of a biosynthetic gene cluster, or is within a proximity zone relative to at least one gene of a second biosynthetic gene cluster which second biosynthetic gene cluster encodes enzymes that produce the biosynthetic product that is produced by the enzymes encoded by the biosynthetic gene cluster; and
- optionally assaying an effect of the biosynthetic product produced by the enzymes encoded by the biosynthetic gene cluster, or an analog of the product, on the human target.

In some embodiments, the present disclosure provides methods comprising:

- identifying a human homolog of an ETaG that is within a proximity zone relative to at least one biosynthetic gene of a biosynthetic gene cluster, or is within a proximity zone relative to at least one biosynthetic gene of a second biosynthetic gene cluster which second biosynthetic gene cluster encodes enzymes that produce the biosynthetic product that is produced by the enzymes encoded by the biosynthetic gene cluster; and
- optionally assaying an effect of the biosynthetic product produced by the enzymes encoded by the biosynthetic gene cluster, or an analog of the product, on the human target.

In some embodiments, the present disclosure provides methods comprising:

- identifying a human homolog of an ETaG that is within a proximity zone relative to at least one gene of a biosynthetic gene cluster; and
- optionally assaying an effect of the biosynthetic product produced by the enzymes encoded by the biosynthetic gene cluster, or an analog of the product, on the human target.

In some embodiments, the present disclosure provides methods comprising:

- identifying a human homolog of an ETaG that is within a proximity zone relative to at least one biosynthetic gene of a biosynthetic gene cluster; and
- optionally assaying an effect of the biosynthetic product produced by the enzymes encoded by the biosynthetic gene cluster, or an analog of the product, on the human target.

In some embodiments, for biosynthetic gene clusters comprising no biosynthetic genes the proximity zones relative to which contain ETaGs, the mammalian targets, e.g., human targets, of the products (and/or analogs thereof) of such biosynthetic gene clusters can be identified through an ETaG that is in a proximity zone relative to a biosynthetic gene of a second biosynthetic gene cluster that encodes the enzymes producing the same biosynthetic product. In some embodiments, the second biosynthetic gene cluster is in a different organism. In some embodiments, the second biosynthetic gene cluster is in a different fungi strain.

In some embodiments, the present disclosure provides methods for identifying and/or characterizing a human target of a biosynthetic product of a biosynthetic gene cluster, or an analog of the product, comprising:

- identifying a human homolog of an ETaG that is within a proximity zone relative to at least one biosynthetic gene of a second biosynthetic gene cluster which second biosynthetic gene cluster encodes enzymes that produce the same biosynthetic product that is produced by the enzymes encoded by the biosynthetic gene cluster; and
- optionally assaying an effect of the biosynthetic product produced by the enzymes encoded by the biosynthetic gene cluster, or an analog of the product, on the human target.

In some embodiments, provided technologies are useful for assessing interactions of human targets with compounds. In some embodiments, the present disclosure provides methods for accessing interaction of a human target with a compound, comprising:

- comparing nucleic acid sequence of the human target, or the nucleic acid sequence that encodes the human target, with a set of nucleic acid sequences which comprise one or more ETaGs.

In some embodiments, homology with ETaGs (nucleic acid level or protein level, including portions thereof) directs to the related biosynthetic gene clusters of the ETaGs and the biosynthetic products thereof. In some embodiments, such connection between biosynthetic products and human targets indicates interaction and/or modulation of the human targets or products encoded thereby. In some embodiments, such biosynthetic products interact with and/or modulate the human targets or products encoded thereby.

In some embodiments, provided technologies are useful for designing and/or providing modulators for human targets, as, among other things, provided technologies provide connections between biosynthetic gene clusters, ETaGs, and human target genes.

In some embodiments, the present disclosure provides a compound, which compound is a product of enzymes encoded by a biosynthetic gene cluster, wherein, within a proximity zone relative to at least one gene in the biosynthetic gene cluster, exists an ETaG that:

is homologous to the human target, or a nucleic acid sequence that encodes the human target; and is optionally co-regulated with at least one biosynthetic gene in the cluster.

In some embodiments, a provided compound is a product of enzymes encoded by a provided biosynthetic gene cluster. In some embodiments, a provided compound is an analog of a product of enzymes encoded by a provided biosynthetic gene cluster. In some embodiments, a provided biosynthetic gene cluster comprises one or more biosynthetic genes presented in one of FIGS. 5-12 and 20-39. In some embodiments, a provided biosynthetic gene cluster is one of FIGS. 5-12 and 20-39. In some embodiments, a provided compound is a product of enzymes encoded by a provided biosynthetic gene cluster presented in one of FIGS. 5-12 and 20-39. In some embodiments, a provided compound is a product of a provided biosynthetic gene cluster presented in one of FIGS. 5-12 and 20-39, or a biosynthetic gene cluster comprising one or more biosynthetic genes presented in one of FIGS. 5-12 and 20-39. In some embodiments, a provided compound is a product of a provided biosynthetic gene cluster presented in one of FIGS. 5-12 and 20-39. In some embodiments, a provided compound is a product of a provided biosynthetic gene cluster comprising one or more biosynthetic genes presented in one of FIGS. 5-12 and 20-39. In some embodiments, a provided compound is an analog of a product of enzymes encoded by a provided biosynthetic gene cluster presented in one of FIGS. 5-12 and 20-39. In some embodiments, a provided compound is an analog of a product of a provided biosynthetic gene cluster comprising one or more biosynthetic genes presented in one of FIGS. 5-12 and 20-39. In some embodiments, a provided compound modulates a function of a human target. In some embodiments, the present disclosure provides pharmaceutical compositions of provided compounds. In some embodiments, the present disclosure provides pharmaceutical compositions comprising a provided compound or a pharmaceutically acceptable salt thereof. In some embodiments, the present disclosure provides pharmaceutical compositions comprising a provided compound or a pharmaceutically acceptable salt thereof, and a pharmaceutically acceptable carrier. In some embodiments, a provided compound in a provided composition is an analog of a product of enzymes encoded by the biosynthetic gene cluster or a salt thereof. In some embodiments, a provided compound in a provided composition is an unnatural salt of a product of enzymes encoded by the biosynthetic gene cluster.

In some embodiments, the present disclosure provides methods for identifying and/or characterizing a modulator of a human target, comprising:

providing a product or an analog thereof, which product is produced by enzymes encoded by a biosynthetic gene cluster, wherein, within a proximity zone relative to at least one gene in the biosynthetic gene cluster, exists an ETaG that:

is homologous to the human target, or a nucleic acid sequence that encodes the human target; and is optionally co-regulated with at least one biosynthetic gene in the cluster.

In some embodiments, the present disclosure provides methods for identifying and/or characterizing a modulator of a human target, comprising:

providing a product or an analog thereof, which product is produced by enzymes encoded by a biosynthetic gene cluster, wherein, within a proximity zone relative to at least one biosynthetic gene in the biosynthetic gene cluster, exists an ETaG that:

is homologous to the human target, or a nucleic acid sequence that encodes the human target; and is optionally co-regulated with at least one biosynthetic gene in the cluster.

In some embodiments, the present disclosure provides methods for modulating a human target, comprising:

providing a product or an analog thereof, which product is produced by enzymes encoded by a biosynthetic gene cluster, wherein, within a proximity zone relative to at least one gene in the biosynthetic gene cluster, exists an ETaG that:

is homologous to the human target, or a nucleic acid sequence that encodes the human target; and is optionally co-regulated with at least one biosynthetic gene in the cluster.

In some embodiments, the present disclosure provides methods for modulating a human target, comprising:

providing a product or an analog thereof, which product is produced by enzymes encoded by a biosynthetic gene cluster, wherein, within a proximity zone relative to at least one biosynthetic gene in the biosynthetic gene cluster, exists an ETaG that:

is homologous to the human target, or a nucleic acid sequence that encodes the human target; and is optionally co-regulated with at least one biosynthetic gene in the cluster.

In some embodiments, the present disclosure provides methods for treating a condition, disorder or disease associated with a human target, comprising administering to a subject susceptible to or suffering therefrom a biosynthetic product or an analog thereof, wherein:

the biosynthetic product is of a biosynthetic gene cluster, wherein, within a proximity zone relative to at least one gene in the biosynthetic gene cluster, exists an ETaG that:

is homologous to the human target, or a nucleic acid sequence that encodes the human target; and is optionally co-regulated with at least one biosynthetic gene in the cluster.

In some embodiments, the present disclosure provides methods for treating a condition, disorder or disease associated with a human target, comprising administering to a subject susceptible to or suffering therefrom a biosynthetic product or an analog thereof, wherein:

the biosynthetic product is of a biosynthetic gene cluster, wherein, within a proximity zone relative to at least one biosynthetic gene in the biosynthetic gene cluster, exists an ETaG that:

is homologous to the human target, or a nucleic acid sequence that encodes the human target; and is optionally co-regulated with at least one biosynthetic gene in the cluster.

In some embodiments, a human target is a Ras protein. In some embodiments, a human target comprises a RasGEF domain. In some embodiments, a human target comprise a RasGAP domain.

In some embodiments, an ETaG is identified by a provided method.

In some embodiments, a product (e.g., a biosynthetic product) is produced by a fungi. In some embodiments, a product is acyclic. In some embodiments, a product is a polyketide. In some embodiments, a product is a terpene compound. In some embodiments, a product is non-ribosomally synthesized.

In some embodiments, an analog a substance that shares one or more particular structural features, elements, components, or moieties with a reference substance. Typically, an analog shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance. In some embodiments, an analog of a substance is the substance being substituted at one or more of its substitutable positions.

In some embodiments, an analog of a product comprises the structural core of a product. In some embodiments, a biosynthetic product is cyclic, e.g., monocyclic, bicyclic, or polycyclic, and the structural core of the product is or comprises the monocyclic, bicyclic, or polycyclic ring system. In some embodiments, a product is or comprises a polypeptide, and a structural core is the backbone of the polypeptide. In some embodiments, a product is or comprises a polyketide, and a structural core is the backbone of the polyketide.

In some embodiments, an analog is a substituted biosynthetic product. In some embodiments, an analog is or comprises the structural core substituted with one or more substituents as described herein.

In some embodiments, the present disclosure provides compositions of biosynthetic products, or analogs thereof, of provided biosynthetic gene clusters wherein an ETaG exists within the proximity zone relative to at least one gene of the biosynthetic gene cluster. In some embodiments, a provided composition is a pharmaceutical composition. In some embodiments, a provided pharmaceutical composition comprises a pharmaceutically acceptable salt of a biosynthetic product, or an analog thereof, of a provided biosynthetic gene cluster wherein an ETaG exists within the proximity zone relative to at least one gene of the biosynthetic gene cluster, and a pharmaceutically acceptable carrier.

In some embodiments, two events or entities are associated with one another if the presence, level and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of and/or susceptibility to the disease, disorder, or condition (e.g., across a relevant population).

In some embodiments, a disease is cancer. In some embodiments, a disease is an infectious disease. In some embodiments, a disease is a heart disease. In some embodiments, a disease is associated with level of a lipid, protein, human metabolite, etc.

BRIEF DESCRIPTION OF THE DRAWING

FIG. 13 depicts alignments of human Ras genes (KRAS (SEQ ID NO: 42), HRAS (SEQ ID NO: 43), NRAS (SEQ ID NO: 44)) and certain identified Ras ETaGs (ANHP_459_5 (SEQ ID NO: 45), KB73344_288_17 (SEQ ID NO: 46), CM004463 (SEQ ID NO: 47), KV42800_485_5 (SEQ ID NO: 48), AACS_391_8 (SEQ ID NO: 49), JH97138_360_5 (SEQ ID NO: 50), KI911109_c052 (SEQ ID NO: 51), and KE54696_c00122 (SEQ ID NO: 52)). As shown, the human Ras genes and the presented ETaGs share the same amino acid residues at many locations of the KRAS nucleotide binding residues.

FIG. 14 depicts alignments of human Ras genes (KRAS (SEQ ID NO: 42), HRAS (SEQ ID NO: 43), NRAS (SEQ ID NO: 44)) and certain identified Ras ETaGs (ANHP_459_5 (SEQ ID NO: 45), KB73344_288_17 (SEQ ID NO: 46), CM004463 (SEQ ID NO: 47), KV42800_485_5 (SEQ ID NO: 48), AACS_391_8 (SEQ ID NO: 49), JH97138_360_5 (SEQ ID NO: 50), KI911109_c052 (SEQ ID NO: 51), and KE54696_c00122 (SEQ ID NO: 52)). As shown, the human Ras genes and the presented ETaGs share the same amino acid residues at many locations of the KRAS residues that are within 4 Å of BRAF.

FIG. 15 depicts alignments of human Ras genes (KRAS (SEQ ID NO: 42), HRAS (SEQ ID NO: 43), NRAS (SEQ ID NO: 44)) and certain identified Ras ETaGs (ANHP_459_5 (SEQ ID NO: 45), KB73344_288_17 (SEQ ID NO: 46), CM004463 (SEQ ID NO: 47), KV42800_485_5 (SEQ ID NO: 48), AACS_391_8 (SEQ ID NO: 49), JH97138_360_5 (SEQ ID NO: 50), KI911109_c052 (SEQ ID NO: 51), and KE54696_c00122 (SEQ ID NO: 52)). As shown, the human Ras genes and the presented ETaGs share the same amino acid residues at many locations of the KRAS residues that are within 4 Å of rasGAP.

FIG. 16 depicts alignments of human Ras genes (KRAS (SEQ ID NO: 42), HRAS (SEQ ID NO: 43), NRAS (SEQ ID NO: 44)) and certain identified Ras ETaGs (ANHP_459_5 (SEQ ID NO: 45), KB73344_288_17 (SEQ ID NO: 46), CM004463 (SEQ ID NO: 47), KV42800_485_5 (SEQ ID NO: 48), AACS_391_8 (SEQ ID NO: 49), JH97138_360_5 (SEQ ID NO: 50), KI911109_c052 (SEQ ID NO: 51), and KE54696_c00122 (SEQ ID NO: 52)). As shown, the human Ras genes and the presented ETaGs share the same amino acid residues at many locations of the KRAS residues that are within 4 Å of SOS.

FIG. 19 depicts sequence alignment of Sec7 (Human_ARNOSec7_Ter (SEQ ID NO: 53), Human_GBF1Sec7 (SEQ ID NO: 54), and ETaGSec7_NCBI (SEQ ID NO: 55)). (A) Example Brefeldin A interacting Residues. (B) Example sequence alignment.

DETAILED DESCRIPTION OF CERTAIN EMBODIMENTS

1. Definitions

Figure 1:
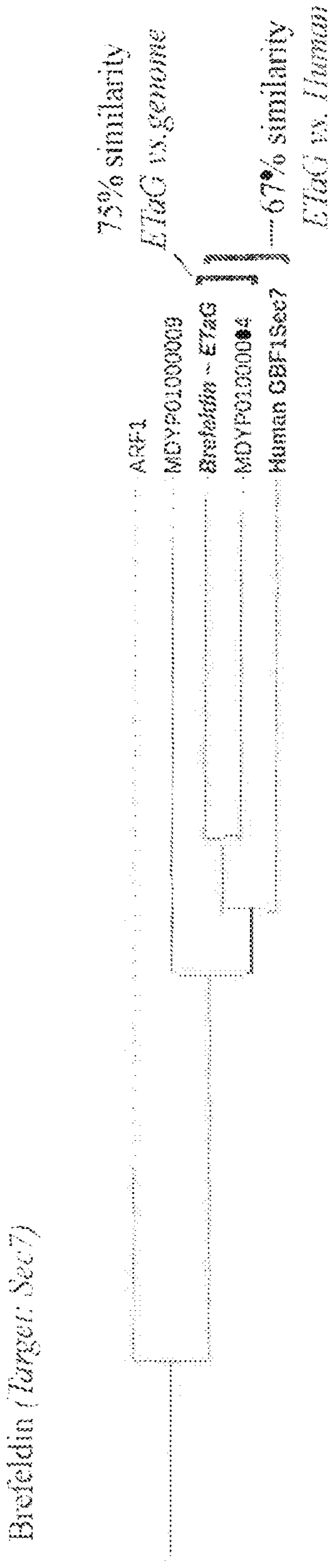
FIG. 1 depicts a Brefeldin A ETaG identified in *Penicillium vulpinum* IBT 29486. The example ETaG identified is the Sec7 guanine-nucleotide-exchange-factor superfamily (pfam01369). Sequence similarity is of the Sec7 domain calculated using MUSCLE alignment algorithm.
Figure 2:
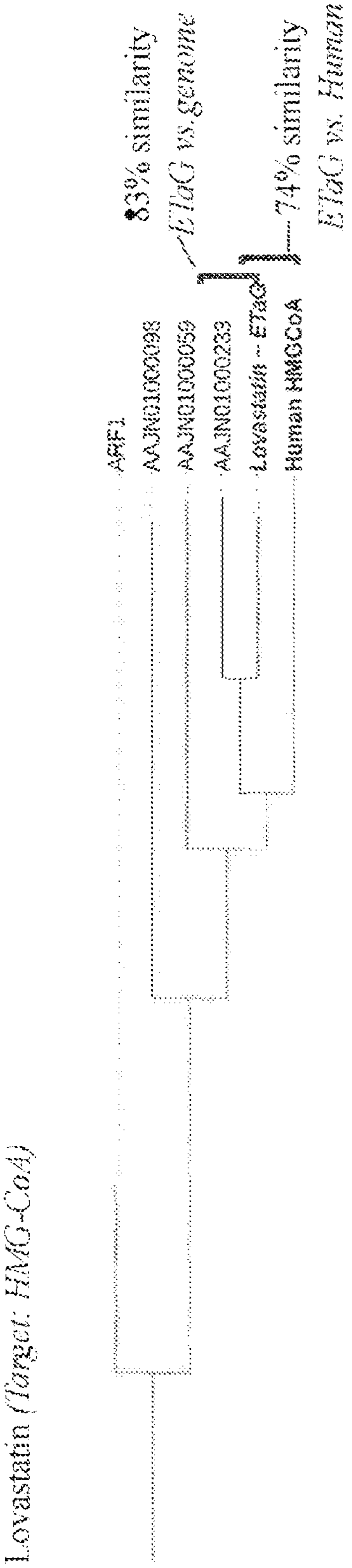
FIG. 2 depicts a Lovastatin ETaG identified in *Aspergillus terreus* ATCC 20542. The example ETaG identified is hydroxymethylglutaryl-coenzyme A reductase (HMG-CoA; pfam00368). Sequence similarity is of the HMG-CoA domain calculated using MUSCLE alignment algorithm.
Figure 3:
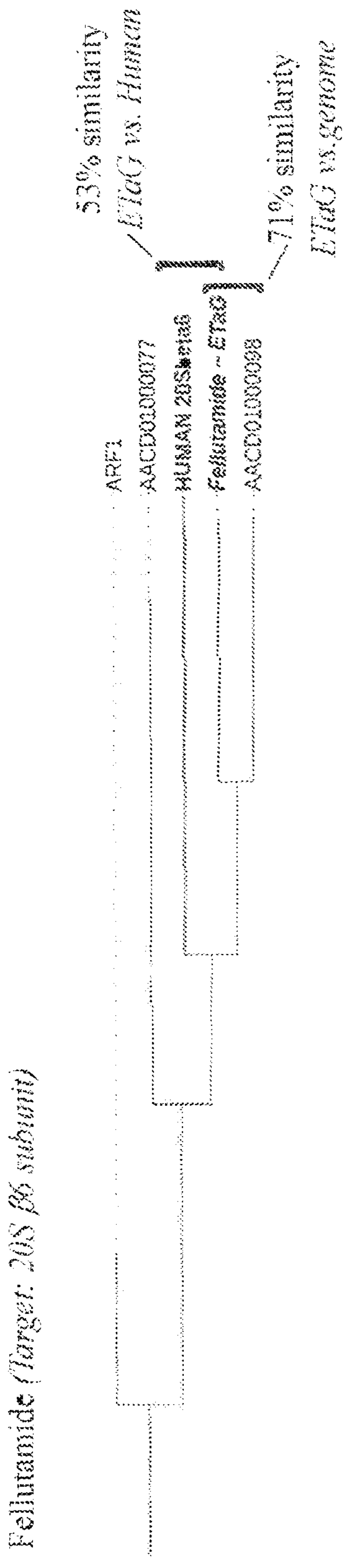
FIG. 3 depicts a Fellutamide ETaG identified in *Aspergillus nidulans* FGSC A4. The example ETaG identified is proteasome 20S beta-subunit (pfam00227). Sequence similarity is of the 20S beta-calculated using MUSCLE alignment algorithm.
Figure 4:
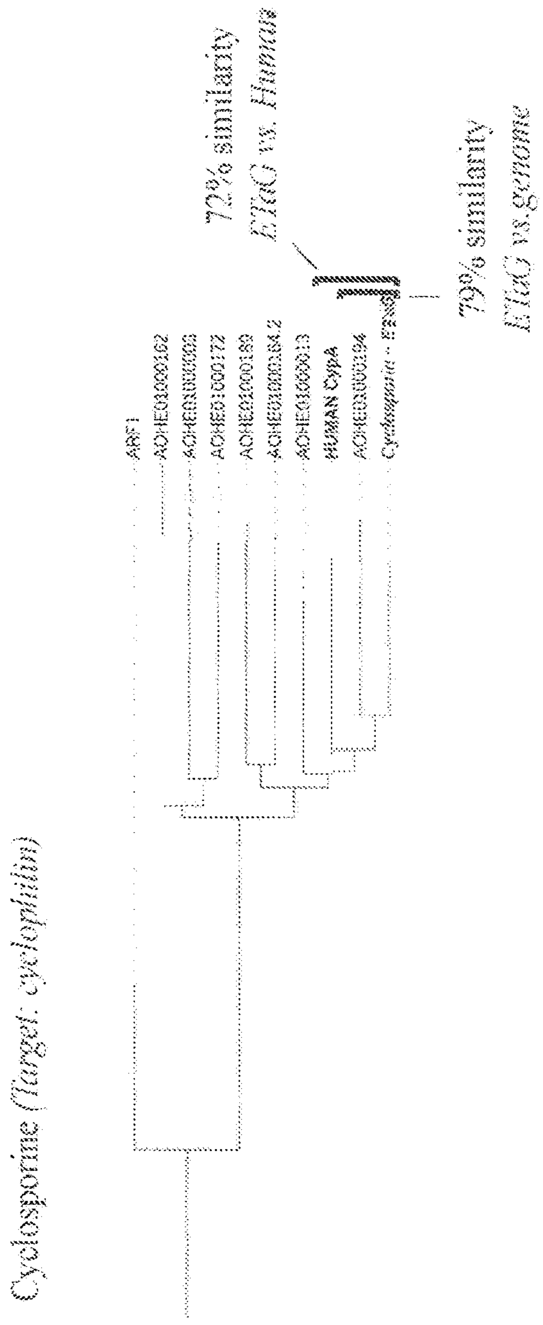
FIG. 4 depicts a Cyclosporine ETaG identified in *Tolypocladium inflatum* NRRL 8044. The example ETaG identified is the cyclophilin type peptidyl-prolyl cis-trans isomerase (pfam00160). Sequence similarity is of the cyclophilin domain calculated using MUSCLE alignment algorithm.

As used herein, the following definitions shall apply unless otherwise indicated. For purposes of this disclosure, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito:

1999, and "March's Advanced Organic Chemistry", $5^{th}$ Ed., Ed.: Smith, M. B. and March, J., John Wiley & Sons, New York: 2001.

Aliphatic: As used herein, "aliphatic" means a straight-chain (i.e., unbranched) or branched, substituted or unsubstituted hydrocarbon chain that is completely saturated or that contains one or more units of unsaturation, or a substituted or unsubstituted monocyclic, bicyclic, or polycyclic hydrocarbon ring that is completely saturated or that contains one or more units of unsaturation, or combinations thereof. Unless otherwise specified, aliphatic groups contain 1-100 aliphatic carbon atoms. In some embodiments, aliphatic groups contain 1-20 aliphatic carbon atoms. In other embodiments, aliphatic groups contain 1-10 aliphatic carbon atoms. In other embodiments, aliphatic groups contain 1-9 aliphatic carbon atoms. In other embodiments, aliphatic groups contain 1-8 aliphatic carbon atoms. In other embodiments, aliphatic groups contain 1-7 aliphatic carbon atoms. In other embodiments, aliphatic groups contain 1-6 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof.

Alkyl: As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, cycloalkyl rings have from about 3-10 carbon atoms in their ring structure where such rings are monocyclic, bicyclic, or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

Aryl: The term "aryl" used alone or as part of a larger moiety as in "aralkyl," "aralkoxy," or "aryloxyalkyl," refers to monocyclic, bicyclic or polycyclic ring systems having a total of five to thirty ring members, wherein at least one ring in the system is aromatic. In some embodiments, an aryl group is a monocyclic, bicyclic or polycyclic ring system having a total of five to fourteen ring members, wherein at least one ring in the system is aromatic, and wherein each ring in the system contains 3 to 7 ring members. In some embodiments, an aryl group is a biaryl group. The term "aryl" may be used interchangeably with the term "aryl ring." In certain embodiments of the present disclosure, "aryl" refers to an aromatic ring system which includes, but not limited to, phenyl, biphenyl, naphthyl, binaphthyl, anthracyl and the like, which may bear one or more substituents. In some embodiments, also included within the scope of the term "aryl," as it is used herein, is a group in which an aromatic ring is fused to one or more nonaromatic rings, such as indanyl, phthalimidyl, naphthimidyl, phenanthridinyl, or tetrahydronaphthyl, and the like, where a radical or point of attachment is on an aryl ring.

Cycloaliphatic: The term "cycloaliphatic," as used herein, refers to saturated or partially unsaturated aliphatic monocyclic, bicyclic, or polycyclic ring systems having, e.g., from 3 to 30, members, wherein the aliphatic ring system is optionally substituted. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic" may also include aliphatic rings that are fused to one or more aromatic or nonaromatic rings, such as decahydronaphthyl or tetrahydronaphthyl, where a radical or point of attachment is on an aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated or that contains one or more units of unsaturation, but which is not aromatic, or a $C_9$-$C_{16}$ tricyclic hydrocarbon that is completely saturated or that contains one or more units of unsaturation, but which is not aromatic.

Halogen: The term "halogen" means F, Cl, Br, or I.

Heteroaliphatic: The term "heteroaliphatic" is given its ordinary meaning in the art and refers to aliphatic groups as described herein in which one or more carbon atoms are replaced with one or more heteroatoms (e.g., oxygen, nitrogen, sulfur, silicon, phosphorus, and the like).

Heteroalkyl: The term "heteroalkyl" is given its ordinary meaning in the art and refers to alkyl groups as described herein in which one or more carbon atoms is replaced with a heteroatom (e.g., oxygen, nitrogen, sulfur, silicon, phosphorus, and the like). Examples of heteroalkyl groups include, but are not limited to, alkoxy, poly(ethylene glycol)-, alkyl-substituted amino, tetrahydrofuranyl, piperidinyl, morpholinyl, etc.

Heteroaryl: The terms "heteroaryl" and "heteroar-," used alone or as part of a larger moiety, e.g., "heteroaralkyl," or "heteroaralkoxy," refer to monocyclic, bicyclic or polycyclic ring systems having, for example, a total of five to thirty, ring members, wherein at least one ring in the system is aromatic and at least one aromatic ring atom is a heteroatom. In some embodiments, a heteroatom is nitrogen, oxygen or sulfur. In some embodiments, a heteroaryl group is a group having 5 to 10 ring atoms (i.e., monocyclic, bicyclic or polycyclic), in some embodiments 5, 6, 9, or 10 ring atoms. In some embodiments, a heteroaryl group has 6, 10, or 14 $\pi$ electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where a radical or point of attachment is on a heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic or polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl group, wherein the alkyl and heteroaryl portions independently are optionally substituted.

Heteroatom: The term "heteroatom" means an atom that is not carbon or hydrogen. In some embodiments, a heteroatom is oxygen, sulfur, nitrogen, phosphorus, boron or silicon (including any oxidized form of nitrogen, sulfur, phosphorus, or silicon; the quaternized form of any basic nitrogen or a substitutable nitrogen of a heterocyclic ring (for example, N as in 3,4-dihydro-2H-pyrrolyl), NH (as in pyrrolidinyl) or $NR^+$ (as in N-substituted pyrrolidinyl); etc.). In some embodiments, a heteroatom is boron, nitrogen, oxygen, silicon, sulfur, or phosphorus. In some embodiments, a heteroatom is nitrogen, oxygen, silicon, sulfur, or phosphorus. In some embodiments, a heteroatom is nitrogen, oxygen, sulfur, or phosphorus. In some embodiments, a heteroatom is nitrogen, oxygen or sulfur.

Heterocyclyl: As used herein, the terms "heterocycle," "heterocyclyl," "heterocyclic radical," and "heterocyclic ring" are used interchangeably and refer to a monocyclic, bicyclic or polycyclic ring moiety (e.g., 3-30 membered) that is saturated or partially unsaturated and has one or more heteroatom ring atoms. In some embodiments, a heteroatom is boron, nitrogen, oxygen, silicon, sulfur, or phosphorus. In some embodiments, a heteroatom is nitrogen, oxygen, silicon, sulfur, or phosphorus. In some embodiments, a heteroatom is nitrogen, oxygen, sulfur, or phosphorus. In some embodiments, a heteroatom is nitrogen, oxygen or sulfur. In some embodiments, a heterocyclyl group is a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where a radical or point of attachment is on a heteroaliphatic ring. A heterocyclyl group may be monocyclic, bicyclic or polycyclic. The term "heterocyclylalkyl" refers to an alkyl group substituted by a heterocyclyl, wherein the alkyl and heterocyclyl portions independently are optionally substituted.

Partially unsaturated: As used herein, the term "partially unsaturated" refers to a moiety that includes at least one double or triple bond. The term "partially unsaturated" is intended to encompass groups having multiple sites of unsaturation, but is not intended to include aryl or heteroaryl moieties.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known. For example, S. M. Berge, et al. describes pharmaceutically acceptable salts in detail in J. Pharmaceutical Sciences, 66: 1-19 (1977). In some embodiments, pharmaceutically acceptable salts include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other known methods such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, pharmaceutically acceptable salts include, but are not limited to, nontoxic base addition salts, such as those formed by acidic groups of provided compounds (e.g., phosphate linkage groups of oligonucleotides, phosphorothioate linkage groups of oligonucleotides, etc.) with bases. Representative alkali or alkaline earth metal salts include salts of sodium, lithium, potassium, calcium, magnesium, and the like. In some embodiments, pharmaceutically acceptable salts are ammonium salts (e.g., $—N(R)_3^+$). In some embodiments, pharmaceutically acceptable salts are sodium salts. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Protecting Group: The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 5th ed.; John Wiley and Sons: Hoboken, NJ, 2014). Exemplary protecting groups (and associated protected moieties) are described in detail below.

Protected hydroxyl groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected hydroxyl groups further include, but are not limited to, esters, carbonates, sulfonates, allyl ethers, ethers, silyl ethers, alkyl ethers, arylalkyl ethers, and alkoxyalkyl ethers. Examples of suitable esters include formates, acetates, propionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Substitution: As described herein, compounds of the disclosure may contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. In some embodiments, example substituents are described below.

Suitable monovalent substituents are halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH═CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)N(R$^\circ$)$_2$; —N(R$^\circ$)C(S)N(R$^\circ$)$_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)N(R$^\circ$)$_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSi(R$^\circ$)$_3$; —(CH$_2$)$_{0-4}$OC(O)R$^\circ$; —OC(O)(CH$_2$)$_{0-4}$SR$^\circ$, —SC(S)SR$^\circ$; —(CH$_2$)$_{0-4}$SC(O)R$^\circ$; —(CH$_2$)$_{0-4}$C(O)N(R$^\circ$)$_2$; —C(S)N(R$^\circ$)$_2$; —C(S)SR$^\circ$; —SC(S)SR$^\circ$, —(CH$_2$)$_{0-4}$OC(O)N(R$^\circ$)$_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$N(R$^\circ$)$_2$; —(CH$_2$)$_{0-4}$S(O)R$^\circ$; —N(R$^\circ$)S(O)$_2$N(R$^\circ$)$_2$; —N(R$^\circ$)S(O)$_2$R$^\circ$; —N(OR$^\circ$)R$^\circ$; —C(NH)N(R$^\circ$)$_2$; —Si(R$^\circ$)$_3$; —OSi(R$^\circ$)$_3$; —P(R$^\circ$)$_2$; —P(OR$^\circ$)$_2$; —OP(R$^\circ$)$_2$; —OP(OR$^\circ$)$_2$; —N(R$^\circ$)P(R$^\circ$)$_2$; —B(R$^\circ$)$_2$; —OB(R$^\circ$)$_2$; —P(O)(R$^\circ$)$_2$; —OP(O)(R$^\circ$)$_2$; —N(R$^\circ$)P(O)(R$^\circ$)$_2$; —(C$_{1-4}$ straight or branched alkylene)O—N(R$^\circ$)$_2$; or —(C$_{1-4}$ straight or branched alkylene)C(O)O—N(R$^\circ$)$_2$; wherein each R$^\circ$ may be substituted as defined below and is independently hydrogen, C$_{1-20}$ aliphatic, C$_{1-20}$ heteroaliphatic having 1-5 heteroatoms independently selected from nitrogen, oxygen, sulfur, silicon and phosphorus, —CH$_2$—(C$_{1-14}$ aryl), —O(CH$_2$)$_{0-1}$(C$_{6-14}$ aryl), —CH$_2$-(5-14 membered heteroaryl ring), a 5-20 membered, monocyclic, bicyclic, or polycyclic, saturated, partially unsaturated or aryl ring having 0-5 heteroatoms independently selected from nitrogen, oxygen, sulfur, silicon and phosphorus, or, notwithstanding the definition above, two independent occurrences of R$^\circ$, taken together with their intervening atom(s), form a 5-20 membered, monocyclic, bicyclic, or polycyclic, saturated, partially unsaturated or aryl ring having 0-5 heteroatoms independently selected from nitrogen, oxygen, sulfur, silicon and phosphorus, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur. Suitable divalent substituents on a saturated carbon atom of R$^\circ$ include ═O and ═S.

Suitable divalent substituents are the following: ═O, ═S, ═NNR*$_2$, ═NNHC(O)R*, ═NNHC(O)OR*, ═NNHS(O)$_2$R*, ═NR*, ═NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* are halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

In some embodiments, suitable substituents on a substitutable nitrogen are —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)ZR$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

Unsaturated: The term "unsaturated" as used herein, means that a moiety has one or more units of unsaturation.

Unless otherwise specified, salts, such as pharmaceutically acceptable acid or base addition salts, stereoisomeric forms, and tautomeric forms, of provided compound are included.

2. Detailed Description of Certain Embodiments

Among other things, the present disclosure encompasses the recognition that many products produced by enzymes encoded by fungi biosynthetic gene clusters may be employed to develop therapeutics toward human targets to treat various diseases. The present disclosure recognizes that one challenge of using the fungi products is to identifying their human targets. In some embodiments, the present disclosure provides technologies for efficient identification of human targets of biosynthetic products produced by enzymes encoded by fungi biosynthetic gene clusters. In some embodiments, a provided technology identifies embedded target genes (ETaGs) in proximity zones of biosynthetic genes of biosynthetic gene clusters, and optionally further identifies human targets of biosynthetic products produced by enzymes encoded by the biosynthetic gene clusters by comparing the ETaG sequences with human nucleic acid sequences, particularly expressed human nucleic acid sequences, including human genes encoding proteins. As readily appreciated by those skilled in the art, the connection between the biosynthetic products from biosynthetic gene clusters, ETaGs, and human targets, once established, can be utilized in various methods. For example, one may start from a biosynthetic product produced by the enzymes encoded by a biosynthetic gene cluster, to an ETaG within proximity zones of a biosynthetic gene of the biosynthetic gene cluster, and then to a human target that is homologous to the ETaG. Once the human target is identified, one can prioritize it (even if it was previously considered undruggable), and develop modulators of the human target using the biosynthetic product, including optional further optimization of the biosynthetic product, for medical use, e.g., by preparing and assaying analogs of the product, using many methods available to those skilled in the art. One may also start from a human target of therapeutic interest, to an ETaG homologous to the human target, then to a biosynthetic gene cluster that contains a biosynthetic gene a proximity zone relative to which contains the ETaG. Once the biosynthetic gene cluster is identified, the biosynthetic product produced by the enzymes encoded by the biosynthetic gene cluster can be characterized and assayed for modulation of the human target or a product thereof. The biosynthetic product can be used as a lead for optimization using a number of methods in the art in accordance with the present disclosure to provide agents useful for many medical, e.g. therapeutics purposes.

Without the intention to be limited by any theory, in some embodiments, the present disclosure encompasses the recognition that ETaGs from eukaryotes and/or products encoded thereby may bear more similarities to mammalian genes and/or products encoded thereby than, for example, their counterparts, in any, in prokaryotes such as bacteria; in some embodiments, eukaryotic ETaGs can be more therapeutically relevant. In some embodiments, ETaGs in fungi may be particularly useful for developing human therapeutics in view of the relative closeness of fungi with mammalians in a phylogenetic tree.

In some embodiments, the present disclosure provides technologies for identifying and/or characterizing ETaGs, which are non-biosynthetic genes in that they are not necessarily involved in synthesis of the products produced by the enzymes encoded by the biosynthetic gene clusters that contain the ETaGs, or the proximity zones relative to whose genes, in some embodiments, biosynthetic genes, contain the ETaGs (enzymes encoded by the biosynthetic gene cluster can produce the biosynthetic product without the ETaG). In some embodiments, ETaGs are not required for the synthesis of the products produced by the enzymes encoded by the biosynthetic gene clusters that contain the ETaGs, or the proximity zones relative to whose genes, in some embodiments, biosynthetic genes, contain the ETaGs (enzymes encoded by the biosynthetic gene cluster can produce the biosynthetic product without the ETaG). In some embodiments, ETaGs are not involved in synthesis of the products produced by the enzymes encoded by the biosynthetic gene clusters that contain the ETaGs, or the proximity zones relative to whose genes, in some embodiments, biosynthetic genes, contain the ETaGs (enzymes encoded by the biosynthetic gene cluster can produce the biosynthetic product without the ETaG). In some embodiments, ETaGs are homologous or comprise sequences that are homologous to human genes, e.g., sharing at least 50%, 55%, 60%, 65%, 70%, 75%, 80%, 85%, 90%, or 95% homology with human proteins or sequences (e.g., functional and/or structural units such as domains, functional structural features (helixes, sheets, etc.), etc.).

In some embodiments, an ETaG is co-regulated with at least one biosynthetic gene in the biosynthetic gene cluster. In some embodiments, an ETaG is co-regulated with the biosynthetic gene cluster in that the expression of the ETaG is correlated to production of the product encoded by the enzymes of the biosynthetic gene cluster. In some embodiments, an ETaG provides a self-protective function. In some embodiments, an ETaG encodes a transporter of the product produced by the enzymes of the biosynthetic gene cluster. In some embodiments, an ETaG encodes a product, e.g., a protein, that can detoxify the product produced by the enzymes of the biosynthetic gene cluster. In some embodiments, an ETaG encodes a resistant variant of a protein whose activities are targeted by the product produced by the enzymes of the biosynthetic gene cluster.

In some embodiments, the present disclosure provides methods comprising:

- querying a set of nucleic acid sequences, each of which is found in a fungal strain and comprises a biosynthetic gene cluster; and
- identifying within at least one of the fungal nucleic acid sequences an embedded target gene (ETaG) sequence characterized in that it:
  - is not involved in synthesis of the product produced by the enzymes encoded by the biosynthetic gene cluster;
  - is within a proximity zone relative to at least one biosynthetic gene in the biosynthetic gene cluster; and
  - is optionally co-regulated with at least one biosynthetic gene in the biosynthetic gene cluster.

In some embodiments, an ETaG is homologous to a mammalian nucleic acid sequence. In some embodiments, the present disclosure provides methods comprising:

- querying a set of nucleic acid sequences, each of which is found in a fungal strain and comprises a biosynthetic gene cluster; and
- identifying within at least one of the fungal nucleic acid sequences an embedded target gene (ETaG) sequence characterized in that it:
  - is not involved in synthesis of the products produced by the enzymes encoded by the biosynthetic gene cluster;
  - is within a proximity zone relative to at least one biosynthetic gene in the biosynthetic gene cluster;
  - is homologous to an expressed mammalian nucleic acid sequence; and
  - is optionally co-regulated with at least one biosynthetic gene in the biosynthetic gene cluster.

Proximity Zone

In some embodiments, an ETaG is typically within a proximity zone relative to at least one gene in a biosynthetic gene cluster. In some embodiments, an ETaG is within a proximity zone relative to at least one biosynthetic gene in a biosynthetic gene cluster. In some embodiments, a proximity zone is no more than 1-100 kb upstream or downstream of a gene. In some embodiments, a proximity zone is no more than 1-50 kb upstream or downstream of a gene. In some embodiments, a proximity zone is no more than 1, 2, 3, 4, 5, 6, 7, 8, 9, 10, 15, 20, 25, 30, 35, 40, 45, 50, 60, 70, 80 or 90 kb upstream or downstream of a gene. In some embodiments, a proximity zone is no more than 1 kb upstream or downstream of a gene. In some embodiments, a proximity zone is no more than 5 kb upstream or downstream of a gene. In some embodiments, a proximity zone is no more than 10 kb upstream or downstream of a gene. In some embodiments, a proximity zone is no more than 15 kb upstream or downstream of a gene. In some embodiments, a proximity zone is no more than 20 kb upstream or downstream of a gene. In some embodiments, a proximity zone is no more than 25 kb upstream or downstream of a gene. In some embodiments, a proximity zone is no more than 30 kb upstream or downstream of a gene. In some embodiments, a proximity zone is no more than 35 kb upstream or downstream of a gene. In some embodiments, a proximity zone is no more than 40 kb upstream or downstream of a gene. In some embodiments, a proximity zone is no more than 45 kb upstream or downstream of a gene. In some embodiments, a proximity zone is no more than 50 kb upstream or downstream of a gene.

In some embodiments, an ETaG is within a biosynthetic gene cluster. In some embodiments, an ETaG is not within a region defined by the first and last genes of a biosynthetic gene cluster, but within a proximity zone relative to the first or last gene of a biosynthetic gene cluster.

Homology

In some embodiments, an ETaG is homologous to an expressed mammalian nucleic acid sequence. In some embodiments, a mammalian nucleic acid sequence is an expressed mammalian nucleic sequence. In some embodiments, a mammalian nucleic acid sequence is a mammalian gene. In some embodiments, a mammalian nucleic acid sequence is an expressed mammalian gene. In some embodiments, a mammalian nucleic acid is a human nucleic acid sequence. In some embodiments, a human nucleic acid sequence is an expressed human nucleic acid sequence. In some embodiments, a human nucleic acid sequence is a human gene. In some embodiments, a human nucleic acid sequence is an expressed human gene. In some embodiments, a human nucleic acid sequence is, or encodes a product which is, an existing target of therapeutic interest. In some embodiments, a human nucleic acid sequence is, or encodes a product which is, a novel target of therapeutic interest. In some embodiments, a human nucleic acid sequence is, or encodes a product which is, a target considered undruggable prior to the present disclosure. In some embodiments, a human nucleic acid sequence is, or encodes a product which is, a target considered undruggable by small molecules prior to the present disclosure. In some embodiments, the present disclosure provides unexpected findings that targets traditionally considered undruggable can be effectively modulated or targeted by small molecules which are the biosynthetic products, or analogs of the biosynthetic products, produced by the enzymes encoded by biosynthetic gene clusters, which biosynthetic gene clusters contain biosynthetic genes the proximity zones relative to which contain ETaGs (or portions thereof, or products encoded thereby and/or portions thereof) that are homologous to the targets.

In some embodiments, the present disclosure provides methods comprising:

- querying a set of nucleic acid sequences, each of which is found in a fungal strain and comprises a biosynthetic gene cluster; and
- identifying within at least one of the fungal nucleic acid sequences an embedded target gene (ETaG) characterized in that it:
  - is not involved in synthesis of the products produced by the enzymes encoded by the biosynthetic gene cluster;
  - is within a proximity zone relative to at least one biosynthetic gene in the biosynthetic gene cluster;
  - is homologous to an expressed human nucleic acid sequence; and
  - is optionally co-regulated with at least one biosynthetic gene in the biosynthetic gene cluster.

In some embodiments, an ETaG and a nucleic acid sequence shares nucleic acid sequence homology. In some embodiments, an ETaG sequence is homologous to another nucleic acid sequence (e.g., an expressed human nucleic acid sequence) in that the ETaG nucleic acid sequence or a portion thereof shares similarity on the level of nucleic acid base sequences with another nucleic acid sequence or a portion thereof. In some embodiments, the sequence of an ETaG shares nucleic acid base sequence similarity with another nucleic acid sequence. In some embodiments, a portion of the sequence of an ETaG shares nucleic acid base sequence similarity with a portion of another nucleic acid sequence.

In some embodiments, homologous portions are at least 50, 100, 150, 200, 300, 400, 500, 600, 70, 800, 900, or 1000 base pairs in length. In some embodiments, the length is at least 50 base pairs. In some embodiments, the length is at least 100 base pairs. In some embodiments, the length is at least 150 base pairs. In some embodiments, the length is at least 200 base pairs. In some embodiments, the length is at least 300 base pairs. In some embodiments, the length is at least 400 base pairs. In some embodiments, the length is at least 500 base pairs.

In some embodiments, homologous portions encode amino acid residues that are of certain structural and/or functional units of encoded proteins. For example, in some embodiments, a homologous portion may encode a protein domain that is characteristic of the family of the encoded protein, that is enzymatically active, that is responsible for interactions with an effector, etc., as described in the present disclosure.

Methods for assessing similarity/homology of nucleic acid sequences are widely known in the art and can be used in accordance with the present disclosure.

In some embodiments, an ETaG and a nucleic acid sequence shares homology in their encoded products, e.g., proteins. In some embodiments, an ETaG and a nucleic acid sequence are homologous in that a product encoded by the ETaG or a portion thereof shares similarity with a product encoded by the nucleic acid sequence or a portion thereof. In some embodiments, an encoded product is a protein. In some embodiments, products encoded by an ETaG and a nucleic acid sequence share similarity across their full length. In some embodiments, products encoded by an ETaG and a nucleic acid sequence share similarity at certain portions.

In some embodiments, an ETaG and a nucleic acid are homologous in that a protein encoded by the ETaG or a portion thereof shares similarity with a protein encoded by the nucleic acid or a portion thereof. Proteins encoded by an ETaG and a nucleic acid sequence can share similarity either at the level of their full lengths or portions. In some embodiments, all amino acid residues in a homologous portion are consecutive. In some embodiments, amino acid residues in a homologous portion are not all consecutive.

In some embodiments, a portion of a protein is a protein domain. In some embodiments, the protein domain forms a structure that is characteristic of the protein family. In some embodiments, the protein domain performs a characteristic function. For example, in some embodiments, a protein domain has an enzymatic function. In some embodiments, such a function is shared by the protein encoded by the ETaG and the protein encoded by the homologous nucleic acid sequence, e.g., a human gene. In some embodiments, a characteristic function is non-enzymatic. In some embodiments, a characteristic function is interaction with other entities, e.g., small molecules, nucleic acids, proteins, etc.

In some embodiments, a portion of a protein is a set of amino acid residues, either consecutive or not consecutive, that are important for a function of a protein. In some embodiments, a function is an enzymatic activity. In some embodiments, a portion of a protein is a set of residues that are required for the activity. In some embodiments, a portion is a set of residues that interact with a substrate, an intermediate, a product, or a co-factor. In some embodiments, a portion is a set of residues that interact with a substrate. In some embodiments, a portion is a set of residues that interact with an intermediate. In some embodiments, a portion is a set of residues that interact with a product. In some embodiments, a portion is a set of residues that interact with a co-factor.

In some embodiments, a function is an interaction with another entity. In some embodiments, an entity is a small molecule. In some embodiments, an entity is a lipid. In some embodiments, an entity is a carbohydrate. In some embodiments, an entity is a nucleic acid. In some embodiments, an entity is a protein. In some embodiments, a portion is a set of amino acid residues that contact with an interacting agent. For example, FIG. 13 illustrates a portion (a set of amino acid) that interact with nucleotide for Ras proteins and their homologous ETaGs, and FIGS. 14-16 illustrates portions that involved in protein-protein interactions.

In some embodiments, interaction of an amino acid residue with an interacting entity can be assessed by hydrogen bonding, electrostatic forces, van der Waals forces, aromatic stacking, etc. In some embodiments, interaction can be assessed by the distance of an amino acid residue to an interacting entity (for example, 4 Å as used in certain cases).

In some embodiments, a similarity is that two structures have a Calpha backbone rmsd (root mean square deviation) within 1, 2, 3, 4, 5, 6, 7, 8, 9, 10, 15, 20, 30, 40, or 50 square angstroms and have the same overall fold or core domain. In some embodiments, a Calpha backbone rmsd is within In some embodiments, a portion of a protein is or comprises a structural element that is essential for protein effector recruitment. In some embodiments, such a portion can be selected based on structural and/or activity data of a protein encoded by a nucleic acid sequence that is homologous to an ETaG, for example, a human gene which encodes a protein that is homologous to an ETaG.

In some embodiments, a portion of a protein comprises at least 2-200, 2-100, 2-50, 2-40, 2-30, 2-20, 2-15, 2-10, 3-200, 3-100, 3-50, 3-40, 3-30, 3-20, 3-15, 3-10, 4-200, 4-100, 4-50, 4-40, 4-30, 4-20, 4-15, 4-10, 5-200, 5-100, 5-50, 5-40, 5-30, 5-20, 5-15, or 5-10 amino acid residues. In some embodiments, a portion of a protein comprises at least 2, 3, 4, 5, 6, 7, 8, 9, 10, 11, 12, 13, 14, 15, 20, 25, 30, 40, 50, 60, 70, 80, 90, 100, or 150 amino acid residues. In some embodiments, a portion comprises at least 2 amino acid residues. In some embodiments, a portion comprises at least 3 amino acid residues. In some embodiments, a portion comprises at least 4 amino acid residues. In some embodiments, a portion comprises at least 5 amino acid residues. In some embodiments, a portion comprises at least 6 amino acid residues. In some embodiments, a portion comprises at least 7 amino acid residues. In some embodiments, a portion comprises at least 8 amino acid residues. In some embodiments, a portion comprises at least 9 amino acid residues. In some embodiments, a portion comprises at least 10 amino acid residues. In some embodiments, a portion comprises at least 15 amino acid residues. In some embodiments, a portion comprises at least 20 amino acid residues. In some embodiments, a portion comprises at least 25 amino acid residues. In some embodiments, a portion comprises at least 30 amino acid residues.

Similarity of nucleic acid sequences and protein sequences can be assessed by a number of methods, including those known in the art, in accordance with the present disclosure. For example, MUSCLE for protein sequences. In some embodiments, similarity is measured based on exact identity, e.g., the same amino acid residues at given position. In some embodiments, similarity is measured based on one or more common properties, e.g., amino acid residues bearing one or more identical or similar properties (e.g., acidic, basic, aromatic, etc.).

In some embodiments, an ETaG is homologous to a nucleic acid sequence (e.g., an expressed human nucleic acid sequence) in that the similarity between the ETaG and the nucleic acid base sequences is no less than a level based on the nucleic acid sequences of the ETaG and the nucleic acid sequence, or portions thereof, or the proteins encoded by the ETaG and the nucleic acid sequences or portions thereof, as described herein. In some embodiments, an ETaG is homologous to a nucleic acid sequence in that the similarity between the ETaG and the nucleic acid sequences is no less than a level based on the nucleic acid base sequences of the ETaG and the nucleic acid sequence, or portions thereof. In some embodiments, an ETaG is homologous to a nucleic acid sequence in that the similarity between the ETaG and the nucleic acid sequences is no less than a level based on proteins encoded by the ETaG and the nucleic acid sequences or portions thereof. In some embodiments, a level is at least 10%-99%. In some embodiments, a level is at least 10%, 20%, 30%, 40%, 50%, 60%, 70%, 80%, 85%, 90%, 91%, 92%, 93%, 94%, 95%, 96%, 97%, 98%, or 99%. In some embodiments, a level is at least 10%. In some embodiments, a level is at least 20%. In some embodiments, a level is at least 30%. In some embodiments, a level is at least 40%. In some embodiments, a level is at least 50%. In some embodiments, a level is at least 60%. In some embodiments, a level is at least 70%. In some embodiments, a level is at least 80%. In some embodiments, a level is at least 90%. In some embodiments, a level is 100%. In some embodiments, a level is lower than 100%. In some embodiments, a level is no more than 90%, 91%, 92%, 93%, 94%, 95%, 96%, 97%, 98%, or 99%.

In some embodiments, an ETaG is homologous to a nucleic acid sequence in that a protein encoded by the ETaG or a portion thereof has a 3-dimensional structure that is similar to that of a protein encoded by the nucleic acid sequence. In some embodiments, similarity is assessed by Calpha backbone rmsd (root mean square deviation), e.g., within 1-100, e.g., 5, 10, 20, 30, 40, 50 square angstroms. In some embodiments, sequences share similarity have Calpha backbone rmsd no more than 10 square angstroms, and also have the same overall fold or core domain. In some embodiments, structural similarity is assessed by interactions with another entity, e.g., small molecules, nucleic acids, proteins, etc. In some embodiments, structural similarity is assessed by small molecule binding. In some embodiments, a protein encoded by an embedded target gene or a portion thereof has a 3-dimensional structure that is similar to a protein encoded by a nucleic acid sequence in that a small molecule binding to a protein encoded by an embedded target gene or a portion thereof also binds to a protein encoded by nucleic acid sequence or a portion thereof. In some embodiments, a binding has a Kd of no more than 1-100 (e.g., 1, 2, 3, 4, 5, 6, 7, 8, 9, 10, 20, 30, 40, 50, 60, 70, 80, 90, 100) μM.

Co-Regulation

In some embodiments, an ETaG is co-regulated with at least one biosynthetic gene in a biosynthetic gene cluster that contains a biosynthetic gene a proximity zone relative to which contains the ETaG. In some embodiments, an ETaG is co-regulated with a biosynthetic gene cluster that contains a biosynthetic gene a proximity zone relative to which contains the ETaG. In some embodiments, an ETaG is co-regulated with a biosynthetic gene cluster in that expression of the ETaG, and/or production of a product encoded by the ETaG, e.g., a protein, is correlated with production of a biosynthetic product produced by the enzymes encoded by the biosynthetic gene cluster. In some embodiments, production of a product encoded by the ETaG, e.g., a protein overlaps timewise with production of a biosynthetic product by the enzymes encoded by the biosynthetic gene cluster. In some embodiments, an ETaG is co-regulated with the biosynthetic gene cluster in that expression of the ETaG is increased, or turned on, when a biosynthetic product produced by the enzymes encoded by the biosynthetic gene cluster is produced. In some embodiments, an ETaG is co-regulated with the biosynthetic gene cluster in that expression of the ETaG is increased, or turned on, when level of a biosynthetic product produced by the enzymes encoded by the biosynthetic gene cluster is produced is increased.

In some embodiments, an ETaG provides advantages to its hosting organism, e.g., fungi, when the biosynthetic product produced by the enzymes encoded by the co-regulated biosynthetic gene cluster is produced. For example, in some embodiments, a protein encoded by an ETaG contributes to transportation of the biosynthetic product out of the cells producing the product. In some embodiments, a protein encoded by an ETaG detoxifies the biosynthetic product so that the biosynthetic product does not harm the organism producing the biosynthetic product but impacts growth or survival of other organisms.

In some embodiments, the present disclosure provides various methods for identifying ETaGs. For example, in some embodiments, a set of homologous biosynthetic gene clusters, e.g., biosynthetic gene clusters whose encoded enzymes produce the same biosynthetic products (based on prediction (e.g., sequence based prediction) and/or identification of the products), typically from different fungi strains, are compared. Non-biosynthetic genes present in only one or a few biosynthetic gene clusters (within the biosynthetic gene cluster or within the proximity zones relative to biosynthetic genes of the biosynthetic gene clusters) but are absent from the majority of biosynthetic gene clusters in the set are identified as ETaG candidates and are optionally further compared with mammalian, e.g., human, nucleic acid sequences to identify the homologous mammalian nucleic acid sequences. In some embodiments, such a method can be used to identify ETaGs on genomic scales, e.g., from sequences of many (e.g., hundreds, thousands, or even more) genomes as illustrated in the Examples. Identified ETaGs can be prioritized based on therapeutic importance of their mammalian homologs, particularly human homologs. In some embodiments, as illustrated in the Figures, an organism comprising an ETaG comprises one or more homologous genes of the ETaG.

In some embodiments, an ETaG is present at no more than 1%, 5%, or 10% of biosynthetic gene clusters of a set. In some embodiments, an ETaG is present at no more than 1%, 5%, or 10% of homologous biosynthetic gene clusters of a set. In some embodiments, an ETaG is present at no more than 1%, 5%, or 10% of biosynthetic gene clusters of a set, which biosynthetic gene clusters encode enzymes that produce the same biosynthetic product. In some embodiments, the percentage is less than 1%. In some embodiments, the percentage is less than 5%. In some embodiments, the percentage is less than 10%.

In some embodiments, the present disclosure provides methods that are particularly effective and efficient for identifying homologous ETaGs for human nucleic acid encoding targets of therapeutic interest by querying provided sets of nucleic acid sequences comprising biosynthetic gene clusters and/or ETaGs within proximity zones relative to biosynthetic genes of the biosynthetic gene clusters.

In some embodiments, the present disclosure provides sets of nucleic acid sequences as described herein. In some embodiments, the present disclosure provides a set of nucleic acid sequences, each of which is found in a fungal stain and comprises a biosynthetic gene cluster. In some embodiments, the present disclosure provides a set of nucleic acid sequences, each of which is found in a fungal stain and comprises an ETaG. In some embodiments, the present disclosure provides a set of nucleic acid sequences, each of which is found in a fungal stain and comprises a biosynthetic gene cluster and an ETaG that is within a proximity zone relative to a biosynthetic gene of the biosynthetic gene cluster. In some embodiments, nucleic acid sequences comprising biosynthetic gene clusters include no more sequences beyond the proximity zones relative to biosynthetic genes of the biosynthetic gene clusters and the sequences of the biosynthetic gene clusters. In some embodiments, the present disclosure provides database comprising provided sets of nucleic acid sequences.

In some embodiments, biosynthetic gene clusters of provided technologies comprise biosynthetic genes encoding enzymes that can participate in synthesis of compounds sharing at least one common chemical attribute. In some embodiments, a common chemical attribute is a cyclic core structure. In some embodiments, a common chemical attribute is a macrocyclic core structure. In some embodiments, a common chemical attribute is a shared acyclic backbone. In some embodiments, a common chemical attribute is that the compounds all belong to a certain category, e.g., non-ribosomal peptides (NPRS), terpenes, isoprenes, alkaloids, etc. In some embodiments, by identifying individual ETaGs for biosynthetic gene clusters, the present disclosure can differentiate compounds sharing common chemical attributes, even though they may be structurally similar.

Provided sets can be of various size and/or diversity. In some embodiments, it is desirable to have more sequences from more species to increase the number of ETaGs and biosynthetic gene clusters. In some embodiments, a set comprises at least 100, 200, 300, 400, 500, 1,000, 1,500, 2,000, 3,000, 5,000, 10,000, 20,000, 50,000, 100,000, 500, 000, 1,000,000, 1,500,000 or 2,000,000 nucleic acid sequences comprising biosynthetic gene clusters. In some embodiments, a set comprises at least 100, 200, 300, 400, 500, 1,000, 1,500, 2,000, 3,000, 5,000, 10,000, 50,000, 100,000, 500,000, 1,000,000, 1,500,000 or 2,000,000 biosynthetic gene clusters. In some embodiments, a set comprises at least 100, 200, 300, 400, 500, 1,000, 1,500, 2,000, 3,000, 5,000, 10,000, 50,000, 100,000, 500,000, 1,000,000, 1,500,000 or 2,000,000 biosynthetic gene clusters related to ETaGs (biosynthetic gene clusters containing biosynthetic genes proximity zones relative to which contain ETaGs). In some embodiments, a set comprises at least 100, 200, 300, 400, 500, 1,000, 1,500, 2,000, 3,000, 5,000, 10,000, 50,000, 100,000, 500,000, 1,000,000, 1,500,000 or 2,000,000 ETaGs. In some embodiments, sequences of a provided set are from at least 100, 200, 300, 400, 500, 1,000, 1,500, 2,000, 3,000, 5,000, 10,000, 20,000, 50,000, 100,000 genomes from different species, e.g., different fungi species.

Among other things, provided databases and/or provided sets are so structured to particularly improve efficiencies for, e.g., identifying ETaGs, identifying ETaGs related to given biosynthetic gene clusters, identifying biosynthetic gene clusters related to given ETaGs, identifying ETaGs homologous to given mammalian nucleic acid sequences (e.g., human genes), identifying biosynthetic gene clusters related to given mammalian nucleic acid sequences (e.g., human genes; optionally through related ETaGs), identifying mammalian nucleic acid sequences (e.g., human genes) homologous to given ETaGs, human genes) homologous to given biosynthetic gene clusters (optionally through related ETaGs), identifying mammalian nucleic acid sequences (e.g., human genes) related to given products (and/or analogs thereof) produced by the enzymes encoded by biosynthetic gene clusters (optionally through related ETaGs and biosynthetic gene clusters), identifying products (and/or analogs thereof) produced by the enzymes encoded by biosynthetic gene clusters related to given mammalian nucleic acid sequences (e.g., human genes; optionally through related biosynthetic gene clusters and ETaGs), etc.

Figure 17:
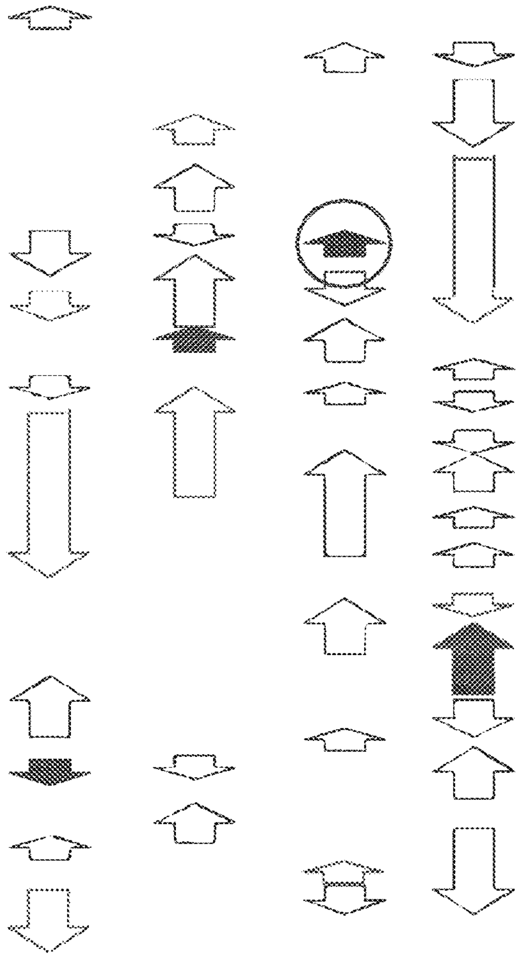
FIG. 17 depicts example sequences wherein ETaGs are indexed/marked (dark color).

For example, in some embodiments, ETaGs in provided sets and/or databases are indexed/marked for searching. For example, FIG. 17 (Applicant notes that provided sets and databases can contain hundreds, thousands or millions of sequences) depicts example sequences from provided sets and/or database wherein ETaGs are specifically indexed/marked (dark color). Among other things, such structural features can greatly improve, for example, query efficiency: instead of searching tens, hundreds, or thousands of genomes for ETaGs homologous to human gene of interests, one can instead using provided technologies to focus searches on indexed/marked ETaGs (for example, skipping non-biosynthetic gene cluster sequences and/or non-ETaG sequences (e.g., empty arrows and sequences in between in FIG. 17)) to quickly locate a hit (for example, the circled ETaG in FIG. 17), thereby saving time and resources for searching a vast majority of unrelated genomic information.

Additionally and alternatively, provided sets of sequences and databases are structured such that ETaGs can be independently annotated with information such as their related biosynthetic gene clusters (a related biosynthetic gene cluster of an ETaG is a biosynthetic gene cluster that contains a biosynthetic gene a proximity zone relative to which the ETaG is in), products produced by the enzymes encoded by the related biosynthetic gene clusters and analogs thereof, their homologous mammalian nucleic acid sequences (e.g., human genes), etc. Similarly, biosynthetic gene clusters can be independently annotated with information such as their related ETaGs (a related ETaG of a biosynthetic gene cluster is an etg within a proximity zone relative to a biosynthetic gene of the biosynthetic gene cluster), biosynthetic products produced by the enzymes encoded by the biosynthetic gene clusters and analogs thereof, homologous mammalian nucleic acid sequences of their related ETaGs and products encoded thereby, etc. By structuring sequence data with indexes and annotations, provided sets and databases can provide a number of advantages. For example, in some embodiments, provided systems provide fast access to ETaGs with useful related information, for example, their related biosynthetic gene clusters and human homologs, and vice versa, while maintaining data size and query cost low.

In some embodiments, at least 10, 20, 50, 100, 200, 500, 1,000, 2,000, 2,500, 5,000, or 10,000, or at least 5%, 10%, 20%, 30%, 40%, 50%, 60%, 70%, 80%, 90%, or 95%, or all, of ETaGs of a set are independently annotated. In some embodiments, at least 10, 20, 50, 100, 200, 500, 1,000, 2,000, 2,500, 5,000, or 10,000, or at least 5%, 10%, 20%, 30%, 40%, 50%, 60%, 70%, 80%, 90%, or 95%, or all, of ETaGs of a set are independently annotated with their related biosynthetic gene clusters and homologous mammalian nucleic acid sequences. In some embodiments, at least 10, 20, 50, 100, 200, 500, 1,000, 2,000, 2,500, 5,000, or 10,000, or at least 5%, 10%, 20%, 30%, 40%, 50%, 60%, 70%, 80%, 90%, or 95%, or all, of biosynthetic gene clusters of a set are independently annotated. In some embodiments, at least 10, 20, 50, 100, 200, 500, 1,000, 2,000, 2,500, 5,000, or 10,000, or at least 5%, 10%, 20%, 30%, 40%, 50%, 60%, 70%, 80%, 90%, or 95%, or all, of biosynthetic gene clusters of a set are independently annotated with their related ETaGs.

In some embodiments, provided sets of sequences and/or databases are embodied in a computer readable medium. In some embodiments, the present disclosure provides systems comprising one or more non-transitory machine-readable storage media storing data representing provided sets of sequences and/or databases. Non-transitory machine-readable storage media suitable for embodying provided data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks. Among other things, provided systems can be particularly efficient due to provided sets and databases having particular structures described herein.

In some embodiments, the present disclosure provides computer systems that can perform provided technologies. In some embodiments, the present disclosure provides computer systems adapted to perform provided methods. In some embodiments, the present disclosure provides computer systems adapted to query provided sets of sequences. In some embodiments, the present disclosure provides computer systems adapted to query provided databases. In some embodiments, the present disclosure provides computer systems adapted to access provided databases.

Computer systems that may be used to implement all or part of provided technologies may include various forms of digital computers. Examples of digital computers include, but are not limited to, laptops, desktops, workstations, personal digital assistants, servers, blade servers, mainframes, smart televisions and other appropriate computers. Mobile devices may be used to implement all or part of provided technologies. Mobile devices include, but are not limited to, tablet computing devices, personal digital assistants, cellular telephones, smartphones, digital cameras, digital glasses and other portable computing devices. The computing devices described herein, their connections and relationships, and their functions, are meant to be examples only, and are not meant to limit implementations of the technology.

All or part of technologies described herein and their various modifications can be implemented, at least in part, via a computer program product, e.g., a computer program tangibly embodied in one or more information carriers, e.g., in one or more tangible machine-readable storage media, for execution by, or to control the operation of, data processing apparatus, e.g., a programmable processor, a computer, or multiple computers.

A computer program for provided technologies can be written in any form of programming language, including compiled or interpreted languages, and it can be deployed in any form, including as a stand-alone program or as a module, part, subroutine, or other unit suitable for use in a computing environment. A computer program can be deployed to be executed on one computer or on multiple computers at one site or distributed across multiple sites and interconnected by a network.

Actions, e.g., associated with implementing programs and technologies, can be performed by one or more programmable processors executing one or more computer programs to perform provided technologies. All or part of the processes can be implemented as, special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks. Non-transitory machine-readable storage media suitable for embodying computer program instructions and data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks.

Each computing device, such as a tablet computer, may include a hard drive for storing data and computer programs, and a processing device (e.g., a microprocessor) and memory (e.g., RAM) for executing computer programs. Each computing device may include an image capture device, such as a still camera or video camera. The image capture device may be built-in or simply accessible to the computing device.

Each computing device may include a graphics system, including a display screen. A display screen, such as an LCD or a CRT (Cathode Ray Tube) displays, to a user, images that are generated by the graphics system of the computing device. As is well known, display on a computer display (e.g., a monitor) physically transforms the computer display. For example, if the computer display is LCD-based, the orientation of liquid crystals can be changed by the application of biasing voltages in a physical transformation that is visually apparent to the user. As another example, if the computer display is a CRT, the state of a fluorescent screen can be changed by the impact of electrons in a physical transformation that is also visually apparent. Each display screen may be touch-sensitive, allowing a user to enter information onto the display screen via a virtual keyboard. On some computing devices, such as a desktop or smartphone, a physical QWERTY keyboard and scroll wheel may be provided for entering information onto the display screen. Each computing device, and computer programs executed thereon, may also be configured to accept voice commands, and to perform functions in response to such commands.

Among other things, provided technologies (methods, sets, databases, systems, etc.) establish connections among biosynthetic gene clusters, products produced by the enzymes encoded by the biosynthetic gene clusters, ETaGs, homologous mammalian nucleic acid sequences, e.g., human genes, of ETaGs, etc. Provided technologies can thus, in some embodiments, be particularly powerful for identifying and/or characterizing human targets of products produced by the enzymes encoded by the biosynthetic gene clusters. Provided technologies can also be particularly powerful for identifying and developing modulators for human targets. For example, in some embodiments, to develop therapeutics for a human target, an ETaG of the human target (or nucleic acid sequences encoding the human target) can be quickly identified using provided technologies, together with information of its related biosynthetic gene clusters and/or biosynthetic products produced by the enzymes of the biosynthetic gene cluster. Products of the related biosynthetic gene cluster can be further characterized and if necessary, analogs thereof can be prepared, characterized, and assayed to develop therapeutics with improved properties. Provided technologies can be particularly useful for human targets that are challenging to target, and/or considered undruggable prior to the present disclosure.

In some embodiments, the present disclosure provides methods for assessing compounds using identified ETaGs and products encoded thereby. In some embodiments, the present disclosure provides a method comprising:

contacting at least one test compound with a gene product encoded by an embedded target gene of a fungal nucleic acid sequence, which embedded target gene is characterized in that it:
- is not required for or is not involved in the biosynthesis of the product of the biosynthetic gene cluster;
- is within a proximity zone relative to at least one biosynthetic gene in the cluster;
- is homologous to an mammalian nucleic acid sequence; and
- is optionally co-regulated with at least one biosynthetic gene in the cluster; and determining that:
- level or activity of the gene product is altered when the test compound is present as compared with when it is absent; or
- level or activity of the gene product is comparable to that observed when a reference agent having a known effect on the level or activity is present.

In some embodiments, the present disclosure provides methods for identifying and/or characterizing a mammalian, e.g., human, target of a product produced by enzymes encoded by a biosynthetic gene cluster, or an analog of the product, comprising:

identifying a human homolog of an ETaG that is within a proximity zone relative to at least one biosynthetic gene of the biosynthetic gene cluster, or is within a proximity zone relative to at least one biosynthetic gene of a second biosynthetic gene cluster which second biosynthetic gene cluster encodes enzymes that produce the same biosynthetic product that is produced by enzymes encoded by the biosynthetic gene cluster; and optionally assaying an effect of the product produced by enzymes encoded by a biosynthetic gene cluster, or an analog of the product, on the target.

In some embodiments, the present disclosure provides methods for assessing compounds using products encoded by mammalian, e.g., human, nucleic acid sequences that are homologous to ETaGs. In some embodiments, the present disclosure provides a method comprising:

contacting at least one test compound with a gene product encoded by a mammalian nucleic acid sequence, which is homologous to an embedded target gene characterized in that the embedded target gene:

is not required for or is not involved in the biosynthesis of the product of the biosynthetic gene cluster;

is within a proximity zone relative to at least one biosynthetic gene in the cluster;

is homologous to the mammalian nucleic acid sequence; and is optionally co-regulated with at least one biosynthetic gene in the cluster; and determining that:

level or activity of the gene product is altered when the test compound is present as compared with when it is absent; or level or activity of the gene product is comparable to that observed when a reference agent having a known effect on the level or activity is present.

In some embodiments, the present disclosure provides methods for identifying and/or characterizing a mammalian, e.g., human, target of a product produced by enzymes encoded by a biosynthetic gene cluster, or an analog of the product, comprising:

identifying a human homolog of an ETaG that is within a proximity zone relative to at least one biosynthetic gene of the biosynthetic gene cluster; and optionally assaying an effect of the product produced by enzymes encoded by a biosynthetic gene cluster, or an analog of the product, on the target.

In some embodiments, provided methods and systems are useful for assessing interactions of human targets with compounds. In some embodiments, the present disclosure provides methods for accessing interaction of a human target with a compound, comprising:

comparing nucleic acid sequence of the human target, or the nucleic acid sequence that encodes the human target, with a set of nucleic acid sequences which comprise one or more ETaGs.

In some embodiments, a compound produced by the enzymes of a biosynthetic gene cluster interacts with a target encoded by a mammalian, e.g., human, nucleic sequence that is homologous to an ETaG related to the biosynthetic gene cluster.

In some embodiments, provided technologies are particularly useful for designing and/or providing modulators for human targets, as, among other things, provided technologies provide connections among biosynthetic gene clusters, ETaGs, and human target genes.

In some embodiments, the present disclosure provides methods for identifying and/or characterizing a modulator of a human target, comprising:

providing a product or an analog thereof, which product is produced by the enzymes encoded by a biosynthetic gene cluster, wherein, within a proximity zone relative to at least one biosynthetic gene in the biosynthetic gene cluster, exists an ETaG that:

is homologous to the human target, or a nucleic acid sequence that encodes the human target; and is optionally co-regulated with at least one biosynthetic gene in the cluster.

In some embodiments, a human target is a Ras protein. In some embodiments, a Ras protein is a HRas protein. In some embodiments, a Ras protein is a KRas protein. In some embodiments, a Ras protein is a NRas protein. In some embodiments, a human target is a protein comprising a RasGEF domain. In some embodiments, a protein is KNDC1, PLCE1, RALGDS, RALGPS1, RALGPS2, RAPGEF1, RAPGEF2, RAPGEF3, RAPGEF4, RAPGEF5, RAPGEF6, RAPGEFL1, RASGEF1A, RASGEF1B, RASGEF1C, RASGRF1, RASGRF2, RASGRP1, RASGRP2, RASGRP3, RASGRP4, RGL1, RGL2, RGL3, RGL4/RGR, SOS1, SOS2, or human guanine nucleotide exchange factor. In some embodiments, a protein is SOS1. In some embodiments, a protein is human guanine nucleotide exchange factor. In some embodiments, a human target is a protein comprising a RasGAP domain. In some embodiments, a protein is DAB2IP, GAPVD1, IQGAP1, IQGAP2, IQGAP3, NF1, RASA1, RASA2, RASA3, RASA4, RASAL1, RASAL2, or SYNGAP1. In some embodiments, a protein is protein p120. In some embodiments, a protein is human guanine nucleotide activating factor.

In some embodiments, the present disclosure provides a method for identifying and/or characterizing a modulator for a human Ras protein, comprising:

preparing an analog of a compound produced by the enzymes encoded by a biosynthetic gene cluster;

wherein, within a proximity zone relative to at least one biosynthetic gene in the biosynthetic gene cluster, exists an ETaG that:

is homologous to the human Ras protein, a RasGEF domain, or a RasGAP domain, or a nucleic acid sequence that encodes the human Ras protein, a RasGEF domain, or a RasGAP domain; and is optionally co-regulated with at least one biosynthetic gene in the cluster.

In some embodiments, a protein comprising the RasGEF domain modulates one or more functions of the human Ras protein. In some embodiments, a protein comprising the RasGAP domain modulates one or more functions of the human Ras protein.

In some embodiments, the present disclosure provides a method for identifying and/or characterizing a modulator for a human Ras protein, comprising:

preparing an analog of a compound produced by the enzymes encoded by a biosynthetic gene cluster;

wherein, within a proximity zone relative to at least one biosynthetic gene in the biosynthetic gene cluster, exists an ETaG that:

is homologous to the human Ras protein, or a nucleic acid sequence that encodes the human Ras protein; and is optionally co-regulated with at least one biosynthetic gene in the cluster.

In some embodiments, the present disclosure provides a method for identifying and/or characterizing a modulator for a protein comprising a RasGEF domain, comprising:

preparing an analog of a compound produced by the enzymes encoded by a biosynthetic gene cluster;

wherein, within a proximity zone relative to at least one biosynthetic gene in the biosynthetic gene cluster, exists an ETaG that:

is homologous to the RasGEF domain, or a nucleic acid sequence that encodes the RasGEF domain; and is optionally co-regulated with at least one biosynthetic gene in the cluster.

In some embodiments, the present disclosure provides a method for identifying and/or characterizing a modulator for a protein comprising a RasGAP domain, comprising:

preparing an analog of a compound produced by the enzymes encoded by a biosynthetic gene cluster;

wherein, within a proximity zone relative to at least one biosynthetic gene in the biosynthetic gene cluster, exists an ETaG that:

is homologous to the RasGAP domain, or a nucleic acid sequence that encodes the RasGAP domain; and is optionally co-regulated with at least one biosynthetic gene in the cluster.

In some embodiments, a biosynthetic gene cluster is an example biosynthetic gene cluster, or a biosynthetic gene cluster comprising one or more biosynthetic genes, illustrated in one of the Figures together with an ETaG homologous to a Ras protein, e.g., FIGS. 5-12, and 20-27. In some embodiments, a biosynthetic gene cluster is an example biosynthetic gene cluster illustrated in one of the Figures together with an ETaG homologous to a Ras protein, e.g., FIGS. 5-12, and 20-27. In some embodiments, a biosynthetic gene cluster is an example biosynthetic gene cluster, or a biosynthetic gene cluster comprising one or more biosynthetic genes, illustrated in one of the Figures together with an ETaG homologous to a RasGEF domain, e.g., FIGS. 28-33, and 35. In some embodiments, a biosynthetic gene cluster is an example biosynthetic gene cluster illustrated in one of the Figures together with an ETaG homologous to a RasGEF domain, e.g., FIGS. 28-33, and 35. In some embodiments, a biosynthetic gene cluster is an example biosynthetic gene cluster, or a biosynthetic gene cluster comprising one or more biosynthetic genes, illustrated in one of the Figures together with an ETaG homologous to a RasGEF domain, e.g., FIGS. 34, and 36-39. In some embodiments, a biosynthetic gene cluster is an example biosynthetic gene cluster illustrated in one of the Figures together with an ETaG homologous to a RasGEF domain, e.g., FIGS. 34, and 36-39. Example ETaG sequences are presented in the present disclosure, and, among other things, can be utilized to locate and identify biosynthetic gene clusters, biosynthetic genes, etc.

In some embodiments, the present disclosure provides methods for modulating a human target, comprising:

providing a product or an analog thereof, which product is produced by the enzymes encoded by a biosynthetic gene cluster, wherein, within a proximity zone relative to at least one biosynthetic gene in the biosynthetic gene cluster, exists an ETaG that:

is homologous to the human target, or a nucleic acid sequence that encodes the human target; and is optionally co-regulated with at least one biosynthetic gene in the cluster.

In some embodiments, the present disclosure provides methods for modulating a Ras protein, comprising:

providing a product or an analog thereof, which product is produced by the enzymes encoded by a biosynthetic gene cluster of one of FIGS. 5-12, and 20-27.

In some embodiments, the present disclosure provides methods for modulating a RasGEF protein, comprising:

providing a product or an analog thereof, which product is produced by the enzymes encoded by a biosynthetic gene cluster of one of FIGS. 28-33, and 35.

In some embodiments, the present disclosure provides methods for modulating a RasGAP protein, comprising:

providing a product or an analog thereof, which product is produced by the enzymes encoded by a biosynthetic gene cluster of one of FIGS. 34, and 36-39.

In some embodiments, an ETaG is identified by a provided method.

In some embodiments, a product is produced by enzymes encoded by a biosynthetic gene cluster is a secondary metabolite produced by the biosynthetic gene cluster.

In some embodiments, an analog of a product comprises the structural core of a product. In some embodiments, a product is cyclic, e.g., monocyclic, bicyclic, or polycyclic. In some embodiments, the structural core of the product is or comprises the monocyclic, bicyclic, or polycyclic ring system. In some embodiments, the structural core of the product comprises one ring of the bicyclic or polycyclic ring system of the product.

In some embodiments, a product is linear, and the structural core is its backbone. In some embodiments, a product is or comprises a polypeptide, and a structural core is the backbone of the polypeptide. In some embodiments, a product is or comprises a polyketide, and a structural core is the backbone of the polyketide.

In some embodiments, an analog is the product substituted with one or more suitable substituents as described herein. In some embodiments, an analog is the structural core substituted with one or more suitable substituents as described herein.

Among other things, the present disclosure provides the following Example Embodiments:

A method comprising steps of:

querying a set of nucleic acid sequences, each of which is found in a fungal strain and comprises a biosynthetic gene cluster; and identifying within at least one of the fungal nucleic acid sequences an embedded target gene (ETaG) sequence characterized in that it:

is not required for or is not involved in the biosynthesis of the product of the biosynthetic gene cluster;

is within a proximity zone relative to at least one gene in the cluster;

is homologous to an mammalian nucleic acid sequence; and is optionally co-regulated with at least one biosynthetic gene in the cluster.

The method of embodiment 1, wherein the ETaG sequence is within a proximity zone relative to at least one biosynthetic gene in the cluster.

The method of any one of the preceding embodiments, wherein a nucleic acid sequence comprising a biosynthetic gene cluster contains no more sequences beyond the nucleic acid sequences of the proximity zones relative to the biosynthetic genes of the biosynthetic gene cluster and the nucleic acid sequence of the biosynthetic gene cluster.

The method of any one of the preceding embodiments, wherein a proximity zone is no more than 1, 2, 3, 4, 5, 6, 7, 8, 9, 10, 20, 30, 40, 50, 60, 70, 80, 90, or 100 kb upstream or downstream of a biosynthetic gene in the cluster.

The method of any one of the preceding embodiments, wherein a proximity zone is no more than 50 kb upstream or downstream of a biosynthetic gene in the cluster.

The method of any one of the preceding embodiments, wherein a proximity zone is no more than 40 kb upstream or downstream of a biosynthetic gene in the cluster.

The method of any one of the preceding embodiments, wherein a proximity zone is no more than 30 kb upstream or downstream of a biosynthetic gene in the cluster.

The method of any one of the preceding embodiments, wherein a proximity zone is no more than 20 kb upstream or downstream of a biosynthetic gene in the cluster.

The method of any one of the preceding embodiments, wherein a proximity zone is no more than 10 kb upstream or downstream of a biosynthetic gene in the cluster.

The method of any one of the preceding embodiments, wherein a proximity zone is a region between two biosynthetic genes of a biosynthetic gene cluster.

The method of any one of the preceding embodiments, wherein the mammalian nucleic acid sequence is an expressed sequence.

The method of any one of the preceding embodiments, wherein the mammalian nucleic acid sequence is a gene.

The method of any one of the preceding embodiments, wherein the mammalian nucleic acid sequence is a human nucleic acid sequence.

The method of any one of the preceding embodiments, wherein an embedded target gene sequence is homologous to an expressed mammalian nucleic acid sequence in that its base sequence or a portion thereof is at least 50%, 60%, 70%, 80%, or 90% identical to that of an mammalian nucleic acid sequence.

The method of embodiment 14, wherein the sequence or a portion thereof is at least 50, 100, 150, or 200 base pairs in length.

The method of any one of embodiments 1-13, wherein an embedded target gene sequence is homologous to an expressed mammalian nucleic acid sequence in that a product encoded by an embedded target gene or a portion thereof is homologous to that of a mammalian nucleic acid sequence or a portion thereof.

The method of embodiment 16, wherein the product is a protein.

The method of embodiment 16, wherein the protein encoded by an embedded target gene or a portion thereof is at least 50%, 60%, 70%, 80%, or 90% similarity to that encoded by a mammalian nucleic acid sequence or a portion thereof.

The method of embodiment 16, wherein the protein encoded by an embedded target gene or a portion thereof has a 3-dimensional structure that is similar to that of a protein encoded by a mammalian nucleic acid sequence or a portion thereof.

The method of embodiment 19, wherein the portion of a protein encoded by an embedded target gene has a 3-dimensional structure that is similar to that of a protein encoded by a mammalian nucleic acid sequence.

The method of any one of embodiments 19-20, wherein the similarity is that the structures have a Calpha backbone rmsd (root mean square deviation) within 10 square angstroms and have the same overall fold or core domain.

The method of any one of embodiments 19-20, wherein a protein encoded by an embedded target gene or a portion thereof has a 3-dimensional structure that is similar to a protein encoded by a mammalian nucleic acid sequence in that a small molecule binding to a protein encoded by an embedded target gene or a portion thereof also binds to a protein encoded by mammalian nucleic acid sequence or a portion thereof.

The method of embodiment 22, wherein the binding of the small molecule to the proteins encoded by the embedded target gene and the mammalian nucleic acid sequence or portions thereof has a Kd no more 100 μM, 50 μM, 10 μM, 5 μM or 1 μM.

The method of any one of embodiments 22-23, wherein the small molecule is produced by a fungi.

The method of embodiment 24, wherein the small molecule is acyclic.

The method of embodiment 24, wherein the small molecule is cyclic.

The method of any one of embodiments 24-26, wherein the small molecule is a secondary metabolite molecule produced by a fungi.

The method of any one of embodiments 24-27, wherein the small molecule is non-ribosomally synthesized.

The method of any one of embodiments 24-28, wherein the small molecule is a biosynthetic product a biosynthetic gene cluster.

The method of embodiment 16, wherein a portion of the protein encoded by an embedded target gene is at least 50%, 60%, 70%, 80%, or 90% similarity to a portion of the protein encoded by an expressed mammalian nucleic acid sequence.

The method of embodiment 30, wherein the portion of the protein is a protein domain.

The method of any one of embodiments 30-31, wherein the portion of the protein is a set of amino acid residues necessary for a function.

The method of embodiment 32, wherein the function is an enzymatic function.

The method of embodiment 33, wherein the set of amino acid residues contact a substrate.

The method of embodiment 33, wherein the set of amino acid residues contact an intermediate.

The method of embodiment 33, wherein the set of amino acid residues contact a product.

The method of embodiment 32, wherein the function is an interaction with another entity.

The method of embodiment 37, wherein the entity is a small molecule.

The method of embodiment 37, wherein the entity is a lipid.

The method of embodiment 37, wherein the entity is a carbohydrate.

The method of embodiment 37, wherein the entity is a nucleic acid.

The method of embodiment 37, wherein the entity is a protein.

The method of any one of embodiments 32-42, wherein each of the residues of the set is within 4 Å of the entity.

The method of any one of the preceding embodiments, wherein the embedded target gene is co-regulated with at least one gene in the cluster.

The method of any one of the preceding embodiments, wherein the embedded target gene is absent from 80%, 90%, 95%, or 100% of all fungal nucleic acid sequences in the set that are from a different fungal strain and comprises a homologous or identical biosynthetic gene cluster.

The method of any one of the preceding embodiments, wherein the set comprises at least 100, 1,000, 5,000, 10,000, 50,000, 100,000, 500,000, 1,000,000, 1,500,000, 2,000,000 or 2,500,000 distinct fungi nucleic acid sequences.

The method of any one of the preceding embodiments, wherein the set comprises nucleic acid sequences from at least 100, 500, 1,000, 5,000, 10,000, 15,000, 20,000, 22,000, 25,000 or 30,000 distinct fungal strains.

The method of any one of the preceding embodiments, wherein the ETaG sequence is not a house-keeping gene.

The method of any one of the preceding embodiments, wherein the ETaG sequence is or comprises a sequence that is homologous to a second nucleic acid sequence or a portion thereof in the same genome.

The method of any one of the preceding embodiments, wherein the ETaG sequence is or comprises a sequence that encodes a product that is homologous to a product or a portion thereof encoded by a second nucleic acid sequence in the same genome.

The method of embodiment 49 or 50, wherein the homology is at least 50%, 60%, 70%, 75%, 80%, 85%, 90%, 91%, 92%, 93%, 94%, 95%, 96%, 97%, 98%, 99% or 99.5%.

The method of embodiment 49, wherein the homology is at least 70%.

The method of embodiment 49, wherein the homology is at least 80%.

The method of embodiment 49, wherein the homology is at least 90%.

The method of any one of embodiments 48-54, wherein the second nucleic acid sequence is or comprises a housekeeping gene.

The method of any one of embodiments 48-55, wherein the ETaG sequences encode a product that provides resistance to a product of the biosynthetic gene cluster while the second nucleic acid sequence does not.

The method of embodiment 56, wherein the ETaG sequences encode a protein that provides resistance to a small molecule product of the biosynthetic gene cluster while proteins encoded by the second nucleic acid sequence do not.

The method of any one of the preceding embodiments, wherein nucleic acid sequences within the set comprise biosynthetic gene clusters whose biosynthetic genes encode enzymes that participate in synthesis of compounds sharing at least one common chemical attribute.

The method of any one of the preceding embodiments, wherein the nucleic acid sequences are from multiple fungi strains.

The method of any one of the preceding embodiments, wherein the common chemical attribute is or comprises a cyclic system.

The method of any one of the preceding embodiments, wherein the common chemical attribute is or comprises a macrocycle.

The method of any one of embodiments 52-61, wherein the common chemical attribute is or comprises an acyclic backbone.

The method of any one of embodiments 52-62, wherein compounds sharing at least one common chemical attribute are polyketides.

The method of any one of embodiments 52-62, wherein compounds sharing at least one common chemical attribute are non-ribosomal peptides.

The method of any one of embodiments 52-62, wherein compounds sharing at least one common chemical attribute are alkaloids.

The method of any one of embodiments 52-62, wherein compounds sharing at least one common chemical attribute are terpenes/isoprenes.

A method comprising steps of:

contacting at least one test compound with a gene product encoded by an embedded target gene of a fungal nucleic acid sequence, which embedded target gene (ETaG) is characterized in that it:

is not required for or is not involved in the biosynthesis of the product of the biosynthetic gene cluster;

is within a proximity zone relative to at least one biosynthetic gene in the cluster;

is homologous to an mammalian nucleic acid sequence; and is optionally co-regulated with at least one biosynthetic gene in the cluster; and determining that:

level or activity of the gene product is altered when the test compound is present as compared with when it is absent; or level or activity of the gene product is comparable to that observed when a reference agent having a known effect on the level or activity is present.

The method of embodiment 67, wherein the ETaG is an ETaG as described in any one of embodiments 1-66.

The method of embodiment 67 or 68, wherein the mammalian nucleic acid sequence is a human Ras sequence.

The method of embodiment 69, wherein the mammalian nucleic acid sequence is a KRas, HRas, or NRas sequence.

The method of embodiment 67 or 68, wherein the mammalian nucleic acid sequence is a sequence encoding a RasGEF domain.

The method of embodiment 67 or 68, wherein the mammalian nucleic acid sequence is a sequence encoding a RasGAP domain.

The method of any one of embodiments 66-72, wherein the ETaG is an ETaG in one of FIGS. 1-39.

The method of any one of embodiments 66-73, wherein the biosynthetic gene cluster is a biosynthetic gene cluster in one of FIGS. 1-39.

The method of any one of embodiments 66-74, wherein the test compound is a biosynthetic product of the biosynthetic gene cluster or an analog thereof.

A method comprising steps of:

contacting at least one test compound with a gene product encoded by an expressed mammalian nucleic acid sequence, which sequence is the expressed mammalian nucleic acid sequence to which the embedded target gene sequence of any one of embodiments 1-75 is homologous.

The method of embodiment 76, wherein the mammalian nucleic acid sequence is a human Ras sequence.

The method of embodiment 77, wherein the mammalian nucleic acid sequence is a KRas, HRas, or NRas sequence.

The method of embodiment 76 or 77, wherein the mammalian nucleic acid sequence is a sequence encoding a RasGEF domain.

The method of embodiment 76 or 77, wherein the mammalian nucleic acid sequence is a sequence encoding a RasGAP domain.

The method of any one of embodiments 76-80, wherein the ETaG is an ETaG in one of FIGS. 1-39.

The method of any one of embodiments 76-81, wherein the biosynthetic gene cluster is a biosynthetic gene cluster in one of FIGS. 1-39.

The method of any one of embodiments 76-82, wherein the test compound is a biosynthetic product of the biosynthetic gene cluster or an analog thereof.

A method comprising:

identifying a human homolog of an ETaG that is within a proximity zone relative to at least one biosynthetic gene of the biosynthetic gene cluster; and optionally assaying an effect of the product produced by enzymes encoded by a biosynthetic gene cluster, or an analog of the product, on the human homolog.

The method of embodiment 77, wherein the ETaG is an ETaG as described in any one of embodiments 1-66.

A method for identifying and/or characterizing a modulator of a human target, comprising:

providing a product or an analog thereof, which product is produced by the enzymes encoded by a biosynthetic gene cluster, wherein, within a proximity zone relative to at least one gene in the biosynthetic gene cluster, exists an ETaG that:

is homologous to the human target, or a nucleic acid sequence that encodes the human target; and is optionally co-regulated with at least one biosynthetic gene in the cluster.

The method of embodiment 86, wherein the ETaG is an ETaG as described in any one of embodiments 1-83.

The method of embodiment 86, wherein the human target is a Ras protein.

The method of embodiment 88, wherein the human target is a KRas, HRas, or NRas.

The method of embodiment 86, wherein the human target comprises a RasGEF domain.

The method of embodiment 86, wherein the human target comprises a RasGAP domain.

The method of any one of embodiments 86-91, wherein the ETaG is an ETaG in one of FIGS. 1-39.

The method of any one of embodiments 86-92, wherein the biosynthetic gene cluster is a biosynthetic gene cluster in one of FIGS. 1-39.

A method for modulating a human target, comprising:

providing a product or an analog thereof, which product is produced by the enzymes encoded by a biosynthetic gene cluster, wherein, within a proximity zone relative to at least one biosynthetic gene in the biosynthetic gene cluster, exists an ETaG that:

is homologous to the human target, or a nucleic acid sequence that encodes the human target; and is optionally co-regulated with at least one biosynthetic gene in the cluster.

The method of embodiment 94, wherein the human target is a Ras protein.

The method of embodiment 94, wherein the human target is a KRas, HRas, or NRas.

The method of embodiment 94, wherein the human target comprises a RasGEF domain.

The method of embodiment 94, wherein the human target comprises a RasGAP domain.

The method of any one of embodiments 94-98, wherein the ETaG is an ETaG in one of FIGS. 1-39.

The method of any one of embodiments 94-99, wherein the biosynthetic gene cluster is a biosynthetic gene cluster in one of FIGS. 1-39.

The method of embodiment 94, wherein the ETaG is an ETaG as described in any one of embodiments 1-93.

A database comprising:

a set of nucleic acid sequences, each of which is found in a fungal strain and comprises a biosynthetic gene cluster;

wherein the set of nucleic acid sequences are embodied in a computer readable medium.

The database of embodiment 102, wherein one or more embedded target genes of any one of embodiments 1-101 are indexed.

A system comprising:

one or more non-transitory machine-readable storage media storing data representing a set of nucleic acid sequences, each of which is found in a fungal strain and comprises a biosynthetic gene cluster.

A system comprising:

one or more non-transitory machine-readable storage media storing data representing a set of nucleic acid sequences, each of which is or comprises a ETaG sequence.

The system of embodiment 105, wherein one or more embedded target genes of any one of embodiments 1-101 are indexed.

A computer system, adapted to perform a method of any one of embodiments 1-101.

A computer system, adapted to access a database of any one of embodiments 95-103.

EXEMPLIFICATION

Non-limiting examples of provided technologies are described below.

Example 1. Construction of Example Databases and their Example Uses

Around 2,000 reported fungi genomes were processed to identify potential biosynthetic gene clusters, using, for example, antiSMASH, and approximately 70,000 identified biosynthetic gene clusters were added to a database. Human targets of interest were used to query the initial database. For example, protein sequence of human Sec7 was used to BLAST search against the initial library to identify ETaGs. Alternatively and additionally, the biosynthetic gene clusters can be compared among themselves. For example, in one process, non-biosynthetic genes present at one or some biosynthetic gene clusters (within a proximity zone relative to at least one biosynthetic gene of the biosynthetic gene clusters) but are absent from most other homologous biosynthetic gene clusters for the same biosynthetic product are identified as potential ETaGs, and are further confirmed by analyzing whether they have homologous mammalian nucleic acid sequences (e.g., human genes) at nucleic acid level and/or, preferably, protein level. Identified ETaGs can be indexed/marked and annotated. The database is searchable by either nucleotide sequence (e.g., BLASTN; tBLASTx) or protein sequence (e.g., tBLASTn).

Results from a BLAST query of a human target were, in some embodiments, listed in order of strength of sequence homology, indicating all putative hits within the database. DNA sequences of all hit biosynthetic gene clusters were then inspected to verify that one or more open reading frame (gene) homologs of the target protein was within the predicted confines of the biosynthetic gene clusters.

In some embodiments, GenBank-formatted sequence files (*.gbk) of each biosynthetic cluster were assembled and curated, from which the ETaG protein sequence was obtained through prediction algorithms, e.g., those comprising antiSMASH and/or methods. The protein families (pfam) function of open reading frames can be predicted by, e.g., antiSMASH, and the nucleotide distance between each identified ETaG and its nearest biosynthetic enzyme predicted by antisSMASH can be determined. In some embodiments, the closer a predicted ETaG is to a biosynthetic enzyme, the higher the likelihood that this open reading frame encodes a legitimate ETaG.

Applicant has successfully identified many biosynthetic gene clusters with related ETaGs beyond the several bona fide ETaG-containing biosynthetic gene clusters (biosynthetic gene clusters for cyclosporine, fellutamide, lovastatin, mycophenolic acid, and brefeldin).

In some embodiments, the present disclosure encompasses the recognition that an ETaG can serve as a functional homolog (an ortholog) of a putative human target protein. In some embodiments, protein sequences of putative ETaG hits were compared to the sequence of human target orthologs. For example, in a project to find ETaGs of human Protein A, n biosynthetic gene clusters were found containing a putative Protein A homolog, and all of the n predicted ETaG proteins were aligned with the human Protein A. In some embodiments, only amino acids within the specific catalytic or structural domain defining the pfam boundaries of the ETaG/target (e.g., based on predictive subfamily domain architecture) were used in an alignment analysis. The ETaG sequences were directly compared to their human counterparts by aligning all ETaGs and human target protein(s), with their phylogenetic relationships yielding quantitative correlative data (e.g. peptide sequence similarity and/or evolutionary tree visualization). Additional analysis can include conservation/similarity of essential structural elements of protein effector recruitment/binding, for example, based on the examination of the tertiary protein structure of the human target. For example, in some embodiments, aligned sequences were compared to the PDB crystal structure corresponding to the target protein residues within 4 Angstrom of the corresponding engaging proteins. Without the intention to be limited by any theory, in cases where these structural motifs are conserved within fungal ETaGs, it may indicate an increased probability that the metabolite produced by the ETaG-related biosynthetic gene cluster is an effector of both fungal and human target proteins, and the metabolite produced can be a drug candidate, or a lead for drug development, toward the human target. In some embodiments, the above analyses were used to prioritize ETaGs and their related biosynthetic gene clusters, and metabolites produced from the biosynthetic gene clusters, with respect to targeting human targets.

Example 2. Modulators for Human Targets—Sec7

Among other things, the present disclosure provides technologies for identifying modulators for human targets. In some embodiments, a human sequence is utilized to query a provided database to identify biosynthetic gene clusters in whose proximity zone exists a homolog of the human sequence.

For example, among other things, the present disclosure provides biosynthetic gene clusters whose biosynthetic products may modulate Sec7 functions. To identify modulators for human Sec7 domain, Sec7 protein sequence was used to query a database, e.g., the database provided in Example 1. An example Sec7-homologous ETaG was identified in *Penicillium vulpinum* IBT 29486 with a related biosynthetic gene cluster—the ETaG is in a proximity zone relative to one of the biosynthetic genes of the biosynthetic gene cluster. See FIG. 1, FIG. 18 and FIG. 19. Among other things, the identified biosynthetic gene cluster shares homology with the biosynthetic gene cluster for Brefeldin A in *Eupenicillium brefeldianum*, and was expected to produce Brefeldin A. Therefore, Brefeldin A was identified as a candidate modulator, and/or a lead compound for modulators, of Sec7. If desired, the result can be optionally validated by expressing the biosynthetic gene cluster of *Penicillium vulpinum* IBT 29486 and isolating and characterizing its product, and then assaying functions of the product against Sec7 using a number of methods available in the art in accordance with the present disclosure. As it has been reported that Brefeldin A targets Sec7 domain of human GBF1, this example illustrates that provided technologies can be successfully utilized to identify modulators of human targets.

Example 3. ETaGs of Lovastatin, Fellutamide, and Cyclosporine

Provided technologies can be utilized to identify ETaGs for various entities. For example, as demonstrated herein, provided technologies can be used efficiently to identify EtaGs related to Lovastatin, Fellutamide, and Cyclosporine. Example results were presented in FIGS. 2-4.

Example 4. Modulators for Human Targets—Ras

Among other things, the present disclosure provides biosynthetic gene clusters whose biosynthetic products may modulate one or more functions of Ras proteins, and/or proteins that comprise RasGEF domain (e.g., KNDC1, PLCE1, RALGDS, RALGPS1, RALGPS2, RAPGEF1, RAPGEF2, RAPGEF3, RAPGEF4, RAPGEF5, RAPGEF6, RAPGEFL1, RASGEF1A, RASGEF1B, RASGEF1C, RASGRF1, RASGRF2, RASGRP1, RASGRP2, RASGRP3, RASGRP4, RGL1, RGL2, RGL3, RGL4/RGR, SOS1, SOS2, etc.) and/or RasGAP domain (DAB2IP, GAPVD1, IQGAP1, IQGAP2, IQGAP3, NF1, RASA1, RASA2, RASA3, RASA4, RASAL1, RASAL2, SYNGAP1; etc.). Ras proteins, e.g., HRas, KRas, and NRas, are connected to many human cancers but are notoriously difficult targets for drug discovery. Among other things, the present disclosure provides technologies for developing Ras modulators, including Ras inhibitors.

Human Ras sequences were used to query provided databases, e.g., the database of Example 1. 8 example ETaGs were identified from different strains with various levels of sequence similarity to the human Ras proteins. The related biosynthetic gene clusters encode enzymes to produce different types of compounds. See FIGS. 5-12 and FIGS. 20-27. Identified ETaGs encoding proteins can be highly homologous to human Ras proteins. For example, see FIG. 13 for similarity of nucleotide binding residues, FIG. 14 for BRAF interacting residues, FIG. 15 for rasGAP interacting residues, and FIG. 16 for SOS interacting residues.

Similarly, biosynthetic gene clusters whose biosynthetic products may modulate RasGEF and RasGAP domains are identified. As demonstrated herein, example identified biosynthetic gene clusters can contain genes and/or modules that involve in synthesis of various types of moieties/products, e.g., terpene, PKS, NRPS, etc. For example identified biosynthetic gene clusters and RasGEF and RasGAP homologs, see FIGS. 28-39.

Figure 5:
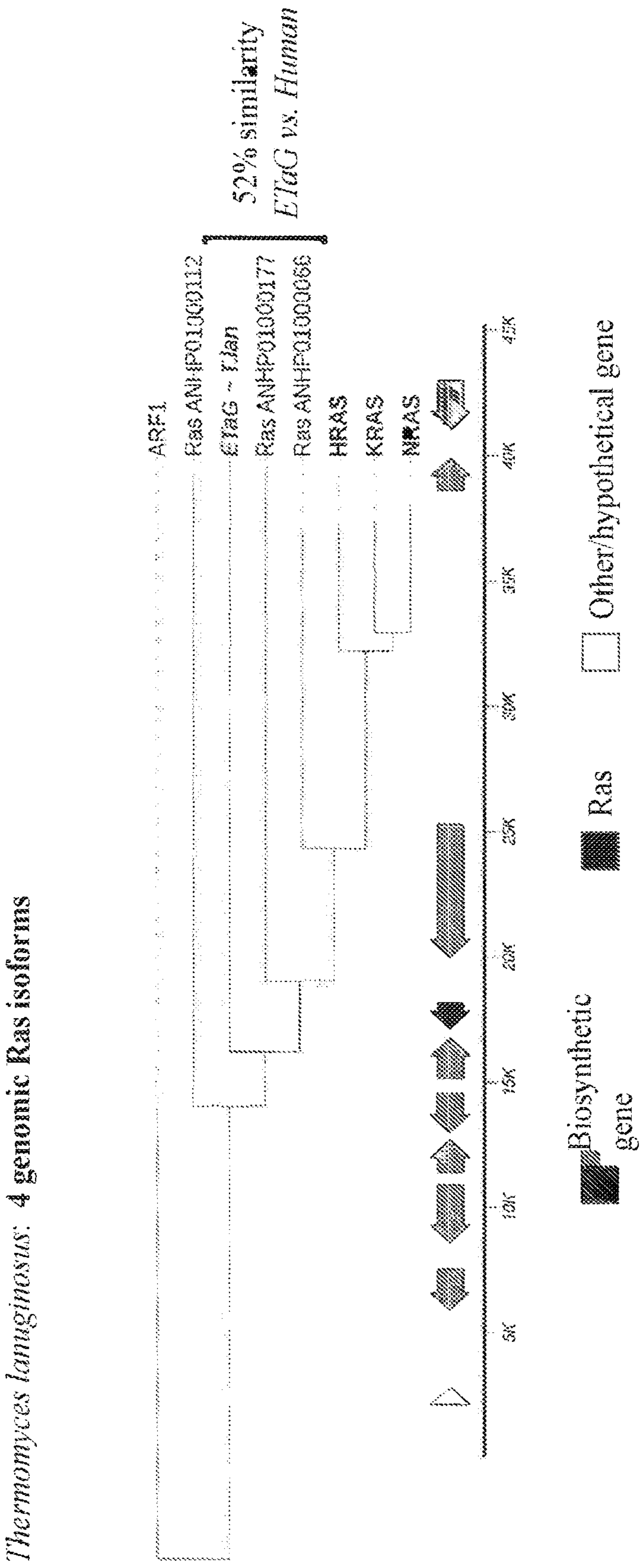
FIG. 5 depicts a Ras ETaG identified in *Thermomyces lanuginosus* ATCC 200065 (public). The example ETaG identified is from the Ras family (pfam00071). Sequence similarity is of Ras domain calculated using MUSCLE alignment algorithm. The ETaG is presented below the scale.

Example identified ETaG sequences are listed below:

FIG. 5: *Thermomyces lanuginosus*. Ras ETaG sequence:

```
ATGCAGCCGCGGTGAGTGTTGGTCGCGCTCCTTGGCAAAGGTCAATACTAATTGGAC
ACAGGCGGGAATATCATATTGTCGTCCTGGGAGCTGGTATGTCGAGAAGAGATTCG
CCACAGCCTATCAGTCGATATGTGTCCCTAACAATGTTATACAGGAGGCGTCGGGAA
GAGCTGCTTGACAGGTATGGACGCGATGGACTGCGGCGACAACATGCGACCGATGG
CTCACTAACTTATCTCATAGCTCAATTTGTACAAAATGTTTGGATTGAGAGTTACGA
CCCGACAATTGAAGATTCCTATCGAAAGCAGATTGAAGTCGATGTGAGTTCCCGTGG
```

CATTGATGCGATTATACCACCTGCTTACGATATTCTATTCGCAGGGTCGACAATGCA
TTCTCGAGATGTACGTCTCTCTTCAGAGCTGTCGCGGAGCTATTTCATCTTACTGATC
ACCGTGCAGTCTGGACACAGCCGGAACAGAGCAATTCAGTACGTCTTAACCTCCCA
ACTCCGATGAAAAGGACCATCCACTAACGATGACGACAGCTGCGATGAGGTATTAC
ACGTCAATGCGGCGCACATGGCCAATGAAGTTGACATGACTGTCCAGGGAAATTTA
CATGAAACAAGGGCAGGGATTCCTGCTAGTCTTCTCGATCACCAGCATGTCATCGCT
GAACGAGTTATCGGAAATCCGGGAGCAGATCCTCCGCATCAAGGACGATGACAAGG
TCCCTATGGTGATCGTCGGCAACAAGTCCGATCTCGAGGAAAACCGAGCTGTGCCTC
GTAGCAAAGCGTTTGCGCTCTCGCAGAGCTGGGCAACGCTCCTTACTACGAAACAT
CCGCTCGACGGCGAGCAAACGTCAACGAGGTCTTCATTGACCTGTGCCGACAGATC
ATCCGCAAGGATCTGCAAGCTACACAGGCAAAGCAAGCGGAAGCCAGACAAGTTA
AGCGAGAGGCGACTCCTCGCAATGACAGGAGCAAGAAGGATAGAAAATCCACAAG
GCGTCGGCATCAATGCGCGATTATGTGA (SEQ ID NO: 1).

Figure 6:
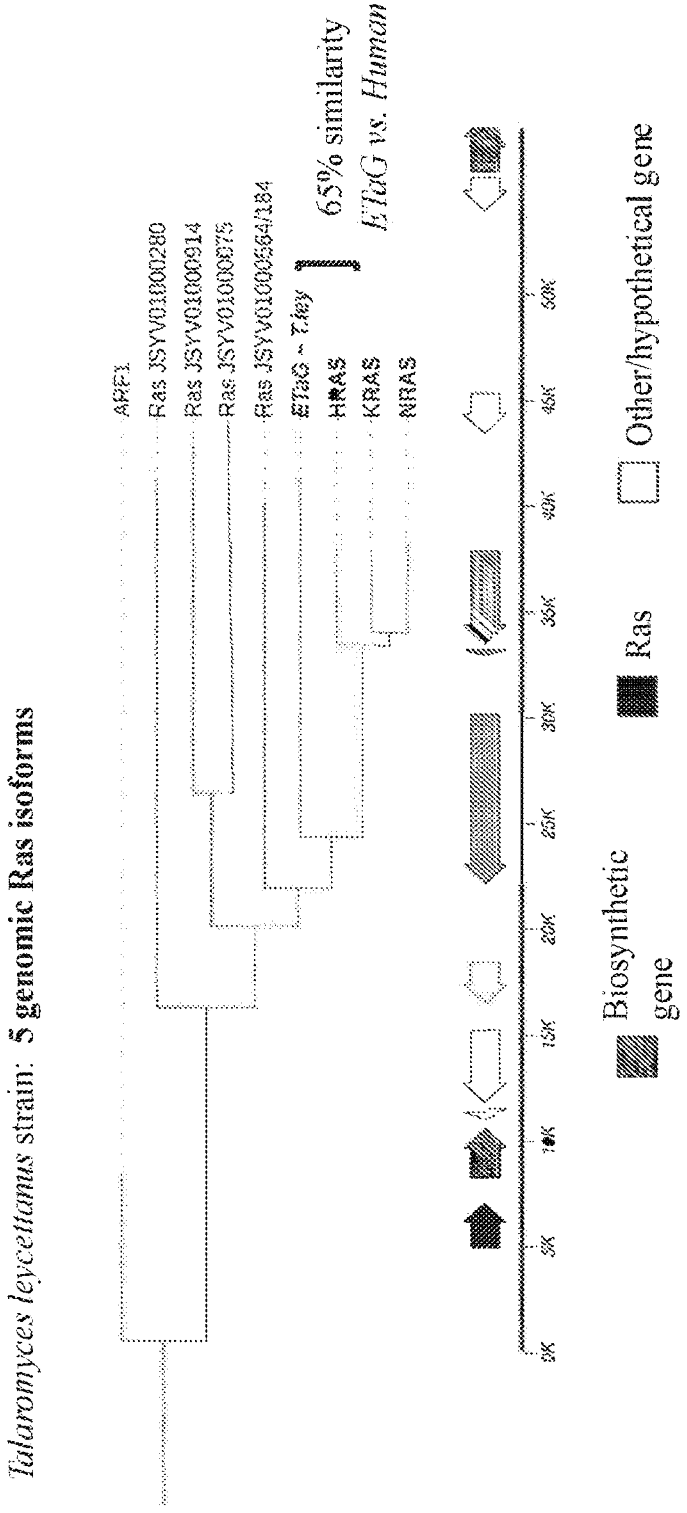
FIG. 6 depicts a Ras ETaG identified in *Talaromyces* leycettanus strain CBS 398.68. The example ETaG identified is from the Ras family (pfam00071). Sequence similarity is of Ras domain calculated using MUSCLE alignment algorithm. The ETaG is presented below the scale.

FIG. 6: *Talaromyces leycettanus* CBS 398.68. Ras ETaG sequence:
ATGCTGGAAGTGCTAGACACAGCGGGCCAGGAAGAGTACACCGCACTGAGAGACC
AGTGGATCCGCGATGGTGAAGGGTTCGTTCTCGTCTATAGCATCACATCGCGAGCGT
CGTTCGCCCGCATACCCAAGTTCTACAATCAGATCAAGATGGTTAAAGAATCGGCAA
GCTCCGGGTCACCCGCTGGAGCCAGCTACTTGACGTCGCCGATCAATTCTCCCTCGG
GACCCCCGCTTCCTGTGCCGGTAATGTTGGTTGGCAACAAGAGCGACAAGGCGATG
GACCGCGCCGTCTCTGCGCAGGAAGGCCAAGCTCTTGCCAAGGAGCTGGGGTGCGA
ATTCGTCGAGGCTTCCGCCAAGAACTGTATCAATGTCGAAAAGGCTTTCTACGACGT
CGTGAGGATGCTTCGGCAGCAGCGACAACAGCAACAGGGAGGACGGGCGCAGGAG
CGGCGACCCGCCGCTTTCGGATCAGGGCCAATGCGCGATCGGGACGCCGGTCCCGA
GTACCCAAAGTCGTTTCGTCCGGATCGATCAAGGCATCGCAATGGCCTCAAATGCGT
TATCCTATGAGCTCCCCCGATGAGTGTTCCGATCGGCGGATCTTTCCAGCTTCTGAC
CTCCGCTTATTCATGACCGTTGCTCTCTAGAATGGATGGTGTCTAGCTCCGTGTTTCT
CTTTCTCGGAGCGTGTGAGCGAGCTTGAGGACAGTCGTTCCACTTGTGCCCCCTCCT
ATCCGCCGCAGGCCCTTGTCGCTGCCGCTTTGCGGACCGCTCGTTTTGTCTACGTTGT
ACTCGAAAGCACGGCCTCTGCTTTCGTGGAAGTCTCCCTTTATGCCAGCTTTGGGTG
CGGTGGTCGATATGCAGATACTGTGTTCTATGCTCGCTGCATGCGATTCAGAGGCGT
CTTGATTCCCCGTGTCAGTATGGGGTGTTCTCGCTATTCAGGGAATCATCTGAAACC
AATTTTTCTCATCCGTTCTGTTTTTGGGAATCGGAACACGGGGGGGATGTCTGGAAA
TCTGGACCTATAACTATAGAAATGTTTCTCACCACCTTTCTCACTCAACCCTCTTGAT
GAATATCCGCCCGGCGTCTTCTACTACTTCCTACCGTCTACTACCACCAATCTCTATT
CTTCTTACCACCCACCTTCTGAGCCACTTCTTACACATCATTCTCGTTTGGTTTGACA
GCAAAGCGGGGAGAGTTCGAAGGACAGATCCCATGCAGGATTGGAGGACGAGAGG
GGAAGAGTCGAAGGGAGAAAAATAATTAAAAAAAAGAAAGGTGCGGGGGCAGAAG
GAGGCAGGTTTGGTTGAGAGTTGCGAATCGGTCCTGTCGCAGTCAAGTCCCAAAAA
AGAAAAGATCGCAGTCGGCGCATTAGCAGGCATTTTGATACGATGATACCCTACAG
CCGAGCTTCGAGTTTTTGTGTTCCTTTTCCTTTTTTGCAAATGCTGATTTAAAAAAAT
AACAATAGAGCTACATACTGAATGTGGATTTTTTTGACCTCTCATCTTTTTGTTGCAG
GGATGACCGCCAATTGGTAAATTCATCCCCAGTCATAATCCGAGCGCAGGATGCATG
AACTCCAGTACCTCATCATATCGCCTGCACGTTCAAGTTCCATCAATCATTCGGCGG
CGCCTACTCTGTACGACTAAGTCTACGGAGTTTGTTCTTGTTGCGGGGAAGGAAGCG
AAAGCCACGACTCCAACAAACAAACTCAGGGTGAATTGAATCCTCAGTTTCTACTCT
GTAGCCGAAGAGCCATCATTACCATTCAGGGGAAGAGCCTAAAGAGCTTGCGAGGT
TGGGCTGAGCTGCTGTGCAGTGAGCAATATATTTGGTCGATGTTTTGGATACGTTAT
CTGGAATGCGCAGATGCAGTGGTTATGCATATCCTCACGTACTCGATTCTGATGATT
CACGGGACCATACGGAGTCGATACCGAGACTCTCGCTACAAACCTGTCAATTGATAT
CGTGTACAGAGTACCGGAGCCGAGACTGGGAAATAGCACAGTCTCAGTCTCAGGTA
GCTATCGATCAATTTGACAAGGTTAGAAGTATCTCGCTAGTAATTGCCAGATGATTC
ATTCCCGGTTGAAAACTTTTCCATTGGCCTTCTTCGCTTAG (SEQ ID NO: 2).

Figure 7:
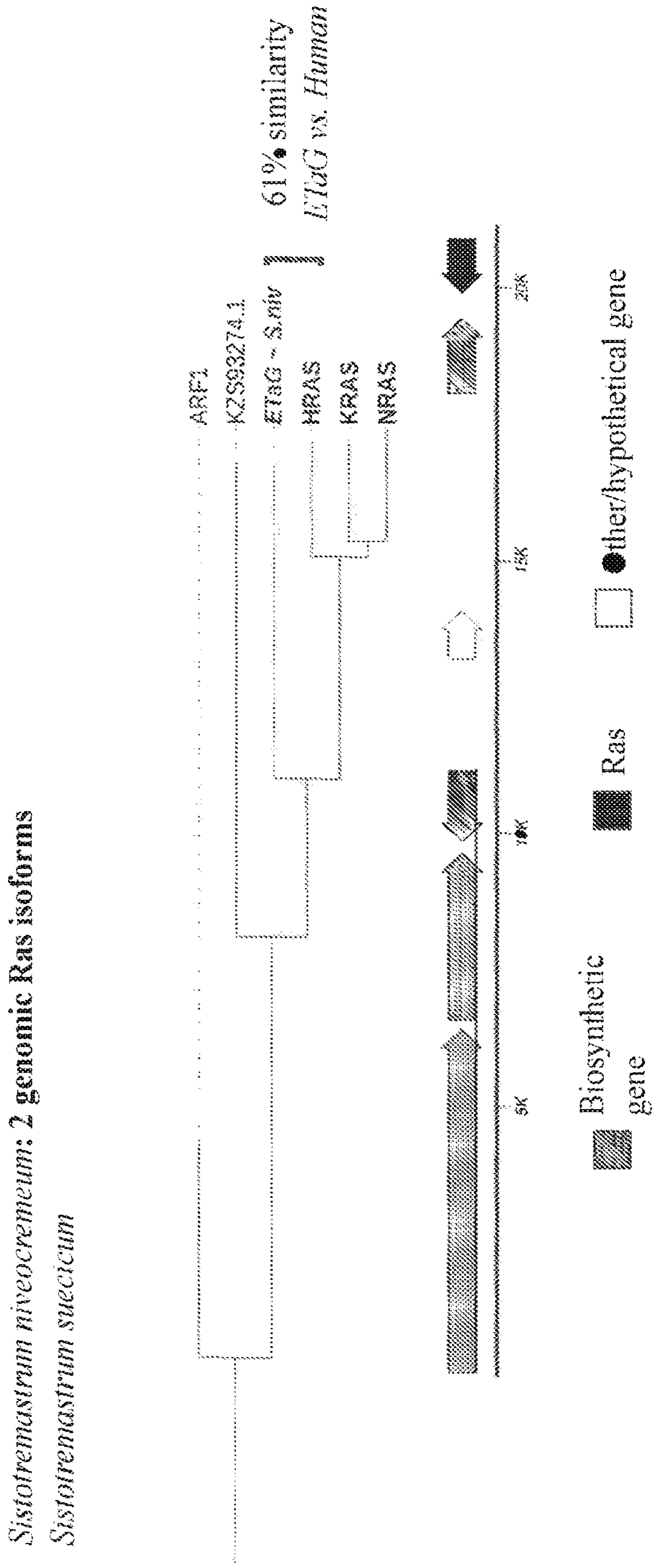
FIG. 7 depicts a Ras ETaG identified in *Sistotremastrum niveocremeum* HHB9708, or in *Sistotremastrum suecicum* HHB10207 (National Forestry Service). The example ETaG identified is from the Ras family (pfam00071). Sequence similarity is of Ras domain calculated using MUSCLE alignment algorithm. The ETaG is presented below the scale.

FIG. 7: *Sistotremastrum niveocremeum*. Ras ETaG sequence:
ATGTCGAGAGTGAGTATTTCTGTTTATTGCGGCTCTATCTTGATCTCACTCGTCGCTA
GTCTGCTGCTCAGGCTTCGTTCCTTCGCGAATACAAGCTCGTCGTCGTCGGTGGTGGT
GGTATGAGCCTTGTCTCTCGTTCTCTGCAATCAAAATCTCACTCGCTTTTCTCTTGTG
CTGCCTAGGTGTTGGCAAATCCGCTCTGACCATTCAATTCATCCAAAGTCATTTCGTT
GACGAGTATGACCCTACTATCGAAGGTCAGCCGACCGCTAGGCAACCATTATCTGAT
CAAACAGCTCATCTCGCACTCGACAGATTCTTACAGAAAGCAATGTGTCATCGATGA
TGAAGTTGCCCTTTTGGATGTGTTAGATACCGCTGGGCAGGAAGAATATGGGTGAGC
TCGTCTCGCAGCCCGATTCCCACGCTTATTGCTAACACGACATCGGCAGCGCAATGC
GAGAACAGTATATGCGAACGGGAGAAGGATTCTTGCTTGTCTACTCGATAACGTCGC
GGAACTCTTTCGAAGAAATCAGCACTTTCCATCAGCAAATTCTTCGAGTAAAAGACA
AGGATGCGTTCCCGGTTATCGTGGTAGCCAACAAGTGTGACCTTGAATATGAGCGAC
AAGTCGGCATGAACGGTGCGTTTTTAGTGTTGTTTCAATCAACATTGTGACTCATCCT
TCGTCAGAGGGCCGTGACCTGGCCAAGCACTTCAACTGCAAATTTATCGAGACCTCG
GCGAAGCAGCGAATCAACGTTGATGAGGCCTTTTCGAACCTTGTTCGAGAGATTCGC
AAATTCAACAAGGTATGTAAGCCCAAACCCGACGGAACTCCCGGCCTGATCTCTTTA
CAGGAACAACAGACCGGACGTCCTGCGACCATGGCTCCGAGCGGCCCTGTGGGTGC
ATTCGGTGGTCCCCCCGGCATGGAAGATGGACCTCATGACGCTGGTTGCTGCTCTGG
ATGTGTCGTTGTATAA (SEQ ID NO: 3).

*Sistotremastrum suecicum*. Ras ETaG sequence:
ATGTCGAGAGTGAGTATTTCTGTTTATTGCGGCTCTATCTTGATCTCACTCGTCGCTA
GTCTGCTGCTCAGGCTTCGTTCCTTCGCGAATACAAGCTCGTCGTCGTCGGTGGTGGT
GGTATGAGCCTTGTCTCTCGTTCTCTGCAATCAAAATCTCATTCGCTTTTCTCTTGTG
CTGCATAGGTGTTGGCAAATCCGCTCTGACCATTCAATTCATCCAAAGTCATTTCGTT GACGAGTATGACCCTACTATCGAAGGTCAGCCGACCGCTAGGCAACCATTATCTGAT
CTAACAGCTCATCTCGCACTCGACAGATTCTTACAGAAAGCAATGTGTCATCGATGA
TGAAGTTGCCCTTTTGGATGTGTTAGATACCGCTGGGCAGGAAGAATATGGGTGAGC
TCGTCTCGCAGCCCGATTCCCACGCTTATTGCTAACACGACATCGGCAGCGCAATGC
GAGAACAGTATATGCGAACGGGAGAAGGATTCTTGCTTGTCTACTCGATAACGTCGC
GGAACTCTTTCGAAGAAATCAGCACTTTCCATCAGCAAATTCTTCGAGTAAAAGACA
AGGATGCATTCCCTGTTATCGTGGTAGCCAACAAGTGTGACCTTGAATATGAGCGAC
AAGTTGGCATGAACGGTGCGATTCTAGTGTTGTTTCTGTCGATATTGGGACTTATCCC
CCTTCAGAGGGCCGTGATTTGGCCAAGCACTTCAACTGCAAATTTATCGAGACATCG
GCGAAGCAGCGAATCAACGTTGATGAGGCCTTTTCCAACCTTGTTCGAGAGATTCGC
AAATTCAACAAGGTATGTAAGCCCAAACCCGACGGAACTCCCGGCCTGATCTCTTTA
CAGGAACAACAGACCGGACGTCCTGCGACCATGGCTCCGAGCGGCCCTGTGGGTGC
ATTCGGTGGTCCCCCCGGCATGGAAGATGGACCTCATGACGCTGGTTGCTGCTCTGG
ATGTGTCGTTGTATAA (SEQ ID NO: 4).

Figure 8:
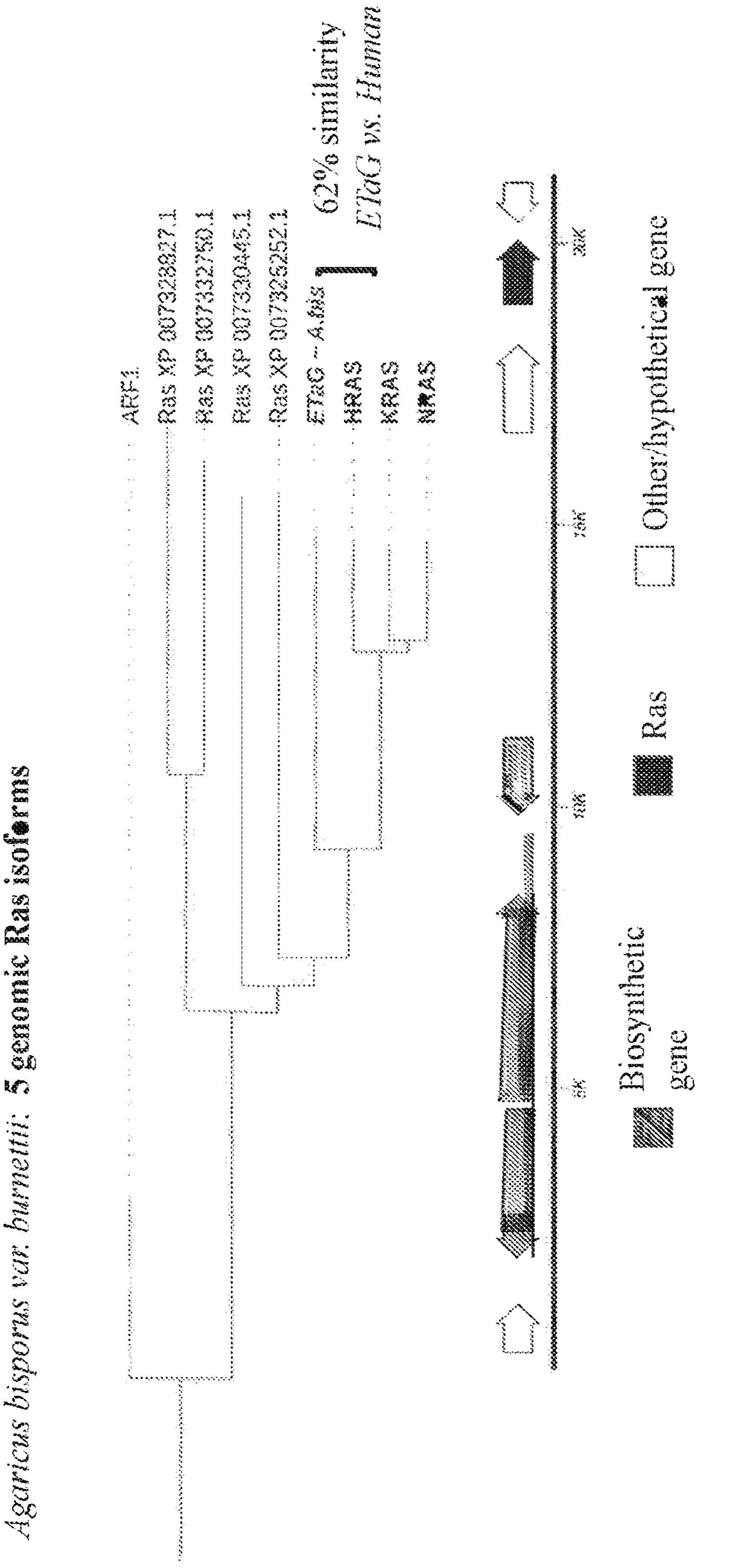
FIG. 8 depicts a Ras ETaG identified in *Agaricus bisporus* var. *burnettii* JB137-S8 (Fungal Genome Stock Center). The example ETaG identified is from the Ras family (pfam00071). Sequence similarity is of Ras domain calculated using MUSCLE alignment algorithm. The ETaG is presented below the scale.

FIG. 8: *Agaricus bisporus* var. *burnettii* JB137-S8. Ras ETaG sequence:
ATGGCAAACAACGCTGCGTCCAGAGTATGTCCTCCCCACAAACCACCCTCAGTTGCC
TGGCTTATGCTCTATTTCAGGCTGCTCAGGCCCAGTTCCTGAGAGAATACAAGCTCG
TAGTGGTCGGAGGAGGAGGCAAGTGCTACCCGCCCTTACAAGCTAGCAAGTCCTAA
AGTCGTGTACAGGTGTTGGAAAATCTGCATTGACTATCCAATTCATTCAAAGCCATT
TCGTGGACGAGTACGACCCAACTATCGAGGGTGAGCTTCTTTCTCACCAATCAATCC
CCTTCCAGGTTATGACATTTCGGAACATTTGTGCTAACATTCTCGTCTTAAAACAGAC
TCGTACAGGAAACAATGCGTCATTGATGAAGAGGTCGCCCTTCTCGATGTCCTGGAT
ACCGCTGGTCAAGAAGAATATGGGTCAGTGTGCTCTCCTGAATAAATTCCGAAGCA
GTCCCCGATTTTTTTTCCTTTCGTCTCGTGATTCGACTATGAAAATGGTCTTCCACGA
GGCGAAGCTTTCATTTCCCGGCATAATTCAGTTATACGACCCTGGATCTAACCCTAT
ATGTACTTATTTTCCAGTGCCATGCGGGAGCAATACATGCGTACTGGGGAGGGATTT
CTTCTCGTCTACAGCATCACCGCGCGTAGCTCCTTTGAAGAAATCAACCAGTTTTAC
CAGCAAATTTTGAGGGTCAAAGATCAAGATTCTTTCCCTGTTATTGTCGTTGCAAAC
AAGTGCGATTTGGAATATGAACGCCAAGTTGGTATGAACGGTATGTTATCAAACCTT
GGAGTATATCAGGGCCCCAGTAGTGACGCAACCTACAGAGGGCCGAGATCTCGCGA
GACATTTTGGCTGCAAATTCATCGAGACGTCTGCCAAACAACGAATAAACGTGGAT
GAAGCTTTCAGCAATCTTGTTCGTGAAATCCGAAAATATAACAAGGTCGGTTTTCCG
CATCACACGCAGAGATTTTACAAACTCATTGGTGCTTTTATAGGACCAACAAACAGG
CCGCCCTCTCCACGGCAGCGGTGGTGGAGCCGGCGGTTATGGTGGCAAGGACCACA
ATGACGATGGAGGTGCTGGCTGCTGCGGCGGTTGCGTTATTCTTTAA (SEQ ID NO: 5).

Figure 9:
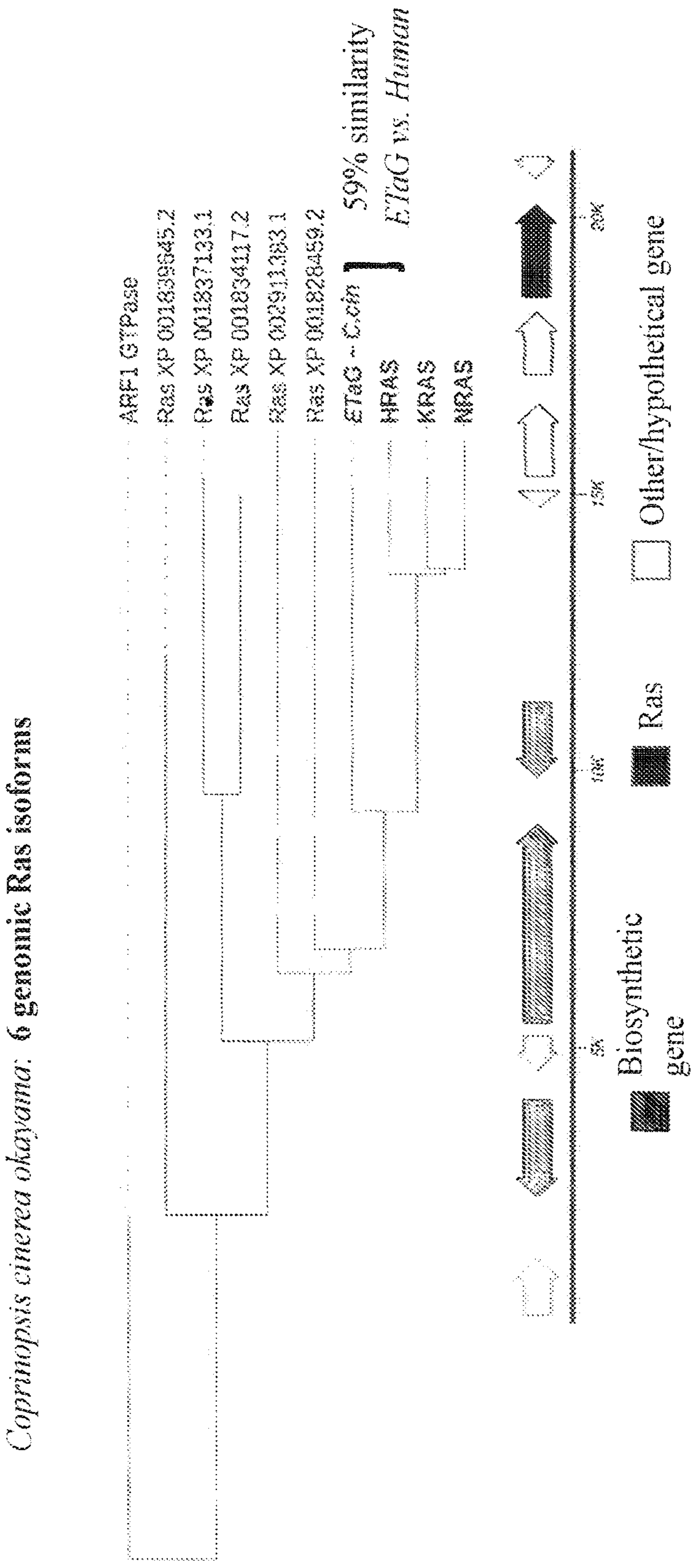
FIG. 9 depicts a Ras ETaG identified in *Coprinopsis cinerea* okayama 7 #130 (Fungal Genome Stock Center). The example ETaG identified is from the Ras family (pfam00071). Sequence similarity is of Ras domain calculated using MUSCLE alignment algorithm. The ETaG is presented below the scale.

FIG. 9: *Coprinopsis cinerea okayama*. Ras ETaG sequence:
ATGCCTGAGGTGATGAATGCTATGTACGCCACGAAAGGCGGTATCTTCGACGTCAGC
GAGAATGATAAGGTTTGGCGTTTGCAGTGTTTCAAAGCTGGCCTCTGTTGTGTTGGA
GAATACTCGGATGCTGATATACATATGGTTTATCGAATACAAGTACGCGTATAAGGA
AAGCTGGGGTAGACAAGGGACTATAGCTGGATCTTAACTCCCAGGAGGGGACGACA
TGAGAGAATGCGGTCTACAGCAATTCTGATGCTCGAAAATCCATCAGCAGAGGTCA
ACCTTGGGTTTCTAGCGAAAAGAAGGGAGATAGGAAGCCCGGAATATCAAAACACG
CGTCGGATTGTGGTCCAAATTGAAAAATGACCGAGAGCCTCGAGCTCGTGTCGCGA
GATGTTTGCACTTGAGATTTAAACTCCGCTGATGATGGCCTTTGAAGTGAGTTTGGTT
ACGATGTTTAGAGGAACCCAGTCGCCCCCTGCTCCCGCTCAACTCCCTAAATACCCT
TCCTGACCATCTTCTTTCTTTCCCAAATCTTTTTCTTCTCTTTCAACAGATTTCATTTCT
GAAGCATGGCTGCCAGGGTCCGTCAAATCCCACAGTCTGCACCGTGGAACCTCAGC
AAACTCACACAGCGTCCAACAGGCTCAGTTCTTGAGGGAGTACAAGCTCGTCGTCGT
AGGTGGTGGTGGTATGTTGCACAGCTCTTAGAACGGAATGTAGTCTCACCTGTGGTG
CCCCAGGTGTTGGAAAGTCGGCCCTGACTATTCAGTTCATCCAATCCCACTTCGTGG
ATGAATATGACCCGACTATCGAAGGTCCGTATAACAAGGCCTTCTCTCGCAAGGATG
CAATAGCTTATGCTTATTCGACACAGACTCGTACAGAAAACAGTGCATCATCGACGA
CGAGGTCGCACTCCTCGACGTTCTCGATACCGCCGGACAGGAAGAGTATGGGTGAG
TACCCGCGCTGCACCCCTCTATTTTCCACCGAATGCTTCGTGGACAGCCCAACTTTTG
ATCCTCGTATCCCATACCACCGCTTTCCTTGTTCCCGGAATCTTTGCATCACCACCTC
TCCACCTTGCCCTCTTCTTCGGGACGTTCCGTGATTAACACACACCTACAGAGCCAT
GCGGGAGCAATACATGCGCACGGGCGAAGGCTTCCTTCTCGTCTACTCTATCACCTC
CAGAAACTCGTTTGAGGAAATCAGCATTTTCCACCAACAAATTTTGCGAGTCAAGGA
CCAGGATTCCTTCCCCGTCATTGTTGTGGCTAACAAGTGCGATCTCGAATATGAACG
TCAAGTTGGCATGAACGGTGTGTAGTCCATCTTTATGTCCCTTGCCGACATGACATG
AACAACGTATTGCAGAGGGGCGTGATCTCGCCAAACACTTTGGTTGCAAATTCATCG
AAACCTCGGCCAAGCAACGAATCAACGTCGACGAGGCATTCAGCAACCTCGTTCGG
GAGATTCGCAAGTCAACAGGGTGAGCAATCCTCTCTTCCAAGGTATTCTGACTAGCA
TTCAAACTGTCTCATGCCCCCAGGAACAACAAACCGGTCGTCCTGCCATCGCAGCAG
GTGGAGGTGGTCCAGCCGGCTCCTACACCCAGGACAGGCACCACGATGAGGCACCT
GGATGCTGTGCCGGATGTGTTATTGCCTAA (SEQ ID NO: 6).

Figure 10:
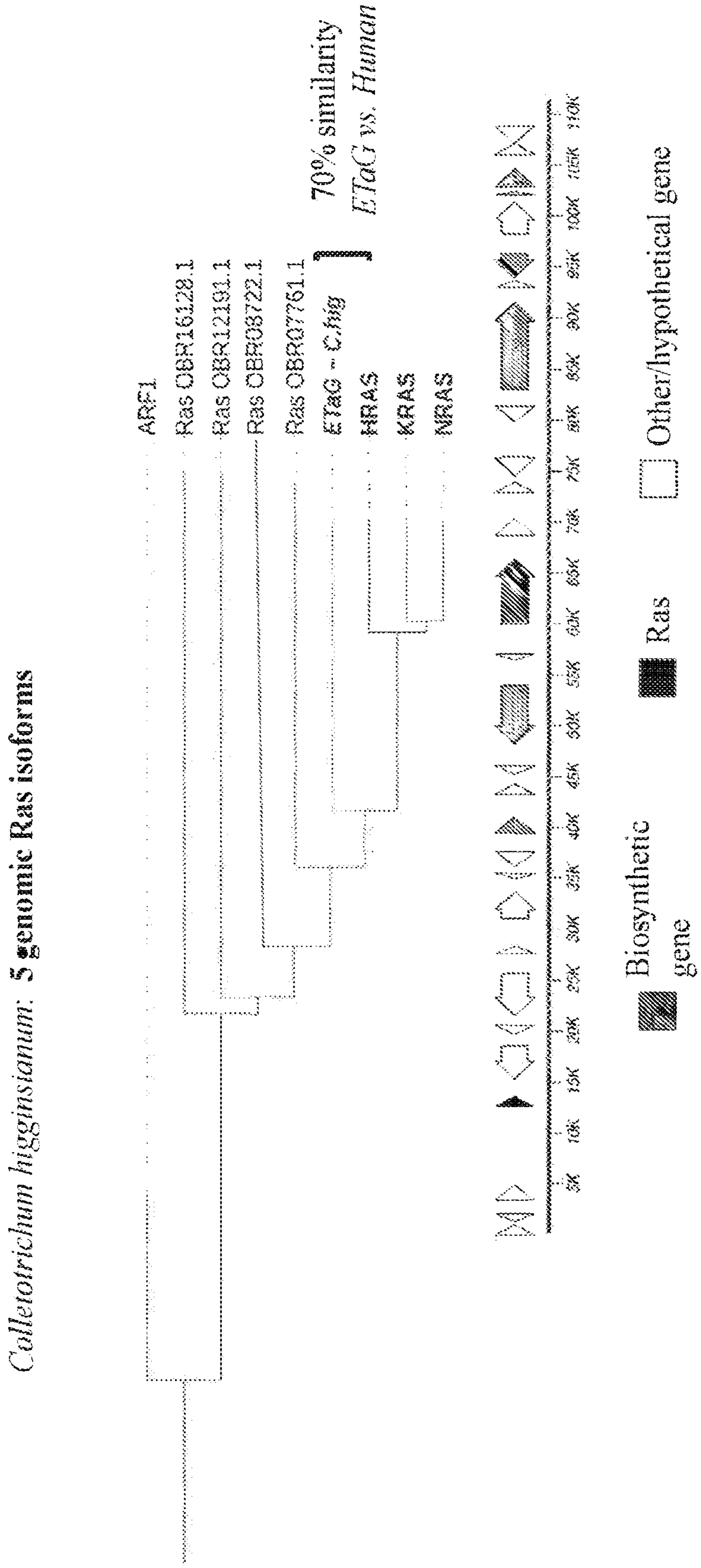
FIG. 10 depicts a Ras ETaG identified in *Colletotrichum higginsianum* IMI 349063 (CABI). The example ETaG identified is from the Ras family (pfam00071). Sequence similarity is of Ras domain calculated using MUSCLE alignment algorithm. The ETaG is presented below the scale.

FIG. 10: *Colletotrichum higginsianum*. Ras ETaG sequence:
ATGGCGTCCAAGGTTCGTCGTCGCCACCTCCCGTTTCCCTTCATTTCTTTTGCCGCCT
CGTCGCTCCATCGCTCCATCGCCCCATCGATCCGTTGCTAACCAGTTGCCATCTCGCA
GTTTCTGAGGGAGTACAAGTTGGTCGTCGTCGGCGGCGGTGGTGTCGGTAAATCCTG
CTTGACCATCCAATTGATTCAGAGCCACTTTGTCGACGAATATGACCCGACGATCGA
AGGTGCGTCGTCCCGAACTTCTTGCTCCACCGTTCGATGCGACGGCTTCGAATCAAT
CGCATGCTAATGTGGATCTCACCCATTTCAGATTCCTACCGCAAGCAGTGCGTCATC
GACGAGGAGGTCGCTCTACTCGATGTCCTCGACACGGCCGGTCAGGAGGAGTACTC
CGCCATGAGGGAGCAGTACATGAGGACGGGAGAGGGTTTCCTTCTGGTTTACTCCAT
CACTTCGCGACAGAGCTTCGAGGAGATCACCACATTCCAGCAGCAGATTCTGAGAG TAAAGGACAAGGACTACTTCCCCATGGTCGTCGTCGGCAACAAGTGCGATCTGGAG
AGCGAGAGAGAAGTCACACGACAAGGTATGATTCTGATTCCTGCTGTGCCGCGACA
CCGCATGAGGCGGCTCCTTTCGAGGCCCAGGCCCGGTGTGGATTCATTGATGGAATG
AAAAGTAGCTGACATCATTCACTCGTGCGCGCTACAGAGGGAGAGGCCCTTGCCAA
GTCATTCGGCTGCAAGTTCATCGAGACGTCGGCCAAGTCTCGCATCAACGTCGACAA
GGCTTTCTATGATATTGTCCGAGAAATCCGTCGGTACAACCGCGAGATGCAGGGCTA
CTCTACCGGCAGTGGCGGCGCCTCGGGCATCAACGGCCCCCCGAAGCCCATGGACG
TCGAGAACGGCGAGCAAGAGGCAGGCTGCTGCTCCAAGTGCGTACTAATGTGA
(SEQ ID NO: 7).

Figure 11:
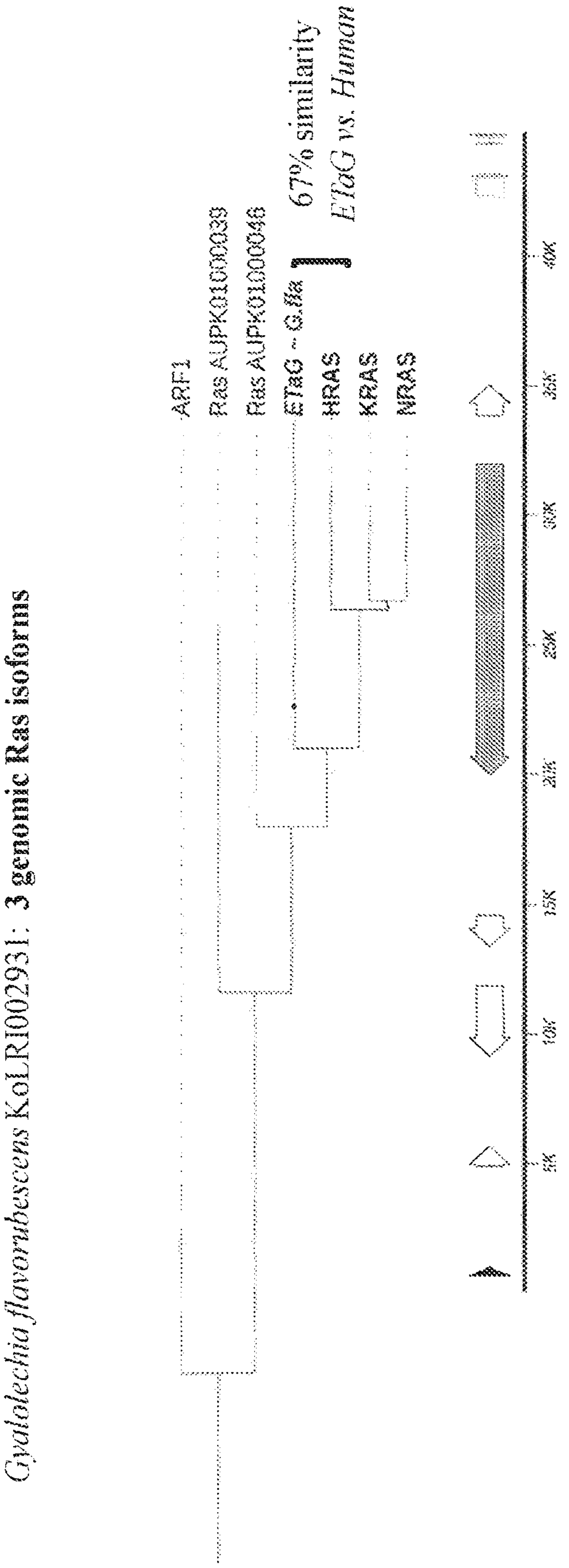
FIG. 11 depicts a Ras ETaG identified in *Gyalolechia flavorubescens* KoLRI002931. The example ETaG identified is from the Ras family (pfam00071). Sequence similarity is of Ras domain calculated using MUSCLE alignment algorithm. The ETaG is presented below the scale.
Figure 12:
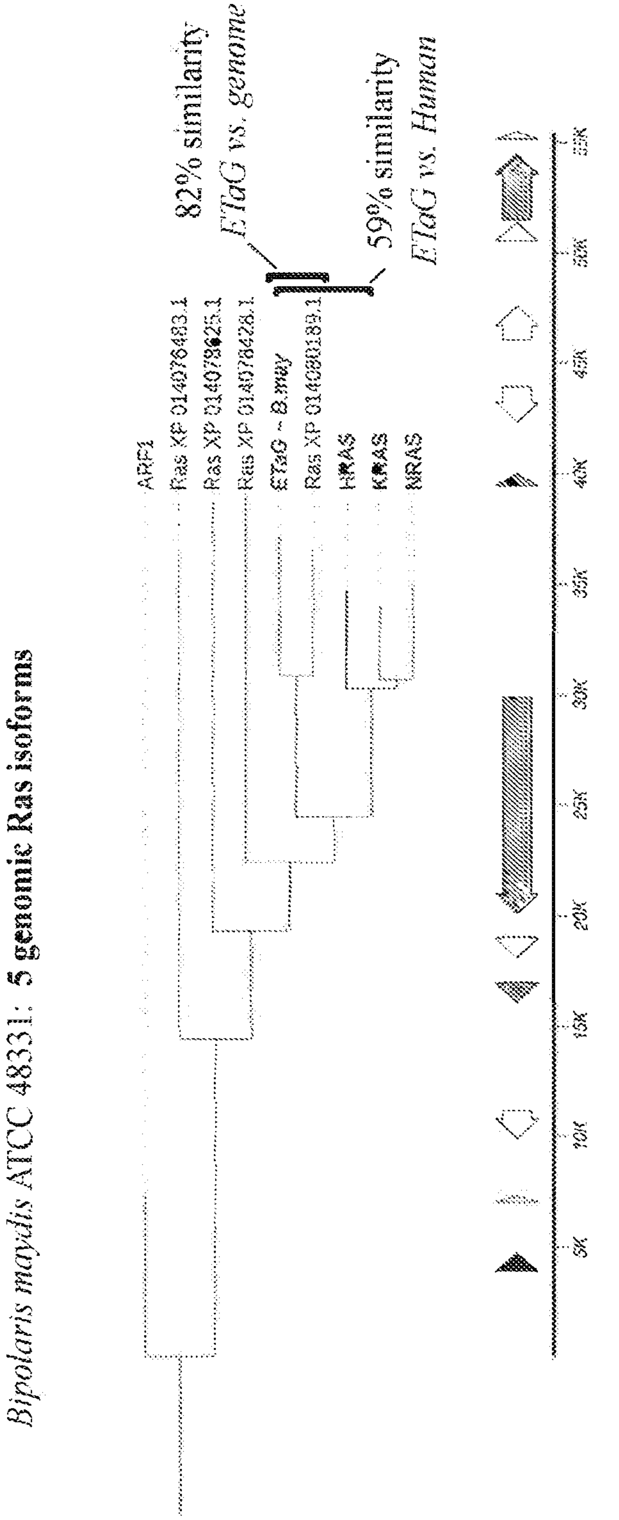
FIG. 12 depicts a Ras ETaG identified in *Bipolaris maydis* ATCC 48331. The example ETaG identified is from the Ras family (pfam00071). Sequence similarity is of Ras domain calculated using MUSCLE alignment algorithm. The ETaG is presented below the scale.

FIG. 11: *Gyalolechia flavorubescens* KoLRI002931. Ras ETaG sequence:
ATGGCTTCAAAGGTAAGTCCATCTGTCTCTTTAGAGTATTCTCATTGCTCTTTGCTAC
CGAGCTTCTCCATGGACGCTGACCCTTACCTGCTCAAGTTCCTACGGGAATACAAGC
TCGTCGTCGTTGGCGGAGGAGGTGTGGGCAAGTCCTGCTTGACCATCCAGCTCATCC
AGAGTCACTTCGTCGACGAATACGATCCCACCATTGAAGGTAAATAGATTCGTCCTA
TCCACCCATTGCGCTTTTACTGATCGAAGCGATTTGCAAGACTCCTACCGGAAGCAA
TGCGTCATCGACGAAGAAGTCGCCTTACTCGATGTACTAG (SEQ ID NO: 8).

IG. 12: *Bipolaris maydis* ATCC 48331. Ras ETaG sequence:
ATGTTCTTGCCTCAACTCTACTCCCTCAACCCTGCCTTGGCTGCCAAACATGCTGATC
CTCTTGCTCCTACAGCCCAGTTTGTGCAAAACGTGTGGATAGAGAGCTATGATCCCA
CCATCGAGGACTCGTACCGAAAGGTCCTCGAAGTAGACGTGCGTACACGACACTCT
TACTAGCCGCGTTTTTTTCACTGACCCACTCTCCCTCCCAGGGCCGTCATGTCATTCT
CGAGATCTTGGATACTGCCGGCACAGAGCAGTTTAGTAAGTGATTACATACATAGCC
CCACCCCACGTGGACCCAAGACTAACACGACAATAGCTGCCATGAGGTAGAGTTTC
CTACTACCCCCTTACTCGGTAAACATCAAAACTTACACGGATGCAGAGAACTGTACA
TGAAAACGGGCCAAGGATTCCTTTTGGTCTTCAGCATCACATCAGAATCTTCCTTTTG
GGAGCTTGCCGAGCTGCGTGAGCAGATACGACGCATCAAGGAAGACAGCAACGTAC
CCATGGTTCTCATTGGCAACAAGTCGGACCTAGAAGACGACCGTGCCGTGCCGCGC
CCACGAGCATTTGCCATTTCGCGTGAATGGAACGTTCCTTATTTCGAAACCAGTGCT
CGAAGGAGAGCCAATGTCGACGAAGCCTTTGTCGACCTCTGCAGGCAAATCATCCG
CAAGGATCAGAACGAACGAAACCGCATGGCCCCACCGGATTCCCCGAGGCCTGGCG
GTCCCAGGAGCAGAACTCACACGGGACGGCCAAAGCGCAAGGCTCACCGGCCCCAT
TGTACCATTCTTTAA (SEQ ID NO: 9).

Figure 18:
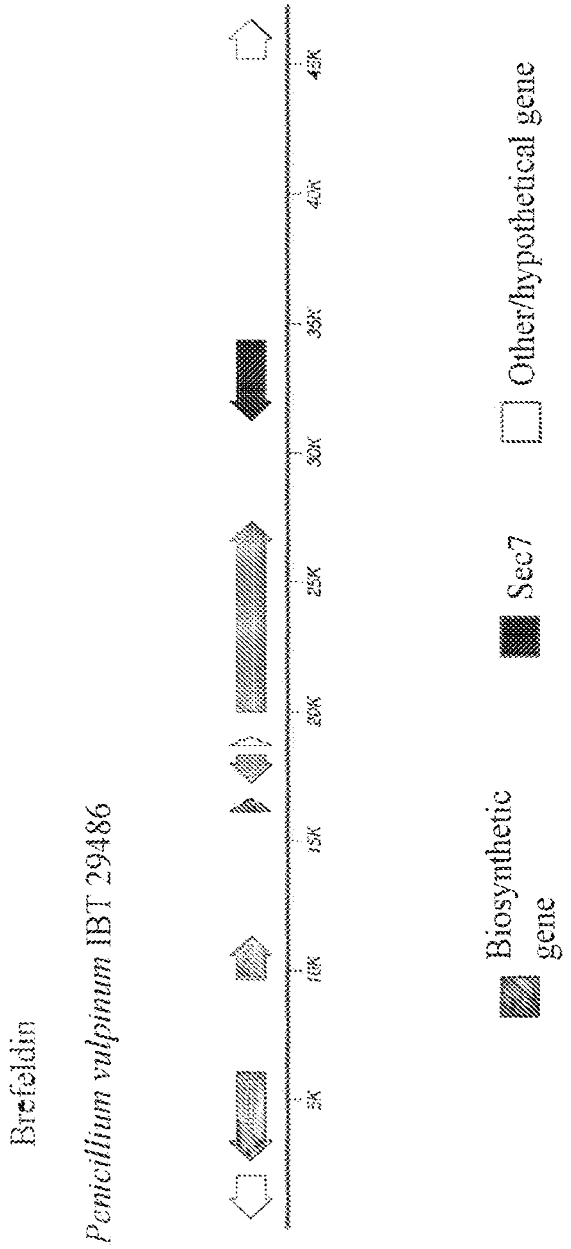
FIG. 18 depicts a biosynthetic gene cluster with Sec7 homolog in *Penicillium vulpinum* IBT 29486.

FIG. 18: *Penicillium vulpinum* IBT 29486. Sec7 ETaG sequence:
ATGGAAGTTGAAAGGCCGGATGGTTGGCATCATCACTGCTGACCACGAAC
AGACATCACGAAATATGACACACCTGCTCTACTACACCCCTTCCTCCAAGTAATACG
ATCATCCTCAACCTCTGCTGCGATCACCTCCCTCGCTCTCATCGCCATCACGAAATTC
CTCTCCTACAAAATAATCTCCGGTGACTCCGCTCGGCTGGCTGAAGCCATGCAGCTC
CTCTCATCAGCTCTCACGCACTGCCGGTTCGAGGCAAGCGATTCAGCAACGGACGA
AATTGTACTCCTGCAGGTACTGAATCTCATGGAAAGCATTATCTTGAGTCCAGGAGG
TGAATCTCTCTGCAATGAGAGCGTTTCTGAGATGATGCAAACTGGACTGAGCATGTG
CTGCCAACCCAGGCTTTCGGAACTCCTACGACAGTCTGCTGAGATTGCCATGGTCTC
TATTTGCCAATTGGTCTTCGAGCGATGGAAGCACCTAGAAGAAGAGGTGGGCGAAG
AGCTAGGGGCCTTGGATCAGGATGTCAGGGCCGATATGGGCACGATGAAGCTCCTT
GATTCAAAAATGCAGACCTCCTTGACCGGTCCAAACTCCAAGAATCTTAAATCTGAG
GAGAAGACACGGTCTTTTGCGAGCGTGGAGAAGCTGATCAATGAGTCCACAGGGAT
GACACTGCAAAAGGGCGACGCCACAATTGATCTACCGTCAATGCACGATGAACAGG
ATGAAGGCGAGGCGCTCCCAATCAAGCCATACTCCCTGACGTTGATACGAGAGCTT
CTTGTGATCCTCATCAATATACTAGATCCTGAGGACAAGAAACAAACAGACACAAT
GCGTATCACGGCACTGCGCATTCTGCATGTTGTGTTGGAAGTAGCGGGCCCATCAAT
CGTCAACCATACTAGTCTAGCAACCCTGACAAAGGACACGCTATGCCGATACTTGCT
CCAATTGGTTCGCTTGGATAACATGAAGATTATCAGCGAGTTGCTCTGTGTGTGTGT
TACTTTATTTGCAACATGCCGAGGTGTACTCAAGCTACAGCAGGAGCTATTCCTATC
GTATGTGGTGACCTGTGTGTTTCCGACAATGGATATTCCGCTAGAGCCTGGTATCGA
CCCTTCTCTTTACGAGGGTGTACCGCAGTCATTCAGCCTCCTCAAGCAATCAAAATC
ACAGTCACCTGCGCAAAAATCTACAAGTGGCAAATCGACGCCCAAGTCTGCCAAGG
ATCGACAGAAGCTGGGACCCGAAGACAGCATAAGGACACCCGATGCTCGTGAGGCG
ATATTAGAGAGCGTGAGCGCCTTGGTTAGGATCCCCTCTTTTATGGTCGAGCTGTTC
GTCAACTACGATTGCGATATTGATAGAAGCGACCTATGTTCGGATCTGGTTGGACTT
CTTTCGCGGAACGCTTTCCCAGACTCAGCCCAGGGGAGTACAACAAACCTCCCACCG
CTATGTTTGGACTCTCTTCTATCCTATGTGCAATCCATTGCAGATAGACTCGATGATG
CGCCCCTGATAGAGGGCTTCCGTGACCCCAATGCCCTACGACAGCAGCGGTCACGT
AAGAGTATGATTATGAAGGGTGCCTCGAAATTCAATGAGAACCCAAAGGCTGGCAT
CGCATTTCTAGTCGCCCAAGGGGTCATACAAGAGCCTGAGAATCCTAAGAACATTGC
GGAGTTTATCAAAGGCACTACGAGAATTGACAAGAAGATCCTGGGGGAGTTTATTT
CAAAGAAAACAAACGAAAATATATTGAACGAGTTCATGAAGCTTTTTAACTTCGCC
GGAAAACGAATTGACGAGGCTATACGCGAGTTACTGGGTGCATTCCGCCTTCCTGGT
GAGTCGGCACTTATAGAGCGAATTGTGGAGGTGTTCGCTGCACAGTATATGGACGA
CGCCAAACCCGCAGGAATTGCAGACTCCACTGCAGCATTTGTTCTCGTGTATGCCAC
CATCTTGTTAAACACAGATCAGCATAATCCCAATTTCAGGGGCCAGAAACGTATGAC
CATTGAGAACTTTGCCCAGAATCTCAGGGGTGTTAACGATCAGGGGGACTTTGATTC
CAACTTCCTTCAGGAAATCTTTGATTCTATCCGGACACATGAGATTATCCTGCCAGA
GGAGCATGATGATAAGCATGCCTATGATTACGCTTGGAATGAGCTGTTGATCAAGGC
CGAATCCACTTCAGACTTGGTGTCTTGCAACACCAACATTTTTGATGCGGATATGTTC
GCGGCAACATGGAAGCCAATCGTCGGGACACTATCATATATGTTCATATCCGCGACT
GACGACGCTGTGCTTTCAAAAATAGTAACCGGTTTCGGCCAGTGCGGTCAGATTGCT
GCGAAGTACAGACTAAGTGATGCCTTGGATAGGATAGTAGCCTGTCTGTCGCATATC -continued AGCACGCTTGCTCCAGAAGTCACACCAAGCACGAGTCTCAAAATCGAGGTCCAGCA
TGAGAAACTTAGTGTAATGATCTCCGAAACCGCCGTTCGATTTGGGCGTGATGACAG
AGCCCAGCTTGCAACAGTAGTGCTGTTCCGAATTCTCAATGGTAACGAGGGTGCAAT
TCGGGATGGATGGGAACAGGTAAGACTTCCATCAACAAAAGCAATTGAGATATATA
AGCTCACAGCTGTAGATTCTGCGAATATTGCTGAATCTTTTTATAAATTCTTTGATAC
CCTCCTCGTTCTCCTCAGCTCGCAAATCGCTTGAACTTCCATCTATCCCGCTACAAAG
CCCCACTCAGATCATCAACAAAGATGATAGAGCAGCGGACACCAGCCTGTTTTATG
CCTTTGCTTCTTATGTTTCGAGTTTCGCGAACGGTGAGCCACCGGAACCTTCAGACG
AAGAGATTGAGAACACCTTGTGTACAATCGATACTATCAGCGCTTGTTCGTTGGACG
AAATCACATCCAACATCTTGTAAGTCATAAACCGCGTGGCTAATCAGGACATGAATT
AACAAGACCTCTAGCGACATGTCCACAGAGGCTTTGAGACCTCTGTTCATGGCGCTT
TTGTCACGACTACCCGAAGATACATCGCTCCACGGTATTGCAGTAA (SEQ ID NO: 10).

Figure 20:
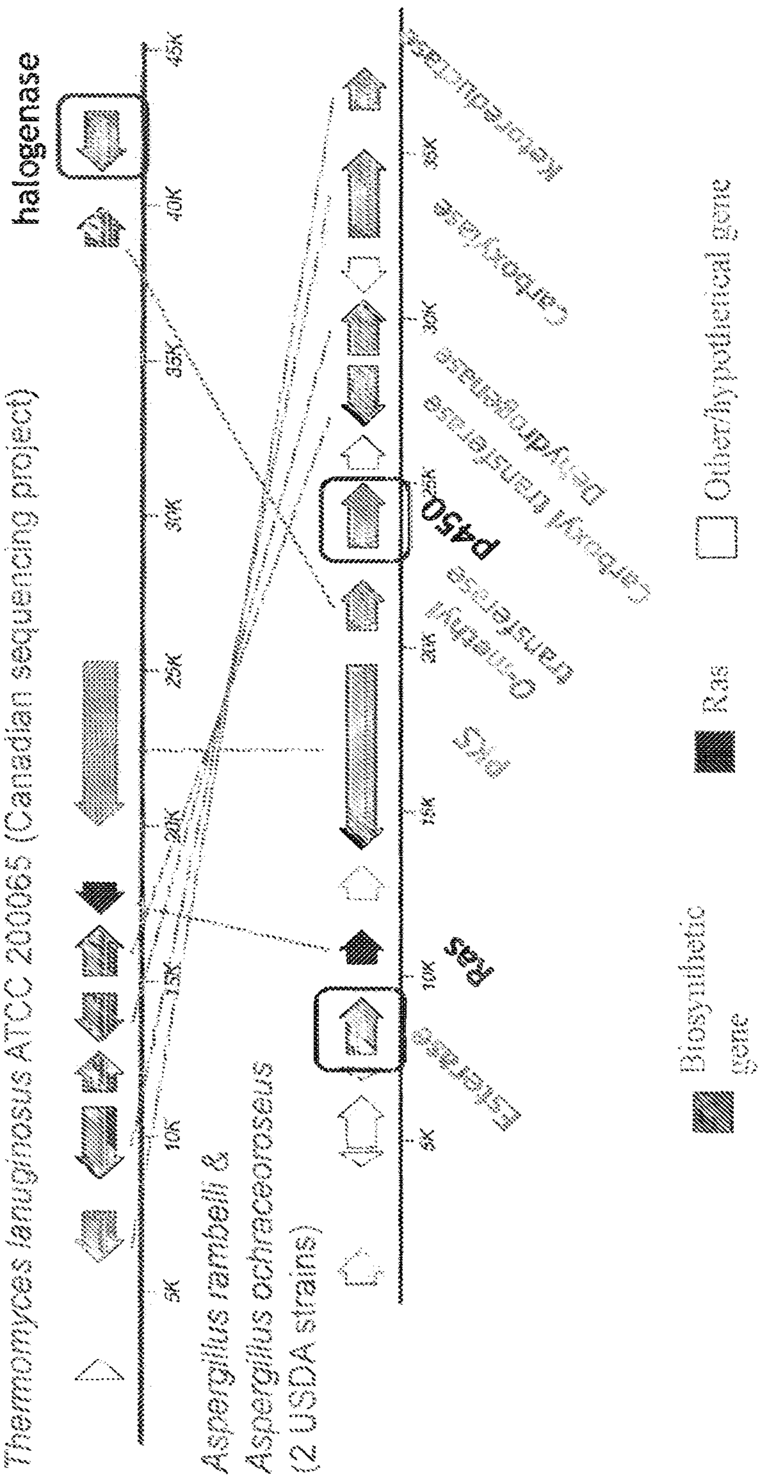
FIG. 20 depicts example biosynthetic gene clusters related to Ras, e.g., from *Thermomyces lanuginosus* ATCC 200065, *Aspergillus rambelli*, and *Aspergillus ochraceoroseus*. Illustrated Ras homologs are indicated in black.

FIG. 20: *Thermomyces lanuginosus* ATCC 200065. Ras ETaG sequence:
ATGCAGCCGCGGTGAGTGTTGGTCGCGCTCCTTGGCAAAGGTCAATACTA
ATTGGACACAGGCGGGAATATCATATTGTCGTCCTGGGAGCTGGTATGTCGAGAAG
AGATTCGCCACAGCCTATCAGTCGATATGTGTCCCTAACAATGTTATACAGGAGGCG
TCGGGAAGAGCTGCTTGACAGGTATGGACGCGATGGACTGCGGCGACAACATGCGA
CCGATGGCTCACTAACTTATCTCATAGCTCAATTTGTACAAAATGTTTGGATTGAGA
GTTACGACCCGACAATTGAAGATTCCTATCGAAAGCAGATTGAAGTCGATGTGAGTT
CCCGTGGCATTGATGCGATTATACCACCTGCTTACGATATTCTATTCGCAGGGTCGA
CAATGCATTCTCGAGATGTACGTCTCTCTTCAGAGCTGTCGCGGAGCTATTTCATCTT
ACTGATCACCGTGCAGTCTGGACACAGCCGGAACAGAGCAATTCAGTACGTCTTAA
CCTCCCAACTCCGATGAAAAGGACCATCCACTAACGATGACGACAGCTGCGATGAG
GTATTACACGTCAATGCGGCGCACATGGCCAATGAAGTTGACATGACTGTCCAGGG
AAATTTACATGAAACAAGGGCAGGGATTCCTGCTAGTCTTCTCGATCACCAGCATGT
CATCGCTGAACGAGTTATCGGAAATCCGGGAGCAGATCCTCCGCATCAAGGACGAT
GACAAGGTCCCTATGGTGATCGTCGGCAACAAGTCCGATCTCGAGGAAAACCGAGC
TGTGCCTCGTAGCAAAGCGTTTGCGCTCTCGCAGAGCTGGGGCAACGCTCCTTACTA
CGAAACATCCGCTCGACGGCGAGCAAACGTCAACGAGGTCTTCATTGACCTGTGCC
GACAGATCATCCGCAAGGATCTGCAAGCTACACAGGCAAAGCAAGCGGAAGCCAG
ACAAGTTAAGCGAGAGGCGACTCCTCGCAATGACAGGAGCAAGAAGGATAGAAAA
TCCACAAGGCGTCGGCATCAATGCGCGATTATGTGA (SEQ ID NO: 11).

*Aspergillus rambelli*. Ras ETaG sequence:
ATGCTGGGAATAGCGGTCACTAATAATGCCTCCTTCGGTGTGACCGGTAG
ACGGGAATATCACATTGTCGTGTTGGGTGCTGGAGGAGTGGGAAAAAGTTGTCTTAC
TGGTATGATTCTCGGTCGCGTCGGCTTCGTGCTTGCCTCGGAAGGCCGTCTCTGCTCT
CTAGACCAATCAGTCGCTTACTTGTGGCAGCGCAATTTGTGCAAAACGTTTGGATTG
AAAGCTATGATCCGACGATTGAAGACTCTTATCGCAAGCATATCGAGGTAGATGTAT
GTTTATCCTGCTCTCAACTTCATTCTCGGGTTCATTCTCAAGTCGCTGACATTTTCTA
GGGCCGACAATGTATTCTGGAAATGTATGTCACAAGGAACACGGATGGTGGTTCGG
AATTGCGCTTTACGTGTAAACAAACACGGCTGGCTGACCCTTGACCTGTCAACAGAC
TTGATACAGCGGGGACAGAACAATTTAGTGAGTTATCTTGCTCTTGATGCTGGGTTT
TCTCTCCACTAACGTTTTCCCAGCGGCCATGAGGTAATGAATGCTATATCCATGGGG
TCATCGGGACTCACATCTCTCAGTTGCCAGATCTCGATCGCTAACATGTGAATCCTG
CAGAGAACTATATATGAAGCAAGGCCAGGGCTTTTTGCTTGTATTCTCTATCACTAG
CATGTCGTCTCTGAACGAGCTGTCCGAATTACGAGAACAAATTATTCGCATTAAAGA
CGACGAGAAAGTTCCCATCGTCATTGTGGGCAATAAATCGGATTTGGAGGAAGACC
GCGCAGTCCCACGTGCTCGTGCATTTGCTCTTTCTCAGAGCTGGGGCAACGCTCCCT
ACTATGAAACATCGGCGCGTCGACGAGCCAATGTTAATGAGGTCTTCATTGACCTGT
GTCGACAGATTATACGGAAGGACCTCCAGGGAAGTTCGACCAGCGATTATGATGCT
GCCGCACGTAAACGCGAGGGTCAAACCCGACAAGACCGAAAGCGAGAGAGAAAAC
GACAAGTGCGGCGAAAGGGTCCTTGTGTCATTCTCTAA (SEQ ID NO: 12).

*Aspergillus ochraceoroseus*. Ras ETaG sequence:
ATGCTGGGAATAGCGGTCACTAATAATGCCTCCTTCGGTGTGACCGGTAG
ACGGGAATATCACATTGTCGTGTTGGGTGCTGGAGGAGTGGGAAAAAGTTGTCTTAC
TGGTATGATTCTCGGTCGCGTCGGCTTCGTGCTTGCCTCGGAAGGCCGTCTCTGCTCT
CTAGACCAATCAGTCGCTTACTTGTGGCAGCGCAATTTGTGCAAAACGTTTGGATTG
AAAGCTATGATCCGACGATTGAAGACTCTTATCGCAAGCATATCGAGGTAGATGTAT
GTTTATCCTGCTCTCAACTTCATTCTCGGGTTCATTCTCAAGTCGCTGACATTTTCTA
GGGCCGACAATGTATTCTGGAAATGTATGTCACAAGGAACACGGATGGTGGTTCGG
AATTGCGCTTTACGTGTAAACAAACACGGCTGGCTGACCCTTGACCTGTCAACAGAC
TTGATACAGCGGGGACAGAACAATTTAGTGAGTTATCTTGCTCTTGATGCTGGGTTT
TCTCTCCACTAACGTTTTCCCAGCGGCCATGAGGTAATGAATGCTATATCCATGGGG
TCATCGGGACTCACATCTCTCAGTTGCCAGATCTCGATCGCTAACATGTGAATCCTG
CAGAGAACTATATATGAAGCAAGGCCAGGGCTTTTTGCTTGTATTCTCTATCACTAG
CATGTCGTCTCTGAACGAGCTGTCCGAATTACGAGAACAAATTATTCGCATTAAAGA
CGACGAGAAAGTTCCCATCGTCATTGTGGGCAATAAATCGGATTTGGAGGAAGACC
GCGCAGTCCCACGTGCTCGTGCATTTGCTCTTTCTCAGAGCTGGGGCAACGCTCCCT
ACTATGAAACATCGGCGCGTCGACGAGCCAATGTTAATGAGGTCTTCATTGACCTGT
GTCGACAGATTATACGGAAGGACCTCCAGGGAAGTTCGACCAGCGATTATGATGCT
GCCGCACGTAAACGCGAGGGTCAAACCCGACAAGACCGAAAGCGAGAGAGAAAAC
GACAAGTGCGGCGAAAGGGTCCTTGTGTCATTCTCTAA (SEQ ID NO: 13).

Figure 21:
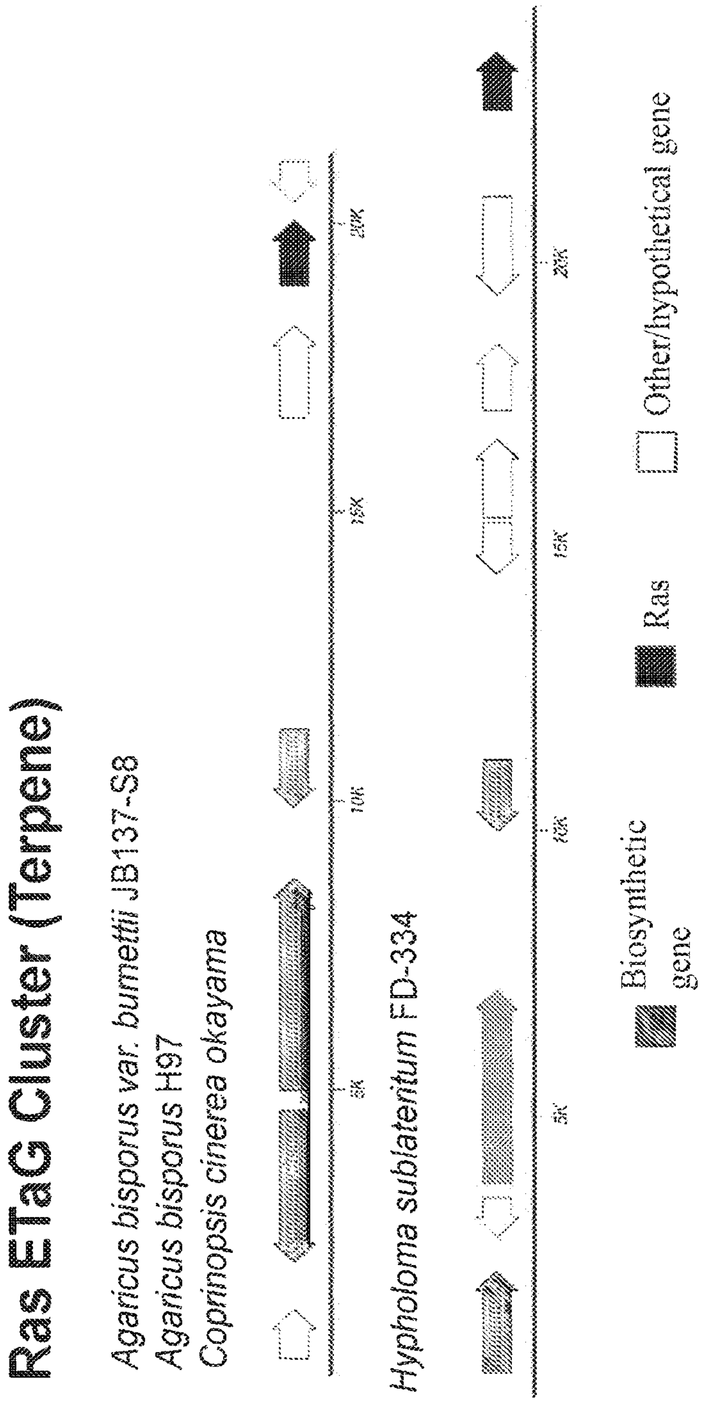
FIG. 21 depicts example biosynthetic gene clusters related to Ras, e.g., from *Agaricus bisporus* var. *burnettii* JR 137-S8, *Agaricus bisporus* H97, *Coprinopsis cinerea okayama, Hypholoma sublateritum* FD-334. Illustrated Ras homologs are indicated in black.

FIG. 21: *Agaricus bisporus* var. *burnettii* JB137-S8. Ras ETaG sequence:
ATGGCAAACAACGCTGCGTCCAGAGTATGTCCTCCCCACAAACCACCCTCAGTTGCC
TGGCTTATGCTCTATTTCAGGCTGCTCAGGCCCAGTTCCTGAGAGAATACAAGCTCG -continued TAGTGGTCGGAGGAGGAGGCAAGTGCTACCCGCCCTTACAAGCTAGCAAGTCCTAA
AGTCGTGTACAGGTGTTGGAAAATCTGCATTGACTATCCAATTCATTCAAAGCCATT
TCGTGGACGAGTACGACCCAACTATCGAGGGTGAGCTTCTTTCTCACCAATCAATCC
CCTTCCAGGTTATGACATTTCGGAACATTTGTGCTAACATTCTCGTCTTAAAACAGAC
TCGTACAGGAAACAATGCGTCATTGATGAAGAGGTCGCCCTTCTCGATGTCCTGGAT
ACCGCTGGTCAAGAAGAATATGGGTCAGTGTGCTCTCCTGAATAAATTCCGAAGCA
GTCCCCGATTTTTTTTCCTTTCGTCTCGTGATTCGACTATGAAAATGGTCTTCCACGA
GGCGAAGCTTTCATTTCCCGGCATAATTCAGTTATACGACCCTGGATCTAACCCTAT
ATGTACTTATTTTCCAGTGCCATGCGGGAGCAATACATGCGTACTGGGGAGGGATTT
CTTCTCGTCTACAGCATCACCGCGCGTAGCTCCTTTGAAGAAATCAACCAGTTTTAC
CAGCAAATTTTGAGGGTCAAAGATCAAGATTCTTTCCCTGTTATTGTCGTTGCAAAC
AAGTGCGATTTGGAATATGAACGCCAAGTTGGTATGAACGGTATGTTATCAAACCTT
GGAGTATATCAGGGCCCCAGTAGTGACGCAACCTACAGAGGGCCGAGATCTCGCGA
GACATTTTGGCTGCAAATTCATCGAGACGTCTGCCAAACAACGAATAAACGTGGAT
GAAGCTTTCAGCAATCTTGTTCGTGAAATCCGAAAATATAACAAGGTCGGTTTTCCG
CATCACACGCAGAGATTTTACAAACTCATTGGTGCTTTTATAGGACCAACAAACAGG
CCGCCCTCTCCACGGCAGCGGTGGTGGAGCCGGCGGTTATGGTGGCAAGGACCACA
ATGACGATGGAGGTGCTGGCTGCTGCGGCGGTTGCGTTATTCTTTAA (SEQ ID NO: 14).

*Agaricus bisporus* H97. Ras ETaG sequence:
ATGGCAAACAACGCTGCGTCCAGAGTATGTCCTCCCCACAAACCGCCCTC
AGTTTCTTGGCTTATGCTCTATTTCAGGCTGCTCAGGCCCAGTTCCTGAGAGAATACA
AGCTCGTAGTGGTCGGAGGAGGAGGCAAGTGCTACCCGCCCTTACAAGCTAGCAAG
TCCTAAAGTCGTGTACAGGTGTTGGAAAGTCTGCATTGACTATCCAATTCATTAAAA
GCCATTTCGTGGACGAGTACGACCCAACTATTGAGGGTGAGCTTCTTTCTCACCAAT
CAATCCCCCTCCAGGTTATGACATTTCGGAACATTTGTGCTAACATTCTCGTCTTAAA
ACAGACTCGTACAGGAAACAATGCGTCATTGATGAAGAGGTCGCCCTTCTCGATGTC
CTGGATACTGCTGGTCAAGAAGAATATGGGTCAGTGTGCTCTCCTGAATAAATTCCG
AAGCAGTCCCCGATTTTTTTTCCTTTCGTCTCGTGATTCGACTATGAAAATGGTCTTC
CACGAGGCGAAGCTTTCATTTCCCGGCATAATTCAGTTATACGACCCTGGATCTAAC
CCTATATGTACTTATTTTCCAGTGCCATGCGGGAGCAATACATGCGTACTGGGGAGG
GATTTCTTCTCGTCTACAGCATCACCGCGCGTAGCTCCTTTGAAGAAATCAACCAGT
TTTACCAGCAAATTTTGAGGGTCAAAGATCAAGATTCTTTCCCTGTTATTGTCGTTGC
AAACAAGTGCGATTTGGAATATGAACGCCAAGTTGGTATGAACGGTATGTTGTTAA
ACCTTGGAGTATATCAGGGCCCAGTAGTGACGCAACCTACAGAGGGCCGAGATCTC
GCGAGACACTTTGGCTGCAAATTCATCGAGACGTCTGCCAAACAACGAATAAACGT
GGATGAAGCTTTCAGCAATCTTGTTCGTGAAATCCGAAAATATAACAAGGTCGGTTT
TCCACATCACACGCAGATTTTACAAACTCATTGGTACTTTTATAGGACCAACAAACA
GGCCGCCCTCTCCACGGCAGCGGTGGTGGAGCCGGCGGTTATGGTGGCAAGGACCA
CAATGACGATGGAGGTGCTGGCTGCTGCGGCGGTTGCGTTATTCTTTAA (SEQ ID NO: 15).

*Coprinopsis cinerea okayama*. Ras ETaG sequence:
ATGCCTGAGGTGATGAATGCTATGTACGCCACGAAAGGCGGTATCTTCGACGTCAGC
GAGAATGATAAGGTTTGGCGTTTGCAGTGTTTCAAAGCTGGCCTCTGTTGTGTTGGA
GAATACTCGGATGCTGATATACATATGGTTTATCGAATACAAGTACGCGTATAAGGA
AAGCTGGGGTAGACAAGGGACTATAGCTGGATCTTAACTCCCAGGAGGGGACGACA
TGAGAGAATGCGGTCTACAGCAATTCTGATGCTCGAAAATCCATCAGCAGAGGTCA
ACCTTGGGTTTCTAGCGAAAAGAAGGGAGATAGGAAGCCCGGAATATCAAAACACG
CGTCGGATTGTGGTCCAAATTGAAAAATGACCGAGAGCCTCGAGCTCGTGTCGCGA
GATGTTTGCACTTGAGATTTAAACTCCGCTGATGATGGCCTTTGAAGTGAGTTTGGTT
ACGATGTTTAGAGGAACCCAGTCGCCCCCTGCTCCCGCTCAACTCCCTAAATACCCT
TCCTGACCATCTTCTTTCTTTCCCAAATCTTTTTCTTCTCTTTCAACAGATTTCATTTCT
GAAGCATGGCTGCCAGGGTCCGTCAAATCCCACAGTCTGCACCGTGGAACCTCAGC
AAACTCACACAGCGTCCAACAGGCTCAGTTCTTGAGGGAGTACAAGCTCGTCGTCGT
AGGTGGTGGTGGTATGTTGCACAGCTCTTAGAACGGAATGTAGTCTCACCTGTGGTG
CCCCAGGTGTTGGAAAGTCGGCCCTGACTATTCAGTTCATCCAATCCCACTTCGTGG
ATGAATATGACCCGACTATCGAAGGTCCGTATAACAAGGCCTTCTCTCGCAAGGATG
CAATAGCTTATGCTTATTCGACACAGACTCGTACAGAAAACAGTGCATCATCGACGA
CGAGGTCGCACTCCTCGACGTTCTCGATACCGCCGGACAGGAAGAGTATGGGTGAG
TACCCGCGCTGCACCCCTCTATTTTCCACCGAATGCTTCGTGGACAGCCCAACTTTTG
ATCCTCGTATCCCATACCACCGCTTTCCTTGTTCCCGGAATCTTTGCATCACCACCTC
TCCACCTTGCCCTCTTCTTCGGGACGTTCCGTGATTAACACACACCTACAGAGCCAT
GCGGGAGCAATACATGCGCACGGGCGAAGGCTTCCTTCTCGTCTACTCTATCACCTC
CAGAAACTCGTTTGAGGAAATCAGCATTTTCCACCAACAAATTTTGCGAGTCAAGGA
CCAGGATTCCTTCCCCGTCATTGTTGTGGCTAACAAGTGCGATCTCGAATATGAACG
TCAAGTTGGCATGAACGGTGTGTAGTCCATCTTTATGTCCCTTGCCGACATGACATG
AACAACGTATTGCAGAGGGGCGTGATCTCGCCAAACACTTTGGTTGCAAATTCATCG
AAACCTCGGCCAAGCAACGAATCAACGTCGACGAGGCATTCAGCAACCTCGTTCGG
GAGATTCGCAAGTCAACAGGGTGAGCAATCCTCTCTTCCAAGGTATTCTGACTAGCA
TTCAAACTGTCTCATGCCCCCAGGAACAACAAACCGGTCGTCCTGCCATCGCAGCAG
GTGGAGGTGGTCCAGCCGGCTCCTACACCCAGGACAGGCACCACGATGAGGCACCT
GGATGCTGTGCCGGATGTGTTATTGCCTAA (SEQ ID NO: 16).

*Hypholoma sublateritum* FD-334. Ras ETaG sequence:
ATGGCTGCTAGGGTACGTCCCTTCACATAACTAGCCAACGTCGCGTAGCTCATGCCC
TCTCAGGCTCAGTTCTTGCGAGAATACAAGTTGGTGGTGGTGGGCGGAGGAGGTCA GCAAATCCTGGCGCCATTTCCCGGTCTTTCTCCTGCTCACAGTTTCCTTCAGGTGTCG
GAAAGTCTGCTTTGACTATTCAGTTCATTCAAAGCCATTTCGTTGACGAGTACGATC
CCACCATCGAGGGTGAGAGTTTCGTGCTTCCAGTGCCGCCGCGACGCTGACCGAAGT
CAAGATTCGTACCGTAAGCAATGCGTAATCGACGAGGAGGTTGCTCTCCTCGACGTT
CTGGACACTGCTGGTCAGGAGGAGTACGGGTACGTGTCTGTCTTTACCATTAACATT
GTCCTCCCCCTGTTCTTTTTTGGCTCGCGCCTCGAGGCGCGTTCTTGCTCTGGTGCTA
TTCTTATCATGGCTGTTCTCTGACGGAAATACGTATAGTGCTATGCGCGAACAATAC
ATGCGTACCGGCGAGGGTTTCTTGCTCGTCTACTCCATTACATCCCGCGACTCCTTCG
AGGAAATAAGCACATTCCACCAACAGATTCTGCGGGTCAAGGACCAGGACTCGTTC
CCCGTTATCGTTGTTGCGAACAAGTGCGATTTGGAGTACGAGCGCCAGGTTGGCATG
AATGGTACGGCAGTAGACCACCAGGCTGGAAGATGCTAATCAACTATCTCTCTCAG
AGGGCCGTGACCTTGCCAAGCACTTCGGTTGCAAGTTCATCGAAACGTCAGCCAAG
CAGCGGATCAACGTCGATGAGGCTTTCAGCAACCTTGTTCGCGAGATTCGGAAGTAT
AATAAGGTTAGTACGTTATGTTATTCTACCTCTCCCTATCTGACAGATATTGTCCACC
AGGAACAACAAACTGGTCGCCCGGCCCTTGCCGGCAATGGAGGAAGCACTGGCGCA
TACGATGGGAAAGACCAGCACGATGATACTCCTGGGTGTTGTTCCGGCTGTGTTGTC
CTCTAA (SEQ ID NO: 17).

Figure 22:
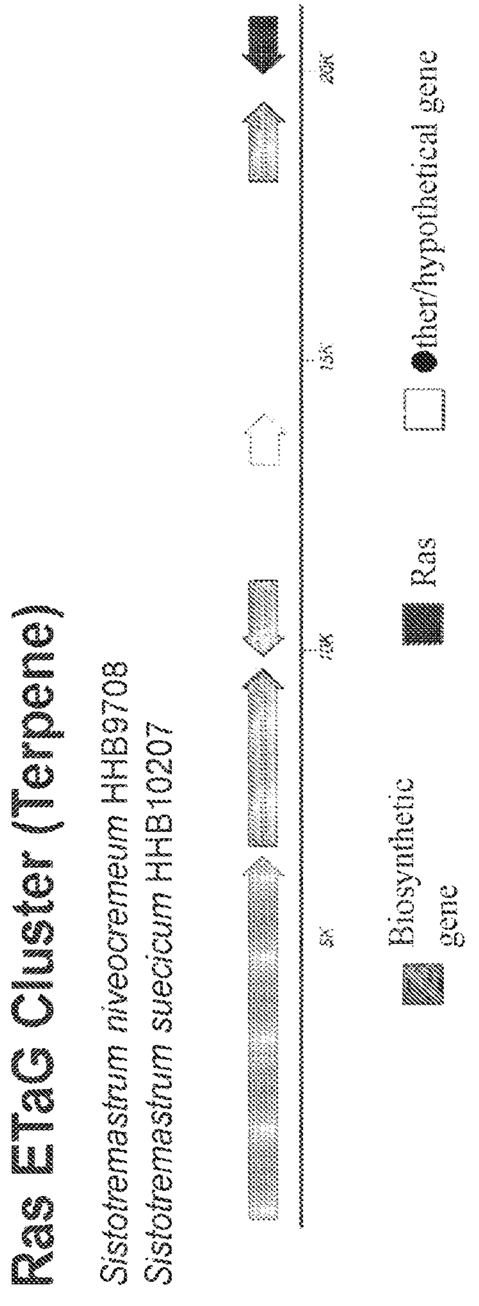
FIG. 22 depicts example biosynthetic gene clusters related to Ras, e.g., from *Sistotremastrum niveocremeum* HHB9708 and *Sistotremastrum suecicum* HHB10207. Illustrated Ras homologs are indicated in black.

FIG. 22: *Sistotremastrum niveocremeum*. Ras ETaG sequence:
ATGTCGAGAGTGAGTATTTCTGTTTATTGCGGCTCTATCTTGATCTCACTCGTCGCTA
GTCTGCTGCTCAGGCTTCGTTCCTTCGCGAATACAAGCTCGTCGTCGTCGGTGGTGGT
GGTATGAGCCTTGTCTCTCGTTCTCTGCAATCAAAATCTCACTCGCTTTTCTCTTGTG
CTGCCTAGGTGTTGGCAAATCCGCTCTGACCATTCAATTCATCCAAAGTCATTTCGTT
GACGAGTATGACCCTACTATCGAAGGTCAGCCGACCGCTAGGCAACCATTATCTGAT
CAAACAGCTCATCTCGCACTCGACAGATTCTTACAGAAAGCAATGTGTCATCGATGA
TGAAGTTGCCCTTTTGGATGTGTTAGATACCGCTGGGCAGGAAGAATATGGGTGAGC
TCGTCTCGCAGCCCGATTCCCACGCTTATTGCTAACACGACATCGGCAGCGCAATGC
GAGAACAGTATATGCGAACGGGAGAAGGATTCTTGCTTGTCTACTCGATAACGTCGC
GGAACTCTTTCGAAGAAATCAGCACTTTCCATCAGCAAATTCTTCGAGTAAAAGACA
AGGATGCGTTCCCGGTTATCGTGGTAGCCAACAAGTGTGACCTTGAATATGAGCGAC
AAGTCGGCATGAACGGTGCGTTTTTAGTGTTGTTTCAATCAACATTGTGACTCATCCT
TCGTCAGAGGGCCGTGACCTGGCCAAGCACTTCAACTGCAAATTTATCGAGACCTCG
GCGAAGCAGCGAATCAACGTTGATGAGGCCTTTTCGAACCTTGTTCGAGAGATTCGC
AAATTCAACAAGGTATGTAAGCCCAAACCCGACGGAACTCCCGGCCTGATCTCTTTA
CAGGAACAACAGACCGGACGTCCTGCGACCATGGCTCCGAGCGGCCCTGTGGGTGC
ATTCGGTGGTCCCCCCGGCATGGAAGATGGACCTCATGACGCTGGTTGCTGCTCTGG
ATGTGTCGTTGTATAA (SEQ ID NO: 18).

*Sistotremastrum suecicum*. Ras ETaG sequence:
ATGTCGAGAGTGAGTATTTCTGTTTATTGCGGCTCTATCTTGATCTCACTCGTCGCTA
GTCTGCTGCTCAGGCTTCGTTCCTTCGCGAATACAAGCTCGTCGTCGTCGGTGGTGGT
GGTATGAGCCTTGTCTCTCGTTCTCTGCAATCAAAATCTCATTCGCTTTTCTCTTGTG
CTGCATAGGTGTTGGCAAATCCGCTCTGACCATTCAATTCATCCAAAGTCATTTCGTT
GACGAGTATGACCCTACTATCGAAGGTCAGCCGACCGCTAGGCAACCATTATCTGAT
CTAACAGCTCATCTCGCACTCGACAGATTCTTACAGAAAGCAATGTGTCATCGATGA
TGAAGTTGCCCTTTTGGATGTGTTAGATACCGCTGGGCAGGAAGAATATGGGTGAGC
TCGTCTCGCAGCCCGATTCCCACGCTTATTGCTAACACGACATCGGCAGCGCAATGC
GAGAACAGTATATGCGAACGGGAGAAGGATTCTTGCTTGTCTACTCGATAACGTCGC
GGAACTCTTTCGAAGAAATCAGCACTTTCCATCAGCAAATTCTTCGAGTAAAAGACA
AGGATGCATTCCCTGTTATCGTGGTAGCCAACAAGTGTGACCTTGAATATGAGCGAC
AAGTTGGCATGAACGGTGCGATTCTAGTGTTGTTTCTGTCGATATTGGGACTTATCCC
CCTTCAGAGGGCCGTGATTTGGCCAAGCACTTCAACTGCAAATTTATCGAGACATCG
GCGAAGCAGCGAATCAACGTTGATGAGGCCTTTTCCAACCTTGTTCGAGAGATTCGC
AAATTCAACAAGGTATGTAAGCCCAAACCCGACGGAACTCCCGGCCTGATCTCTTTA
CAGGAACAACAGACCGGACGTCCTGCGACCATGGCTCCGAGCGGCCCTGTGGGTGC
ATTCGGTGGTCCCCCCGGCATGGAAGATGGACCTCATGACGCTGGTTGCTGCTCTGG
ATGTGTCGTTGTATAA (SEQ ID NO: 19).

Figure 23:
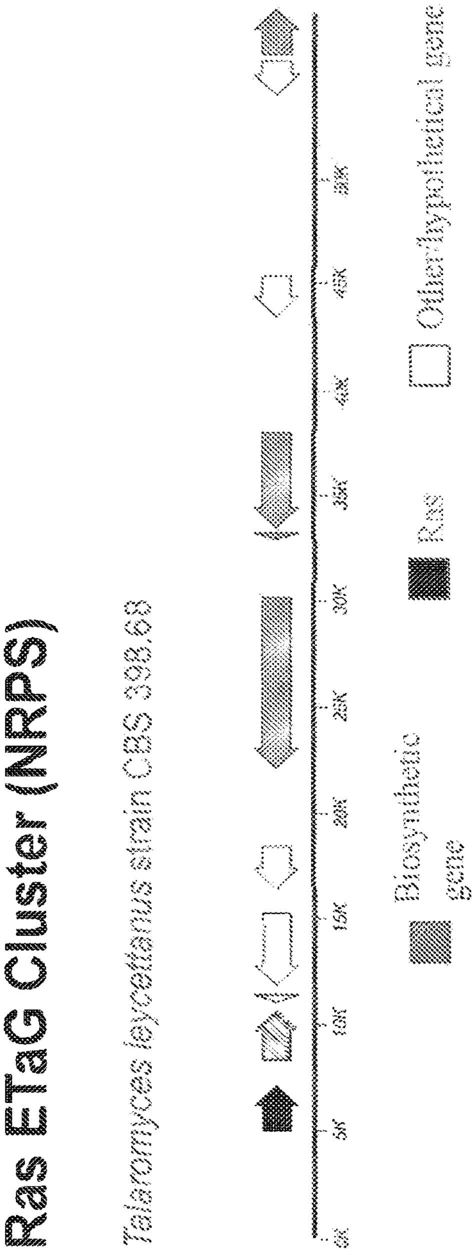
FIG. 23 depicts example biosynthetic gene clusters related to Ras, e.g., from *Talaromyces leycettanus* strain CBS 398.68. Illustrated Ras homolog is indicated in black.

FIG. 23: *Talaromyces leycettanus* CBS 398.68. Ras ETaG sequence:
ATGCTGGAAGTGCTAGACACAGCGGGCCAGGAAGAGTACACCGCACTGAGAGACC
AGTGGATCCGCGATGGTGAAGGGTTCGTTCTCGTCTATAGCATCACATCGCGAGCGT
CGTTCGCCCGCATACCCAAGTTCTACAATCAGATCAAGATGGTTAAAGAATCGGCAA
GCTCCGGGTCACCCGCTGGAGCCAGCTACTTGACGTCGCCGATCAATTCTCCCTCGG
GACCCCCGCTTCCTGTGCCGGTAATGTTGGTTGGCAACAAGAGCGACAAGGCGATG
GACCGCGCCGTCTCTGCGCAGGAAGGCCAAGCTCTTGCCAAGGAGCTGGGGTGCGA
ATTCGTCGAGGCTTCCGCCAAGAACTGTATCAATGTCGAAAAGGCTTTCTACGACGT
CGTGAGGATGCTTCGGCAGCAGCGACAACAGCAACAGGGAGGACGGGCGCAGGAG
CGGCGACCCGCCGCTTTCGGATCAGGGCCAATGCGCGATCGGGACGCCGGTCCCGA
GTACCCAAAGTCGTTTCGTCCGGATCGATCAAGGCATCGCAATGGCCTCAAATGCGT
TATCCTATGAGCTCCCCCCGATGAGTGTTCCGATCGGCGGATCTTTCCAGCTTCTGAC
CTCCGCTTATTCATGACCGTTGCTCTCTAGAATGGATGGTGTCTAGCTCCGTGTTTCT
CTTTCTCGGAGCGTGTGAGCGAGCTTGAGGACAGTCGTTCCACTTGTGCCCCCTCCT
ATCCGCCGCAGGCCCTTGTCGCTGCCGCTTTGCGGACCGCTCGTTTTGTCTACGTTGT
ACTCGAAAGCACGGCCTCTGCTTTCGTGGAAGTCTCCCTTTATGCCAGCTTTGGGTG
CGGTGGTCGATATGCAGATACTGTGTTCTATGCTCGCTGCATGCGATTCAGAGGCGT
CTTGATTCCCCGTGTCAGTATGGGGTGTTCTCGCTATTCAGGGAATCATCTGAAACC
AATTTTTCTCATCCGTTCTGTTTTTGGGAATCGGAACACGGGGGGGATGTCTGGAAA
TCTGGACCTATAACTATAGAAATGTTTCTCACCACCTTTCTCACTCAACCCTCTTGAT
GAATATCCGCCCGGCGTCTTCTACTACTTCCTACCGTCTACTACCACCAATCTCTATT -continued CTTCTTACCACCCACCTTCTGAGCCACTTCTTACACATCATTCTCGTTTGGTTTGACA
GCAAAGCGGGGAGAGTTCGAAGGACAGATCCCATGCAGGATTGGAGGACGAGAGG
GGAAGAGTCGAAGGGAGAAAAATAATTAAAAAAAAGAAAGGTGCGGGGGCAGAAG
GAGGCAGGTTTGGTTGAGAGTTGCGAATCGGTCCTGTCGCAGTCAAGTCCCAAAAA
AGAAAAGATCGCAGTCGGCGCATTAGCAGGCATTTTGATACGATGATACCCTACAG
CCGAGCTTCGAGTTTTTGTGTTCCTTTTCCTTTTTTGCAAATGCTGATTTAAAAAAAT
AACAATAGAGCTACATACTGAATGTGGATTTTTTTGACCTCTCATCTTTTTGTTGCAG
GGATGACCGCCAATTGGTAAATTCATCCCCAGTCATAATCCGAGCGCAGGATGCATG
AACTCCAGTACCTCATCATATCGCCTGCACGTTCAAGTTCCATCAATCATTCGGCGG
CGCCTACTCTGTACGACTAAGTCTACGGAGTTTGTTCTTGTTGCGGGGAAGGAAGCG
AAAGCCACGACTCCAACAAACAAACTCAGGGTGAATTGAATCCTCAGTTTCTACTCT
GTAGCCGAAGAGCCATCATTACCATTCAGGGGAAGAGCCTAAAGAGCTTGCGAGGT
TGGGCTGAGCTGCTGTGCAGTGAGCAATATATTTGGTCGATGTTTTGGATACGTTAT
CTGGAATGCGCAGATGCAGTGGTTATGCATATCCTCACGTACTCGATTCTGATGATT
CACGGGACCATACGGAGTCGATACCGAGACTCTCGCTACAAACCTGTCAATTGATAT
CGTGTACAGAGTACCGGAGCCGAGACTGGGAAATAGCACAGTCTCAGTCTCAGGTA
GCTATCGATCAATTTGACAAGGTTAGAAGTATCTCGCTAGTAATTGCCAGATGATTC
ATTCCCGGTTGAAAACTTTTCCATTGGCCTTCTTCGCTTAG (SEQ ID NO: 20).

Figure 24:
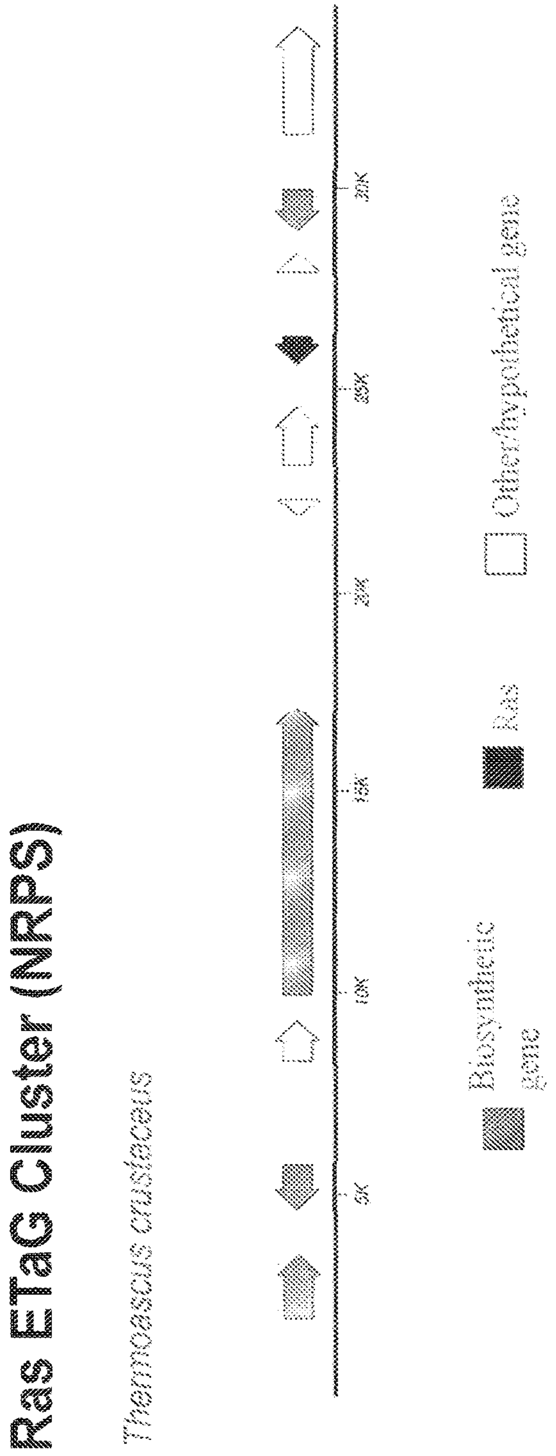
FIG. 24 depicts example biosynthetic gene clusters related to Ras, e.g., from *Thermoascus crustaceus*. Illustrated Ras homolog is indicated in black.

FIG. 24: *Thermoascus crustaceus*. Ras ETaG sequence:
ATGACCCAACAATCGAAGGTTGGTCACCGTTAAGCAAACCACGATGGGAGCGTCCC
GACCATGATGGCTCATTAGATCTCTTCTTCTCCAGACTCGTACCGCAAGCAGTGTGTT
ATTGACGATGAGGTCGCCCTGTTGGACGTCCTGGATACCGCCGGCCAGGAGGAATA
CTCAGCCATGCGAGAACAGTACATGAGAACGGGAGAGGGGTTCCTTCTGGTGTACT
CTATAACTTCGCGTCAGTCGTTCGAGGAAATCATGACCTTCCAACAACAGATCTTGC
GAGTCAAGGACAAGGATTATTTCCCCATCATTGTCGTCGGCAACAAGTGTGATCTGG
AGAAGGAGAGAGTGGTCACGCAAGAAGGTATGTCTTTAAGCTCTCCGTCGGCTTTTG
AAACTTGGCTGGAGTGCCTTGCTAATCACATTACCGCTTCTCAACAGAGGGTGAGGC
TCTCGCGAAGCAATTCGGCTGCAAATTCCTGGAAACCTCGGCGAAGTCGCGTATTAA
TGTTGAAAACGCGTTCTACGAACTTGTGCGTGAGATCCGCCGCTACAACAAAGAGAT
GTCATCCTCGTCCGGTGGCGGTGCGGGCGCGCGCGCCCCTGAGGGCAAGATGGATG
TTAATGACCCAGGCGAGAGCGCTGGCTGCTGTGGAAAGTGCATTGTTATGTAA (SEQ
ID NO: 21).

Figure 25:
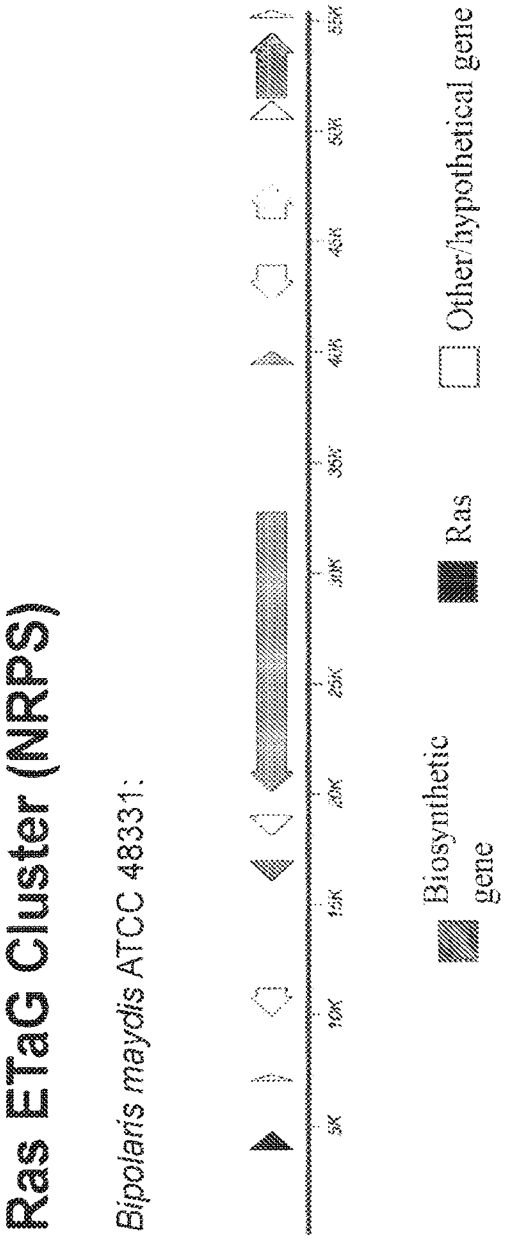
FIG. 25 depicts example biosynthetic gene clusters related to Ras, e.g., from *Bipolaris maydis* ATCC 48331. Illustrated Ras homolog is indicated in black.

FIG. 25: *Bipolaris maydis* ATCC 48331. Ras ETaG sequence:
ATGTTCTTGCCTCAACTCTACTCCCTCAACCCTGCCTTGGCTGCCAAACATGCTGATC
CTCTTGCTCCTACAGCCCAGTTTGTGCAAAACGTGTGGATAGAGAGCTATGATCCCA
CCATCGAGGACTCGTACCGAAAGGTCCTCGAAGTAGACGTGCGTACACGACACTCT
TACTAGCCGCGTTTTTTTCACTGACCCACTCTCCCTCCCAGGGCCGTCATGTCATTCT
CGAGATCTTGGATACTGCCGGCACAGAGCAGTTTAGTAAGTGATTACATACATAGCC
CCACCCCACGTGGACCCAAGACTAACACGACAATAGCTGCCATGAGGTAGAGTTTC
CTACTACCCCCTTACTCGGTAAACATCAAAACTTACACGGATGCAGAGAACTGTACA
TGAAAACGGGCCAAGGATTCCTTTTGGTCTTCAGCATCACATCAGAATCTTCCTTTTG
GGAGCTTGCCGAGCTGCGTGAGCAGATACGACGCATCAAGGAAGACAGCAACGTAC
CCATGGTTCTCATTGGCAACAAGTCGGACCTAGAAGACGACCGTGCCGTGCCGCGC
CCACGAGCATTTGCCATTTCGCGTGAATGGAACGTTCCTTATTTCGAAACCAGTGCT
CGAAGGAGAGCCAATGTCGACGAAGCCTTTGTCGACCTCTGCAGGCAAATCATCCG
CAAGGATCAGAACGAACGAAACCGCATGGCCCCACCGGATTCCCCGAGGCCTGGCG
GTCCCAGGAGCAGAACTCACACGGGACGGCCAAAGCGCAAGGCTCACCGGCCCCAT
TGTACCATTCTTTAA (SEQ ID NO: 22).

Figure 26:
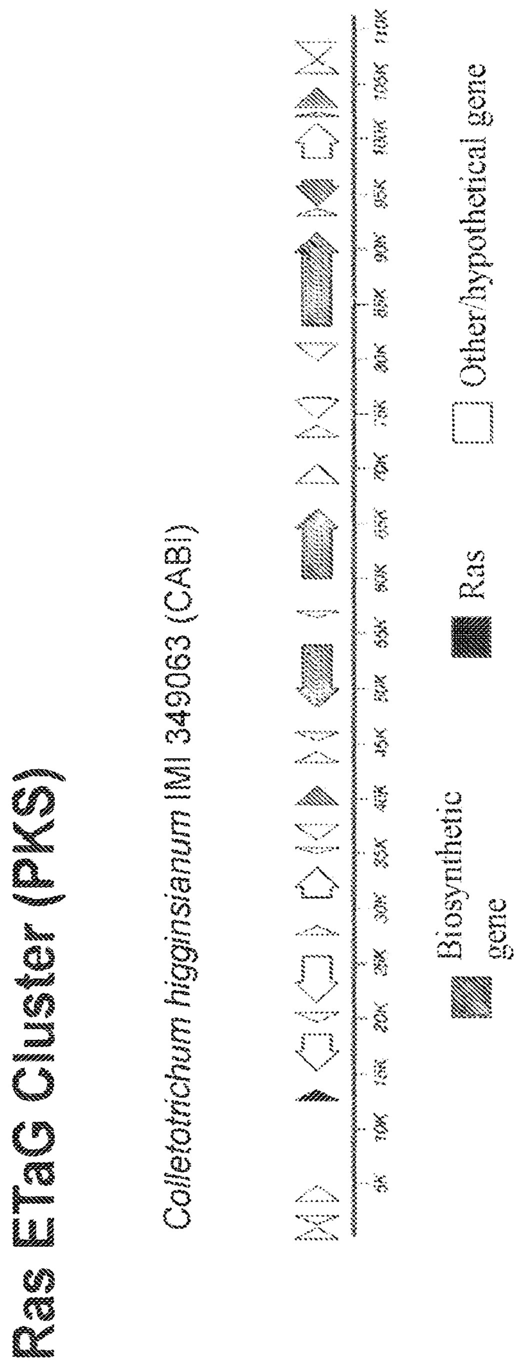
FIG. 26 depicts example biosynthetic gene clusters related to Ras, e.g., from *Colletotrichum higginsianum* IMI 349063 (CABI). Illustrated Ras homolog is indicated in black.

FIG. 26: *Colletotrichum higginsianum* IMI 349063. Ras ETaG sequence:
ATGGCGTCCAAGGTTCGTCGTCGCCACCTCCCGTTTCCCTTCATTTCTTTTGCCGCCT
CGTCGCTCCATCGCTCCATCGCCCCATCGATCCGTTGCTAACCAGTTGCCATCTCGCA
GTTTCTGAGGGAGTACAAGTTGGTCGTCGTCGGCGGCGGTGGTGTCGGTAAATCCTG
CTTGACCATCCAATTGATTCAGAGCCACTTTGTCGACGAATATGACCCGACGATCGA
AGGTGCGTCGTCCCGAACTTCTTGCTCCACCGTTCGATGCGACGGCTTCGAATCAAT
CGCATGCTAATGTGGATCTCACCCATTTCAGATTCCTACCGCAAGCAGTGCGTCATC
GACGAGGAGGTCGCTCTACTCGATGTCCTCGACACGGCCGGTCAGGAGGAGTACTC
CGCCATGAGGGAGCAGTACATGAGGACGGGAGAGGGTTTCCTTCTGGTTTACTCCAT
CACTTCGCGACAGAGCTTCGAGGAGATCACCACATTCCAGCAGCAGATTCTGAGAG
TAAAGGACAAGGACTACTTCCCCATGGTCGTCGTCGGCAACAAGTGCGATCTGGAG
AGCGAGAGAGAAGTCACACGACAAGGTATGATTCTGATTCCTGCTGTGCCGCGACA
CCGCATGAGGCGGCTCCTTTCGAGGCCCAGGCCCGGTGTGGATTCATTGATGGAATG
AAAAGTAGCTGACATCATTCACTCGTGCGCGCTACAGAGGGAGAGGCCCTTGCCAA
GTCATTCGGCTGCAAGTTCATCGAGACGTCGGCCAAGTCTCGCATCAACGTCGACAA
GGCTTTCTATGATATTGTCCGAGAAATCCGTCGGTACAACCGCGAGATGCAGGGCTA
CTCTACCGGCAGTGGCGGCGCCTCGGGCATCAACGGCCCCCCGAAGCCCATGGACG
TCGAGAACGGCGAGCAAGAGGCAGGCTGCTGCTCCAAGTGCGTACTAATGTGA
(SEQ ID NO: 23).

Figure 27:
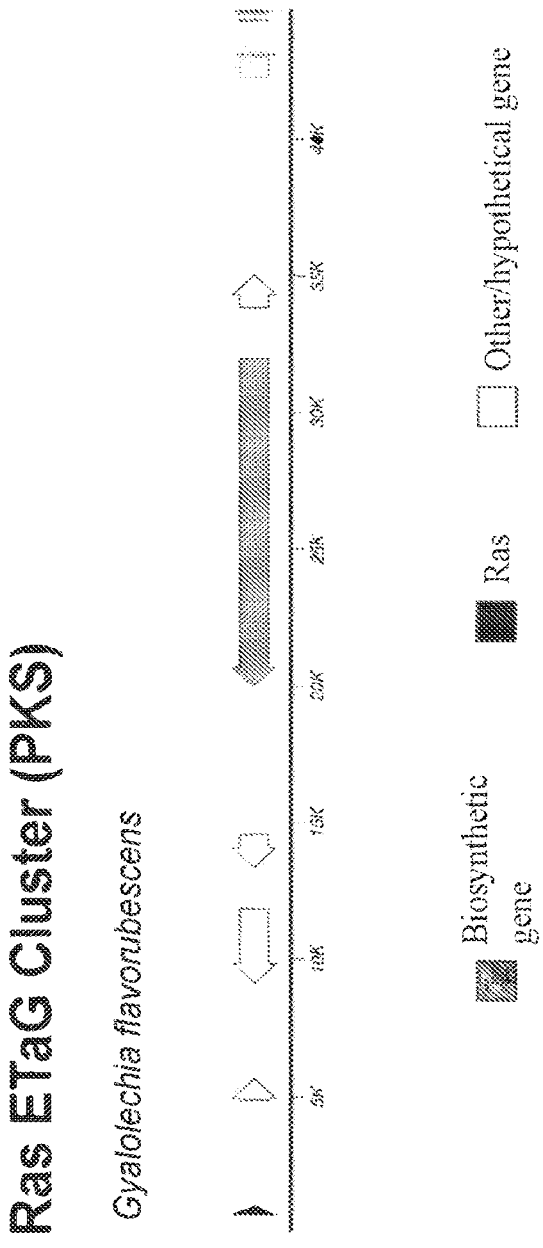
FIG. 27 depicts example biosynthetic gene clusters related to Ras, e.g., from *Gyalolechia flavorubescens*. Illustrated Ras homolog is indicated in black.

FIG. 27: *Gyalolechia flavorubescens*. Ras ETaG sequence:
ATGGCTTCAAAGGTAAGTCCATCTGTCTCTTTAGAGTATTCTCATTGCTCTTTGCTAC
CGAGCTTCTCCATGGACGCTGACCCTTACCTGCTCAAGTTCCTACGGGAATACAAGC
TCGTCGTCGTTGGCGGAGGAGGTGTGGGCAAGTCCTGCTTGACCATCCAGCTCATCC
AGAGTCACTTCGTCGACGAATACGATCCCACCATTGAAGGTAAATAGATTCGTCCTA
TCCACCCATTGCGCTTTTACTGATCGAAGCGATTTGCAAGACTCCTACCGGAAGCAA
TGCGTCATCGACGAAGAAGTCGCCTTACTCGATGTACTAG (SEQ ID NO: 24).

Figure 28:
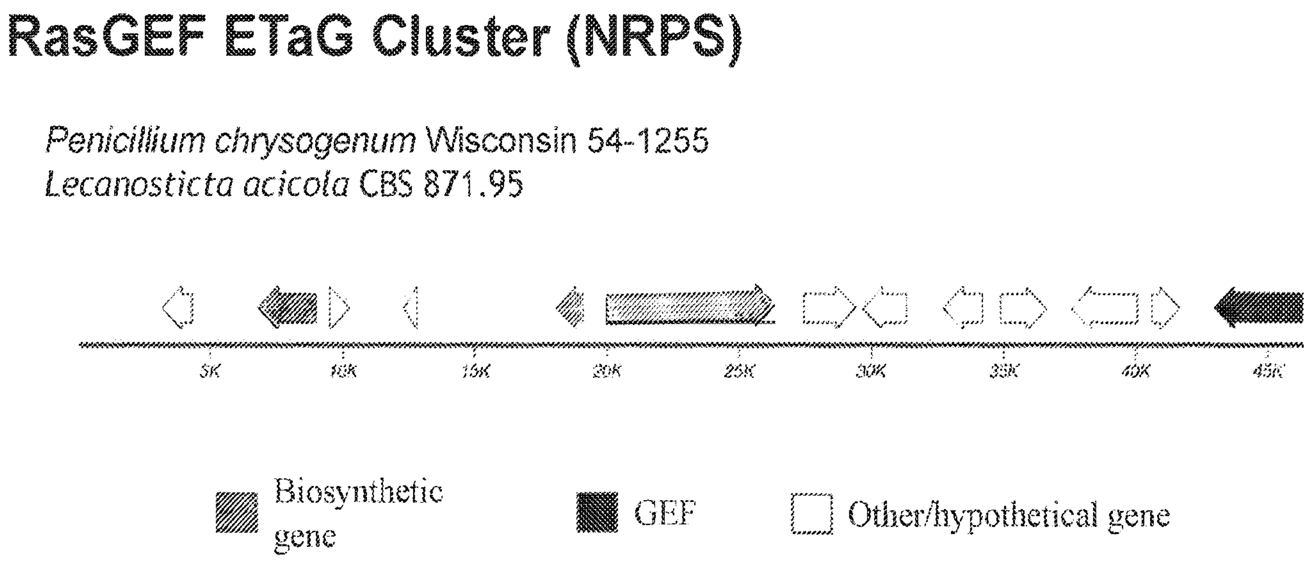
FIG. 28 depicts example biosynthetic gene clusters related to RasGEF, e.g., from *Penicillium chrysogenum* Wisconsin 54-1255 and *Lecanosticta acicola* CBS 871.95. Illustrated RasGEF homologs are indicated in black.

FIG. 28: *Lecanosticta acicola* CBS 871.95. RasGEF ETaG sequence:
ATGGAGCTCCCTTTCGAGAACCCGACCGCAACAACTGAACCAGGCCCGCG
AGATCGAAATAATTTCTTTGTCCCCGACCAGACACGGCCACCTCCAGAGCTGATGGC
GCGTGGCTTTGAGCGGGATGAGGACGAGTACGATGGATCTGCATCGGAGGCAGAAG
GAGAGTCACTGATGTTAGGCTCGCATGACTCGATTTCTCGCCGACGCCAGTCCGTGA
TGGATGGAGTATCCCCTGCCACGTCCATGGATTCCTTGTACGCCGCAGGATCTAAAG
ATTTCAAAACGCCGCAGCCGCCGAGCAAGAGCCCGCAAAAGTCACACAGCCTCGGC
GGAAACAGTACCAGCACATCTGTGACCGAAAGCTTTTCCAGACCTTCTATTTCCTCC
AACCCCCCTCAACACTTTGTCGACGATGGCTTCGCACCGCCAATCACCTGGCCTTTG
CTTGTCGATAATATGCGGTACGCCGTGGAAGCCTATCGCCAGGTGCTTTTCAACGGT
GAGCGTGCAGAGTACGTAAGAAAGGCCGAGGACATATCTGACCATCTTCGCATGCT
GCTGGCTGCTGGATCTGACACGACGGATAACCACTCTGGTAACCCATCTATCATTTC
CACAAACAAGGCGCTATATCCTTACTTCCGGGACATGATGTCTAAGTTCTCGAAGCT
GGTTCTTTCATCACATATTGCCGCCGCTGATTGGCCTGGTGCCGACTCGGCCAATAA
ATGTTTGCAGGAGGCCGATGGAGTTATGCAAGGCGTGTATGGCTATGTGCAAGTGG
CTCAACATCAGCGCGGCGATGCCATCCATCGCATCGTGCCTGGCTTCGTCAGCGGCA
GCTCTTCGGGTGGTAGCTGGCAGAACAACGGTGTTTCCTTGAATACTTCAGGCCCGA
CATCATTCCTCGTTCCGGATGGAGGGGACTCGCGAGTAGAGCCATCGGTCTCTCTTG
ACACCGCCTTTTTGGATTCAATCGACATCCTCAGAAGATCTTTTGTTGGTAGTATTCG
GCGACTAGAAGAACGGCTGGTTATAAACCGGAATATCGTTACAGTGGAGGAACATG
GAGACATTGCCGATGCGATCTCAGCTGCTGCAATCAAGGTGATTGAACAGTTCCGCC
CATGGATCTCCTCGGTGGAGTCGATGAATTTAGCTCCGTTGGGAACCAGCTTCCAGA
ACCCCCAGCTAGTAGACTTCAGCTTGCAAAAGCAGAGAGTCTACGATGCTATTGGA
GATTTTGTCCTGAGCTGTCAAGCAGTCTCTGCCCCTCTGGCTGATGAGTGGGCAGAG
CTCCGTGGTAATTCTCTCGACGATCGTGTGAATGCCGTGCGAGGCATCGTTAGACAG
TTGGAGAACTATGTCTCCCAGATTGGCTTCTCATTGTCGCTGCTCCTCGAGCAAATCC
CCACCGAACCAGCATCATCTCTAAGACGGGATAGCCGCCAAGAAGCGGAAGATGAG
TCGTACAAGATAATGCATAGCCGAGGCGAGTCCAAGGCCAAGATTGCCACAGAGTC
AATCGGGATTCCGTCCTCCTACGCTCCTGAAAAGGAAAGTGGCACAGATAAAGTAC
GAAGAAATATGGACAAGGCACAACGTTTCTTTGGCCAGGCACCCCCAACGGCTATC
ACCCGAGAGCCAATCCGTGAGCCAGTCCGTGAGCCCGAAGAAACTCCCTGGTTCTT
GAAAATGGCCCATGAAGGCGAAGTGTTCTACGATAACAAGGGAGACTTGCCCATCC
TCAAATGTGGAACACTCGCCGGATTGGTTGAACACCTCACCCGCCACGATAAGCTTG
ATGCATCCTTCAACAACACATTCCTCCTCACCTATCGCTCTTTCACTACTGCCACCGA
ACTATTTGAATTGCTTGTCCAGCGGTTTAACATTCAGCCTCCATTTGGCCTGAATCAA
GATGACATGCAAATGTGGATTGACCGGAAACAGAAGCCGATTAGATTCCGTGTCGT
CAACATTCTTAAGAGCTGGTTCGATCACTTCTGGATGGAGCCCAATGATGAACTGCA
CATGGATCTCCTGCGACGTGTCCATACCTTTACCAGCGACTCCATCGCTACCACGAA
GACCCCAGGAACCCCTACATTATTGGCCGTGATCGAACAACGACTTCGAGGACAAG
ATACCACTGTTAAGCGCCTTGTTCCGACTCAGAGCACCGCCGCACCAACACCAATCA
TCCCTAAGAATATGAAGAAACTGAAGTTCCTCGACATTGATCCAACGGAGTTTGCTC
GGCAGTTGACCATCATTGAGTCGCGCCTCTACTCCAAAATCCGGCCCACTGAGTGTT
TGAACAAGACATGGCAGAAGAAGGTCGGCCCTGATGAGCCGGAACCATCTCCCAAT
GTCAAGGCCTTGATTCTTCACTCGAACCAGCTTACCAACTGGGTCGCGGAAATGATT
CTCGCCCAAGGCGATGTTAAGAAGCGGGTTGTAGTCATCAAACACTTTGTGAACGTG
GCTGATGTATGTGTTTACTCTGCTTGCTTGACAAATCCCGGCCTCACTAACTCAATCA
TACAGAAATGTCGCCATCTGAACAATTATTCTACCCTGACTTCCATCATCTCGGCTCT
TGGAACTGCACCCATTCATCGTCTAGGTAGAACGTGGGGCCAGGTTAGCGGACGCA
CGTCCGCAATTCTGGAACAGATGCGCCGGCTTATGGCTAGTACGAAGAACTTTGGCG
AATACCGAGAAACCCTGCATCTCGCTAACCCGCCCTGTATTCCATTTTTCGGTATGC
GTCACGGTCATTTCAAGCAGATTCAAGTIGTCTTGGAGTATCTCACCCCCTTGACTCT
GTAGCTAACACATCTTAGGTGTCTATCTCACGGATTTGACCTTCATTGAAGACGGTA
TCCCGTCTCTAACACCATCAGAATTGATCAACTTCAATAAGCGGGCCAAGACCGCAG
AAGTCATCCGGGATATCCAACAATACCAGAACGTGCCTTACCTTTTGCAACCCGTCG
GCGAACTTCAAGATTACATCCTCAGTAACCTCCAAGGTGCTGGCGATGTACATGACA
TGTACGACCGGAGTCTGGAGATCGAGCCTAGGGAGCGCGAGGACGAAAAGATTGCA
AGGTATGCTGAAGCCACAAGCAGAGACAAGGGCTCCTTGTTATTTGCATCCACCGTC
GCTATCTTGCGATAA (SEQ ID NO: 25).

*Penicillium chrysogenum* Wisconsin 54-1255. RasGEF ETaG sequence:
ATGGAGCTCCCTTTCGAGAACCCGACCGCAACAACTGAACCAGGCCCGCG
AGATCGAAATAATTTCTTTGTCCCCGACCAGACACGGCCACCTCCAGAGCTGATGGC
GCGTGGCTTTGAGCGGGATGAGGACGAGTACGATGGATCTGCATCGGAGGCAGAAG
GAGAGTCACTGATGTTAGGCTCGCATGACTCGATTTCTCGCCGACGCCAGTCCGTGA
TGGATGGAGTATCCCCTGCCACGTCCATGGATTCCTTGTACGCCGCAGGATCTAAAG
ATTTCAAAACGCCGCAGCCGCCGAGCAAGAGCCCGCAAAAGTCACACAGCCTCGGC
GGAAACAGTACCAGCACATCTGTGACCGAAAGCTTTTCCAGACCTTCTATTTCCTCC
AACCCCCCTCAACACTTTGTCGACGATGGCTTCGCACCGCCAATCACCTGGCCTTTG
CTTGTCGATAATATGCGGTACGCCGTGGAAGCCTATCGCCAGGTGCTTTTCAACGGT
GAGCGTGCAGAGTACGTAAGAAAGGCCGAGGACATATCTGACCATCTTCGCATGCT
GCTGGCTGCTGGATCTGACACGACGGATAACCACTCTGGTAACCCATCTATCATTTC
CACAAACAAGGCGCTATATCCTTACTTCCGGGACATGATGTCTAAGTTCTCGAAGCT
GGTTCTTTCATCACATATTGCCGCCGCTGATTGGCCTGGTGCCGACTCGGCCAATAA
ATGTTTGCAGGAGGCCGATGGAGTTATGCAAGGCGTGTATGGCTATGTGCAAGTGG
CTCAACATCAGCGCGGCGATGCCATCCATCGCATCGTGCCTGGCTTCGTCAGCGGCA
GCTCTTCGGGTGGTAGCTGGCAGAACAACGGTGTTTCCTTGAATACTTCAGGCCCGA
CATCATTCCTCGTTCCGGATGGAGGGGACTCGCGAGTAGAGCCATCGGTCTCTCTTG
ACACCGCCTTTTTGGATTCAATCGACATCCTCAGAAGATCTTTTGTTGGTAGTATTCG
GCGACTAGAAGAACGGCTGGTTATAAACCGGAATATCGTTACAGTGGAGGAACATG -continued GAGACATTGCCGATGCGATCTCAGCTGCTGCAATCAAGGTGATTGAACAGTTCCGCC
CATGGATCTCCTCGGTGGAGTCGATGAATTTAGCTCCGTTGGGAACCAGCTTCCAGA
ACCCCCAGCTAGTAGACTTCAGCTTGCAAAAGCAGAGAGTCTACGATGCTATTGGA
GATTTTGTCCTGAGCTGTCAAGCAGTCTCTGCCCCTCTGGCTGATGAGTGGGCAGAG
CTCCGTGGTAATTCTCTCGACGATCGTGTGAATGCCGTGCGAGGCATCGTTAGACAG
TTGGAGAACTATGTCTCCCAGATTGGCTTCTCATTGTCGCTGCTCCTCGAGCAAATCC
CCACCGAACCAGCATCATCTCTAAGACGGGATAGCCGCCAAGAAGCGGAAGATGAG
TCGTACAAGATAATGCATAGCCGAGGCGAGTCCAAGGCCAAGATTGCCACAGAGTC
AATCGGGATTCCGTCCTCCTACGCTCCTGAAAAGGAAAGTGGCACAGATAAAGTAC
GAAGAAATATGGACAAGGCACAACGTTTCTTTGGCCAGGCACCCCCAACGGCTATC
ACCCGAGAGCCAATCCGTGAGCCAGTCCGTGAGCCCGAAGAAACTCCCTGGTTCTT
GAAAATGGCCCATGAAGGCGAAGTGTTCTACGATAACAAGGGAGACTTGCCCATCC
TCAAATGTGGAACACTCGCCGGATTGGTTGAACACCTCACCCGCCACGATAAGCTTG
ATGCATCCTTCAACAACACATTCCTCCTCACCTATCGCTCTTTCACTACTGCCACCGA
ACTATTTGAATTGCTTGTCCAGCGGTTTAACATTCAGCCTCCATTTGGCCTGAATCAA
GATGACATGCAAATGTGGATTGACCGGAAACAGAAGCCGATTAGATTCCGTGTCGT
CAACATTCTTAAGAGCTGGTTCGATCACTTCTGGATGGAGCCCAATGATGAACTGCA
CATGGATCTCCTGCGACGTGTCCATACCTTTACCAGCGACTCCATCGCTACCACGAA
GACCCCAGGAACCCCTACATTATTGGCCGTGATCGAACAACGACTTCGAGGACAAG
ATACCACTGTTAAGCGCCTTGTTCCGACTCAGAGCACCGCCGCACCAACACCAATCA
TCCCTAAGAATATGAAGAAACTGAAGTTCCTCGACATTGATCCAACGGAGTTTGCTC
GGCAGTTGACCATCATTGAGTCGCGCCTCTACTCCAAAATCCGGCCCACTGAGTGTT
TGAACAAGACATGGCAGAAGAAGGTCGGCCCTGATGAGCCGGAACCATCTCCCAAT
GTCAAGGCCTTGATTCTTCACTCGAACCAGCTTACCAACTGGGTCGCGGAAATGATT
CTCGCCCAAGGCGATGTTAAGAAGCGGGTTGTAGTCATCAAACACTTTGTGAACGTG
GCTGATGTATGTGTTTACTCTGCTTGCTTGACAAATCCCGGCCTCACTAACTCAATCA
TACAGAAATGTCGCCATCTGAACAATTATTCTACCCTGACTTCCATCATCTCGGCTCT
TGGAACTGCACCCATTCATCGTCTAGGTAGAACGTGGGGCCAGGTTAGCGGACGCA
CGTCCGCAATTCTGGAACAGATGCGCCGGCTTATGGCTAGTACGAAGAACTTTGGCG
AATACCGAGAAACCCTGCATCTCGCTAACCCGCCCTGTATTCCATTTTTCGGTATGC
GTCACGGTCATTTCAAGCAGATTCAAGTTGTCTTGGAGTATCTCACCCCCTTGACTCT
GTAGCTAACACATCTTAGGTGTCTATCTCACGGATTTGACCTTCATTGAAGACGGTA
TCCCGTCTCTAACACCATCAGAATTGATCAACTTCAATAAGCGGGCCAAGACCGCAG
AAGTCATCCGGGATATCCAACAATACCAGAACGTGCCTTACCTTTTGCAACCCGTCG
GCGAACTTCAAGATTACATCCTCAGTAACCTCCAAGGTGCTGGCGATGTACATGACA
TGTACGACCGGAGTCTGGAGATCGAGCCTAGGGAGCGCGAGGACGAAAAGATTGCA
AGGTATGCTGAAGCCACAAGCAGAGACAAGGGCTCCTTGTTATTTGCATCCACCGTC
GCTATCTTGCGATAA (SEQ ID NO: 26).

Figure 29:
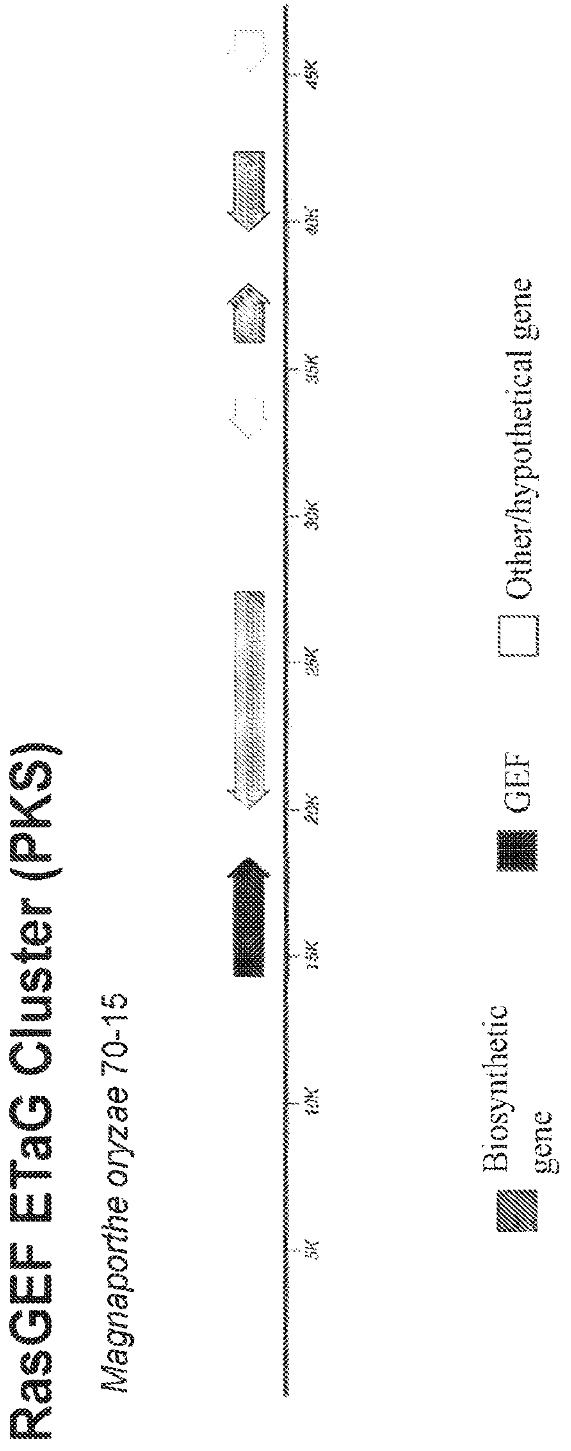
FIG. 29 depicts example biosynthetic gene clusters related to RasGEF, e.g., from *Magnaporthe oryzae* 70-15. Illustrated RasGEF homolog is indicated in black.

FIG. 29: *Magnaporthe oryzae* 70-15. RasGEF ETaG sequence:
ATGGTAATGCCCGGCGACCATTCCATGCAGCGGGCGAGCCTTCAAGTGGC
ACCCCTCGCCATCCGTAACAAGGGCTCCCGTCTCGGCCACGGCTCTGACACCGAGAA
CGATGCTTCTTTCACGTCAGTCTCGAGCAACAACAGTGACGCCACCATCACGGACTC
GAGGTCCGACGCAACAAACCTCAACAAGACAACAGCAACCACCACCACCACCACAA
CAACAACGACCACCACGAGCACAACCAAGAAACCAAACGCCGCGATCGATTCGTCC
AACGGCTCCCACATGAAGTCGTCGTCGCGCAATGGCTCGCGAGAGGAACCGCTGGA
GGCGGATCCGGACATGGCTCCGCCCGTCTTCCACAACTTCTTGCGGGCCTTCTTCCA
CTTCAAGCCGAGCTTCCTCATGACGGACTCGACTGTTACACTGCCGCTGGCCGAGGG
CGACGTAATCCTGGTGCACTCGATACACACCAATGGCTGGGCAGACGGCACCCTGC
TGGCAACCGGCGCCAGAGGCTGGCTGCCGACCAACTACTGCGAACCATACGGACCC
GACGAACTCACGAACCTTTTGAACGCCTTGCTTAACTTTTGGGATCTTTTGCGTAGCA
CGTCGGTCAACGACCACGAGATATTCAGCAACCAGGAGTTCATGAAGGGCATAATA
GCCGGCGTCCGATACCTACTGGTAGGTTTTTGCTCTTTGTTTTTCTTTTGTCTTTTTAT
GACTTTGCTTAGCCCCGAGCCTTGCGCCTGGCGTGGGATGAAAAAAAAGACCAAAA
AGCCCTCCGAGGCCTGTGCGACTGACGCTGATTAATTGGGTGGCACAGGAACGCAC
AAACTCTCTTACTAGAGAGGCCCCTCTCATTCAGCGCCACGAGGGCCTCAGACGCAG
CAGGAAATCGCTATTGTCCGAGCTTAGCTCGCTGGTCAAGACGGCCAAACGCCTCCA
GGAGCACCAGCGTATGATTCAGCCCATTGAGGACACTAACGATATCATTGACGAGA
TGATCCTCAAGGCATTCAAGATTGTGACCAAGGGTACTCGCTTTCTAGACATTCTGG
ATGAGGACAGGAAATCTCGAGCACCATCAGTCACGGTCATGGCAACCGTCATGGAG
GAGGTGACGCCGCCCGTCGACGGAAAGCCTGCAAATAGCGAACAGGCAAAGGCAC
TGCGGGCGTTGACGGCAGGTGCAGGCGAAGACTCGTCTGCCGTGGACGACACCACG
GAGCAGACGGTCGTTGTACGTCCTACTAACAGGCGCATGTCGACCATCACATCGCCA
ATTTCGGCAACCAACACGAGGAGAATGTCGCTGGGTAGCAACCCCCACCGGGTGTC
GACGGCAATCTCGCACCGAGTCTCGCTTGTCCCATCACCATCCACCAAGGCCCAGAA
CCTCATCTCACAGCAATTGAGCGACAGCCACGATACCTTCCTGTCATACCTGGGTTC
GTTCATCGGCCGCCTGCACCTGCAGTCCCAGTCTAGGCCGCATTTGGCGCTTGCCGT
CAAGCAGTCGGCAACGTCGGGTGGCGAGCTGCTGGTGGTTGTCGATGTGGTGTGCG
CCCACAACCGCATGAGCCAGGATTTCCTTGATGCTTACCGCGATGCCATGTTTGCAC
GTCTCCGAGACCTTGTCTTGGCGGCACAGGATGTCCTGACCAGCCGCGGTCGCGAGA
TGGAGGACGTCATCTTTCCCCAGGACAACAGCAGACTGCTTCAGGCGGCCACGGGT
TGCGTGCGGGCCACGGGCGAGTGTGTTGCCAAGACCAAATGGTTCCTCGAAAAGAT
TGGCGACTTTGAGTTTGAGCTGGAACGGGGAGCTTCGGCTCTGAACATGGATCTTGG
CTTTTTGGAGATTAAAGTTGCCGAGGACAGGGATAAGGACCAGGGCATGGACGCCA
CCAGCATCGCCGAGTCCAACAAATCAGGCTCTACCGAAACCTCGACGGTAACGGCA
ACTACGACACAGTCCGCCGCGTCGACAACCGCCACGGTGCGGCCGACGGCCCTGGC
CACCAACAAGCCGCTTCCTGAGGTGCCCCAATCCACAACCCCCGACGAGGAGGCCC
CGCGGCCTCAACGATCCCCCGCTTCCTCACGACCGACCTCGCTTGTGGAGGAGGGCC
CTGCCAGCATGGCTTCCTCTGTGGCGTCGCTGCGTCCTATGCTGCCGCCTCTGCCCAG GCTTTCCACCTCGCTTATGACGCAGGATGAGTACAGCCCGTCGGAGCACTCGGCTGG
CCACGACAGCGACAACTACCATGGCTCGTTCCGCTCTGAGAGCATGACAGCCTCCA
GCTCCGGAACCGGCAGCACATATATCAGCCGCGACTCGGAGTCAAGCCTGGTCTCA
CAGTCGTCAACGCGTGCGACAACGCCAGACATTCCCTTGGCGAACCAAAAGTCGCT
CTCGGATATTAGCAACTCTGGCAGCGGAGCTTGTGTGGTTGAGGAGGATGACGTCG
AGTCGAGGCTGCTCGAGAGGACATATGCGCACGAGCTCATGTTCAACAAGGAGGGC
CAAGTTACCGGCGGCTCACTCCCCGCTCTGGTCGAGAGGCTGACCACTCACGAGTCC
ACCCCCGACGCCATGTTCGTGTCGACCTTTTACTTGACTTTCAGGCTCTTCTGCACAC
CCGTAAAATTGGCCGAGAGCTTGATCGACCGATTCGACTACGTTGCCGAGTCTGCTC
ACATGGCAGGTCCCGTTCGTCTGCGTGTCTACAACGTCTTCAAGGGCTGGCTCGAGT
CCCACTGGAGGGACGAGACGGACCGCGAAGCCCTGAGTCTCATCGAGCCGTTTGCT
ACTTTCAAACTTGGCGAGGTGCTTCCCTCGGCCGGCAAGCGTATCCTCGAGCTTGTC
GATCGCGTCTCTGCGTGCGGCGGTGGTGCATTGGTCCCACGCCTGGTGTCTTCGATG
GGCAAGACCAACACATCCATCTCTCAATACGTTCCCGCCGACACTCCCCTGCCAAAC
CCGGTATTCACCAAGAGCCACGCGCACCTGCTGGCCAACTGGAGGAACGGCGGCAG
CTGCCCTAGCATCCTCGACCTTGATGCTCTCGAGATTGCCCGGCAGCTTACCATCAA
GCAGATGAACATCTTTTGCTCGATAATGCCCGAGGAGCTCCTAGGCTCTCAGTGGAT
GAAGAATGGAGGTGCCGAGTCGCCCAACGTCAAGGCCATGTCGACCTTTTCCAACG
ACTTGTCCTCGCTGGTGTCGGACACAATCCTGCACTACAACGAGGTCAAGAAGCGTG
CAGCCGTGCTCAAGCAGTGGATCAAGATTGCCCACCAGTGCCTGGACTTGAACAAC
TATGACGCCCTCATGGCGATCATCTGCAGTCTCAACAGCTCCACCATCACGCGCCTC
CGGCGCACATGGGAGGCCGTCTCGCCTCGTCGCCGTGAGCTCCTCAAGCAGCTCCAA
GCCATTGTCGAGCCGTCTCAGAACAACAAGGTCCTGCGCGGTCGCTTGGCCGGCCAC
GTCCCGCCCTGCCTGCCATTCCTCGGCATGTTCCTCACCGACCTGACCTTTGTCGACA
TTGGCAACCCGGCCATCAAGCAGCTCCCTGGTAACGAGGGCGACGGCAAGGCTCCG
GCCATCACCGTCATCAACTTTGACAAGCACGCCCGCACGGCCAAGATCATCGGCGA
GCTGCAGCGCTTCCAGATTCCTTACCGGCTGCAGGAGCTTACCGAGGTGCAGGAGTG
GATCCAGGCCCAGATTGCACGACTCCGCGAGCTCGAGACGCCCAACGATAACGTCC
AGGTCGCCTACTACCGCAAGAGTCTGCTGCTCGAGCCCCGCGAGGTCACGGCCACG
CCCCAGACGCTACGGAACTCGTCCGAGACGTTTTCCTCGTCGTCGGCCACGCTCGCA
CCTCCAAGCGCCAGAGACTCGACCGCTGCCAACGGCAGAGCAGCAGAGAGAACTGC
TCAGTCGCAGAGGACGGATTATTTTGGCTGGATGCGAGGATCTGGGGGCAGCCACA
GAGATCATCCTGCTGCTTGA (SEQ ID NO: 27).

Figure 30:
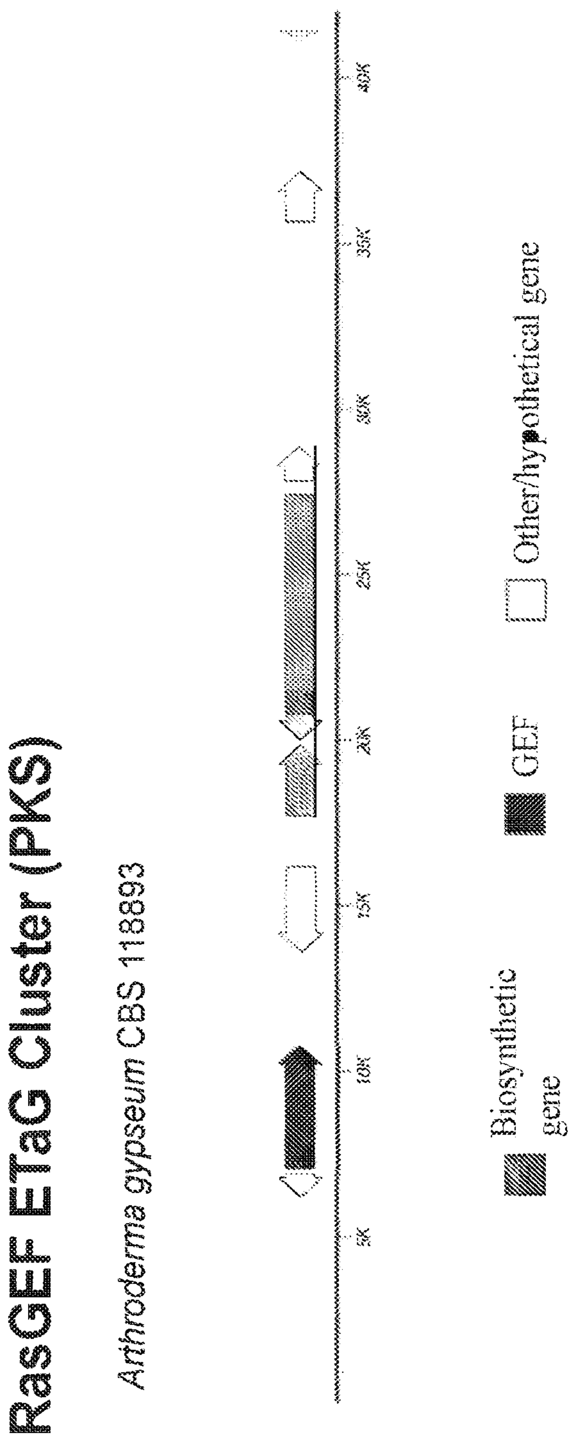
FIG. 30 depicts example biosynthetic gene clusters related to RasGEF, e.g., from *Arthroderma gypseum* CBS 118893. Illustrated RasGEF homolog is indicated in black.

FIG. 30: *Arthroderma gypseum* CBS 118893. RasGEF ETaG sequence:
ATGGCTGCTCGCGATGGCTACTCCAGCCAGGGCGCTGCTGGTGCGGCGAA
TGACGATGGTCTGTACCAAAATTTACTTCCTCTTCTTCCGGTTCTACCCACGTCGTAT
TAACCGCATTTCACAGGCTACGTATCACCAACAGAGGCGCCTCCGGCTCTCTATGTT
AGAGCTCTGTACAAGTACACCTCAGACGACCACACCAGCCTTAGCTTCGAGCAAGG
CGACATTATTCAGGTGCTGAATCAGCTCGAGACCGGCTGGTGGGACGGTGTGATTGG
TGATGTCCGTGGCTGGTTCCCAAGTAACTACTGCGCTGTCGTTCCTGGGCCCGAGGC
TCTCAACGAGCACGCCGGTGATGCCAGTGCCGAATCTGGCGCAGACGATGACTACG
AGGACGACGTTGACGGCCTTGACACTACCCTGAGAGACGACGACCTGCCTATTGAA
AGCAATGGAGCAGACGGCGGCGAGCCCGAAGAGGCCGCCTTCTGGATCCCCCAGGC
CACCGCAGACGGGCGCCTGTTCTACTACAACACATTGACCGGCTACAGCACAATGG
AACTTCCCCTGGAGACGCCGACTTCCGTCAACGAGTCTGGCCCTCGGGACCGTACAA
ACGTCTACGTGCCCGAACACACCAGGCTGCCACCTGAGATGATGGCCCGTGGCATC
GATCGCTACGAAGATGACTATGATGGCTCTGCCTCAGAGGCTGAAGGTGACTCCCTC
TTAATGGCATCGCAGCGCCGACATTCGTTCATTTCTGATGGCGTCTCTCCTGCTACAT
CCTTAGGTTCCGTCAATCCTTCACCAATCACCAAACACTATGATCTCAAATCAGCTT
ATCCTCCCCATTTCGTTGCAAACGGTGGAAACGCTGGCATGGACTCTATCCCTATCA
TGGGCACTCCCATGTCCACCCACTCGAACGCGACTGATCGATCTCTGCCCTTTGGCA
TCTCAACCTCTATCCCTCGCTATTTCCTGGATGACTCCACCGCTCCTCATCCTACCTG
GAACTCGCTCGTCAGCAACATGCGAGATGCAATTGAGGCGTATCGACAGGCCATCA
TCGAAGGTCGGCGGTCAGAGTACGTTCGCAGGGCCGAGGATGTGTCCGATCACCTG
CGGATGCTTCTCGCGGCAGGCTCCGATACTACAGATAACCACTCGGGCAACCCGTCA
ATCATCTCTACAAACAAGGCGCTATACCCGCATTTCCGCGATATGATGTCCAAATTC
TCCAAGCTCGTCCTATCCTCACATATTGCCGCGGCTGACTGGCCGGGACCAGACTCT
GCGACCAAATGTCTCCATGAAGCCGAGGGCGTTCTACAGGGCGTTTACGGCTACGTC
GAAGTGGCCAAGCAGCAGCGAGGAGACGATATCCGCCGTCTGACACCTGGCTTTGT
CGCCGGCAGCACTTCTGGCGGTCACTGGCAGAACAACAACCTCGCTCGAAGGGATC
CAACGTCTTTCCTCGAGCATGACTCTGAGTCTCACCGCACTCCGTCGGTCTCGCTTGA
CTCAAAGCTTCTAGAGCGAATCGAAGAGCTTCGCAAGATGCTAGCTGTCAGCTCCCG
CAGGCTAGAAGAGCAGCTCTCATCCTTCAAGGGTAAAATTGTTACGCCAAAAAGCC
ATGCCGAGATTGGCGACGCTGTATGTGAAGCTGGCGTGCCGATAGTCGAAAACTTTC
GCCCGTGGGTGGCGCTCATCGAGTCTATCGACTTGTCACACTTTGGCTCTGATCTCCA
GAACCCGCAATTAGCGGACTTCAGCGTTCAGAAGCAGCGCGTGTACGACAGCATCT
CGGACCTCGTTATGAGCTGCCAGCACATCTCTGCTCCGCTAGGCGACGAGTGGGCCG
AGATCAGGGGCGATTCGCTTGAGACTCGTCTAAATAATACCCGCATGATGTCAAGGC
AGCTCACTAATTGCGTTCAACAGATTGGATTCTCGTTGACCTTACTATTGGAACAAG
CTCCACAACAACAAATACAAAATGGAGATGGATATAACAAATCTGCTCCCAAGGTA
CGCAAGAGTCCGCCATCATCTATTGGCATACCTTCCAGCTATGGCGTGGGCGATGAC
CATGATAAGCCACCACGGTCTCTGGATAAGGCGCAGCGGTTCTTTGGCCAACCCGTG
CCGAGGGAGCCGACTTCTGCCAGAGAACCCGAGGAAACACCGTGGTTCCTGAAACT
CGACCATGAGGCCGAGGTGTTTTACGACGTCAAGGGTGACGTGCAGCAGCTCAAGT
GCGGTACGCTGGCAGGACTAGTTGAACAGCTTACCCGCCATGACAAGCTTGATCCCT
CCTTCAAGGATACCTTCCTTCTCACATACCGGTCCTTCACCACGGCTTCGGAGCTTTT
TGAGATGGTGGTACATCGCTTCACACTCCAGCCTCCCTACGGCCTGACCAAAGCAGA
GCTACAAATCTGGACCGAACAAAAGCAAATACCCATCCGGATCCGTGTCGTCAACA -continued TCCTCAAGAGTTGGTTCGAGAACTTCTGGATGGAACCAAATGATGAGGCAAACACA
CATTTACTTGGCCGTATACACTCCTTCGTTACCGAGGCAGTTGCATCGACTAAGACG
CCTGGCGCGCAACAACTAGTCAGTTTGATAGAGCAACGCCTACGTGGAGAAGAAAC
TACCGCCAAACGCCTGGTACCCACCATTAGCTCCAATGCACCCACTCCCATCACACC
CAAGAACATGAGGAGGATCAAGTTCTTGGATATCGACCCAACGGAGTTTGCGCGCC
AGTTGACTATCATCGAGTCGCGGCTGTATGCTAAGATTAAGCCTACGGAGTGTTTGA
ATAAGACCTGGCAGAAAAAGGCTGGACCAGGCGAGGCCGAGCCGGCGCCGAACGT
CAAGGCTCTTATTCTACATTCTAACCAGCTTACCAACTGGGTGGCTGAGATGATTTT
GACCCAGTCGGACGTCAGGAGACGAGTCGTCGTTATCAAACACTTTGTCTCCGTTGC
TGATGTAAGTTGATTTATCTTCTTACCCCCTTAACACATAAAAATTATGCTAACAAAT
TTGATAGAAATGCCGACAACTTAACAATTATTCTACTTTGACATCTATTATCTCTGCG
CTTGGCACCGCGCCAATCCATCGACTGGCTCGTACATGGGCGCAAGTCAGCCAGAG
AACCGCTGGAACCCTCGAGATGATCCGCAAACTCATGGCTAGCACAAAGAACTTTG
GCGAATACCGTGAAACCCTTCACCTAGCCAATCCCCCTTGCATTCCTTTCTTCGGTAA
CGACAATTTCCTATTTTTTTTTATCGGCGCAGAGCCACTAACACACGCACAGGTGTCT
ACCTAACGGATCTTACCTTCATCGAAGACGGCATTCCCTCACTCACTCAATCCGATC
TAATCAACTTCAACAAACGCACCAAGACCGCGGAGGTGATCCGCGATATCCAGCAG
TACCAGAATGCGCCTTACCAGCTCATTCCCGTGCCGGAGCTGCAGGAGTACGTGCTG
AATAATATGCAGGCTGCAGGCGATGTGCACGACATGTACGACCGCAGTCTTGAAAT
CGAACCCCGAGAAAGGGAAGACGAGAAAATCGCAAGGTATGGTAAACACTACTAC
GACCCATCGGTCGTTGCACTCTCCCTGACGGTTGGCATACATTGA (SEQ ID NO: 28).

Figure 31:
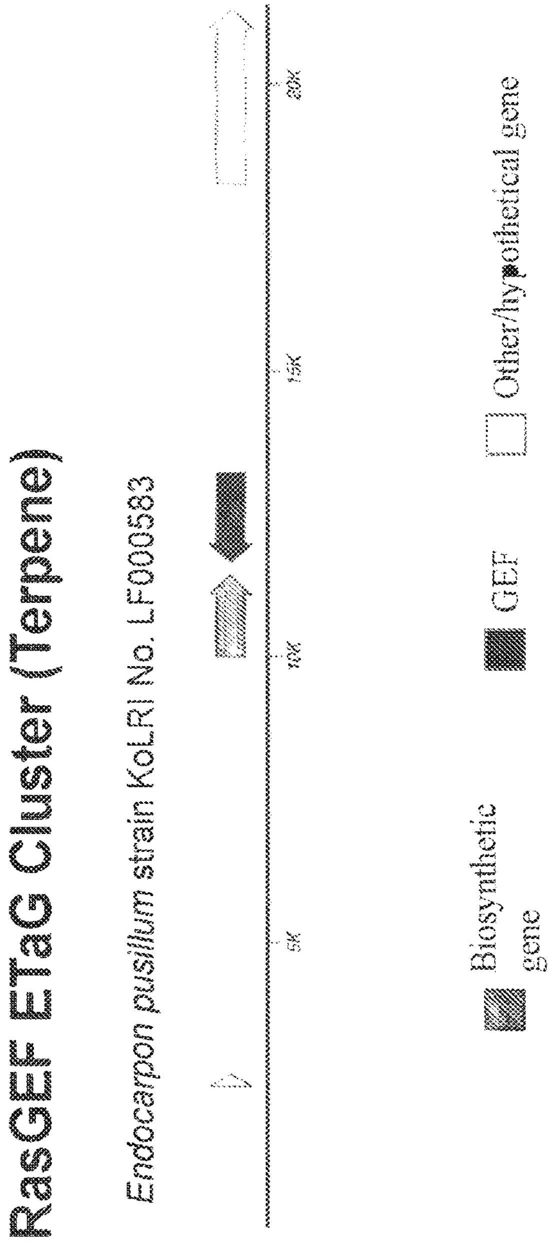
FIG. 31 depicts example biosynthetic gene clusters related to RasGEF, e.g., from *Endocarpon pusillum* strain KoLRI No. LF000583. Illustrated RasGEF homolog is indicated in black.

FIG. 31: *Endocarpon pusillum* strain KoLRI No. LF000583. RasGEF ETaG sequence:
ATGGAGGAGAATGACGGAGAGAGCAGGAAGCTTCTCGACAGGATCTACT
CATTTGCTAAAGACTCAATTGCCACGACCAAGACACCAGGCTCAGGACCTTTGATGG
CGGTGGTTGAGCAGAGGCTGAAGGGTCAGGACACTTCTGCTAAAAGACTTGTGCTA
ACATTGACGAATTCTGCTCCCGCCCCGATCTTGCCAAAAAATATGAAGAAGCTCAAG
TTCCTCGACATAGACGCAACAGAATTCGCACGACAGCTTACCATTATCGAGTCTAAG
CTCTATGGAAAGATCAAACCAACTGAATGTTTGGGCAAGACGTGGCAGAAAAAGGT
TGGTCCTGAGGAGCCCGACCCAGCACCCAATGTGAAGTCCTTGATCCTCCATTCCAA
CCAGCTCACGAACTGGGTTGCGGAGATGATACTATCACAGTCCGAGGTTAAGAAGC
GAGTACTCGTCATCAAGCACTTTGTTTCGATTGCAGATGTGAGTCCAGCCGTAAACG
CCAATTCGCAAAGACTGACCCATACAGAAATGCCGCAACATGAATAATTTCTCAAC
CCTTACCTCTATTGTTTCTGCTCTGGGAACTGCTCCAATACACCGGCTTAATCGAACA
TGGACCCAAGTCAGCCCAAAGACCATGACTTCTCTGAGTGTGATGCGACAGCTTATG
GCCAGCACCAAGAACTTTGGTGAATATCGGGAGAGGCTACGCCGGGCAAACCCGCC
ATGCATACCCTTCCTAGGTGTTTATCTTACGGATCTGACATTCATTGAAGATGGAATC
GCGTCGATCGTCAAGAACTCCAACCTCATTAATTTTGCCAAGCGGACCAAGACGGCC
GAGGTCATTCGTGACATCCAGCAGTACCAGAACGTACCGTACTCGCTCAACCCTGTT
CCTGATCTTCAGGAGTATATACTCAGCAACATGAGAGAAGCTGGCGATGTACATGA
GATGTATGATAAGAGCTTGCAAATCGAACCAAGGGAGCGAGAGGATGAGAAGATC
GCAAGGTGAGTGTGTACAAGGAAATCTTCACACCCCCAACGATGCAGATGGGTCTG
ACTCACGTCTCTCCTCGATTATAGATTGCTGTCTGAGTCTGGTTTCCTTTGATCCGTG
AGCAGGACTCGCGATTCGCTGGTTTCTCAACATACCTTTTGAGTTGAATAGCCGCGG
GGTTTGCAGGTGCCGAATCTCCCTTGTCCCTAACTATGATGTCAATTCTACATAAGTA
CTGGGGATGCTACACAAGGCCGGTCCTACGTAACAAGCCATTGCATGGATACTTGG
ATGGTTGGGGGTTTTTCTGGTAGATATCTGATTCAGGCTTGGTGGCATGGTATTGGA
CGTCTGACATGAAATTGCACGAGCAAACGAGTCGATGAGACACTTATCTGGACATG
GTCAAACATCAACGAAGCTCATGGATAGGAGCGATACTAATTCAGGCTGATCTCGG
AGCTTGTGATGGGGAATCTGCGATATCTAGTGCTTTTGAATATACATTTTTGTTGCTA
ATGCAGAATGAGTAGCTGCATTTTTGCGCAGTCGATCGGTTTTCTAG (SEQ ID NO: 29).

Figure 32:
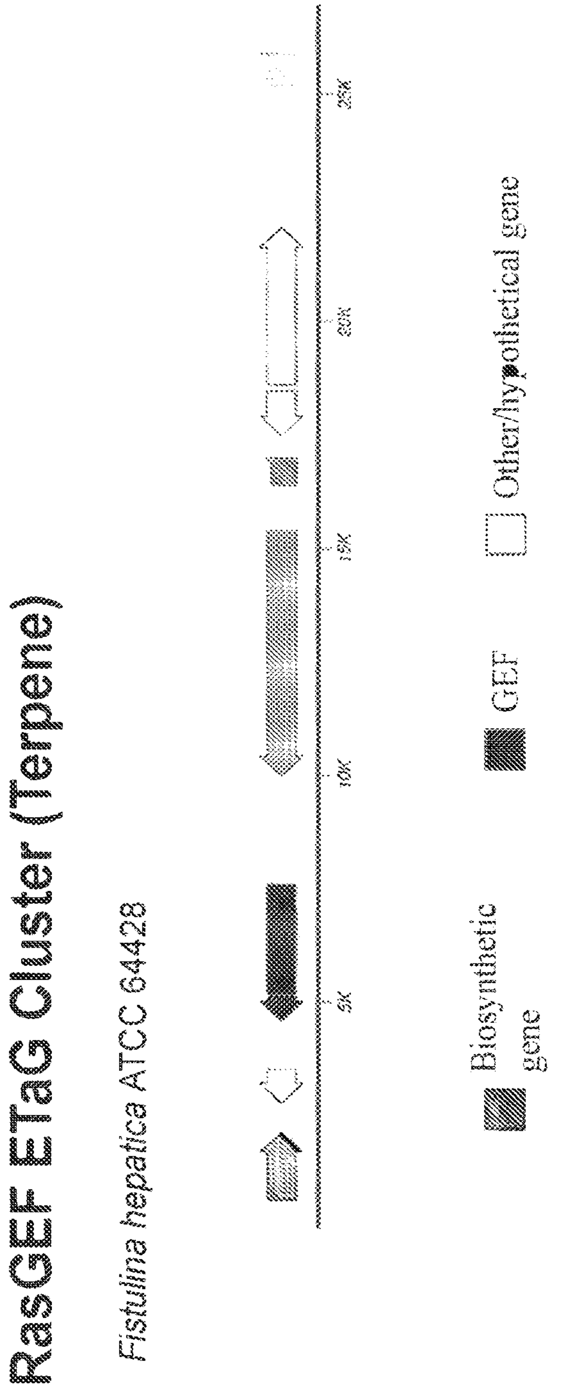
FIG. 32 depicts example biosynthetic gene clusters related to RasGEF, e.g., from *Fistulina hepatica* ATCC 64428. Illustrated RasGEF homolog is indicated in black.

FIG. 32: *Fistulina hepatica* ATCC 64428. RasGEF ETaG sequence:
ATGTACGATCTCGTACACGAAATTGTTGCCATTGTGTGCAAGCTACTTACC
ATCGCGGACGCTGTAATGCTGCACCCAGACATCCCGCCAAACAAAGTCAAGAACCT
CAGCCACTCAAAGAATGCGCTGTACGATTCGACGACGGCATTGATGGAATGTGTCC
AGACGTTGACGCAACCACTCGCGCCGACGGTGACGGAAGAGGATGAGAAGAGCGC
GTTACTGGTCACCGCCACATCCGCAGTAAAGGTTGGTGCAGACTGCGTGGCCGCGAT
CAAGATGTGCCTGTCGCGTTCGGTGGGCGAACGGCCATTCGTACTGCAGCTGCCCGA
CAAGAATCACCCTCCTGTGGCAGTGCCTTTACAACGACCAAAGCTCGGCAAGGCAA
CAAGCCTTGGCTCGTTGAATACGTCCACTAACGTGCCTGAAGACCACGATGACACCA
TCCGGCCGCCCGTACCACCACTTCCACAACAGTGTTCGCGTGATCTTTCTTCTGGATC
GGAAAAGAGCGACGCGTCGGCACAGAGTTCGACGAGCTCACGAGACACAGGCTTTA
CGTCGTTGGACGCCTTGAAGCTGGTTTCACCGAAAGAGAAGCCTCTGCCCGCTCTCC
TTAAGCTTACAAAAGCCGCCGTCGAAAAAGATCTCCCCTCGCCCACATCTCTTGCTC
CCACTGAAGCTGCAAGTACATGGGAAGGTGCTCCATCACATTACTTGCACTCGCTCG
GTAAATCATCAACCACTTCATCAAATGCGGCGCTCAGCTTGCAATCTATCCCACAAT
CCTTGCCATCACTGCCGGCGCTTGTCAATGCACATGACTATTCCGACGACGAGGTGG
CATGCAATAGCGAGGGACACATCGTCGGTGCAACGATGAGCGTGTTAGTGGCACGG
ATGACGCCACATGACAATCTCGTCGATGCCGCCTTCGCCGCAGTCTTCTTCATGACG
TTCCGCTTGTTTTCGTCGCCCGAAGAGCTCGTTGACACTCTGATAGCTCGGTACAAC
ATCCAGCCGCCTGAATTCCTGAGTCAGGCGGACAAGGAGTTGTGGATGCATCAAAA
GGGCATGCCCATTCGACTTCGTGCGGCGAACCTTGTAAAGAGCTGGGTTGAAAGTTA
TTGGCGCCCTGGTGTTGACGATGCAGTGTCGCAGACCATCTACGAATTTGCAGAGAC
TTGTGTGCATAAGACCTTTGCGTCGGTCGCCAACCGTATTGTGGAACTGCTGGAGGT
GCGGCAAACGACAAGTAACGCGGTAATCACGCCGAAAGGCGATCGCACACGCGAC
CCCGGCATGTCAATTAACCCTCCGATTGTGAATTCGCCGTCCGAAATTCCGCGACCG -continued ATCGTGTCCAAACCATTGTTTGCGGCGTTGAGGAATCGGAATTTCTCGTCGATCAGT
GTGCTTGACTTCGATGCATTGGAATTGGCCCGCCAACTCACGCTTATGGAATGCACG
CTCTATTGTGCAATACGGCCGGAGGAAGTGCTCGAACCTGGCCAGCCGGGAAAGCC
GAACATGAATGTCAAGGCGATGAGCACGCTGAGCACTGTTATCACAGGTTGGGTAA
CTGAGTCTATACTCAGTGAACAAGATGCGAAGAAACGGACTACGCTGGTTAAGTTCT
TCGTCAAGGTCGCAGATGTACGTGTTCGTTCTATGTCAACCGTCTGTAAAGATTTTG
AACTCCTTGTCAGAGATGTGTCTCACTGAACAATTTCAGTACCTCGTGGTCCCTTCTA
GCGGCTCTCGATTCTTCTACCATTTCACGGCTTCATCAGACCTGGACCGTAAGTACC
AAATTTGTCTCTTGTTCTCTCGTTAAAATATGATTCTTGCTTCCAGGGCCTGCCTCAG
AAGAATCGGCAACAGCTTGATGCACTTCGCAAGTTATCGGACCGTGCTCGGAATTAC
CGCGAGTACAGAAATAAATTGCGGAACACCGCGCCGCCAGCTGTTCCGTTCTTGGGT
TTGTGCACTGTTTCTGCTCCTTTTCGCGATGAGACGGATTAACAATGGTTTTCAGGCC
TCTACCTGACGGATGTGACATTTTGTCGTGAGGGCAATCCCTCCACTAAACCGTCGC
CTCTAGATCCCAATAAGCAGCTCATCAACTTCAATAAATATCATAAGTTGGCGCGAA
TCGTGCAAGGTATTTTCACATGCGCGTGCCGCACTATGTCATAATGCTTGAACTTCG
GTTTGCAGATATGCAGCGTTTCCAAGTGCCTTACAATTTCAAGGCTATACCTGTTATC
CAGGAATATTTGAACGTCGCGTTCGAGACTTCGAAGAAGAACAGCGATCTTCAAGA
CTTGTACCGTCGTAGGCAAGTACACAGTATGAATTCTTCTGTGGCCATAATCGCTGA
TGATGTGCTCAGTCTTATGATCGAGCCAAAGCGGCCGGTCGACACGCCACCCGCGA
GCGCGAGCGATACGCGATTGTTCCATTGGGCTTCGAAGTCCCAAACACCATCTCAGA
CTGTAGCTGCTCCATTCTAGATGTCCCTGCTTATTTGTACTATTTTCACTATGTTTATA
CATGGGTTCCGTGCACACGGTTGCTCATATTTGTGTCTCTTTCTTTTTTTTGGCGGAC
CCGTTCGCGTGTTTTCGATGACTTTCTCTCTCCGTCCTCGGTGTTCACATATTAACTC
GACTCTCTGTCTCTCTGTCTCTTTCGCTCTTGTTATTCATTTCGCTTTGTTGTTAGGTT
ATATATACATTATATTGTCAAGCCATCTGTACGTTCACCCATCCACTGCATTGGTTTA
GCCTCACTACTTTTGTCTGCTTGAATACACTGGTTCGTCCATCACCCGTGTCGTCTCT
GGCCAGTAGGGAAGGGAGCACGCATCGTTTCACTATACATAGGTCAGTCAGGTCGA
GTCTTTCTTCTTCTGGGTTCATCCCTCAGGTCATGAGGTGCGTCATGCAGCGACTTGT
TATTCTCAATCTGATTATGGTCAGTTATATCAGCGGTGAAACTCTTCACGAATAG
(SEQ ID NO: 30).

Figure 33:
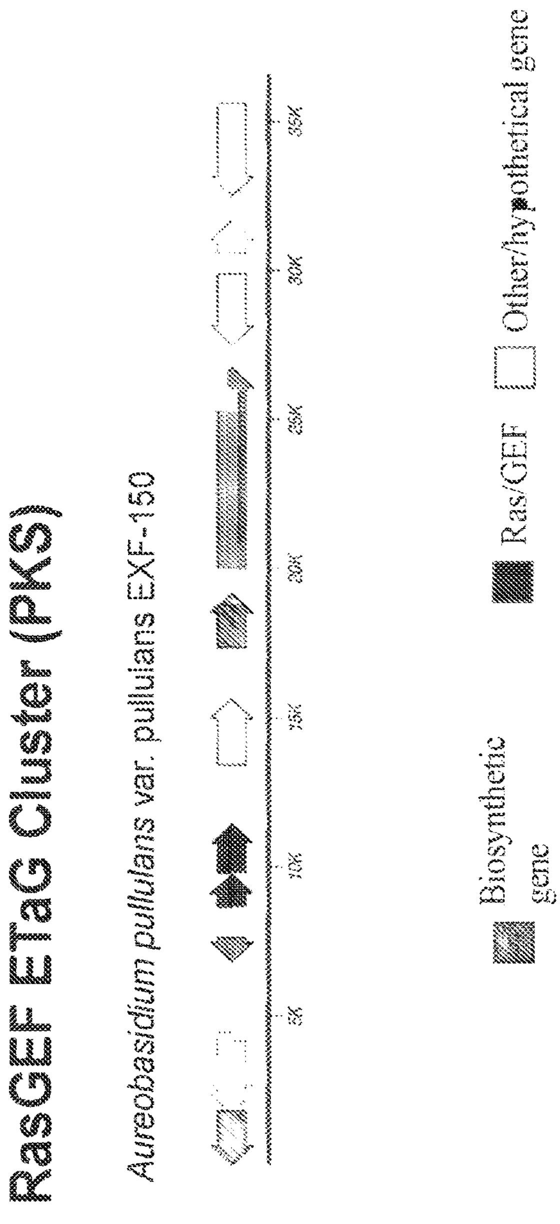
FIG. 33 depicts example biosynthetic gene clusters related to RasGEF, e.g., from *Aureobasidium pullulans* var. *pullulans* EXF-150. Illustrated RasGEF homolog is indicated in black.

FIG. 33: *Aureobasidium pullulans* var. *pullulans* EXF-150. RasGEF ETaG sequence:
ATGGTGACAACCCCTTCAGCCTCCACAAATCCGCCCCTCGACATTGACAC
GAATTTGGACGAATCACGCGACGACATTACAGACTCATCTCGTTCTGAGCACGCCTC
CTCATCTGAGGATGGCGGTCTTGATGTCGATAGTCAATCAGAGGCCCCATCCGATGA
GCGGGGATACTCCTTTGACAACCTCGTCGACCGTCTCCTGGGGCTACCGCGATCAAA
AGCCGACACACGATTCGGCTCTGTCTTTCTTGCCCTCTATCGGAAATTCGCTGCACCC
GGACAGTTGCTGGAAGCTATAGTTCATCGCTTCGAAGCCTTGGAAAAAGAAAACTG
TCCTTTCATGACAAAGACTGTCTCACAATTACGCTACTTATCTGTCATTGAGCAATGG
ATTGGAACATACCCTGGAGACTTTGCACACACAAAAACCCGCCGTCGCATGCGCAT
CTTCGTCGCCAAGCTGTCCAACACACGCATCTTCTCTGCTGCCGCTCGTGAGATGAG
CTGTGACTTGGACGTTGTGACAGAAGACGATGATACAAATTGGGCTTGTTGTGACAT
GGATCGTGAAAAACGCGGTCTCCTGAGCCCCGATCTCGGCTGGTCATCCCGTGTGAG
CACACTCCTGGACGATCCCGAATTTGACTTTAGCGACAACCTGGGAAGCCTGTCTCT
CGATGGCGGCCAGGGTAGAAATGCAGCCCATTCCTTACATACCGACTTTGGCATGCT
GCAGACCGTGGACGCAGCACGTAGACAAGGCCCATCTCTGGTTCCCGTCCCCAAGA
TTCCAATCAGCAAGATGCATTGGCACATGCTTATGGAAACACCAACGGATCACATCG
CTTGCGAACTGACACGCATTGACTGGATCATGTTCAGTGCAGTACGTCCGCGTGATT
TGGTGCGGCACGTTTCCTTATCGCAAACTCAGAAGGCACAGTGCAAATCCATAGTAC
ATGTCAGCCGCATGATCGACCATTTCAATCACATTCGAGACTGGGTGGCCAACTTCA
TCTTGCTTAGAGAGAAGGCGAAACACCGTGTACTGATGTTGGAAAAGCTCATGCAT
GTCGCCCGTAAGCTGCGAGAGATGAACAACTACAACTCGCTGGGGGCGTTCCTTGC
CGGTATCAGCAGTGCAGCCGTACACCGACTTGCCGCTACTCGAGAACTGGTTTCACC
CGAGACCGGCAAGGATTGGATGAAGCTGGAGATATTGATGTCTCCCACTCGCTCTTA
TTCTGCTTATCGCCTGGCTTGGGAGAACTCAAGCGGAGAGAGAATCCCTTTCCTCCC
TCTACCCATCCGAGATCTTGTGGCCGCCGAGGAAGGCAACAAGACCTTTGTCGGCG
ACGAAGTGAATGGCAGAATCAACTGGCGCAAGTTCGAAGTCATGGGAGAAACGGTC
GTCGGGATTCAAAAGGCGCAAGGTCTGCCTTATAGGAACTCCATGCTCGGCCCTAGG
AATGATGAGTTGAGAGCATTGATCCTGAACAGTAACATGATCAGAGATGACGAGGT
AAGTTCTTCAGAGATCAAGGTATTTGCAGACACACGACTAACTGAATCTTCCAGGCT
CTTTATGACCGTAGCTGTTCTCTCGAATCTACCAACGACAGAAGGGGGCTGCGAGAT
ATCTTCAGACGCGCATAG (SEQ ID NO: 31).

Figure 34:
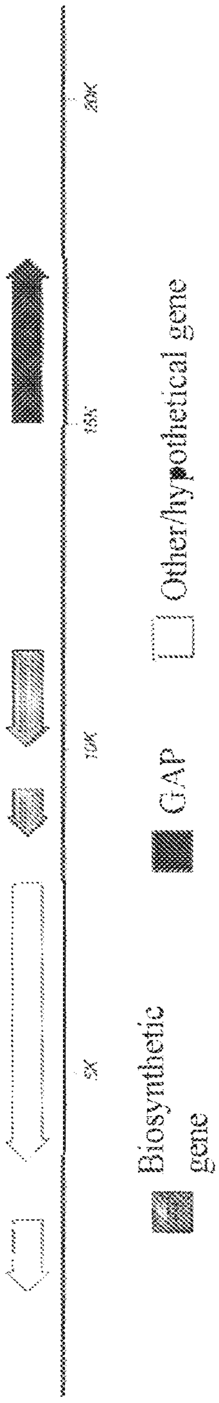
FIG. 34 depicts example biosynthetic gene clusters related to RasGAP, e.g., from *Acremonium furcatum* var. *pullulans* EXF-150. Illustrated RasGAP homolog is indicated in black.

FIG. 34: *Acremonium furcatum*. RasGAP ETaG sequence:
ATGTCTGTGATGCTGCAAGCTCCTTCCCGAGCCTCCACTGCATCCTCCTCC
TCCATCCAGCCCCTCTCCCGACAGAACACCATGTCTTCCTACGATGGCTCGCGGTCC
GCCCGCCAGTCGAAGCGGTACTCCATGTCCGCGCTGTACATGTCCATGTCAGCCAAC
GACGGAGAGCTCGAGATCGAAGACGATCTGGCCAAAGGTAGGCTACATGCATTCCC
AGTTGCACTACGACTGGATTCTCTCGCTAACACGCTCAAAACACAGCCCAGAAAATC
CTGCGAGAACTCAAGTCCAAGATCTCCTCCCAGTCCAAGAAGAACTTCGTCCTCGAG
AAGGATGTTCGATATCTCGACTCTCGAATCGCCCTTCTCATCCAGAACCGCATGGCT
CTGGAGGAACAGAACGAAGTCGCCAGCCATCTTGAAGACGCCACAGACATGCAAGA
GGGAGCCTTCCCGAACGACGACAAGACCCAGAAATATGGCAACCTCATGTTTTTGCT
GCAGTCCGAGCCGAGGCACATCGCCCATCTGTGCCGTCTTGTGTCCATGGCTGAGAT
CGACTCGCTGCTCCAGACCGTCATGTTCACGATCTATGGAAATCAGTACGAGAGCCG
CGAAGAGCACCTGCTTCTTACCATGTTCCAGGTCCGCCTGCCTACCTGCACTATATC
AGATCATTGCTAACAAGGACTTCCAGTCTGTTCTGACCTATCAGTTCGACAACACCC
CTGAGTACTCCTCGCTCCTGCGCGCAAATACCCCCGTCTCTCGCATGATGACGACAT -continued ACACGAGGAGAGGCCCTGGACAGAGTTTCCTCAAGTCTGTTCTGGCCGATAGGATC
AACAGCCTGATCGAACTGAAGGACCTCGACCTTGAAATCAACCCCTTGAAGGTGTAT
GAGCGCATGATCGAGCAGATCGAAGAGGACACAGGAAGCCTACCCGCATCCCTGCC
AAAGGGAATCACTGCTGAGCAGGCGGCGGAAAACCCTCAAGTCCAGGCCATCATCG
AACCCCGTCTGACGATGCTGACGGATCTCGCCAATGGCTTCTTGTCGACCATCATCG
AGGGGCTCGATGAAGCTCCTTATGGGATCCGTTGGATTTGCAAGCAGATCCGCAGCT
TGACCAAGCGCAAGTATCCTGATGCTAATGATCAGGTTGTTTGCACCCTCATCGGCG
GTTTCTTCTTCCTGCGCTTCATCAACCCTGCCATTGTCACGCCCAAGTCCTACATGCT
CATCGAAGGCCAGCCTGCCGAGCGACCCAGGCGCACCTTGACCTACATTGCCAAGA
TGCTCCAGAACCTGGCCAACAAGCCCTCGTATGCCAAGGAGCCGTACATGGCGAAG
CTTCAGCCCTTCATTCAGCACAACAAGGACCGGGTCAACAAGTTCATGCTCGACCTC
TGCGAGGTGCAAGATTTCTACGAAAGCCTCGAGATGGACAACTACGTGGCCCTGTCC
AAGAAGGACCTGGAGCTGTCCATCACACTGAACGAAATCTACGCCATGCACTCACT
GATCGAGAAGCATCATGATGAGCTCTGCAAGGACGCCAATTCTCACCTGGCAATCAT
CATGTCTGAACTGTCTTCGGCCCCGGCCCAAGTCCCACGCAAGGAGAACAGGGTCG
TCAACTTGCCCCTATTCAGTCGCTGGGAGACAGCCATGGATGACCTCACTGCCGCAC
TTGACATTACGCAAGAGGAGGTGTTCTTTATGGAAGCCAAGTCCATCTTCGTACAGA
TCATGCGGTCCATCCCGTCCAACAGCAGCGTTTCTCGACGCCCCCTGCGCCTCGAGA
GGATCGCTGACGCAGCAGCCACCAGCCGAAACGATGCGGTTATGGTCCGCAAGGGC
ATTCGAGCCATGGAGCTGCTTTCACAGCTTCAGGAGCTGAGGGTCATTGATAAGAGC
GACCATTTCAGTCTGCTCCGCGATGAGGTGGAGCAAGAGCTGCAGCACCTGGGGTC
GCTCAAGGAAGCCGTCATCCGTGAGACATCGAAGCTCGAGGAGGTTTTCAAGACCA
TTCGCGACCATAACACGTACCTGGTCGGCCAGCTCGAGACGTACAAAAGCTATCTTC
ACAACGTCCGCTCGCAGAGCGAAGGAACGAAGAGGAAGCAGCAGAAGCAGCAGGT
CCTTGGTCCTTACAAGTTCACCCATCAGCAGCTTGAAAAGGAGGGCGTCATCCAGAA
GAGCAATGTCCCCGACAACCGACGGGCGAACATTTACTTCAACTTCACGAGCCCTTT
GCCGGGCACTTTCGTCATTTCCCTTCACTACAAGGGTGAGTATTCCTCATTGCCGCGC
CCTCATTGATTCATGCTTACAACTGCGTAGGACGCAACCGAGGATTGCTGGAGCTTG
ATCTCAAGCTGGACGACCTTCTGGAGATGCAGAAGGACGGGCAAGACGACCTCGAC
CTTGAGTACGTGCAGTTCAATGTGCCCAAGGTCCTGGCGCTCTTGAACAAGCGCTTC
GCGAGGAAGAAGGGGTGGTAA (SEQ ID NO: 32).

Figure 35:
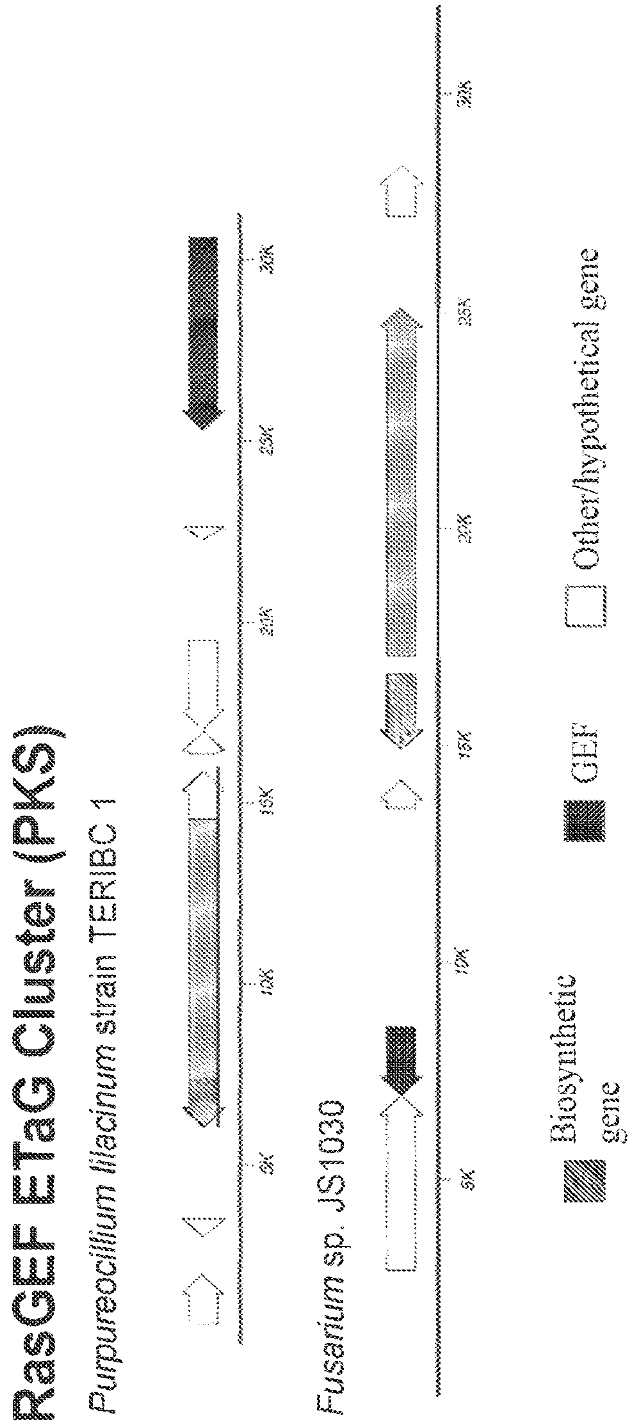
FIG. 35 depicts example biosynthetic gene clusters related to RasGEF, e.g., from *Purpureocillium lilacinum* strain TERIBC 1 and *Fusarium* sp. JS1030. Illustrated RasGEF homologs are indicated in black.

FIG. 35: *Purpureocillium lilacinum* strain TERIBC 1. RasGEF ETaG sequence:
ATGGTCAGGGACTCAGGGTCACGTCCAGGACGGGAAGACGTCTGGCTGTT
GGCTGTCTTTCTCGTCGCCCCAAGAAAGGGTAGGGAGTCTTGGCTGCTCCGCAGAGA
CTTGTATTTGCATGGCCGCCATCCCATCGGCGCCGTGTGTGGCATGGCACGGGTGCT
GCTGCGTGCTTCGTTCGAATGGGGTCGATGATGCCCAATTCCTCGGGGATCCTCGTC
GTGGTATATTACCTTACCTTTGCATCTACCTAATCGACGGCGGCGGCGCCAGGCAAA
TGGAAGCTGGCCGCCGGCAAGGTCACCGCCCACGGCACCCCTAATCGTCAATTACG
ACAGACGCCCGACCAACGACACCCACCTCTGTGGCCGGGGCTGCACACCCGAGTGT
AGGTTCAAGGTTGATCTTGCGTACCTCACGGAGTACAGGCGAGGTACTGCAGCGCGT
GCCTTCCTTGCCCGTGGCCGGACCGCGCCAACACCGACGAGTACCTGCCCCGTACTC
CGTGGAGTGCTCCGCGCCGTGCCTTGCTTGCCTCGAGTACAAAGCCAGGGTACTTCC
GTACATTGCCCCTCGACCAGGCCACCACCCAGACCCGCAAAAAAGACAACGACAAG
ACAACAGCGTCACCCTTCCCCTTGTCCGTGCTCCAGCAAGCCCGCTTGTCCTCGACC
GGTGCTGTCTCGCCGGCGCGCGCGCCTCGATACCATACCCTCTCTTTTCTACAATTGC
ACTCACTTTCCCCATCCGTCGGGGCTTTGCGTTTTTCGGCCCAGAATAGCCGTCGAC
GGTACTGTGCGCCATTGCCAGAGAGCTTGATCTGTTGTTGCGGCGCCAAACACCGAA
CGCTCTTTATACTTTCCTGTGCCCCTTGACCTGAACGCAGTCGCAGCGTTCTCGCCCT
TCGACCCCGGCATCGAGCTTGGAAACCGACAAGCAGCTCCCCCACAATCCTGGCCT
GCCGCTTTCTCCGCATCGCCTCGTCCGCCTTTCGTAACGACTGCTTCGTCGCCCGCGT
TCGACTCCGCCTGGCCTCGAACCTCGAGGCGCCTGCGTGTAAGTCAGTCACCTTGCG
TGCTTTGATCCTGCGGCTCAGCTGCAGCCCCCCCACCAGCAGTTTGCCCTTGCTTCAG
GTCCTGCTGTCATGTCGTCCACGCTCTCAGCAGTTCTCTTGTACTTCTTAGTTCACCC
TGCATTCCTCGCCACGCCCGCCCCGTCCCCCTCTGGCCTGCATTCCAGACACGGGTC
ATTGGCTCTTGCCACAACATCCAGGTCGCGCTCCGGCCTTGCTAACATCCAATCTCG
CCTCCAGACAAACGAGCGTCGCGTACATCTCACAACTGCTGGTTGCGCCCACCTGCG
TTGACCTGCGCCTCGGTGGTCGCGGCCGTCGTTGTCACATCCCTGGGTCCTCGCCAG
CACCAGCATACCCCCCCTCAAAAAGAACGAACTGTCACGGAACCCCCCCCTGGGGC
TCCTCCACTGCGCTCTTTGGATAACCAAAGCACTTACTTTGGAACCAGGGCGCGGCT
GGCCGTCGCTCTGGGACGGGCCGTCGACGCTAGACCGCGAGGCCTCGACCAGATGA
TCTTGACACTCGTCTCTACCTTCTCACAGGCGCAATGCTGAGCGACCAACCGTCGCG
AACTGCTTTACACGTGGCCCCGCTGGAGATACCCGCGTCGCAGCCACAGGACGGTG
CCAATGGCTTGTGCCATCAAGAACATCAGACGAATCTCTACTCACAGACCCCTATGA
CTCCGCCGGAAACACCTAACGGCTCCCAGGAGGACCTGACGCCGGAGCCTCTCGCC
CCGCCCGTCTTTCACAATTTCCTTAGGGCCTTCTACCCGTTTCACCCCGGCTACGCCT
TGTCCGACTCGAGCGTCACGCTGCCACTGGACGAAGGCGATGTCGTACTTATACACT
CTGTACACACCAATGGTTGGGCGGACGGTACTCTTTTGGCAACCGGCGCCAGGGGCT
GGCTGCCAACTAACTACTGCGATGCCTACGAGCCCGAGGATATGCGGAGCCTTCTG
AAGGCGCTTCTCAACTTTTGGGACCTCCTACGTAGCGCATCAGTAAACAATGAGATC
TTCAGGAACCAAGAATTTATGAAGGGCGTCATAGCTGGAGTTCGGTTTCTCTTGGTA
GGCTTGCGCTATCTTCTCCCCCACAAGGGCTCATTGTCTTTGCTAATGACAATGTGCT
CAGGAACGCACAAACTGCTTAAACCGAGAATCGACCATCATTCAGCGCAGTGACAG
TTTAAGGAGATGTCGCAAATCATTGCTCTCAGAACTCTCATCATTGGTCAAGACAGC
GAAGAAAACACAGGAGTGCCAAAAGGGGACACTCCACCCACCGCAGGATGTCAAC
GACATCATTGACGAGATGATACTCAAGGCATTCAAGATTGTCACCAAAGGCGTCCG
GTTTCTCGATGTTCTCGAGGACGAACGGAGGGCTCGCGCACCAGCAGCTGTCACTGT
CATGGCCACTGTCGCCGAGGAATCATACATTCCACCTACACCCCCTGCGGAGCGCTT
GGCTTTCGACGATCAAAGTTTGAACAATGGCAGCGAGACGGCTTCCCGCGGAACGG CCGACAGTGTGGTTGGCAGCAGCGCCACTTCGGAACCCAGCGTTGCATCACTCAATC
CATGGAACAGGCGCATGTCGTCTCTGGGTGGATCTCAAGGCACGGCGGCCCAGAAT
CGATGGTCTCAAGGAAGTCTCCAACAAGTCAACCGTTTGTCCACAAGTATGGCGCAC
AGAGTCTCGCTGGCCGGCCCATCCCCGCTGTCGAGGCCTCAACATTTGGTATCGGAG
CGCCTCAACCGCAGCCATGACAAATTCCTCTCGCACCTCGGATCTTTCATTGGGCGA
CTGCACTTGCAGTCACACTCGCAACCGGAACTGGCACTCGCGATCAAGCAATCTGCC
ACATCGGGCGGTGAATTACTGGCAGTCATCGACGGTGTCTGCGAGTACAACAGCTCT
AGTGCCGCGGCGCTCGCTATTGTCCGAGATGCCATGTTTGAGCGCATTCAGATCTTG
GTCCACTCTGCCAGAGATATTTTGGCCAATGCCGCTACTGAAGGGGCCGACATAATC
CTGCCACAAGACAATGGGGTTTTGCTCATGGCAGCCACTGGTTGCGTGAAAGCCGCA
GGAGAATGCGTCGCCAAGGCCAAGGCCGCCATTGAGAGGGCGGGGGACTTCGAGTT
CGAGCTGGAAGAGAACACGCTCGGGATAGACCTGAGCATCTTGGACATTGTCGTGG
ACGAGCGGGCGAGAACGCCCTCGGTAACGGATCGATCGGACCCTATGAGCAGCGTT
GCAGAATCGTTCCAGACCCCCGAATCGACTGTTCAGCCTCAAAAGCGGCCGATCGC
ACCCGCCGTCGACAAGCCGCTTCCCCAAGTACCCAGAATCACCATCCCCGCAGACTC
GCACAGTCGTCAAAGCAACTCCCCAGTGTCCTCTCGACCCCCGTCCCTCAACGAGGA
CAATGCTTCTAGCGTCGCGTCGTCTGTTTCGTCTATTCGCCCTGTTCTCCCGCCCCTC
CCTGAGGTTTCCACAACACCGCAGCCTCTGGATCGCGATGGTTCCGACACGACAACA
ATCGAGTCGGACGCCCATACCTCGAGGTTCGACGCCTTGGCGGCGTCCAGCGCGGG
CAGCAGTACCACTTACCTCAGCCGGGACTCTGAAACGAGCATGATGTCGCAGACGT
CGACGCGAGCGACGACGCCGGATCACACCTTGGTGCCTCGCAGCCAGCCCTCGATG
TCGGAGCTGAGTACGGCCGGCAGCTTCTCCCAGGCCGAAGAGGCGGATGACGTCGA
AACAAGACTTATGGAGAGGACGTACGCTCACGAGCTCATGTTCAATAAGGAAGGTC
AAGTCACTGGCGGATCGCTCCAGGCTCTGGTCGAACGTCTCACCACGCACGAGTCG
ACTCCGGACGCGGCTTTTGTCTCGACTTTCTACCTCACATTCCGACTGTTTTGCTCAC
CGGTCAGGTTGACGGAAGCGCTCATCGAACGTTTCGATTACGTTGGAGAATCGCCTC
ACATGTCGGGCCCCGTGCGTTTGAGGGTATACAATGCTTTCAAAGGCTGGCTGGAAT
CCCACTGGAAGGAGCAGACTGATCGAGACGCACTACAGCTCATGATTCCCTTTGCG
GAAGGAAAGCTGGCTTCGGTTCTGCCATCAGCGGGACGCCGCCTGTCCGAGCTGGC
CAAGCGTGTCTCCGGAGAAGGGTCTCTGGTGCCGCGGCTTGTCTCGTCAATGGGAAA
GACGAGCACGTCCATTGCTCAATTTGTCCCGGCTGATAGCCCCGTGCCGCAGCCTAT
CATTTCAAAAAGCCAGCAGAATTTGCTTACGTCCTTCAAAATTGGCAGTGGGATGCC
AACCATCCTCGACTTTGACCCTCTCGAGCTGGCACGACAGATCACTCTGAGGCAGAT
GGGCATTTTCTGCTCCATCCAACCGGAAGAGCTGCTTGCATCGCAGTGGATGAAGAA
CGGTGGTGTAGATGCACCACACGTCAAGGCTATGTCAGCGCTGTCGACGGACTTGTC
GAATCTGGTGGCAGAGACCATCCTTCAGTACACCGAGATCAAGAAGCGAGCCGCTG
CCATCAAGCAGTGGATTAAGATCGCCCATAAATGCCACGAACTGCACAACTACGAC
GGGCTCATGGCCATAATTTGCAGCCTGAACAGCAGCACGATCAGCCGCCTTCGCAA
AACCTGGGACGCGATTTCTGCAAAGCGAAAGGAGGTGTTACGCGCACTGCAGGAGA
TCGTGGAACCATCTCAGAACAACAAAGTTCTGCGGACGCGACTACACGATCACGTA
CCTCCTTGCCTGCCCTTCCTCGGCATGTACCTCACGGATCTCACCTTTGTGGACATTG
GCAACCCCGCGACGAAGCAGATGTCCCTGGGCACCCAGTCGGAAGAGGACAGCACG
GGCGGCTTGACTGTTGTCAACTTTGACAAGCACAGTCGCACTGCCAAAATCATTGGC
GAGCTTCAACGTTTCCAAATCCCGTATCGGCTGGTGGAAGTGTCTGACATGCAGGAC
TGGCTGGCCGCTCAGGTGCGGCGTGTGCGCGAAGGTGACCAAGGCAACGTCCAGGT
CACTTACTATCGCAAGAGCCTGCTCCTGGAACCCCGCGAGAGCGCTTCGCGACGCG
AAGCCGAGCCGCCTACACCTGGTTCAACTGGTGTTGGCAGCTCTCGCACCGACTTGT
TTGGCTGGATGTCCCGCGACCGAAGCGGACAAACCGCTACACCAGCACCCGTATAG
(SEQ ID NO: 33).

*Fusarium* sp. JS1030. RasGEF ETaG sequence:
ATGCACAAGGGCACCGGTGCTGTGCAAAATTGCCTCATTGCAGCTGAAAG
GCAGTCTACAAAGCGTTTGACGACCATCGATGAAACTAGTGACGCCCGTCGTCCAA
GCTTGAGGGACGATTCACTATCCCATCCCCGACTTCATCTGAACGAGAACGCTGAGG
TGACTGGAGGCACCCTTCCGGGCCTTGTGGGCCATCTCACCTCTCGACAATCCGCAT
CCGACATCATGTTCCCGTACGCTTTCTTTCTTACATTCCGACAATTCTGCAAGCCACG
AGAGCTCGCAGAACAGCTTGTCGAGAGATTCGATAGTGCCAACGACTCTTCCTTTGC
CGAAGATACGCAGTTGAGGGTCTGCGACGGTTTCAAGCTTTGGCTCGAAATGTACTG
GCGAGTGGAGACTGACCAAGAGGCTCTACCGGTTATCAAGCCCTTTATCACATCGAG
CTTGTCTTCTATCATCCCAGCCGCGAGTAGGAAGCTAGCTCGGTTGATCGAGCACCT
TCCAGCTCGAGAGCCTTGTTTGTTGCCTCTAGCAGATCATGATAAACTCATAACAAC
TGTTTTTGACTCACCTAGAGTCAGGAGACATCGAGCTCAGCCTAATGATTCAGCGAC
GCATCAATGGGGCTTTTTGAGGACGCTGAGGAACAGTAAAAGCTCGTCGACTTTCCT
CAGCTTTGGCTGTATAGAGTTTGCCCGACAGTTGAGCATTGAGCAGACGACTCTATT
CTGCCGCATTCCTCCCCAAGAGTTCCTGGGTTGTGCGTGGGTATGCAAAACTGGCAA
CATGGCGCCTAATATCAGAGCAATGGTGTCTTTCACTAGTCAGCTTTCAAACCTTGT
GGTGGAAACCATTCTCGACCATCAAACGGCTCGCAAGCGGGCTGCTGCCATTAACC
ACTGGGTCAACATCGCACAGGAGTGCTCAAACTTTCGCAACTACGATGGCCTTGTGG
CCCTCCTCTCAGGCTTGGGCCACAGTGCCATTCTCCGGCTACGTCAGACATGGAATC
TGGTATCACCCAAGTACATAAACACCTTACAATTCCTTAAGACGCGTATGGACCGCT
CCGATAATCACAAATCACTTCGCGCATTATTGGAAACCCATGACAACCCATGTCTGC
CCTTTCTTGGCATGTATCTAACAGAGCTGGCTTTTGTGGAGATGGGTCAGTCTTGGAT
CGATCCGCAAAATCCTCACGACGAAACAACATCTGAGCAGCCCTTTATTGACTTTGC
TAAATATGCTCGGACGGCTAAGATTGTAAGGCAGCTTCAGCGTTTCCAGACGCCATC
CAAGTTAACAGCTCACCCTCGTCTACAAAATTGGTTGTCTTTTAAAATCTCAGAACTT
GATTGCAATAATGACCCTAAACTGGATGTTAGCTTTTTTGATAGAAGTGTGTCATTG -continued GAGCCGTACAGGATAAAAAAGTAGTTGTGGCCCGCTCTCTCTAAATAAAATAATCGT
AATGTCTAAAGCAGTGTTTGTTTAATCCGTGCCAGTATATGACCCTTATTTGCGGATT
CCTTGCGCTCAAATAGCCGTAAACATGCGTTCTAGTCCCCCAAGCTAGGCG (SEQ ID
NO: 34).

Figure 36:
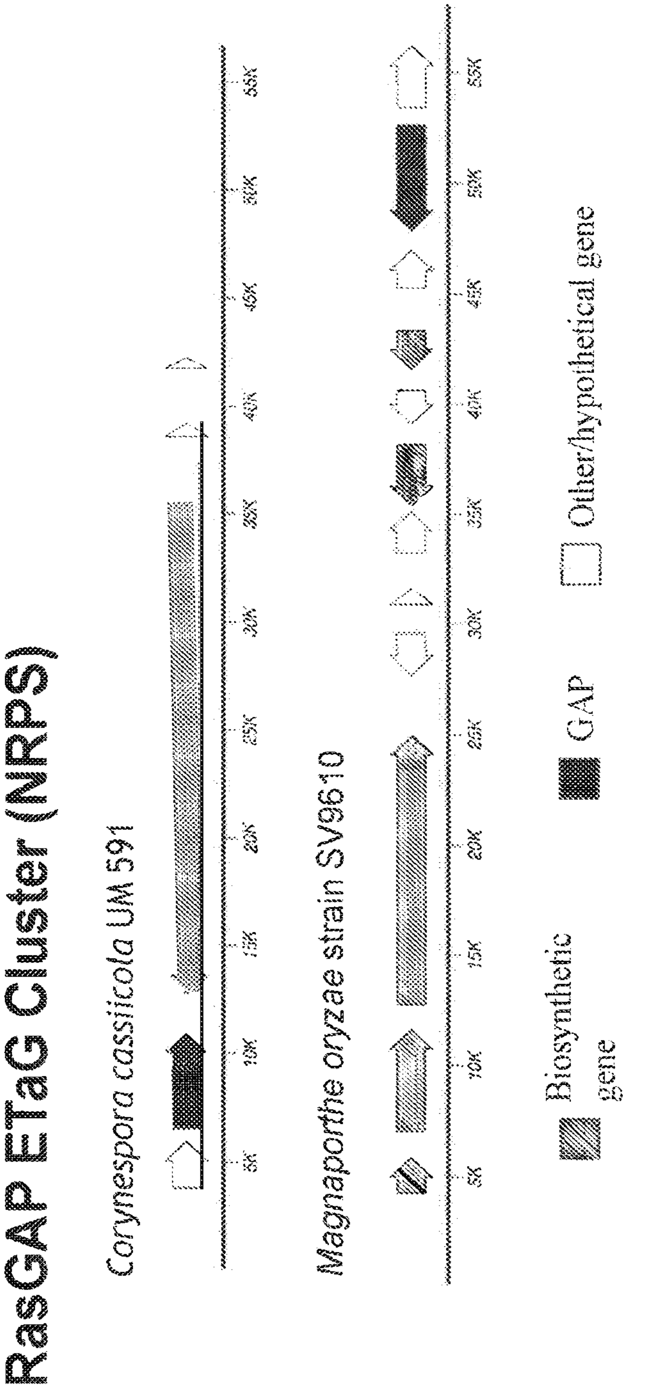
FIG. 36 depicts example biosynthetic gene clusters related to RasGAP, e.g., from *Corynespora cassiicola* UM 591 and *Magnaporthe oryzae* strain SV9610. Illustrated RasGAP homologs are indicated in black.

FIG. 36: *Corynespora cassiicola* UM 591. RasGAP ETaG sequence:
ATGGACCAAACAAGGCAGAGTCGGCGCAACAGGAGGGAGATTGGCGCTC
CGGAAGCAACTCAGCCTCTGCCACGCGACCAACGGCGAGACGATCGCGGCTCGTAC
AATTCGGCGACGATCCGTACCGTCACCCCCGATTCCATCCCAGAGGACAGCGTTGCC
AGCCAGACGTACACTACCTCCCCGCCCATCTCGCCGCGCTCCAACAGTACCTCCCAG
TCCGCCCGCAACAGCAACCCGCGCACCTTTGTTGCCCGCGCAAACTCGAACGACGC
AGAATACTCGCTCAGGGCTGCCCGTGAGACTCAGACTCGTCCGCGGACCAGGACCC
TGGAGGAGCGCTCAACGCGCGATCGCTCTCCGCCGAATCTATTCGTAACCAGCCGCC
ACCGCATCGGCTCGGTGCACAGCGCTGCGCCCTCCAATTTCCAGAGCCTCGAGGAGT
CGGTCGTCACCTCCATCGGCCATCCCTCTACCATATCCGCCGGCCCTACCGCCCCTCC
GCCTCGAACCTCGAGCAGCAACCGAAGCCGCATCATAAAACAGCAGGCCCAGCCGC
AACCGCCCCAGCGTGCCACCTCGCCCACCTCCTCGACCGCCGTCTCTCCCAATGCCC
AGCAGCCAGACTCGTGGGTGTCGCCTGTGCCGGCTTCAGACGCCCGCAAGGTCCTG
AAGCTCATGCGCGCCACATGCGGCAAGATGCAGGGCATGCTGGCCTTCCGCAGAGG
AGAGTCGAATCCGTGGTCGCTCTCCTACTGCTACATCAATGAGGAGGCCGGGAGCTT
GGTGTACGAGCCAAAGAGTGACACATCGTACCACAGGACGCTGGTGCCGGACCTGC
GCGGCTGTCGTGTCAAGACTGCCTACGATGCCGAGTCGTACACCGCCTACATTCACG
TTCTGGGCCACAACTCCAAGCTCGAGGTGTTTTTGCGCCCGCCCACCCAAGAAGAAT
TTGACTCTTGGTTTGCCGCACTTCTCTGCTGGGGCCCCATCCGCCCCAAGGGCATCC
ACAACAAGATGGCGAAGCCCCAGACGCCAATGGTGACGGAACGGCGACTCGCCGAT
AGCAGGAGACACTCCGAGGTGTCTCTGCTCAAAGAGGCGCCCATCATCAAAGTCGG
AAAGATGATCTACTGGGATACCAGCGTGACATATAGCAACACAGGAACCCCCAAGG
CCACTGGAGTCGCCAGGCCCCAAGCCTACCGGATACAAAGCCATGGCTCCCGCAGG
TGGAGAAGAGTATCGTGCACCTTGCGAGAGAACGGAGAGCTCAAGCTATACTCCGA
CACTGATGTCACTCTAGTCTCGGTCGTTCAGCTTTCCCAGCTGTCGCGGTGCGCCGTC
CAGCGCCTGGACCCATCTGTTCTGGATAACGAATTCTGCATCGCTATCTACCCGCAA
TACACCTCGACGTCGACGTCATTATCACTACTACGCCCCATTTTCCTATCGCTGGAAT
CACGAGTTCTTTACGAAGTGTGGATTGTTCTGTTACGAGCATTTACCATTCCGCAACT
CTACGGCCCGAAACAGCCGACCCTAAACGACGAAGGCGCCCTCTCGCCTTCGTTCG
GTACACAAGACATGTTCCGCATGGAGCGTTCGCTACTGGTCAGAGTCATCGAGGCA
AGGTTGATACCACCGATAAGCCCCAAGGTCTCAGAAAACAGCGGGCGGCCGACGTC
CTCGGCGAATATGAACGCCGGAGGTTACTACGTCGAAGTCTTGTTGGATGGAGAAG
CGCGAGCCCGGACCATGGCCAAGAATGAGGGCAACAATCCATTTTGGCGGGAGGAA
TTTGAGTTTCTTGACCTACCTGCAGTCCTCTCAACAGCTTCTTTGCTGTTGAAGAAGC
GACCTCCGAGCCAAGCCCGCAACGACAAGAACTTTTACGAGACACAGCTCAACTCC
GAATCCTTCAACTCGGACGGTGCAGGTGGCTATGCCGGCATCTCTTTCGATCAGACA
TGCGGCAAGACAGACATCTATCTTGACGACCTGGGTCCGAATCAGGAAGTTGAGAA
GTGGTGGCCGCTTGTCAACATGTACGGCAACAGTGTCGGCGAAGTCCTCGTCAAGGT
TAGCGCTGAAGAGTGTGTCATTCTCATGGCTCGAGATTACCAGCCCATGTCGGAGCT
TCTGCATCGCTTCTCCAATGGTCTGACATTGCAGATTGCGCAGATGATCCCGAATGA
GCTCAAGAAGCTGTCAGAATACCTCCTCAATATATTTCAAGTTTCGGGCCAGGCCGG
CGAGTGGATCATGGCTCTTGTTGAGGAAGAGATTGATGGCACCCTCAAGGAAAGCC
CGGCGAGTCGTCTGCGTTTCAGCAAGAGACTGGGATCTAGCGAGTCTAGCGAGTCCT
TCGGCTCGTCGAGTGACCGCGAACTCTTTTTGAGAGACATGGGCAACAATGCTAAGC
TGGAGGCGAACTTGTTGTTCCGCGGCAACACCCTCTTGACTAAGTCCCTGGACTTCC
ACATGAAACGGCTCGGAAAGGAGTACCTGGAAGAGACTCTTAGCGAAAGACTGCGA
GAGATCAACGAAAAGGACCCCGAGTGCGAGGTGGATCCAAACAAGATCACATCCCA
AAATGAGCTTGACCGCAACTGGAGGAGACTCATCAACATCACCGAGGATCTCTGGC
GTGCCATTTACAATTCCGTCTCGCGTTGCCCCCAGGAACTGAGGCTGATCTTTCGAC
ACATTCAAGCTTGTGCCGAGGATCGTTATGGCGATTTCCTCAGGACGGTCAAGTACA
GCAGCGTTTCGGGCTTTCTTTTCCTCCGCTTCTTCGTCCCAGCCGTGCTTAATCCGAA
GCTGTTCGGCTTACTGAAAGGTATGTGGTGACTTCTTGCCAACAGGTTGGGCGATAC
TAAATAATGCAGACCACCCGAAACCCAGAGCACGCAGAACATTTACACTGGTAGCC
AAGTCCCTACAGGGCCTTGCCAACATGTCATCTTTTGGTACAAAAGAGGCATGGATG
GAGCCGATGAACTCCTTCCTCTCATCGCACCGTCAAGAGTTCAAGACTTACCTAGAC
AACATCTGCTCCATCTCCTCGACAACCTCGCCTGCCCCTCCTATACCTCCTTCGTACA
GCACCCCTCTTGCGATTCTGCAGCGCCTACCACCCACTTCTCGAGAAGGTTTTCCTTC
TCTTCCGTATCTCATCGACCATGCACGCAACTTTGCTGCTCTGGTAGACCTATGGCTC
CAGAATACGAGAAGCAGCGCGCCGAATATCCAGTCAACAGATGGCGATCTTCTCCG
CTTTCACAACATCTGCGTGGCTCTACATGAACGCACAGATGATTGCCTGAACAGGGC
AGAACGTGCCGAACGTCCTAGCTCGTCGTTGAGTGTCAAATGGGAAGAGTTGGTCG
AGCAACTGCAGGGTTCTGCAAGCTTTGACAGCTCAAGGGGCGCTGCCACAAGGAAT
CGAGGAGCAACAATCAAAGAAGAGGAGAGGGAGTATCTGCCAATATCCCCGGGAA
CGTGCGACGAAATGACTAGTTCCTCGTCCACGAGCACCCCTGTGACCATGAAGCCTG
TTCGACAACCCAAGGGGCGGCATCAGCAGAACAGTTCCATATCTGCGTCTACTAATT
CAGTCGCCAGCAATAACTCAGGCACCATGACCTTTCCAAACCCCTTTGCACCAAAGA
CTGCCCGCAGTGCAGGTTATCCGCCCTCAGTAAACGATTCGGTATCCGCTTCCCAGT
CTGCATCGGCCTCCGCCAGCGCATCTGCATCCGCAAATGAGGAAACGCCACCTGGG
AGCTCCGATGGCTTGCACATGGCACCTGCCCCTGCTTATCCACAGACTCATACCCAC
CCATCCGCCTCTACGAATTCTTTCACGTATGCGAACCCCAATGCACACATTAACACG
GGGACGATGGCATCAGGAGCCCTTACACGCCCTCCTCGTAGTGCAGGCGGCCACAG
TCTGGAAAACTCCGATGCAGGAAGCACGCACGAGGAAGAGTACACTACGGCACTCC
CTGCCTTCTCCAAGGACTCGCAGAAGGAGAAGAAGGAGCGTGGCTTCCGCGGTGTT
TTGCCATTCCAACGCAAGCGTAAAGACAAGGATAAGGATAAGGACAAGGATAAGG -continued ACAAGGACAGGGAAAAGGATAAAGACAAAGATAAAGACAGGGAGAAGGACAAAG
ACAAGGACAAAGACAAGGAGAGGGGCAAAGAAAAAGACAGGGACAAAGAGAAAG
AAAAAGACAAGGGCAAGCTCCGAGAAAGGGAACGAAGCGTGGAACGGAATGACCG
TGGTGGACACTCTGCCATGGGCGAATACCACAGCCACAGTAGCCTTCGGGGTCGAG
CGCAGAACGAAGAGTTCTGA (SEQ ID NO: 35).

*Magnaporthe oryzae* strain SV9610. RasGAP ETaG sequence:
ATGTCTAAGAAGCATGAGCGCGGACAGAGTCTGGACATGAGCAAACTCGCCATCTT
CGAACAAGAGAAGACGGTCACACCCGCACCAGCGCCGCCGCCCAGGATGGGGAGC
TTGCGGCCAACGTCGATGCTCCTCACTCGATCTGACACGATCAACCGAGGGGGAAG
TGCCGCTGTCGCCCATGCCCATGGCCCCGCCTCGCCTCCGCCCTTGCACCATCCACA
GGCAGTCCAACTGCCCGGATCCGATCTTGAGATCCTTGGCCGCTCATCCACAAACCA
ACTTCGTACCCTCTCGAAACTTGCACAGTCTGGAGAGGCTGATGAGTTTGCCATCAC
GTCACCGGCGCAAGAGGTTGTCGGACTAAAAGGCCGCCGCAGGCTTCAGAGAGCCG
ACAGGTCAAATGCTGGCCGCCTCGGTCAGAAGTCTAGCGGATATGGGTGGGAAGGG
AGAAATTGGATGGACAAACAACGACAATTCCTTCAGGCATACGAATATCTTTGTCAC
ATCGGTGAGGCAAAAGAGTGGATCGAAGATGTTATGAACAAATCTATTGGTGAGAT
TGTGAAGCTGGAAGAGGAGCTTAGGAACGGCGAGACTCTGGCGGAGGTGGTTCAAG
CGCTGAACCCGGACCGAAGATATCGTATTTTCCGGCACCCTCGTCTACAGTACCGCC
ATTCGGACAACATTGCAATCTTCTTCCGGTACCTCGACGAGGTTGAACTACCCGACC
TCTTCCGATTTGAACTGATCGATCTTTACGAAAAGAAAAACATCCCAAAGGTCATCT
ACTGCATACATGCTCTCAGCTGGCTCTTATACCGCAAAGGAATTGTCGATTTCCGAA
TCGGAAACCTGGTTGGTCAACTTGAGTTTGAGCACCACGATCTTGAAGCTATGCAGA
AGGGCCTGGATAAGCTAGGGGCCAGTATGCCGACCTTTGGTGACATGGGCGCTGAC
TTTGGGGTTGAGCCGGAACCGGAACCCGAAGAAACGGAAGAGGAGCGGATAGAAA
GGGAACTTGGAGAAAATGAGGAGTCCATCGTCGAGCTGCAAGCTCAAGTACGCGGT
GCATTATTGCGAATGCGGCTTGGGGAGACAATGCAGGAACTCTGGGACTCGGAGAA
CTGGCTTGTCGACCTTCAGGCCCGGATTCGTGGTGATTTTGCGCGCCAGATCATCGA
CTACCGACTAAACATGAGGCGCTTCGCAGTGAATCTACAGAGTGCCGCACGCGGGT
TCCTCGTTCGGTCGCGGCAAGCAGAGAGAGAGTACATGTGGAAGCGCTCAGAGCCC
GCCGTTCTGAAGCTACAGAGTCTCTTCCGGGCTGCAAAGGTCCGCGATGAGGTACGA
GACGTGCGATCTCAATTGTCAGAGGCTACAGGTCCTGTACGCGAGATCCAAGCGGTT
ATGCGAGGCTTTCTCGCCCGCAAGGGTGTGCGCACCCAGGTGCAAGAGACGAGTCG
AACGTCGGGAGCCGCACCGGGTCTCCAGGCGGCCATTCGTGGTATGCTGCTGAGGA
ACAGGCTTGATCATGACAGGGCTATTCTTGCCGAGGAAGCTGTTTCGATCTGCAGCT
TTCAGGCCGCCTCCCGTGCCTTGCTCACAAGAAAACAGGTCGCCCTTCAACGGGAGT
CACTAGCAAGCTTCACGGCGCAGTGGGAGGGTCTTCAATCCGCCTCCAGGGGGATG
TTCGCCAGGAACAGCATCCATGTCACCAAGGCGGAGCTCCGGGGACACTCTCCTGC
CATTGGCCTCCTGCAGGCTTTTTCAAGGGCCGGTGCTGTACGACGTGAAACGACCCG
GGTGTTGGACGCCATCGCTGTACACGAGCCGCAGGTGGTTGAGCTTCAGGGCTTGAT
CCGCGGCGCCATTCAACGCCAACGTATTGCCGCCGACTACCAGGACCTTGAGGAAC
AAGTCCCTCAGATTACCGACCTGCAGTCTCAGATCCGTGGTATGCTCTGCCGCAAAG
AGCAAGGTGAGCTTCTTGATCAGCTCCAGAGCAACGAAGAGCAAATCATCACTTTG
CAGGCCCAGATCAGGGCTATGATCCTGCGAAACAACTTGGATGTAGTGCTGGCCGA
GCTCGAAGAGCAAGAAGGGACGATTGTGCAGCTGCAGGCTGCGGCCAGGGGTGTGA
TTGTACGCAAGAGGTTCGAGGAGAAGAAGCGTCACTTCAAGGAGAACATGTCCAAG
GTCATCAAGATCCAAAGTTTTGTTCGTGGAAAGCTCCAAGGTGAAGCCTACAAGAG
CCTCACAACAGGCAAGAGCCCGCCCGTCAGTGCCGTCAAGAACTTTGTCCATCTGCT
GAACGACAGCGATTTTGACTTCAACGAGGAGGTTGAGTTTGAGCGGATGCGCAAGA
CTGTGGTACAACAGGTGCGGCAAAACGAGATGTTGGAGCAGTACATCGACCAGCTG
GACATCAAGATCGCTCTGCTCGTCAAGAACAAGATCACTCTGGACGAGGTAGTTAG
GCACCAGAGCAACTTTGGTGGCCACACCAGCAATCTGATAGCGAACAGCTCCATCG
CTTCAGTGAACCAGTATGATCTCAAGGCCCTGAACAAGACGTCGAGGAAGAAGCTC
GAGTCATACCAGCATCTCTTCTACAACCTACAAACGCAACCGCAATATCTGGCACGC
CTGTTCCGCAGGATACGTGAGCAAGGCACGGCCGAGAAGGAGTGCAAGCGCATCGA
GCATCTCATCATGGGTCTCTTTGGGTATGCACAAAAGAGGAGAGAAGAGTACTACCT
CCTCAAGCTAATTTCTCGCTCTATCTGGGAGGAGGTTGAAGCTAGCCACATGGTACA
AGACTCACTACGTGGTAACCTCTTCTGGTCTAAGCTCCTAGGCAACTATTCGAGGTC
ACCTCGCGACAGGAAGTACCTGCGAGACCTGCTCGGCCCTCTGATTCGTGACAACAT
TATCGAGGACCCTGCTCTCGACCTTGAAAGCGATCCTCTCCAGATCTATCGATCCGC
CATCAACAACGAGGAGCTGCGGACGGGCATGCCAAGCCAAAGGCCACTCGACGTCC
CCAGGGAAGTAGCCATCAAGGATCCCGAGACGAGGGAGCTGTTCATTGATCATCTT
CGGGATCTCCGTGAGATTTGCGACCAGTTCTTGCTTGCCCTCGAAGACCTGCTTCCTC
GACTGCCATATGGCCTCAGATACATATGCCGCCAGATGTTTGATGCCTTGTGCCAAC
ATTTCAAGCGTGAGCCGCAGCACATATTGCTACAGATGGTGGGCAACTGGTTCTGGC
GCTTTTACCTGCAGCCTGCCCTGACGGCTCCTGAGAACGTCGGCGTGATGGAGAAGG
GGTTGAGCCCGCTGCAGAAGCGCAACCTGGGTGAGGTTGCCAAGGTTCTCGGCCAG
GTAGCCTCTGGCCGTCCGTTTGGCGGTGATAATATCTACCTGCAGCCATTAAACGCC
TTTGTCGCTGAGTCCATGGAGCGTTTAGGCCATATCCTGGGCGAGCTGATCTCAGTC
GCCGATGCCGAAAGTACATTTGACATTGATGAGTTCAACGACCTTTACGCCAAAAAC
CGGCCCACGCTTTATATCAAGCTTGCAGATATCTTCGCCATACACAACCTGATCTCG
TCAGACCTTCCCACTATTTGTCCCAACCGCGACGACATGCTCCGGGAGATCATGCAG
GAGCTCGGTAGTGCCAAGAACAACGAGAGTGAGATGACGGCTACCGGCTCGTCCGA
CATCCAGATGTTCCTCACTCCCAAGCTGCACGATGTCGAAGATCCCGAGGCAGAGAT
CAAGGCTCTCTTCATGGAGACGAAGCGCTGCATCCTGTACATTATTCGTGTCCAGTC
AGGCTCAACCCTCCTCGAGATCCTGGTCAAGCCCGTCACGCAAGAGGACGAGCGCA
AGTGGATGGCGGTGCTGCACGACGACTTTAGTGACGGCGGGTCCACAAAGGGAGCT
TATTCCGACGTTAATATGGTCGACGTTACCCGTATGTCGTACCTCGACCTCAAGCGC
ACGGCACTCGAGAACGTCATGAGGCTGGAGCACGCCGGCAGGATCTCCAAGCACAA -continued CCACTACCAAGATATATTGAACGCCATTGCACTCGATATCCGGACCAAAAGCAGGA
GGAGAGTTCAGAGGCAGCGCGAGCTCGACGGGGTCCGCATGACGCTTTCTAATCTC
CACGAGAAGGCAAAGTACCTAGAGCAACAGCGCAAGAGCTACGATGACTACATTGA
GCAGGCCATGGCGACTCTGCAGAATAGGAAAGGGTAAGTCGACCTACGATACCAAC
ATGCTTCTCGTCTGAACAAGTAAAGGCTAACCTCGTTGGTTTGTTAACTTTGAACAG
CAAGAAACGGTTCCTGCTTCCATTCACAAAGCAGTACAACCACCAACGCGAGCTCG
AGCGTAGCGGCCGGGTGCCCAAGTTCGGATCGTACAAGTACAGCGCACGCCAGCTC
GCCGACAAGGGCGTACTTGTCAGCTGGGCGGGAGTGTCGGAGCGCGACCTGAGCCA
GATCAACCTCACTATCTCTTGCGACGAGGTGGGCGTATTTGTCATCGAGGGCTCGCG
TGGCCACATCCAGATCCCCGGCGCGAGTGCCCTAGTCCCTATCGAGGACCTGCTGCA
AGCCCAGTTTGAGTCGCATCAGTTCATGAACCTCTTCGAGGGCAACCTGAGGCTCAA
TGTCAATATCTTGCTGCATCTGCTTTATAAGAAATTTTATAGGACACAATAAATGGT
CGGGGCGAATTGGGGAGGGTCTAA (SEQ ID NO: 36).

Figure 37:
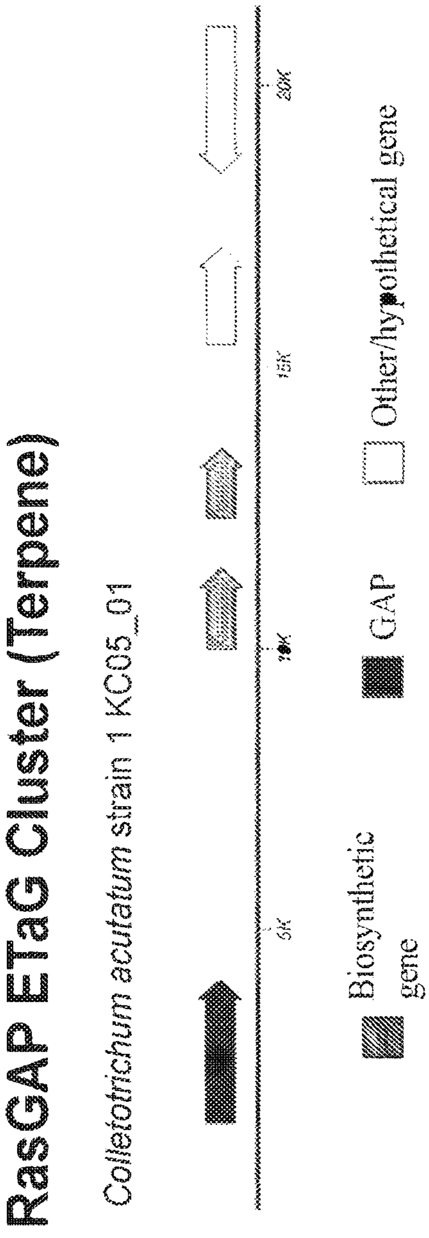
FIG. 37 depicts example biosynthetic gene clusters related to RasGAP, e.g., *Colletotrichum acutatum* strain 1 KC05_01. Illustrated RasGAP homolog is indicated in black.

FIG. 37: *Colletotrichum acutatum* strain 1 KC05_01. RasGAP ETaG sequence:
ATGTCCGTCATGCTCCAAACACCATCTCGAGCTTCTACCGCCTCCTCCTCCTCCTTCC
AACCCCTTTCCCGCCAAAACACCATGTCTTCTTACGATGGATCGCGGTCCGCCCGCC
AATCGAAGCGTTACTCCATGTCCGCGCTGTACATGTCCATGTCAGCGAACGAGACTG
ATCTGGAGATTGAGGATGACTTGGCCAAAGGTAGGCTCTGTAACCTCCGCAGTTTCC
TTGCCCTTTTGCCCTACTGACGATGGATTTTACAGCCCAGAAGATTCTCAGAGAGCT
CAAGTCCAAGATCTCTTCGCAGTCCAAAAAGAACTTCGTACTGGAAAAGGATGTAC
GATATCTTGATTCACGAATCGCCCTCCTCATCCAGAACCGAATGGCTCTCGAGGAAC
AGAACGAAGTCGCGAGCCACTTGGAAGACGCGACGGATATGCAAGAAGGCGCCTTT
CCTAACGACGACAAGACGCAAAAGTATGGCAACTTGATGTTCTTGTTGCAATCCGAG
CCGAGGCATATTGCACACCTCTGCCGTCTGGTGTCAATGTCGGAAATCGACTCTCTG
CTGCAGACTGTCATGTTCACCATCTACGGAAACCAATACGAGAGTCGCGAAGAACA
TCTGCTCTTGACTATGTTCCAGGTTTGTGACCCGTGACTATACTACGCGATCTGGCAA
GCTGACTCTTGACCCATTAGTCTGTTCTGACCTACCAATTCGACAACACCCCCGAAT
ATTCTTCGCTTCTGCGTGCGAACACCCCCGTCTCGAGAATGATGACCACGTATACGC
GGAGAGGACCAGGACAGAGCTTTCTCAAGTCAGTTCTCGCTGATAGAATCAACAGT
CTGATCGAGTTGAAGGATCTCGACCTGGAGATCAACCCCCTCAAGGTCTACGAGCG
CATGATTGAGCAAATTGAGGAGGACACTGGCAGTCTGCCTGCATCGCTTCCCAAGG
GCGTTACTGCTGAGCAGGCTGCGGAGAACCCCCAAGTTCAAGCCATCATCGAGCCG
CGTCTGACAATGCTCACCGAGATTGCTAATGGCTTCTTGACAACCATCATTGACGGA
CTCGACGAAGCGCCGTACGGTATTCGGTGGATTTGCAAACAGATTCGCAGCTTGACG
AAGCGCAAGTACCCTGATGCCAATGATCAGGTCATTTGCACTCTTATCGGCGGATTC
TTCTTCTTGCGGTTCATCAACCCGGCAATCGTGACACCAAAGTCATACATGCTCATT
GACGGTCAGCCGGCTGATCGCCCGAGAAGAACGCTGACTTTGATTGCAAAGATGCT
GCAAAACCTTGCTAACAAGCCCTCCTACGCCAAGGAGCCATACATGGCCAAGCTGC
AACCCTTCATCTACCAGAACAAGGAGCGTATCAACAAATTCATGCTTGACTTGTGTG
AAGTTGGCGACTTTTATGAGAGCTTGGAAATGGATAACTACGTCGCACTCTCGAAGA
AGGATTTGGAACTGTCCATCACCTTGAACGAAATCTATGCCATGCATGGCCTGATTG
AGAAGCACAACGGAGAGCTCTGCAAGGACGACAACTCGCACTTGGGCATCATCATG
TCTGAGCTAGGAGGCGCACCCCCACAGGTTCCTCGCAAGGAGAACCGCGCCATCAA
CCTCCCCCTCTTTAGCCGATGGGAAACAGCGATCGACGACTTGACAGCGGCGCTCGA
CATCACGCAAGAGGAAGTGTACTTTATGGAAGCCAAGTCCGTCTTTGTGCAAATTAT
GCGATCGATCCCATCCAACAGCAGTGTTGCACGAAGACCTCTGCGACTCGAGCGGA
TTGCCGACGCCGCAGCTACGAGCCGAAACGACGCCGTGATGGTTCGCAAAGGTATC
AGAGCGATGGAGCTGCTCTCACAGCTGCAGGAACTGAAAGTCATCGATAAGAGCGA
TCAATTCGGCCTGCTGCGTGACGAAGTCGAGCAGGAACTGCAACACCTTGGATCGCT
CAAGGACGGAGTCATTCAAGAGACTGGCAAATTGGAAGAAGTCTACAAGACCATTC
GCGACCACAACAACTATCTCGTTGGCCAATTGGAGACGTACAAGAGCTACCTGCAC
AACGTGCGTTCGCAAAGCGAGGGAACCAAGCGCAAGCAGCAGAAGCAACAGGTCC
TCGGGCCTTACAAATTCACTCACCAGCAGCTGGAGAAGGAGGGTGTCATTCAAAAA
AGCAACGTCCCGGATAACCGGAGGGCCAACATTTACTTCAACTTTACCAGCCCTTTG
CCGGGAACTTTTGTTATCTCTCTTCACTACAAGGGTACGTTGCCTCGATTGGTCATTG
CGCAACTTTTACTGACTTTTGTACAGGACGCAACCGCGGTCTTCTTGAACTGGATCTC
AAGCTCGACGACCTGCTTGAGATGCAGAAAGACGGCCAGGACGACCTAGATCTGGA
GTACGTCCAGTTCAACGTCACCAAGGTTCTCACTTTGTTGAACAAGCGATTTGCGAG
AAAGAAGGGGTGGTAA (SEQ ID NO: 37).

Figure 38:
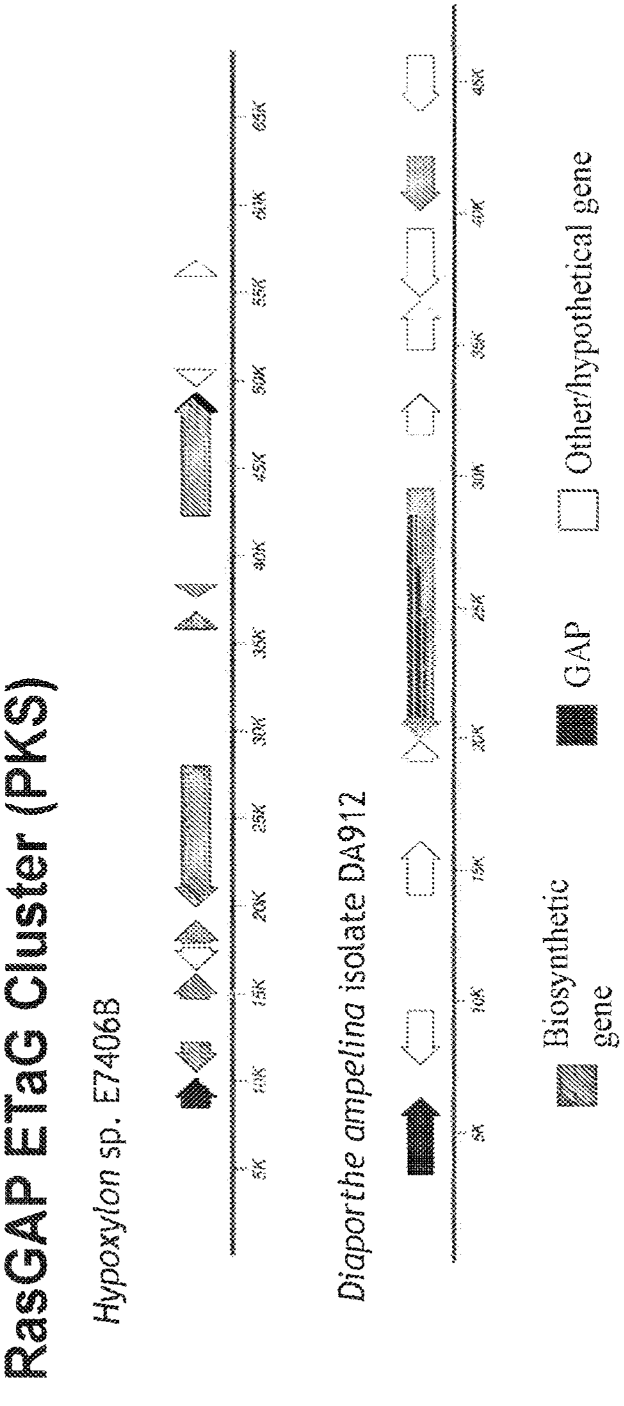
FIG. 38 depicts example biosynthetic gene clusters related to RasGAP, e.g., from *Hypoxylon* sp. E7406B and *Diaporthe ampelina* isolate DA912. Illustrated RasGAP homologs are indicated in black.

FIG. 38: *Hypoxylon* sp. E7406B. RasGAP ETaG sequence:
ATGACTACCTACACTAGGCGTGGACCAGGACAGAGCTTCTTGCGAACGGTACTGGC
GCAAAGAATCAACAGCCTAATTGAGTTGACAGATCTAGACCTTGAGATCAACCCCTT
GAAAGTCTATGAACGCATGTGTCAACAAATTGAAGAAGACACCGGTAGTCTTCCCC
CCTCTCTACCTAGAGGAATCACAGGCGAACAAGCTGCCGAGAATCCCCAAGTGCAA
GCCATCATAGAGCCTCGTTTAACGATGCTAACGGAGATTGCCAATGGCTTCCTGACC
ACAATTATCGAGGGCCTCGAAGAGGCTCCCTATGGCATTAGATGGATATGCAAGCA
GATTCGGAGTTTGACCAAACGAAAATATCCTGATGCGAATGACCAGGTCATTTGCAC
ACTGATCGGCGGCTTTTTCTTCCTGCGCTTTATCAATCCTGCTATCGTTACACCCAAG
TCCTACATGCTCATCGATGGAGTGCCTTCTGAACGACCACGCCGAACGTTAACCCTG
GTTGCCAAGATGCTTCAGAACTTGGCCAATAAACCATCGTATGCTAAAGAACCGTAC
ATGGCGAAGTTGCAACCATTTATCCAGCAGAACAAGGATCGTGTCAACAAGTTTATG
CTTGATCTCTGCGAGGTCCAGGACTTCTACGAGAGTCTCGAGATGGACAACTATGTT
GCACTTTCAAAGAAAGACCTAGAGCTCTCCATTACGCTGAATGAGATATACGCCATG
CACGCCTTGATCGAAAAGCACAGTGGAGAACTCTGTAGGGACGAGAACTCCCACTT
GTCACAAATCATCCAGGAGCTCGGCAAAGCACCCGCGCAGGTACCTCGGAAGGAGA
ATAGGGCGATTAATCTTCCCCTGTTTAGCCGATGGGAGACAGCTATAGATGATTTGA
CTGCCGCCCTAGATATCACGCAGGAGGAAGTGTATTTCATGGAAGCAAAGTCAATCT -continued TTGTACAAGTTATGCGGTCCATTCCTGCTAACAGCTCGGTTGCTCGGCGACCTCTAC
GCCTAGAGAGAATTGCTGATGCGGCTGCCACATCAAGGAACGACGCAGTGATGGTC
CGGAAAGGTATCCGGGCCATGGAGCTGCTTAGTCAACTACAGGAGATGAAGGTTAT
TGATAAGTCAGACCAGTTCAGCCTCCTGAGGGATGAGGTCGAACAAGAGTTACAAC
ATCTAGGTTCCCTGAAGGATGGTGTCATTGCCGAAACCGCGAAGCTCGAAGAGGTTT
ACAAGACGATTAGGGATCATAACTCGTACCTCGTCGGCCAGCTAGAGACTTACAAG
AGCTATCTCCACAACGTGCGAAGTCAGTCCGAAGGCACGAGACGGAAACAGCAAAA
GCAGCAAGTTCTCGGGCCTTACAAGTTTACTCACCAGCAACTAGAGAAGGAAGGCG
TCATCCAGAAGAGTAATGTTCCGGACAATAGAAGGGCTAACATCTACTTCAATTTCA
CAAGTCCTTTACCTGGAACTTTTGTGATTTCATTACACTACAAAGGTCAGTCAGAAG
GGACATTCCACTTCAGTCACGGGCTAACAAATGAATAGGACGCAATCGTGGTCTTCT
AGAACTCGACCTTAAGTTGGACGATCTGTTAGAAATGCAGAAGGACAATCAAGATG
ACTTGGACCTCGAATACGTGCAGTTCAACGTCACGAAGGTATTGGCCTTGTTAAACA
AGCGCTTTGCCAGGAAGAAGGGCTGGTAA (SEQ ID NO: 38).

*Diaporthe ampelina* isolate DA912. RasGAP ETaG sequence:
ATGTCTGTGATGCTGCAAACTCCTTCCCGGGCCTCAACCGCATCCTCCTCCTCCTACC
AGGCCCTCTCCCGCCAGAACACCATGTCTTCCTACGATGGCTCGCGGTCAGCCCGCC
AATCGAAACGGTACTCCATGTCGGCATTGTACATGTCCATGTCGGCACAGGAAACCG
ACTTGGAAATAGAAGACGATCTTGCTAAAGGTTTGTTCCCAACCCCTCTCATCCAGG
CCGAAATCTTGACCGAAGTCCCATTACTTACTGTCCCCAGCCCAAAAGATACTACGG
GACTTGAAGTCCAAGATTTCCTCCCAATCCAAGAAGAACTTCGTGCTTGAAAAGGAC
GTGCGGTACCTCGACTCACGTATTGCATTGCTGATTCAGAATCGCATGGCTTTGGAG
GAGCAGAACGAAGTCGCCAGCCACTTAGAAGACGCGACAGATATTCAGGAAGGGGT
CTTTCCAAACGACGACAAGACGCAGAGATATGGCAACCTCATGTTTCTCTTGCAATC
AGAGCCCAGGCACATTGCGCATCTCTGCCGGCTTGTGTCCATGTCCGAGATCGACTC
CCTGCTGCAGACAGTCATGTTCACCATCTATGGAAACCAGTACGAGAGCCGAGAAG
AGCATCTGCTGCTAACTATGTTTCAGGTTTGCCTACCTTCTATTTCAACGTGAGTGCT
CATGCTAACTCTTGCCACCAGTCCGTTTTGACGTATCAGTTCGATAACACGCCTGAA
TATTCGTCGCTGCTTCGCGCCAACACACCAGTCTCCCGGATGATGACAACATACACG
AGGAGAGGCCCGGGTCAGAGTTTTTTGAGATCGGTGCTTGCGCACAGGATTAATGG
CCTTATCGAGCTGCACGATCTGGATCTCGAGATCAACCCCCTCAAAGTTTACGAGCG
CATGTGCGAACAAATCGAGCAGGACACGGGCAGCCTTCCGCCGTCTCTGCCAAAGG
GCATCACTGCTGAACAGGCCGCGGAGAATGCTCAGGTCCAAGCTATCATCGAGCCG
AGACTCACCATGCTTACCGAGATCGCGAATGGCTTTTTGTCGACCATCATCGACGGC
CTGGACGAAGCGCCGTACGGAATTCGATGGATCTGCAAACAAATTCGCAGCTTGAC
GAAGCGGAAGTACCCCGATGCCAACGACCAGGTCATTTGTACACTGATCGGAGGAT
TTTTCTTCCTGCGCTTCATAAACCCTGCCATCGTTACGCCGAAGTCGTACATGCTGAT
AGATGGAACACCGGCGGATCGGCCGAGGAGGACCTTGACGCTGATCGCAAAAATGC
TGCAAAACCTTGCGAACAAGCCATCCTACGCGAAGGAGCCCTACATGGCCAAGCTG
CAGCCGTTTATCCAATCGAACAAAGAACGGATCAACAAGTTCATGCTTGATCTTTGC
GATGTGCAAGACTTCTACGAAAGTCTGGAGATGGACAACTACGTGGCGCTTTCAAA
GAAGGATCTGGAGCTGTCCATAACACTGAACGAGATCTATGCCATGCACGGCCTCAT
TGACAAGCACCGGAATGAAATTTGCAAGGACGAGAACTCGCACCTACACATCATCA
TGTCCGAGCTTGGCCCTTCTCCTCCGCAGGTGCCCAGGAAGGAGAACCGGGTGATCA
ACTTACCACTGTTCAGCAGATGGGAGTCGGCCATGGATGACTTGACCGCCGCGCTCG
ATATCACCCAGGAGGAGATTTATTTCATGGAGGCCAAAAACGTATTTGTACAGATCA
TGCGTTCCATTCCATCGAATAACTCGGTTCAGCGAAGGCCTCTTCGCCTCGAGCGTA
TCGCCGATGCAGCAGCGACATCTCGGAACGACGCGGTTATGGTCCGCAAAGGTATC
CGTGCTATGGAACTGCTGAGTCAACTCCAGGAGCTGCGAGTCATAGACAAATCCGA
CCAGTTCAGCCTGCTACGAGATGAGGTCGAGCAAGAGCTACAGCATCTGGGCTCTCT
TAAGGATGCGGTCCTTGTGGAGACTTCCAAGCTTGACGAGGTCTACAAGACAATCCG
CGACCACAACACGTATCTGGTCGGCCAGCTGGAAACGTACAAGAGCTATCTGCACA
ATGTCCGCAGCCAGAGTGAGGGTACACGGCGGAAACAGCAGAAGCAGCAGGTTCTC
GGTCCCTACAAGTTCACACACCAACAATTGGAGAAGGAAGGGGTTATCCAGAAGAG
CAATGTGCCGGACAACAGGCGGGCCAACATATATTTCAACTTCACAAGCCCCCTTCC
GGGAACATTCGTGATTTCTCTGCACTACAAGGGCAAGTATAGCAGCTCGAGGGCTG
AGGACCATCCGGCATCATTCGTGAATTTATTACTGACATCCATCCCAGGGCGTAACC
GCGGGCTCTTGGAGCTTGATCTCAAGCTCGACGATCTCCTGGAGATGCAGAAAGAC
GGACAGGACGAGCTGGACCTCGAGTATGTCCAATTCAATGTGCCGAAAGTGCTCGC
CCTTCTGAACAAGCGGTTCGCTCGGAAGAAGGGTTGGTAAATAACGGATTGCCACA
CGTTATTCTGCCTTGTGTGCATCCTAGAAGATGAGGCAAGCGGTGGTCCATCCACAG
TGGCCTACTTCTTCACAACACATATCTCACGATCGATCATTCTGCCATCTCCAACATA
CAACATCATGTATCGCTAAGGGACTGTCGGCGTTTTGGGGCCGGCGTGCACTTTTAT
AATCCTTGATACCATCGTCTATACGCAACATCGTCTTTCAGGTCGCCCGCCTACACCT
TCACCTTTCCCCACTATATATCCCGACCGAGAGAGCCCTCTCTCGTACTGCACGCCC
CCCGCCCCCTGGGGCAGCACATCAACAGCCTCTATCAATATCTAA (SEQ ID NO: 39).

Figure 39:
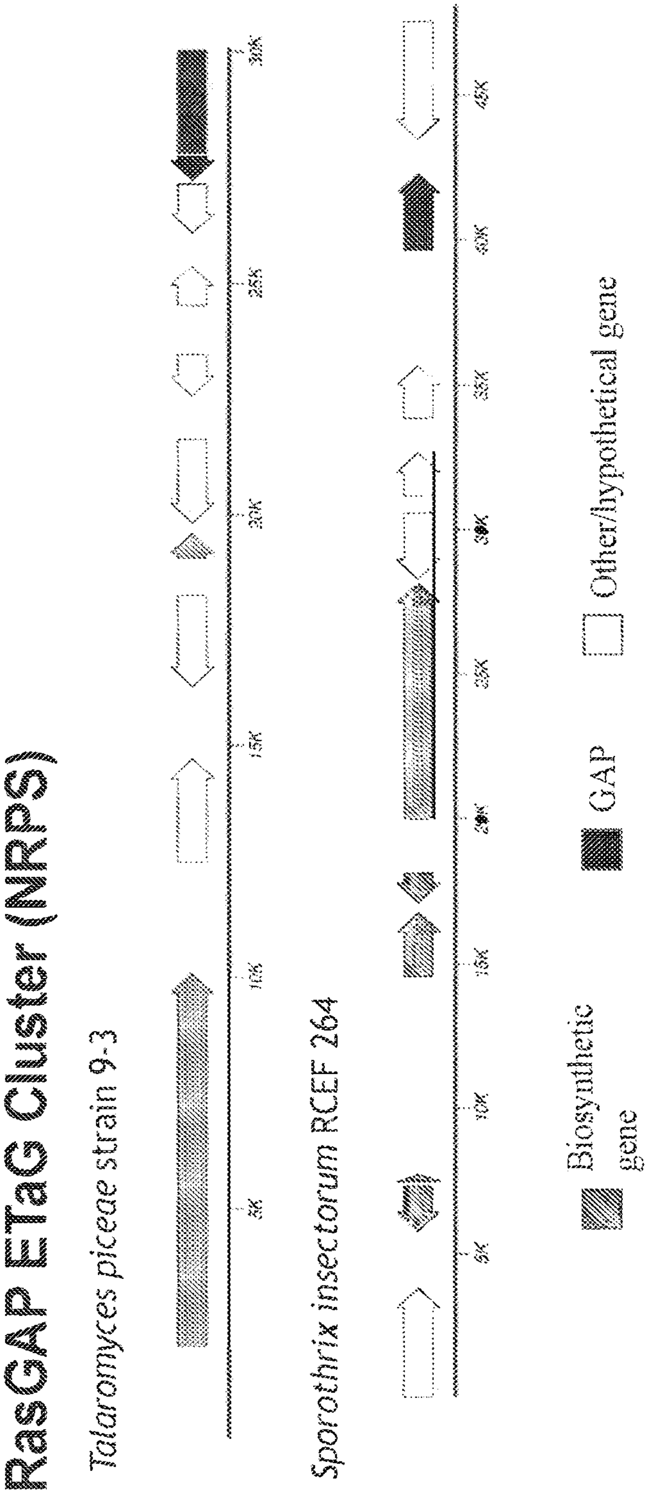
FIG. 39 depicts example biosynthetic gene clusters related to RasGAP, e.g., from *Talaromyces piceae* strain 9-3 and *Sporothrix insectorum* RCEF 264. Illustrated RasGAP homologs are indicated in black.

FIG. 39: *Talaromyces piceae* strain 9-3. RasGAP ETaG sequence:
TTCGACAACACGCCCGAGTACTCGTCGCTTCTCCGTCAAAACACCCCCGTT
TCCCGCATGATGACCACCTACACCCGCCGCGGTCCCGGTCAAAGCTACCTGAAACAT
GTCTTGGCTGAACAGATCAATACGCTCATTGACTTGCACGATGTCGATCTCGAGATC
AACCCCTTGAAGGTGTACGAAAGTATGGTGCAGCAGCTTCAGGAAGACACGGGCAG
TTTGCCCGACTACCTGCCCCGAGCAGTCACCGCCGAAGTCGCTGCCGAGAACGAGC
AGGTCCAGGCGATTATTGCTCCGCGCCTGAAGATGTTGACGGACCTTGCCAACAATT
TTCTCAACACCATCATCGAGGGGCTCGAAGATGCTCCGTACGGGATCCGCTGGATCT
GCAAACAAATCCGAAGTCTCTCCCGACGCAAGTACCCGGACGCTCAGGACCAGACC
ATCTGCACGCTTATCGGCGGCTTCTTTTTCCTTCGCTTCATCAACCCGGCCATTGTGA
CGCCTCGGTCGTACATGCTCATTGAGGCGACCCCGACCGACAAGCCCCGCCGGACCT TGACCCTGATCGCCAAGATGCTGCAGAACTTGGCCAATAAGCCGTCGTACGCCAAA
GAACCGTACATGGCCAAATTGAGCCCCTTTATCGACGAGAACAAAGACCGCGTGAA
CAAATTCTTGCTCGATCTGTGTGAAGTCCAGGACTTTTACGAGAGCCTGGAGATGGA
CAACTATGTCGCCCTGACGAAGCGGGACCTGGAGCTGCAGATCACGTTGAACGAGG
TGTATGCCACACACGCGCTGCTGGAGAAACACAGCGCCAGCCTGGCGGCTTCAGAC
CAACACTCTCACTTGCAAGCTCTTCTCCAGGAACTAGGGCCGGCACCGAGCCAGGTT
CCCCGGAAAGACAATCGCGCGATCAACCTGCCGCTGTTTAGCAAGTGGGAGACCTC
GGTCGACGATCTCACGGCGGCCCTGGATATCACCCAGGAAGAGATTTTCTTTATGGA
AGCCAAGTCGACCTTTGTCCAGATCCTGCGTTCGCTACCCTCCAACTCGGCTGTCAT
GCGGCGTCCTTTGCGGCTGGATCGCATCGCCGAGGCCGCGGCAACTCTGAAGAACG
ATGCCGTCATGGTTCGAAAGGGGATTCGTACGATGGAGCTCCTGAGCCAGCTCCAG
GAGCTGGGCGTGATTGATCGATCCGATGAGTTTGGGCTGTTGCGCGACGAAGTCGA
ACAGGAACTCGTCCATCTGGGTTCGCTCAAGGAGAAAGTGGTGCAAGAGACTCGGC
AGTTGGAGGAAGTGTACAAGACCATTCGCGATCACAACGCCTACTTGGTCGGCCAG
CTCGAAACCTACAAGTCGTATCTGCACAACGTGCGCAGCCAGTCCGAAGGCAAATC
CCGGAACAAAAAGGAGAAGAACCAGGAGCTCGGTCCGTACAAGTTTACCCACCAGC
AACTTGAAAAGGAGGGAGTCATCCGCAAAAGCAACGTGCCCGAGAATCGGCGTGCC
AACATCTATTTTATGTTCAAGAGTCCGCTGCCGGGCACATTTGTCATCAGTCTACACT
ACAAAGGTGAGCTTTCGTCCTTTTGTTTTCCTGGTTTGCTGAAGCCCCGCCCCAAACT
AACTATCACCAGGACGAGCCCGCGGTCTTCTCGAGCTCGACTTGAAACTGGACGAC
CTTTTGGAGATGCAAAAAGACAACCAAGAGGACCTTGATCTTGAATACGTTCAATTC
AACGTCACCAAAGTACTGACCCTGCTGAACAAGCGCTTTGCGCGTAAAAAGGGGTG
GTAATGGCCCCTTGACGACTTTCCATGACCCTGGCACCCCGTTGTGCTTTACCTAACC
CGTATCCTTTTGTTTTCGAAACACAGTGCTTGCGTTGTCCGTGTGAGTTCAACAGCTT
GCCATGATACCCCGCTCCGGCTCGAATTTAGTCTACATCTTGATTATGCTATTGATCG
TTTGCGCATACCCCTGTTGGTTTTTGGTTCACCTGAATTGTTGGTTTGATTTTTGGAA
AATGGATTAAAAAAAGCACAAAAAAAAAGAAGAAGAAGAAGAAAAAGAGGAAAA
AAAAAAAAAAAAGAGGAAGTCAAAGTCTCCATGGGGATATCCTGTTATGGATGTCG
GGAAATGTGGTGAATTGCTTACATGACTTGCGTCCACCGTTCGCTGGCTCGAAAGGT
GTATTGTTTGTGTTTGGTGATTGTTTGCGTGTCGTGCGCTTTGGTGTTTGAGTCTCTG
GACCGTATACAGAGCGGCTTGAAGCATTTTTTGTTTGCGTGCGTTTCGATGGTTGGG
ATTGTTATGCTGATCCGACCACGTGTAATAATATATATATATATATATATATATCAAT
CATAGGCTTTCATGACAATCACTTCTTGTCTCTCCTCCCCTTGGTCCATATCGCCATA
TCTGGTCAGACCAGGGTGGCGAGCGAATCAGCACAGACAACCAAACTAGGCAAAGC
TAGTCGCAACTTTGCCGCCAACTGCAACACCAGCCACAACTGCCGCCCGCCGCTGCT
CCCCCAGCCCACTTGGCCCGATCAGCGCACGCCAGACCTTTGTTTTCTAGTTTCTCCT
CAGCTGCAATCACACTTTACCCTTCAGACCGCAACTTCAGACTTGTGTGTTCTGCAAT
TCCTTCCCTTTTCCTCTTTTCCTCGCTGTGTCCTCTATCCGCACCTGCCGGGCACAAAT
CGAATTGACCGCAGTCATCATCGACTCACCACCAGTCAATCTCGCCGGACCCCGCTA
TCCCGCTTGA (SEQ ID NO: 40).

*Sporothrix insectorum* RCEF 264. RasGAP ETaG sequence:
ATGTCTGTCATGCTGCAGACGCCTTCTCGAGCCTCCACTGCCTCTTCTTCGTCCTTTC
AACCCATCTCCAGACAGAACACCATGTCGTCCTACGATGGCACGCGGTCCGCCCGCC
AATCCAAGCGGATTTCCATGTCCGCCCTCTACATGTCCATGTCGGCCAACGAAACCG
ACTTGGAGATTGAGGACGAGCTGGCCAAAGGTTGGTCCAAAGCCCCTGCCTGCTGCT
GCCTTCTGTGGACGTTTTTGTCTGGTTTGCAAACTGCCCATGATGTACTAATGCCGTG
TTCTCTTCTCCCTGCCACAGCACAAAAGAAGCTTCGCGATCTCAAAGCCAAAATCTC
GATGCAATCGAAACAGAACTTTGTCCTCGAGAAGGACGTGCGGTATCTCGATTCGA
GAATTGCCTTGCTGATTCAAAATCGCATGGCCTTGGAAGAGGTATGCATTGAAGCGG
CTGCGGATTACAGAAACAACAAATGACCCATACTCCGTTGTTGTTGATGTCGTTCTT
GTTCTCTTGTTCCCTTTCCTAACGCCAATTGTGCTTTAGCAAAACGAAGTGGCGAGCC
GTCTCGAAGACGCACTCGAATTGCAAGTCGGCGCCTTTCCGAACGACATGCAAACC
CAAAAATACGGCAACCTGATGTTCCTGCTACAGTCCGAGCCTCGGCACATTGCGCAT
CTCTGCCGCCTGGTGTCCATGTCCGAAATCGACTCACTGCTGCAGACGGTCATGTTC
ACCATCTACGGCAACCAGTACGAGAGCCGCGAAGAGCACCTGCTCCTGACCATGTT
TCAGTCTGTGCTCACCTACCAATTCGACAACACCCCCGAATACTCCTCGCTGCTGCG
GGCCAACACCCCCGTCTCGCGCATGATGACGACGTACACGCGACGCGGACCCGGCC
AGAGCTTTCTCAAGACCATCCTCGCCGACCGGATCAACAGCCTCATCGAGCTCCAAG
ACCTCGACCTGGAAATCAACCCGCTCAAGGTCTACGAGCGCATGGTCGCCCAGATC
GAAGAAGACACGGGCAGCCTCCCCGCGTCCCTCCCCAAGGGCATCACGGCCGAACA
GGCCGCCGAAAACCCACAGGTCCAGGCCATCATCGAGCCGCGCCTGACCATGCTCA
ACGAGATCGCCAACGGGTTCCTCGCCACCATCATTGACGGCCTGGAGGAGGCGCCG
TACGGCATCCGCTGGATCTGCAAGCAGATCCGCAGCCTCACGAAGCGCAAGTACCC
CGACGCCAACGACCAGGCCATCTGCACCCTGATCGGCGGCTTCTTCTTCCTGCGCTT
CATCAACCCGGCCATTGTCACCCCCAAGTCGTACATGCTGATCGACGGCACGCCCGC
CGACCGGCCGCGCCGGACCTTGACGCTGATCGCCAAGATGCTGCAGAACCTGGCCA
ACAAGCCCTCGTACGCCAAGGAGCCGTACATGTCCAAGCTGCAGCCCTTCATCCACC
ACAACAAAGACCGTGTCAACAAGTTCATGCTGGACCTGTGCGAGGTGCAGGATTTCT
ACGAGAGCCTGGAGATGGACAACTACGTGGCGCTGTCCAAGAAGGACCTCGAGCTG
TCCATCACCCTCAACGAGATCTACGCCATGCACGGCCTGATCGAAAAGCACAGCGG
CGAGCTCTGCAGCGACGCGAACTCGCATCTGGCCGTCATGATGGCCGACCTCGGTGC
CGCGCCCGCGCAGCTCCCCCGCAAGGAAAATCGCGTGATCAACCTGCCCCTGTTCAG
CCGCTGGGAAGCCGCGCTCGACGACCTGACGGCGGCGCTCGACATCACCCAGGAGG
AGGTGTACTTCATGGAGGCCAAGTCCATCTTTGTGCAAATCATGCGGTCCATCCCGC
AGAACTCGTCCGTGGCGCGCCGGCCCCTGCGCCTCGAACGCATCGCCGACGCCGCG
GCCACGTTCAAAAACGACGCCGTCATGGTGCGCAAGGGCATCCGCGCCATGGAGCT
ACTGAGCCAGTTGCAGGAGATGAAGGTCACCGATAAGTCCGATGGCTTCTCTCTGTT
GCGCGACGAGGTGGAGCAGGAGCTGCAGCACCTCGGCTCGCTGAAGGAGGGCGTCC -continued

```
TCACCGAAACGAAGAAGCTGTCCGAGGTGTTTGCGACCATCACCGACCACAACACG
TACCTGAACGGCCAGCTCGAGACGTACAAGAGCTACCTGCACAACGTGCGCAGCCA
GAGCGAAGGCACGCGCCGGAAACCCCAGAAACAGCAGGTACTCGGCCCGTACAAG
TTCACACACCAGCAGCTAGAGAAGGAGGGCGTCATCCAGAAGAGCAATGTCCCCGA
CAACCGCCGAGCCAACATCTACTTCAACTTTACCAGTCCTCTGCCGGGCACCTTTGT
CATCTCCCTGCATTATAAAGGTAAGGCGCTCCTCTGCCGCATTTGCGTTGTCCCATTA
TGCATTTGTACGGTTTCGGTACTCACTAACGCATGCAGGGCGCACCCGGGGCCTGTT
GGAGCTGGATCTCAAACTCGACGATCTCCTGGAGATGCAGAAAAACAACTTGGACG
AGCTCGATTTGGAATACGTTCGGTTCAACGTCCCCAAGGTGCTGGCCCTGTTGAACA
AGCGCTTTGCAAGGAAGAAGGGCTGGTAG (SEQ ID NO: 41).
```

With the identified biosynthetic gene clusters, a number of methods can be utilized to identify and characterize compounds produced by the enzymes of these biosynthetic gene clusters (e.g., those described in Clevenger, et al., Nat. Chem. Bio., 13, 895-901 (2017) and references cited therein) in accordance with the present disclosure. The compounds, once identified, can be assayed to assess their capability for modulating human Ras proteins. Additionally and alternatively, the compounds can used as lead compounds to prepare more analogs for, e.g., SAR studies, to further improve affinity, efficacy, selectivity, etc. for modulating Ras activities. It is expected that useful compounds will be developed from biosynthetic gene clusters related to the identified ETaGs.

While various embodiments have been described and illustrated herein, those of ordinary skill in the art will readily envision a variety of other means and/or structures for performing the functions and/or obtaining the results and/or one or more of the advantages described in the present disclosure, and each of such variations and/or modifications is deemed to be included. More generally, those skilled in the art will readily appreciate that all parameters, dimensions, materials, and configurations described herein are meant to be example and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described in the present disclosure. It is, therefore, to be understood that the foregoing embodiments are presented by way of example only and that, provided technologies, including those to be claimed, may be practiced otherwise than as specifically described and claimed. In addition, any combination of two or more features, systems, articles, materials, kits, and/or methods, if such features, systems, articles, materials, kits, and/or methods are not mutually inconsistent, is included within the scope of the present disclosure.

The invention claimed is:

1. A method for identifying a modulator of a human target, comprising steps of:

a) querying a set of nucleic acid sequences, each of which is found in a fungal strain and comprises a biosynthetic gene cluster; and b) identifying within at least one of the fungal nucleic acid sequences an embedded target gene (ETaG) sequence characterized in that:

the ETaG is not required for or is not involved in the biosynthesis of the product of the biosynthetic gene cluster;

the ETaG is within a proximity zone relative to at least one biosynthetic gene in the cluster, wherein the proximity zone is no more than 100 kb upstream or downstream of the at least one biosynthetic gene in the biosynthetic gene cluster;

the ETaG is optionally co-regulated with at least one biosynthetic gene in the cluster; and the ETaG or a portion thereof, is a homolog of a nucleic acid sequence that encodes the human target;

c) assaying an effect of the product of the biosynthetic gene cluster, or an analog of the product, on the human target.

2. The method of claim 1, wherein a proximity zone is no more than 1, 2, 3, 4, 5, 6, 7, 8, 9, 10, 20, 30, 40, 50, 60, 70, 80, 90, or 100 kb upstream or downstream of a biosynthetic gene in the cluster.

3. The method of claim 1, wherein a protein encoded by the ETaG or a portion thereof has a 3-dimensional structure that is similar to the human target in that a small molecule binding to the protein encoded by the ETaG or a portion thereof also binds to the human target.

4. The method of claim 3, wherein the binding of the small molecule to the protein encoded by the embedded target gene and the human target has a Kd no more 100 μM, 50 μM, 10 μM, 5 μM or 1 μM.

5. The method of claim 3, wherein the small molecule is a biosynthetic product of the biosynthetic gene cluster.

6. The method of claim 1, wherein the set comprises nucleic acid sequences from at least 100, 500, 1,000, 5,000, 10,000, 15,000, 20,000, 22,000, 25,000 or 30,000 distinct fungal strains.

7. The method of claim 1, wherein step c) comprises determining that:

level or activity of the human target is altered when the product of the biosynthetic gene cluster, or an analog of the product is present as compared with when it is absent; or level or activity of the human target is comparable to that observed when a reference agent having a known effect on the level or activity is present.

8. The method of claim 1, wherein a proximity zone is a region between two biosynthetic genes of a biosynthetic gene cluster.

9. The method of claim 3, wherein the similarity is that the structures have a Calpha backbone rmsd (root mean square deviation) within 10 square angstroms and have the same overall fold or core domain.

10. The method of claim 1, wherein the ETaG sequence is or comprises a sequence that is homologous to a second nucleic acid sequence or a portion thereof in the same genome.

11. The method of claim 1, wherein the ETaG sequence is or comprises a sequence that encodes a product that is homologous to a product or a portion thereof encoded by a second nucleic acid sequence in the same genome.

12. The method of claim 11, wherein the homology is at least 50%, 60%, 70%, 75%, 80%, 85%, 90%, 91%, 92%, 93%, 94%, 95%, 96%, 97%, 98%, 99% or 99.5%.

13. The method of claim 11, wherein the second nucleic acid sequence is or comprises a house-keeping gene.

14. The method of claim 11, wherein the ETaG sequences encode a product that provides resistance to a product of the biosynthetic gene cluster while the second nucleic acid sequence does not.

15. The method of claim 14, wherein the ETaG sequences encode a protein that provides resistance to a small molecule product of the biosynthetic gene cluster while proteins encoded by the second nucleic acid sequence do not.

16. The method of claim 1, wherein the human target is a Ras protein.

17. The method of claim 16, wherein the human target is a KRas protein, HRas protein, or NRas protein.

18. The method of claim 17, wherein the human target is a RasGEF domain.

19. The method of claim 18, wherein the human target is a RasGAP domain.

* * * * *